(12) United States Patent
Naganawa et al.

(10) Patent No.: US 8,088,802 B2
(45) Date of Patent: Jan. 3, 2012

(54) N-PHENYLARYLSULFONAMIDE COMPOUND, PHARMACEUTICAL COMPOSITION COMPRISING THE COMPOUND AS ACTIVE INGREDIENT, SYNTHETIC INTERMEDIATE FOR THE COMPOUND AND PROCESS FOR ITS PREPARATION

(75) Inventors: Atsushi Naganawa, Mishima-gun (JP); Tetsuji Saito, Mishima-gun (JP); Kaoru Kobayashi, Mishima-gun (JP); Takayuki Maruyama, Mishima-gun (JP); Yoshihiko Nakai, Mishima-gun (JP); Shinsuke Hashimoto, Sakai-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 12/603,194

(22) Filed: Oct. 21, 2009

(65) Prior Publication Data

US 2010/0041708 A1 Feb. 18, 2010

Related U.S. Application Data

(60) Division of application No. 11/239,406, filed on Sep. 30, 2005, now Pat. No. 7,629,369, which is a continuation of application No. 10/471,673, filed as application No. PCT/JP02/02245 on Mar. 11, 2002, now Pat. No. 7,235,667.

(30) Foreign Application Priority Data

| Mar. 12, 2001 | (JP) | ................................. 2001-068498 |
| Sep. 17, 2001 | (JP) | ................................. 2001-281569 |
| Jan. 16, 2002 | (JP) | ................................. 2002-007760 |

(51) Int. Cl.
*A61K 31/41* (2006.01)
*C07D 421/00* (2006.01)
*C07D 417/00* (2006.01)
*C07D 413/00* (2006.01)
*C07D 285/08* (2006.01)
*C07D 271/06* (2006.01)
*C07D 257/04* (2006.01)
*C07D 307/00* (2006.01)

(52) U.S. Cl. ..... 514/359; 514/362; 514/381; 546/268.1; 546/268.7; 546/269.1; 548/129; 548/132; 548/250; 549/429

(58) Field of Classification Search ................... 514/359, 514/381, 362; 546/93, 268.1, 268.7, 269.1; 548/132, 250, 129; 549/429
See application file for complete search history.

(56) References Cited

U.S. PATENT DOCUMENTS

| 4,066,636 | A | 1/1978 | Sera et al. |
| 6,448,290 | B1 | 9/2002 | Ohuchida et al. |

FOREIGN PATENT DOCUMENTS

| CH | 615660 A5 | 2/1980 |
| EP | 947500 A1 | 10/1999 |
| EP | 1 201 238 A1 | 5/2002 |
| JP | 50-117711 A | 9/1975 |
| JP | 52-93469 A | 8/1977 |
| WO | 98/27053 A1 | 12/1989 |
| WO | 00/69465 A1 | 11/2000 |
| WO | 02072145 A1 | 9/2002 |

OTHER PUBLICATIONS

Stock, Jeffrey L., "The prostaglandin $E_2$EP1 receptor mediates pain perception and regulates blood pressure," the Journal of Clinical Investigation, vol. 107, No. 3, pp. 325-331, Feb. 2001.
Oka, Kae, et al., "PGE 2 receptor subtype $EP_1$ antagonist may inhibit central interleukin1 B-induced fever in rats," The American Physiological Society, vol. 275, (6 Pt 2), R1762-5 (1998).
Kouji Watanabe et al., *Cancer Research*, vol. 59, pp. 5093-5096 (1999).
*Am. J. Physiol.* 267, R289-294 (1994).
European Search Report dated Nov. 7, 2006.
Canadian Office Action dated Feb. 24, 2010 in corresponding Canadian Application No. 2439604 (Inventor: Naganawa et al.).
Norwegian Office Action dated Mar. 25, 2010 in corresponding Norwegian Application No. 20034007 (Inventor: Naganawa et al.).

*Primary Examiner* — Taylor Victor Oh
(74) *Attorney, Agent, or Firm* — Sughrue Mion, PLLC

(57) ABSTRACT

An N-phenylarylsulfonylamide compound of formula (I)

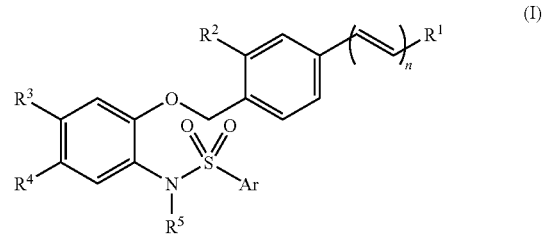

($R^1$ is COOH etc.; $R^2$ is hydrogen, methyl, etc.; $R^3$ and $R^4$ are a combination of methyl and methyl, etc.; $R^5$ is isopropyl etc.; Ar is thiazolyl, pyridyl, 5-methyl-2-furyl each optionally substituted with methyl; n is zero or 1), a synthetic intermediate for the compound and a process for its preparation. The compound of formula (I) binds to a prostaglandin $E_2$ receptor, especially an $EP_1$ subtype receptor, and antagonizes it. It is less affected by protein binding, so it has a satisfactory in vivo activity. Therefore, it is considered to be useful as an analgesic, an antipyretic agent, an agent for the treatment of pollakiuria (frequent urination) and/or lower urinary tract disease syndrome or an antineoplastic agent.

8 Claims, No Drawings

N-PHENYLARYLSULFONAMIDE COMPOUND, PHARMACEUTICAL COMPOSITION COMPRISING THE COMPOUND AS ACTIVE INGREDIENT, SYNTHETIC INTERMEDIATE FOR THE COMPOUND AND PROCESS FOR ITS PREPARATION

This is a divisional of application Ser. No. 11/239,406, filed Sep. 30, 2005 (allowed), which is a continuation of application Ser. No. 10/471,673, filed May 17, 2004 (now U.S. Pat. No. 7,235,667, which issued Jun. 26, 2007), which is a U.S. National Stage Application of PCT/JP02/02245, filed Mar. 11, 2002, which claims benefit of Japanese Application Nos. 2001-68498, filed Mar. 12, 2001, 2001-281569, filed Sep. 17, 2001 and 2002-7760, filed Jan. 16, 2002 the disclosure of each of which is incorporated herein by reference in its entirety.

TECHNICAL FIELD

The present invention relates to an N-phenylarylsulfonamide compound.

More detailed, the present invention relates to
(1) an N-phenylarylsulfonamide compound of formula (I)

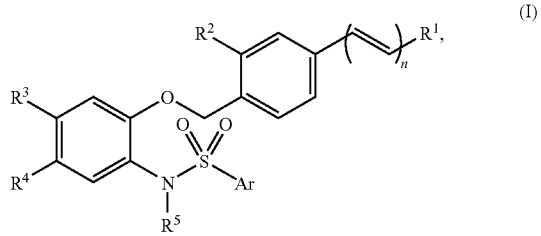

wherein all symbols have the same meanings as defined hereinafter,
(2) a prostaglandin $E_2$ receptor ($EP_1$) antagonist which comprises the compound as an active ingredient,
(3) a compound of formula (II)

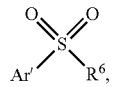

wherein all symbols have the same meanings as defined hereinafter, and
(4) a process for its preparation.

BACKGROUND ART

Prostaglandin $E_2$ (abbreviated as $PGE_2$) has been known as a metabolite in the arachidonate cascade. It has also been known that $PGE_2$ possesses a cyto-protective activity, a uterine contractive activity, a pain-inducing effect, a promoting effect on digestive peristalsis, an awakening effect, a suppressive effect on gastric acid secretion, a hypotensive effect, a diuretic activity and so on.

In a recent study, it was found that a $PGE_2$ receptor is divided into some subtypes which possess different physical roles from each other. At present, four receptor subtypes are known and they are called $EP_1$, $EP_2$, $EP_3$ and $EP_4$ respectively (Negishi M. et al., *J. Lipid Mediators Cell Signaling*, 12, 379-391 (1995)).

$PGE_2$ possesses a variety of physiological activities, so the undesired action other than the aimed one is shown as side effect. The research for the role of each receptor subtype and the investigation of the compound which only shows the effect on the specific subtype have been carried out to overcome such a problem.

Among these subtypes, it has been known that $EP_1$ subtype relates to induction pain, pyrexia (induction fever) and diuresis (ref *Br. J. Pharmacol.*, 112, 735-740 (1994); *European J. Pharmacol.*, 152 273-279 (1988); *Gen Pharmacol.*, September 1992, 23(5) 805-809). Therefore, compounds which antagonize this receptor are considered to be useful as analgesics, as antipyretic agents and as agents for treating pollakiuria (frequent urination).

It has also been known that $EP_1$ antagonists possess a suppressive effect on aberrantcryptfoci and formation of intestinal polyps, and that they indicate an effective anti-tumor activity (ref. WO00/69465).

After drugs are absorbed in the body, they mainly migrate into the bloodstream. Then they are transported in the blood and are delivered to target organs. Finally they exert their potency. However, some drugs do not exert their potency because they combine with some proteins, which is contained in blood as nutritive substances. While some compounds are effective in in vitro experiment, it may often turn out that they are not effective in in vivo experiment. And it has been well known that there is not a specific structure-activity relationship on binding between drugs and proteins, and that it is very difficult to find out the ordinality.

The present inventors found a useful compound which is an $EP_1$ antagonist, and filed a patent application. In the specification of WO98/27053 (EP947500), it is disclosed that a sulfonamide compound of formula (A)

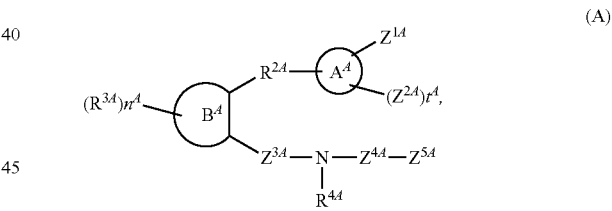

wherein the group

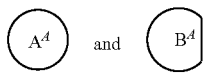

are each independently C5-15 carbocyclic ring etc.; $Z^{1A}$ is —$COR^1$ etc.; $Z^{2A}$ is hydrogen etc.; $R^{1A}$ is hydroxy etc.; $Z^{3A}$ is single bond etc.; $Z^{4A}$ is $SO_2$ etc.; $Z^{5A}$ is 5 to 7 membered heterocyclic ring containing one or two oxygen, sulfur or nitrogen atom(s), which may be substituted with 1 to 5 $R^{5A}$ etc.; $R^{5A}$ (if two or more $R^{5A}$, each independently) is hydrogen, C1-6 alkyl etc.; $R^{2A}$ is $Z^{7A}$-C1-4 alkylene etc.; $Z^{7A}$ is oxygen etc.; $R^{3A}$ is trifluoromethyl etc.; $R^{4A}$ is C1-8 alkyl etc.; $n^A$ and $t^A$ are each independently 1 to 4 (as excerpt),
binds to a $PGE_2$ receptor, especially the $EP_1$ receptor, to show an agonistic or an antagonistic activity. The specification disclosed that the compound having the antagonistic activity is useful for the prevention of abortion, as an analgesic, as an antidiarrhoic, as a hypnagogic agent and for treating pollakiuria (frequent urination), while the one having an agonistic activity is useful for abortion, as an abstergent, as an antiulcer agent, as an antigastritis agent, as an antihypertensive agent, as a diuretic agent.

In this patent application, for example, the following compounds are disclosed specifically.

(1) Example 18(93)

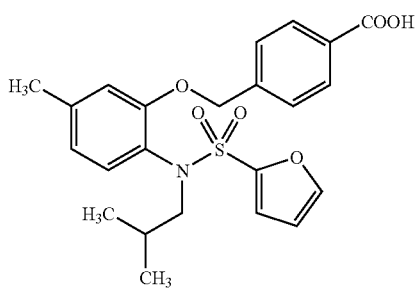

(2) Example 18(113)

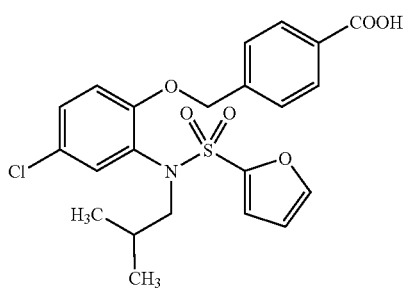

(3) Example 18(125)

(4) Example 18(121)

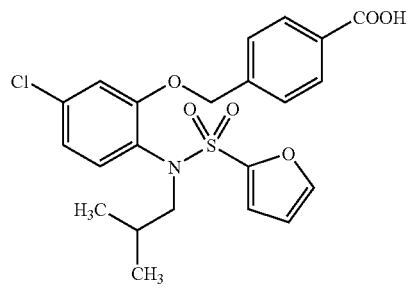

(5) Example 18(126)

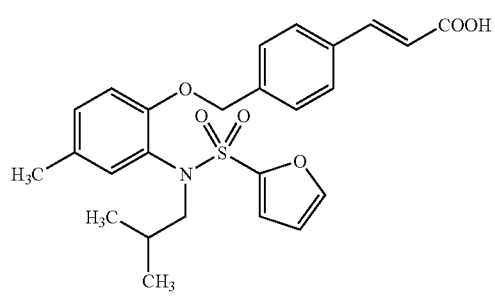

(6) Example 18(59)

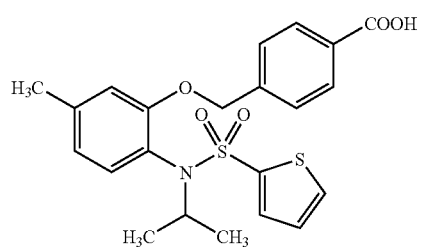

(7) Example 18(124)

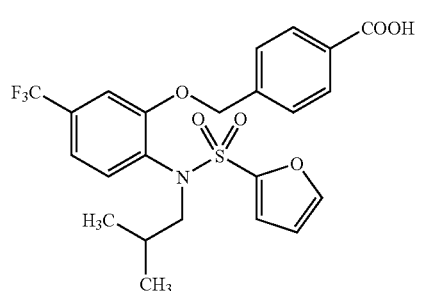

(8) Example 18(94)

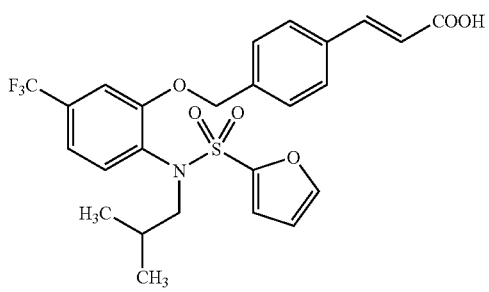

(9) Example 21(13)

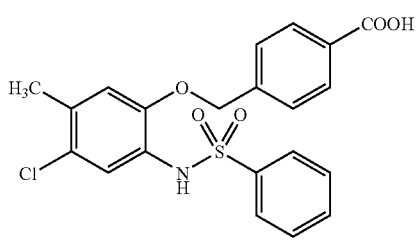

(10) Example 21(14)

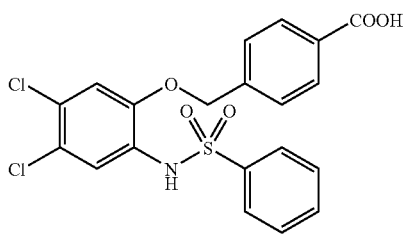

In the process of the researches about these compounds, it was revealed that these compounds have some problems that they are susceptible to the influence of protein binding and that they do not have a satisfactory in vivo activity.

DISCLOSURE OF THE INVENTION

As a result of an energetic investigation to find those compounds which selectively bind to $EP_1$ subtype receptor and have a satisfactory in vivo activity owing to being less affected by protein binding, the present inventors have found that the only N-phenylarylsulfonamide compound of formula (I) has a very strong in vivo activity and completed the present invention.

The present inventors have also found that a novel intermediate of formula (II)

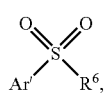
(II)

wherein all symbols have the same meanings as defined hereinafter, which is used for the preparation of the compound of formula (I) and a method for the preparation thereof.

Various compounds are disclosed in the specification of WO 98/27053, as referred to above, but no compounds of the present invention are disclosed, and there are neither description nor suggestion as to above problems nor methods for the resolution.

The present invention relates to (1) an N-phenylarylsulfonylamide compound of formula (I)

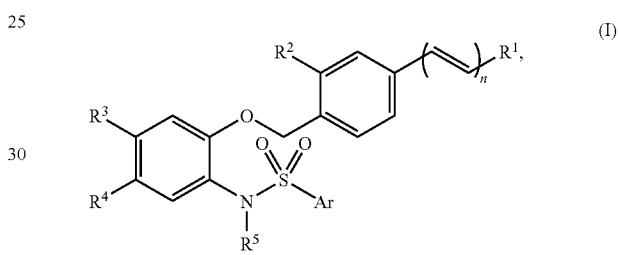

wherein $R^1$ is COOH, 5-tetrazolyl, 5-oxo-1,2,4-oxadiazolyl, $CH_2OH$ or 5-oxo-1,2,4-thiadiazolyl;

$R^2$ is hydrogen, methyl, methoxy or chloro;

$R^3$ and $R^4$ are a combination of (1) methyl and methyl, (2) methyl and chloro, (3) chloro and methyl or (4) trifluoromethyl and hydrogen, or $R^3$ and $R^4$ are taken together with the carbons to which $R^3$ and $R^4$ are attached to form (5) cyclopentene, (6) cyclohexene or (7) benzene ring;

$R^5$ is isopropyl, isobutyl, 2-methyl-2-propenyl, cyclopropylmethyl, methyl, ethyl, propyl or 2-hydroxy-2-methylpropyl;

Ar is thiazolyl optionally substituted with methyl, pyridyl or 5-methyl-2-furyl; and n is zero or 1, and when $R^1$ is 5-tetrazolyl, 5-oxo-1,2,4-oxadiazolyl or 5-oxo-1,2,4-thiazolyl, n is zero, an ester thereof or a non-toxic salt thereof, (2) a method for the preparation thereof, (3) an antagonist of $PGE_2$ receptor, $EP_1$ subtype receptor, comprising it as an active ingredient, (4) a compound of formula (II)

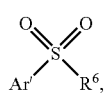
(II)

wherein Ar' is an optionally substituted 5 to 10 membered heterocyclic ring and $R^6$ is

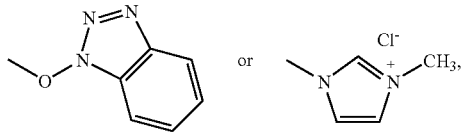

which is an intermediate for the compound of formula (I), and (5) a method for the preparation of the compound of formula (II).

The present inventors synthesized almost all combinations of the compounds of formula (I) of the present invention, and confirmed their activities. And all compounds thereof are preferable.

More preferable compound(s) have or has Ar of 5-methyl-2-furyl, 2-thiazolyl, 5-methyl-2-thiazolyl, 2-pyridyl and 3-pyridyl.

Specifically, preferable compounds are:
4-[2-[N-isobutyl-N-(5-methyl-2-furylsulfonyl)amino]-5-trifluoromethylphenoxymethyl]cinnamic acid,
4-[2-[N-isopropyl-N-(5-methyl-2-furylsulfonyl)amino]-5-trifluoromethylphenoxymethyl]benzoic acid,
4-[2-[N-isobutyl-N-(5-methyl-2-furylsulfonyl)amino]-5-trifluoromethylphenoxymethyl]benzoic acid,
4-[2-[N-isobutyl-N-(5-methyl-2-furylsulfonyl)amino]-4-chloro-5-methylphenoxymethyl]benzoic acid,
4-[2-[N-isopropyl-N-(5-methyl-2-furylsulfonyl)amino]-4,5-dimethylphenoxymethyl]benzoic acid,
4-[2-[N-isobutyl-N-(5-methyl-2-furylsulfonyl)amino]-4,5-dimethylphenoxymethyl]benzoic acid,
3-methyl-4-[2-[N-isobutyl-N-(5-methyl-2-furylsulfonyl)amino]-4-methyl-5-chlorophenoxymethyl]benzoic acid,
3-methyl-4-[2-[N-isobutyl-N-(5-methyl-2-furylsulfonyl)amino]-4-chloro-5-methylphenoxymethyl]benzoic acid,
3-chloro-4-[2-[N-isobutyl-N-(5-methyl-2-furylsulfonyl)amino]-4-methyl-5-chlorophenoxymethyl]benzoic acid,
3-chloro-4-[2-[N-isopropyl-N-(5-methyl-2-furylsulfonyl)amino]-4-methyl-5-chlorophenoxymethyl]benzoic acid,
3-methoxy-4-[2-[N-isopropyl-N-(5-methyl-2-furylsulfonyl)amino]-4-methyl-5-chlorophenoxymethyl]benzoic acid,
3-methyl-4-[2-[N-isobutyl-N-(5-methyl-2-furylsulfonyl)amino]-4,5-dimethylphenoxymethyl]benzoic acid,
3-methoxy-4-[2-[N-isopropyl-N-(5-methyl-2-furylsulfonyl)amino]-4,5-dimethylphenoxymethyl]benzoic acid,
3-methoxy-4-[2-[N-isobutyl-N-(5-methyl-2-furylsulfonyl)amino]-4,5-dimethylphenoxymethyl]benzoic acid,
3-methoxy-4-[2-[N-isopropyl-N-(5-methyl-2-furylsulfonyl)amino]-4-chloro-5-methylphenoxymethyl]benzoic acid,
3-chloro-4-[2-[N-isobutyl-N-(5-methyl-2-furylsulfonyl)amino]-4,5-dimethylphenoxymethyl]benzoic acid,
3-chloro-4-[2-[N-isopropyl-N-(5-methyl-2-furylsulfonyl)amino]-4,5-dimethylphenoxymethyl]benzoic acid,
3-methyl-4-[2-[N-isobutyl-N-(5-methyl-2-furylsulfonyl)amino]-4-chloro-5-methylphenoxymethyl]cinnamic acid,
4-[2-[N-isopropyl-N-(5-methyl-2-furylsulfonyl)amino]-4-methyl-5-chlorophenoxymethyl]cinnamic acid,
4-[2-[N-isobutyl-N-(5-methyl-2-furylsulfonyl)amino]-4-methyl-5-chlorophenoxymethyl]cinnamic acid,
4-[2-[N-isobutyl-N-(5-methyl-2-furylsulfonyl)amino]-4,5-dimethylphenoxymethyl]cinnamic acid,
3-methyl-4-[2-[N-isopropyl-N-(5-methyl-2-furylsulfonyl)amino]-5-trifluoromethylphenoxymethyl]cinnamic acid,
3-methyl-4-[2-[N-isopropyl-N-(5-methyl-2-furylsulfonyl)amino]-4,5-dimethylphenoxymethyl]benzoic acid,
3-methyl-4-[2-[N-isopropyl-N-(5-methyl-2-furylsulfonyl)amino]-4,5-dimethylphenoxymethyl]cinnamic acid,
3-methyl-4-[2-[N-isobutyl-N-(5-methyl-2-furylsulfonyl)amino]-4,5-dimethylphenoxymethyl]cinnamic acid,
4-[2-[N-isobutyl-N-(5-methyl-2-furylsulfonyl)amino]-4,5-dimethylphenoxymethyl]cinnamic acid,
N-[4-chloro-5-methyl-2-[2-methyl-4-(5-tetrazolyl)phenylmethyloxy]phenyl]-N-isobutyl-(5-methyl-2-furyl)sulfonylamide,
3-methoxy-4-[2-[N-isobutyl-N-(5-methyl-2-furylsulfonyl)amino]-4-methyl-5-chlorophenoxymethyl]cinnamic acid,
N-[4,5-dimethyl-2-[2-methyl-4-(5-tetrazolyl)phenylmethyloxy]phenyl]-N-isobutyl-(5-methyl-2-furyl)sulfonylamide,
N-[4,5-dimethyl-2-[2-methyl-4-(5-tetrazolyl)phenylmethyloxy]phenyl]-N-isopropyl-(5-methyl-2-furyl)sulfonylamide,
N-[4-chloro-5-methyl-2-[4-(5-tetrazolyl)phenylmethyloxy]phenyl]-N-isobutyl-(5-methyl-2-furyl)sulfonylamide,
N-[4-chloro-5-methyl-2-[4-(5-oxo-1,2,4-oxadiazol-3-yl-1,2,4-oxadiazol-3-yl)phenylmethyloxy]phenyl]-N-isopropyl-(5-methyl-2-furyl)sulfonylamide,
N-[4-chloro-5-methyl-2-[4-(5-oxo-1,2,4-oxadiazol-3-yl)phenylmethyloxy]phenyl]-N-isobutyl-(5-methyl-2-furyl)sulfonylamide,
4-[6-[N-isobutyl-N-(5-methyl-2-furylsulfonyl)amino]indan-5-yloxymethyl]benzoic acid,
4-[6-[N-isopropyl-N-(5-methyl-2-furylsulfonyl)amino]indan-5-yloxymethyl]benzoic acid,
4-[7-[N-isobutyl-N-(5-methyl-2-furylsulfonyl)amino]-1,2,3,4-tetrahydronaphtharen-6-yloxymethyl]benzoic acid,
4-[7-[N-isopropyl-N-(5-methyl-2-furylsulfonyl)amino]-1,2,3,4-tetrahydronaphtharen-6-yloxymethyl]benzoic acid,
N-[4,5-dimethyl-2-[2-methyl-4-(5-oxo-1,2,4-oxadiazol-3-yl)phenylmethyloxy]phenyl]-N-isopropyl-(5-methyl-2-furyl)sulfonylamide,
N-[4,5-dimethyl-2-[2-methyl-4-(5-oxo-1,2,4-oxadiazol-3-yl)phenylmethyloxy]phenyl]-N-isobutyl-(5-methyl-2-furyl)sulfonylamide,
N-[4,5-dimethyl-2-[4-(5-tetrazolyl)phenylmethyloxy]phenyl]-N-isopropyl-(5-methyl-2-furyl)sulfonylamide,
N-[4,5-dimethyl-2-[4-(5-tetrazolyl)phenylmethyloxy]phenyl]-N-isobutyl-(5-methyl-2-furyl)sulfonylamide,
N-[4,5-dimethyl-2-[4-(5-oxo-1,2,4-oxadiazol-3-yl)phenylmethyloxy]phenyl]-N-isobutyl-(5-methyl-2-furyl)sulfonylamide,
3-methyl-4-[2-[N-isobutyl-N-(5-methyl-2-furylsulfonyl)amino]-4-methyl-5-chlorophenoxymethyl]cinnamic acid,
N-[4,5-dimethyl-2-[2-methoxy-4-(5-oxo-1,2,4-oxadiazol-3-yl)phenylmethyloxy]phenyl]-N-isobutyl-(5-methyl-2-furyl)sulfonylamide,
N-[4,5-dimethyl-2-[2-methoxy-4-(5-oxo-1,2,4-oxadiazol-3-yl)phenylmethyloxy]phenyl]-N-isopropyl-(5-methyl-2-furyl)sulfonylamide,
4-[6-[N-isobutyl-N-(5-methyl-2-furylsulfonyl)amino]indan-5-yloxymethyl]cinnamic acid,
3-methyl-4-[6-[N-isobutyl-N-(5-methyl-2-furylsulfonyl)amino]indan-5-yloxymethyl]benzoic acid,
3-methyl-4-[6-[N-isobutyl-N-(5-methyl-2-furylsulfonyl)amino]indan-5-yloxymethyl]cinnamic acid,
4-[2-[N-(2-methyl-2-propenyl)-N-(5-methyl-2-furylsulfonyl)amino]-4,5-dimethylphenoxymethyl]benzoic acid,
3-methyl-4-[6-[N-isopropyl-N-(5-methyl-2-furylsulfonyl)amino]indan-5-yloxymethyl]benzoic acid, 3-methyl-4-[6-[N-isopropyl-N-(5-methyl-2-furylsulfonyl) amino]indan-5-yloxymethyl]cinnamic acid,
4-[6-[N-isopropyl-N-(5-methyl-2-furylsulfonyl)amino]indan-5-yloxymethyl]cinnamic acid,
4-[3-[N-isobutyl-N-(5-methyl-2-furylsulfonyl)amino]-2-naphthyloxymethyl]benzoic acid,
3,5-dimethyl-4-[2-[N-isobutyl-N-(5-methyl-2-furylsulfonyl)amino]-5-trifluoromethylphenoxymethyl]benzoic acid,
3-methyl-4-[6-[N-(2-methyl-2-propenyl)-N-(5-methyl-2-furylsulfonyl)amino]indan-5-yloxymethyl]benzoic acid,
4-[6-[N-cyclopropylmethyl-N-(5-methyl-2-furylsulfonyl) amino]indan-5-yloxymethyl]-3-methylbenzoic acid,
4-[6-[N-isobutyl-N-(5-methyl-2-furylsulfonyl)amino]indan-5-yloxymethyl]-3-methylbenzylalcohol,
3-methyl-4-[6-[N-methyl-N-(5-methyl-2-furylsulfonyl) amino]indan-5-yloxymethyl]benzoic acid,
4-[6-[N-ethyl-N-(5-methyl-2-furylsulfonyl)amino]indan-5-yloxymethyl]-3-methylbenzoic acid,
4-[6-[N-methyl-N-(5-methyl-2-furylsulfonyl)amino]indan-5-yloxymethyl]cinnamic acid,
4-[6-[N-ethyl-N-(5-methyl-2-furylsulfonyl)amino]indan-5-yloxymethyl]cinnamic acid,
4-[6-[N-propyl-N-(5-methyl-2-furylsulfonyl)amino]indan-5-yloxymethyl]cinnamic acid,
4-[4,5-dimethyl-2-[N-(2-methyl-2-propenyl)-N-(5-methyl-2-furylsulfonyl)amino]phenoxymethyl]-3-methylbenzoic acid,
4-[6-[N-(2-methyl-2-propenyl)-N-(5-methyl-2-furylsulfonyl)amino]indan-5-yloxymethyl]cinnamic acid,
4-[6-[N-cyclopropylmethyl-N-(5-methyl-2-furylsulfonyl) amino]indan-5-yloxymethyl]cinnamic acid,
4-[6-[N-(2-propenyl)-N-(5-methyl-2-furylsulfonyl)amino] indan-5-yloxymethyl]cinnamic acid,
3-methyl-4-[6-[N-propyl-N-(5-methyl-2-furylsulfonyl) amino]indan-5-yloxymethyl]benzoic acid,
3-methyl-4-[6-[N-(2-propenyl)-N-(5-methyl-2-furylsulfonyl)amino]indan-5-yloxymethyl]benzoic acid,
4-[4,5-dimethyl-2-[N-methyl-N-(5-methyl-2-furylsulfonyl) amino]phenoxymethyl]benzoic acid,
4-[4,5-dimethyl-2-[N-ethyl-N-(5-methyl-2-furylsulfonyl) amino]phenoxymethyl]benzoic acid,
4-[4,5-dimethyl-2-[N-(5-methyl-2-furylsulfonyl)-N-propylamino]phenoxymethyl]benzoic acid,
4-[3-[N-isopropyl-N-(5-methyl-2-furylsulfonyl)amino] naphthalen-2-yloxymethyl]-3-methylbenzoic acid,
4-[3-[N-isobutyl-N-(5-methyl-2-furylsulfonyl)amino]naphthalen-2-yloxymethyl]-3-methylbenzoic acid,
4-[3-[N-isopropyl-N-(5-methyl-2-furylsulfonyl)amino] naphthalen-2-yloxymethyl]cinnamic acid,
4-[3-[N-isobutyl-N-(5-methyl-2-furylsulfonyl)amino]naphthalen-2-yloxymethyl]cinnamic acid,
3-methyl-4-[3-[N-isopropyl-N-(5-methyl-2-furylsulfonyl) amino]naphthalen-2-yloxymethyl]cinnamic acid,
3-methyl-4-[3-[N-isobutyl-N-(5-methyl-2-furylsulfonyl) amino]naphthalen-2-yloxymethyl]cinnamic acid,
4-[4,5-dimethyl-2-[N-[(5-methyl-2-furyl)sulfonyl]-N-2-propenylamino]phenoxymethyl]benzoic acid,
4-[4,5-dimethyl-2-[N-methyl-N-(5-methyl-2-furylsulfonyl) amino]phenoxymethyl]-3-methylbenzoic acid,
4-[4,5-dimethyl-2-[N-ethyl-N-(5-methyl-2-furylsulfonyl) amino]phenoxymethyl]-3-methylbenzoic acid,
4-[4,5-dimethyl-2-[N-(5-methyl-2-furylsulfonyl)-N-propylamino]phenoxymethyl]-3-methylbenzoic acid,
4-[4,5-dimethyl-2-[N-(5-methyl-2-furylsulfonyl)-N-(2-propenyl)amino]phenoxymethyl]-3-methylbenzoic acid,
4-[4,5-dimethyl-2-[N-(2-hydroxy-2-methylpropyl)-N-(5-methyl-2-furylsulfonyl)amino]phenoxymethyl]-3-methylbenzoic acid,
4-[6-[N-(2-hydroxy-2-methylpropyl)-N-(5-methyl-2-furylsulfonyl)amino]indan-5-yloxymethyl]-3-methylbenzoic acid,
4-[4,5-dimethyl-2-[N-cyclopropylmethyl-N-(5-methyl-2-furylsulfonyl)amino]phenoxymethyl]benzoic acid,
4-[4,5-dimethyl-2-[N-(2-hydroxy-2-methylpropyl)-N-(5-methyl-2-furylsulfonyl)amino]phenoxymethyl]benzoic acid,
4-[6-[N-(2-hydroxy-2-methylpropyl)-N-(5-methyl-2-furylsulfonyl)amino]indan-5-yloxymethyl]cinnamic acid,
4-[4,5-dimethyl-2-[N-cyclopropylmethyl-N-(5-methyl-2-furylsulfonyl)amino]phenoxymethyl]-3-methylbenzoic acid,
4-[2-[N-isopropyl-N-(2-thiazolylsulfonyl)amino]-5-trifluoromethylphenoxymethyl]benzoic acid,
4-[2-[N-isobutyl-N-(2-thiazolylsulfonyl)amino]-5-trifluoromethylphenoxymethyl]benzoic acid,
4-[2-[N-isopropyl-N-(2-thiazolylsulfonyl)amino]-5-trifluoromethylphenoxymethyl]cinnamic acid,
4-[2-[N-isobutyl-N-(2-thiazolylsulfonyl)amino]-5-trifluoromethylphenoxymethyl]cinnamic acid,
4-[2-[N-isobutyl-N-(4-methyl-2-thiazolylsulfonyl)amino]-5-trifluoromethylphenoxymethyl]benzoic acid,
4-[2-[N-isobutyl-N-(4-methyl-2-thiazolylsulfonyl)amino]-5-trifluoromethylphenoxymethyl]cinnamic acid,
4-[2-[N-isopropyl-N-(2-thiazolylsulfonyl)amino]-4-chloro-5-methylphenoxymethyl]benzoic acid,
N-[4-trifluoromethyl-2-[4-(5-tetrazolyl)phenylmethyloxy] phenyl]-N-isobutyl-2-thiazolylsulfonylamide,
N-[4-trifluoromethyl-2-[4-(5-tetrazolyl)phenylmethyloxy] phenyl]-N-isopropyl-2-thiazolylsulfonylamide,
N-[4-trifluoromethyl-2-[4-(5-oxo-1,2,4-oxadiazol-3-yl)phenylmethyloxy]phenyl]-N-isopropyl-2-thiazolylsulfonylamide,
N-[4-trifluoromethyl-2-[4-(5-oxo-1,2,4-thiadiazol-3-yl-1,2,4-oxadiazol-3-yl)phenylmethyloxy]phenyl]-N-isopropyl-2-thiazolylsulfonylamide,
4-[2-[N-isopropyl-N-(4-methyl-2-thiazolylsulfonyl)amino]-4-chloro-5-methylphenoxymethyl]benzoic acid,
4-[2-[N-isobutyl-N-(4-methyl-2-thiazolylsulfonyl)amino]-4-chloro-5-methylphenoxymethyl]benzoic acid,
3-chloro-4-[2-[N-isopropyl-N-(4-methyl-2-thiazolylsulfonyl)amino]-4-chloro-5-methylphenoxymethyl]benzoic acid,
3-methyl-4-[2-[N-isobutyl-N-(4-methyl-2-thiazolylsulfonyl)amino]-5-trifluoromethylphenoxymethyl]benzoic acid,
3-methyl-4-[2-[N-isobutyl-N-(4-methyl-2-thiazolylsulfonyl)amino]-4-chloro-5-methylphenoxymethyl]benzoic acid,
3-methoxy-4-[2-[N-isobutyl-N-(4-methyl-2-thiazolylsulfonyl)amino]-4-chloro-5-methylphenoxymethyl]benzoic acid,
3-methoxy-4-[2-[N-isobutyl-N-(4-methyl-2-thiazolylsulfonyl)amino]-5-trifluoromethylphenoxymethyl]benzoic acid,
N-[4-trifluoromethyl-2-[4-(5-tetrazolyl)phenylmethyloxy] phenyl]-N-isobutyl-(4-methyl-2-thiazolyl)sulfonylamide,
N-[4-trifluoromethyl-2-[4-(5-oxo-1,2,4-oxadiazol-3-yl)phenylmethyloxy]phenyl]-N-isopropyl-(4-methyl-2-thiazolyl)sulfonylamide,
N-[4-trifluoromethyl-2-[4-(5-oxo-1,2,4-oxadiazol-3-yl)phenylmethyloxy]phenyl]-N-isobutyl-(4-methyl-2-thiazolyl) sulfonylamide, 4-[2-[N-isobutyl-N-(4-methyl-2-thiazolylsulfonyl)amino]-4-methyl-5-chlorophenoxymethyl]benzoic acid,
3-chloro-4-[2-[N-isobutyl-N-(4-methyl-2-thiazolylsulfonyl)amino]-4-methyl-5-chlorophenoxymethyl]benzoic acid,
3-methoxy-4-[2-[N-isobutyl-N-(4-methyl-2-thiazolylsulfonyl)amino]-4-methyl-5-chlorophenoxymethyl]benzoic acid,
N-[4-trifluoromethyl-2-[4-(5-tetrazolyl)phenylmethyloxy]phenyl]-N-isopropyl-(4-methyl-2-thiazolyl)sulfonylamide,
3-methyl-4-[2-[N-isobutyl-N-(4-methyl-2-thiazolylsulfonyl)amino]-4,5-dimethylphenoxymethyl]benzoic acid,
3-methyl-4-[2-[N-isopropyl-N-(4-methyl-2-thiazolylsulfonyl)amino]-4,5-dimethylphenoxymethyl]benzoic acid,
3-methoxy-4-[2-[N-isobutyl-N-(4-methyl-2-thiazolylsulfonyl)amino]-4,5-dimethylphenoxymethyl]benzoic acid,
3-chloro-4-[2-[N-isobutyl-N-(4-methyl-2-thiazolylsulfonyl)amino]-4,5-dimethylphenoxymethyl]benzoic acid,
3-chloro-4-[2-[N-isopropyl-N-(4-methyl-2-thiazolylsulfonyl)amino]-4,5-dimethylphenoxymethyl]benzoic acid,
4-[2-[N-isopropyl-N-(4-methyl-2-thiazolylsulfonyl)amino]-4,5-dimethylphenoxymethyl]benzoic acid,
4-[2-[N-isobutyl-N-(4-methyl-2-thiazolylsulfonyl)amino]-4,5-dimethylphenoxymethyl]benzoic acid,
4-[2-[N-isobutyl-N-(4-methyl-2-thiazolylsulfonyl)amino]-4-chloro-5-methylphenoxymethyl]cinnamic acid,
3-methyl-4-[2-[N-isobutyl-N-(4-methyl-2-thiazolylsulfonyl)amino]-5-trifluoromethylphenoxymethyl]cinnamic acid,
3-chloro-4-[2-[N-isobutyl-N-(4-methyl-2-thiazolylsulfonyl)amino]-5-trifluoromethylphenoxymethyl]cinnamic acid,
3-methyl-4-[2-[N-isopropyl-N-(4-methyl-2-thiazolylsulfonyl)amino]-4,5-dimethylphenoxymethyl]cinnamic acid,
3-methyl-4-[2-[N-isobutyl-N-(4-methyl-2-thiazolylsulfonyl)amino]-4,5-dimethylphenoxymethyl]cinnamic acid,
4-[2-[N-isobutyl-N-(4-methyl-2-thiazolylsulfonyl)amino]-4-methyl-5-chlorophenoxymethyl]cinnamic acid,
3-methyl-4-[2-[N-isobutyl-N-(4-methyl-2-thiazolylsulfonyl)amino]-4-methyl-5-chlorophenoxymethyl]cinnamic acid,
3-methyl-4-[2-[N-isobutyl-N-(4-methyl-2-thiazolylsulfonyl)amino]-4-chloro-5-methylphenoxymethyl]cinnamic acid,
N-[4-chloro-5-methyl-2-[2-methyl-4-(5-tetrazolyl)phenylmethyloxy]phenyl]-N-isobutyl-(4-methyl-2-thiazolyl)sulfonylamide,
N-[4-chloro-5-methyl-2-[2-methyl-4-(5-tetrazolyl)phenylmethyloxy]phenyl]-N-isopropyl-(4-methyl-2-thiazolyl)sulfonylamide,
4-[2-[N-isobutyl-N-(4-methyl-2-thiazolylsulfonyl)amino]-4,5-dimethylphenoxymethyl]cinnamic acid,
N-[4-trifluoromethyl-2-[2-methyl-4-(5-tetrazolyl)phenylmethyloxy]phenyl]-N-isopropyl-(4-methyl-2-thiazolyl)sulfonylamide,
N-[4-trifluoromethyl-2-[2-methyl-4-(5-tetrazolyl)phenylmethyloxy]phenyl]-N-isobutyl-(4-methyl-2-thiazolyl)sulfonylamide,
3-chloro-4-[2-[N-isobutyl-N-(4-methyl-2-thiazolylsulfonyl)amino]-4,5-dimethylphenoxymethyl]cinnamic acid,
N-[4,5-dimethyl-2-[2-methyl-4-(5-tetrazolyl)phenylmethyloxy]phenyl]-N-isobutyl-(4-methyl-2-thiazolyl)sulfonylamide,
N-[4,5-dimethyl-2-[2-methyl-4-(5-tetrazolyl)phenylmethyloxy]phenyl]-N-isopropyl-(4-methyl-2-thiazolyl)sulfonylamide,
N-[4,5-dimethyl-2-[4-(5-tetrazolyl)phenylmethyloxy]phenyl]-N-isopropyl-(4-methyl-2-thiazolyl)sulfonylamide,
N-[4,5-dimethyl-2-[4-(5-tetrazolyl)phenylmethyloxy]phenyl]-N-isobutyl-(4-methyl-2-thiazolyl)sulfonylamide,
N-[4-chloro-5-methyl-2-[4-(5-tetrazolyl)phenylmethyloxy]phenyl]-N-isopropyl-(4-methyl-2-thiazolyl)sulfonylamide,
N-[4-chloro-5-methyl-2-[4-(5-tetrazolyl)phenylmethyloxy]phenyl]-N-isobutyl-(4-methyl-2-thiazolyl)sulfonylamide,
N-[4-chloro-5-methyl-2-[4-(5-oxo-1,2,4-oxadiazol-3-yl)phenylmethyloxy]phenyl]-N-isobutyl-(4-methyl-2-thiazolyl)sulfonylamide,
N-[4-chloro-5-methyl-2-[2-methyl-4-(5-oxo-1,2,4-oxadiazol-3-yl)phenylmethyloxy]phenyl]-N-isobutyl-(4-methyl-2-thiazolyl)sulfonylamide,
3-methoxy-4-[2-[N-isobutyl-N-(4-methyl-2-thiazolylsulfonyl)amino]-4,5-dimethylphenoxymethyl]cinnamic acid,
N-[4,5-dimethyl-2-[2-methyl-4-(5-oxo-1,2,4-oxadiazol-3-yl)phenylmethyloxy]phenyl]-N-isopropyl-(4-methyl-2-thiazolyl)sulfonylamide,
N-[4,5-dimethyl-2-[2-methyl-4-(5-oxo-1,2,4-oxadiazol-3-yl)phenylmethyloxy]phenyl]-N-isobutyl-(4-methyl-2-thiazolyl)sulfonylamide,
N-[4,5-dimethyl-2-[4-(5-oxo-1,2,4-oxadiazol-3-yl)phenylmethyloxy]phenyl]-N-isopropyl-(4-methyl-2-thiazolyl)sulfonylamide,
N-[4,5-dimethyl-2-[4-(5-oxo-1,2,4-oxadiazol-3-yl)phenylmethyloxy]phenyl]-N-isobutyl-(4-methyl-2-thiazolyl)sulfonylamide,
N-[4,5-dimethyl-2-[2-methoxy-4-(5-oxo-1,2,4-oxadiazol-3-yl)phenylmethyloxy]phenyl]-N-isopropyl-(4-methyl-2-thiazolyl)sulfonylamide,
N-[4,5-dimethyl-2-[2-methoxy-4-(5-tetrazolyl)phenylmethyloxy]phenyl]-N-isopropyl-(4-methyl-2-thiazolyl)sulfonylamide,
4-[6-[N-isobutyl-N-(4-methyl-2-thiazolylsulfonyl)amino]indan-5-yloxymethyl]benzoic acid,
4-[6-[N-isobutyl-N-(4-methyl-2-thiazolylsulfonyl)amino]indan-5-yloxymethyl]cinnamic acid,
3-methyl-4-[6-[N-isobutyl-N-(4-methyl-2-thiazolylsulfonyl)amino]indan-5-yloxymethyl]benzoic acid,
3-methyl-4-[6-[N-isobutyl-N-(4-methyl-2-thiazolylsulfonyl)amino]indan-5-yloxymethyl]cinnamic acid,
3-methyl-4-[2-[N-(2-methyl-2-propenyl)-N-(4-methyl-2-thiazolylsulfonyl)amino]-4-chloro-5-methylphenoxymethyl]benzoic acid,
4-[2-[N-(2-methyl-2-propenyl)-N-(4-methyl-2-thiazolylsulfonyl)amino]-5-trifluoromethylphenoxymethyl]cinnamic acid,
3-methyl-4-[2-[N-(2-methyl-2-propenyl)-N-(4-methyl-2-thiazolylsulfonyl)amino]-4,5-dimethylphenoxymethyl]benzoic acid,
3-methyl-4-[6-[N-isopropyl-N-(2-thiazolylsulfonyl)amino]indan-5-yloxymethyl]benzoic acid,
3-methyl-4-[6-[N-isobutyl-N-(2-thiazolylsulfonyl)amino]indan-5-yloxymethyl]benzoic acid,
3-methyl-4-[6-[N-isopropyl-N-(4-methyl-2-thiazolylsulfonyl)amino]indan-5-yloxymethyl]benzoic acid,
4-[6-[N-isopropyl-N-(2-thiazolylsulfonyl)amino]indan-5-yloxymethyl]benzoic acid,
4-[6-[N-isobutyl-N-(2-thiazolylsulfonyl)amino]indan-5-yloxymethyl]benzoic acid,
4-[6-[N-isopropyl-N-(4-methyl-2-thiazolylsulfonyl)amino]indan-5-yloxymethyl]benzoic acid,
4-[6-[N-isopropyl-N-(4-methyl-2-thiazolylsulfonyl)amino]indan-5-yloxymethyl]cinnamic acid,
3-methyl-4-[6-[N-isopropyl-N-(4-methyl-2-thiazolylsulfonyl)amino]indan-5-yloxymethyl]cinnamic acid, 4-[2-[N-isopropyl-N-(2-thiazolylsulfonyl)amino]-4,5-dimethylphenoxymethyl]benzoic acid,
4-[2-[N-isobutyl-N-(2-thiazolylsulfonyl)amino]-4,5-dimethylphenoxymethyl]benzoic acid,
4-[2-[N-isopropyl-N-(2-thiazolylsulfonyl)amino]-4,5-dimethylphenoxymethyl]cinnamic acid,
4-[2-[N-isobutyl-N-(2-thiazolylsulfonyl)amino]-4,5-dimethylphenoxymethyl]cinnamic acid,
4-[6-[N-isopropyl-N-(2-thiazolylsulfonyl)amino]indan-5-yloxymethyl]cinnamic acid,
4-[6-[N-isobutyl-N-(2-thiazolylsulfonyl)amino]indan-5-yloxymethyl]cinnamic acid,
3-methyl-4-[2-[N-isopropyl-N-(2-thiazolylsulfonyl)amino]-4,5-dimethylphenoxymethyl]benzoic acid,
3-methyl-4-[2-[N-isobutyl-N-(2-thiazolylsulfonyl)amino]-4,5-dimethylphenoxymethyl]benzoic acid,
3-methyl-4-[2-[N-isopropyl-N-(2-thiazolylsulfonyl)amino]-4,5-dimethylphenoxymethyl]cinnamic acid,
3-methyl-4-[2-[N-isobutyl-N-(2-thiazolylsulfonyl)amino]-4,5-dimethylphenoxymethyl]cinnamic acid,
3-methyl-4-[6-[N-isopropyl-N-(2-thiazolylsulfonyl)amino]indan-5-yloxymethyl]cinnamic acid,
3-methyl-4-[6-[N-isobutyl-N-(2-thiazolylsulfonyl)amino]indan-5-yloxymethyl]cinnamic acid,
4-[3-[N-isobutyl-N-(4-methyl-2-thiazolylsulfonyl)amino]naphthalen-2-yloxymethyl]benzoic acid,
4-[3-[N-isopropyl-N-(4-methyl-2-thiazolylsulfonyl)amino]naphthalen-2-yloxymethyl]benzoic acid,
4-[3-[N-isobutyl-N-(4-methyl-2-thiazolylsulfonyl)amino]naphthalen-2-yloxymethyl]-3-methylbenzoic acid,
4-[3-[N-isopropyl-N-[2-(4-methylthiazolyl)sulfonyl]amino]naphthalen-2-yloxymethyl]-3-methylbenzoic acid,
4-[3-[N-isobutyl-N-(4-methyl-2-thiazolylsulfonyl)amino]naphthalen-2-yloxymethyl]cinnamic acid,
4-[3-[N-isopropyl-N-(4-methyl-2-thiazolylsulfonyl)amino]naphthalen-2-yloxymethyl]cinnamic acid,
4-[4,5-dimethyl-2-[N-methyl-N-(4-methyl-2-thiazolylsulfonyl)amino]phenoxymethyl]-3-methylbenzoic acid,
4-[4,5-dimethyl-2-[N-ethyl-N-(4-methyl-2-thiazolylsulfonyl)amino]phenoxymethyl]-3-methylbenzoic acid,
4-[4,5-dimethyl-2-[N-propyl-N-(4-methyl-2-thiazolylsulfonyl)amino]phenoxymethyl]-3-methylbenzoic acid,
4-[4,5-dimethyl-2-[N-(2-propenyl)-N-(4-methyl-2-thiazolylsulfonyl)amino]phenoxymethyl]-3-methylbenzoic acid,
4-[4,5-dimethyl-2-[N-cyclopropylmethyl-N-(4-methyl-2-thiazolylsulfonyl)amino]phenoxymethyl]-3-methylbenzoic acid,
4-[4,5-dimethyl-2-[N-(2-hydroxy-2-methylpropyl)-N-(4-methyl-2-thiazolylsulfonyl)amino]phenoxymethyl]-3-methylbenzoic acid,
4-[6-[N-(2-methyl-2-propenyl)-N-(4-methyl-2-thiazolylsulfonyl)amino]indan-5-yloxymethyl]benzoic acid,
4-[6-[N-(4-methyl-2-thiazolylsulfonyl)-N-(2-propenyl)amino]indan-5-yloxymethyl]benzoic acid,
4-[6-[N-cyclopropylmethyl-N-(4-methyl-2-thiazolylsulfonyl)amino]indan-5-yloxymethyl]benzoic acid,
4-[3-[N-isobutyl-N-[2-(4-methylthiazolyl)sulfonyl]amino]naphthalen-2-yloxymethyl]-3-methylcinnamic acid,
4-[3-[N-isopropyl-N-(4-methyl-2-thiazolylsulfonyl)amino]naphthalen-2-yloxymethyl]-3-methylbenzoic acid,
4-[6-[N-ethyl-N-(4-methyl-2-thiazolylsulfonyl)amino]indan-5-yloxymethyl]benzoic acid,
4-[6-[N-(4-methyl-2-thiazolylsulfonyl)-N-propylamino]indan-5-yloxymethyl]benzoic acid,
4-[6-[N-methyl-N-(4-methyl-2-thiazolylsulfonyl)amino]indan-5-yloxymethyl]benzoic acid,
3-methyl-4-[6-[N-methyl-N-(4-methyl-2-thiazolylsulfonyl)amino]indan-5-yloxymethyl]cinnamic acid,
4-[6-[N-ethyl-N-(4-methyl-2-thiazolylsulfonyl)amino]indan-5-yloxymethyl]-3-methylcinnamic acid,
3-methyl-4-[6-[N-(2-methyl-2-propenyl)-N-(4-methyl-2-thiazolylsulfonyl)amino]indan-5-yloxymethyl]cinnamic acid,
4-[6-[N-cyclopropylmethyl-N-(4-methyl-2-thiazolylsulfonyl)amino]indan-5-yloxymethyl]-3-methylcinnamic acid,
3-methyl-4-[6-[N-(4-methyl-2-thiazolylsulfonyl)-N-(2-propenyl)amino]indan-5-yloxymethyl]cinnamic acid,
4-[6-[N-(2-hydroxy-2-methylpropyl)-N-(4-methyl-2-thiazolylsulfonyl)amino]indan-5-yloxymethyl]-3-methylcinnamic acid,
3-methyl-4-[6-[N-(4-methyl-2-thiazolylsulfonyl)-N-propylamino]indan-5-yloxymethyl]cinnamic acid,
4-[6-[N-(2-hydroxy-2-methylpropyl)-N-(4-methyl-2-thiazolylsulfonyl)amino]indan-5-yloxymethyl]benzoic acid,
4-[2-[N-isobutyl-N-(2-pyridylsulfonyl)amino]-5-trifluoromethylphenoxymethyl]cinnamic acid,
4-[2-[N-isobutyl-N-(3-pyridylsulfonyl)amino]-5-trifluoromethylphenoxymethyl]benzoic acid,
3-chloro-4-[2-[N-isopropyl-N-(2-pyridylsulfonyl)amino]-4-chloro-5-methylphenoxymethyl]benzoic acid,
3-methyl-4-[2-[N-isobutyl-N-(2-pyridylsulfonyl)amino]-4-chloro-5-methylphenoxymethyl]benzoic acid,
3-methyl-4-[2-[N-isobutyl-N-(3-pyridylsulfonyl)amino]-4-chloro-5-methylphenoxymethyl]benzoic acid,
3-methyl-4-[2-[N-isobutyl-N-(2-pyridylsulfonyl)amino]-4-methyl-5-chlorophenoxymethyl]benzoic acid,
N-[4-trifluoromethyl-2-[4-(5-tetrazolyl)phenylmethyloxy]phenyl]-N-isopropyl-3-pyridylsulfonylamide,
N-[4-trifluoromethyl-2-[4-(5-tetrazolyl)phenylmethyloxy]phenyl]-N-isobutyl-3-pyridylsulfonylamide,
4-[2-[N-isobutyl-N-(3-pyridylsulfonyl)amino]-4-methyl-5-chlorophenoxymethyl]benzoic acid,
3-chloro-4-[2-[N-isobutyl-N-(3-pyridylsulfonyl)amino]-4-methyl-5-chlorophenoxymethyl]benzoic acid,
3-methyl-4-[2-[N-isobutyl-N-(2-pyridylsulfonyl)amino]-5-trifluoromethylphenoxymethyl]cinnamic acid,
3-methoxy-4-[2-[N-isobutyl-N-(2-pyridylsulfonyl)amino]-4,5-dimethylphenoxymethyl]benzoic acid,
3-methoxy-4-[2-[N-isobutyl-N-(3-pyridylsulfonyl)amino]-4,5-dimethylphenoxymethyl]benzoic acid,
3-methyl-4-[2-[N-isobutyl-N-(3-pyridylsulfonyl)amino]-4,5-dimethylphenoxymethyl]benzoic acid,
3-methyl-4-[2-[N-isobutyl-N-(2-pyridylsulfonyl)amino]-4,5-dimethylphenoxymethyl]benzoic acid,
N-[4-trifluoromethyl-2-[4-(5-tetrazolyl)phenylmethyloxy]phenyl]-N-isopropyl-2-pyridylsulfonylamide,
N-[4-trifluoromethyl-2-[4-(5-tetrazolyl)phenylmethyloxy]phenyl]-N-isobutyl-2-pyridylsulfonylamide,
3-methyl-4-[2-[N-isobutyl-N-(3-pyridylsulfonyl)amino]-4-methyl-5-chlorophenoxymethyl]benzoic acid,
4-[2-[N-isobutyl-N-(2-pyridylsulfonyl)amino]-4,5-dimethylphenoxymethyl]benzoic acid,
N-[4-trifluoromethyl-2-[4-(5-oxo-1,2,4-oxadiazol-3-yl)phenylmethyloxy]phenyl]-N-isobutyl-2-pyridylsulfonylamide,
4-[2-[N-isopropyl-N-(2-pyridylsulfonyl)amino]-4-methyl-5-chlorophenoxymethyl]cinnamic acid,
3-methyl-4-[2-[N-isobutyl-N-(2-pyridylsulfonyl)amino]-4-methyl-5-chlorophenoxymethyl]cinnamic acid,
3-methyl-4-[2-[N-isobutyl-N-(2-pyridylsulfonyl)amino]-4,5-dimethylphenoxymethyl]cinnamic acid,
4-[2-[N-isobutyl-N-(3-pyridylsulfonyl)amino]-4,5-dimethylphenoxymethyl]cinnamic acid, 3-methyl-4-[2-[N-isobutyl-N-(3-pyridylsulfonyl)amino]-4,5-dimethylphenoxymethyl]cinnamic acid,
N-[4-trifluoromethyl-2-[2-methyl-4-(5-tetrazolyl)phenylmethyloxy]phenyl]-N-isopropyl-2-pyridylsulfonylamide,
3-chloro-4-[2-[N-isobutyl-N-(3-pyridylsulfonyl)amino]-4,5-dimethylphenoxymethyl]cinnamic acid,
N-[4,5-dimethyl-2-[2-methyl-4-(5-tetrazolyl)phenylmethyloxy]phenyl]-N-isobutyl-2-pyridylsulfonylamide,
N-[4,5-dimethyl-2-[2-methyl-4-(5-tetrazolyl)phenylmethyloxy]phenyl]-N-isobutyl-3-pyridylsulfonylamide,
N-[4-chloro-5-methyl-2-[4-(5-tetrazolyl)phenylmethyloxy]phenyl]-N-isobutyl-3-pyridylsulfonylamide,
N-[4,5-dimethyl-2-[2-chloro-4-(5-tetrazolyl)phenylmethyloxy]phenyl]-N-isobutyl-2-pyridylsulfonylamide,
N-[4,5-dimethyl-2-[2-chloro-4-(5-tetrazolyl)phenylmethyloxy]phenyl]-N-isopropyl-3-pyridylsulfonylamide,
N-[4,5-dimethyl-2-[2-chloro-4-(5-tetrazolyl)phenylmethyloxy]phenyl]-N-isobutyl-3-pyridylsulfonylamide,
3-methyl-4-[2-[N-isobutyl-N-(3-pyridylsulfonyl)amino]-4-chloro-5-methylphenoxymethyl]cinnamic acid,
N-[4,5-dimethyl-2-[4-(5-tetrazolyl)phenylmethyloxy]phenyl]-N-isopropyl-2-pyridylsulfonylamide,
N-[4,5-dimethyl-2-[4-(5-tetrazolyl)phenylmethyloxy]phenyl]-N-isobutyl-2-pyridylsulfonylamide,
N-[4,5-dimethyl-2-[4-(5-tetrazolyl)phenylmethyloxy]phenyl]-N-isobutyl-3-pyridylsulfonylamide,
3-chloro-4-[2-[N-isobutyl-N-(3-pyridylsulfonyl)amino]-5-trifluoromethylphenoxymethyl]cinnamic acid,
N-[4-chloro-5-methyl-2-[2-methyl-4-(5-tetrazolyl)phenylmethyloxy]phenyl]-N-isopropyl-2-pyridylsulfonylamide,
N-[4-chloro-5-methyl-2-[2-methyl-4-(5-tetrazolyl)phenylmethyloxy]phenyl]-N-isobutyl-2-pyridylsulfonylamide,
N-[4,5-dimethyl-2-[2-methyl-4-(5-oxo-1,2,4-oxadiazol-3-yl)phenylmethyloxy]phenyl]-N-isopropyl-2-pyridylsulfonylamide,
N-[4,5-dimethyl-2-[2-methyl-4-(5-oxo-1,2,4-oxadiazol-3-yl)phenylmethyloxy]phenyl]-N-isobutyl-3-pyridylsulfonylamide,
N-[4,5-dimethyl-2-[2-methoxy-4-(5-tetrazolyl)phenylmethyloxy]phenyl]-N-isobutyl-2-pyridylsulfonylamide,
N-[4,5-dimethyl-2-[2-methoxy-4-(5-tetrazolyl)phenylmethyloxy]phenyl]-N-isopropyl-2-pyridylsulfonylamide,
N-[4,5-dimethyl-2-[2-methoxy-4-(5-oxo-1,2,4-oxadiazol-3-yl)phenylmethyloxy]phenyl]-N-isobutyl-2-pyridylsulfonylamide and N-[4,5-dimethyl-2-[2-methoxy-4-(5-oxo-1,2,4-oxadiazol-3-yl)phenylmethyloxy]phenyl]-N-isopropyl-2-pyridylsulfonylamide.

Esters:

Among the compounds of formula (I) of the present invention, the compound of formula (I-B) may be converted into the corresponding ester by methods known per se. The conversion into ester is useful, because of increase of stability and absorbability of the compound. An alkyl ester is preferable. C1-4 alkyl ester is more preferable. The ester of formula (I-B) may be prepared by methods known per se. It may also be obtained as the compound of formula (I-A) in the process of preparing the compound in the present invention.

Salts:

The compound of formula (I) of the present invention may be converted into the corresponding salt by methods known per se. A non-toxic and water-soluble salt is preferable. A suitable salt, for example, includes a salt of alkali metals (potassium, sodium, etc.), a salt of alkaline earth metals (calcium, magnesium, etc.), an ammonium salt, a salt of pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.).

Method for the Preparation of the Compound in the Present Invention:

The compound of formula (I) of the present invention may be prepared by methods described in WO98/27053, or according to the reaction schemes outlined below. Details of the process are described below.

In the schemes, R is C1-4 alkyl, Tf is trifluoromethanesulfonyl and the other symbols have the same meanings as defined hereinbefore.

R: C1-4 alkyl;
Ms: mesyl;
$Tf_2O$: trifluoromethanesulfonic acid anhydride;
Et: ethyl;
TCDI: 1,1'-thiocarbonyldiimidazole.

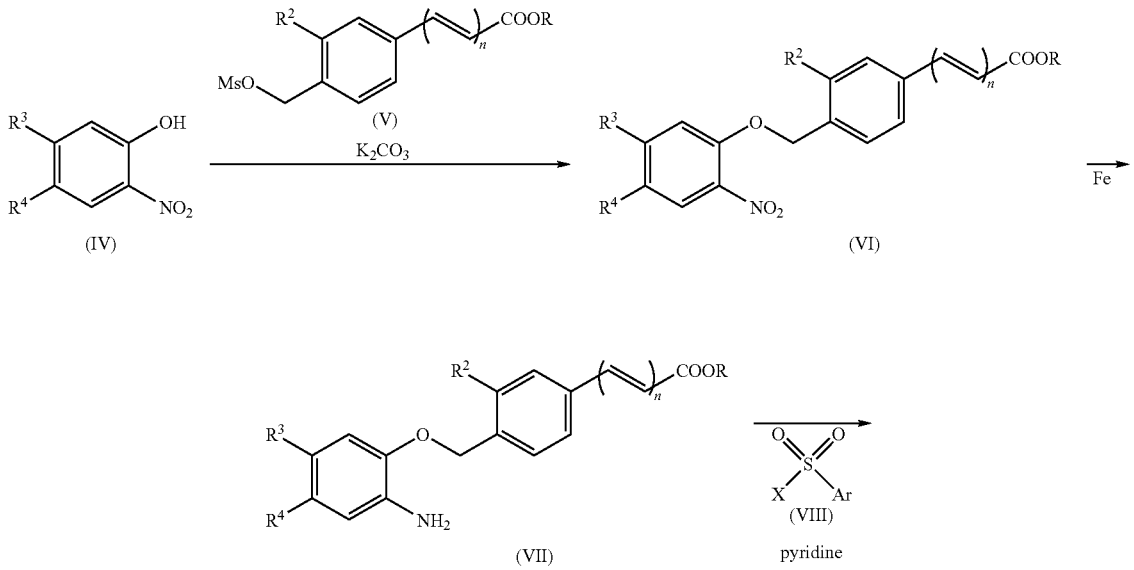

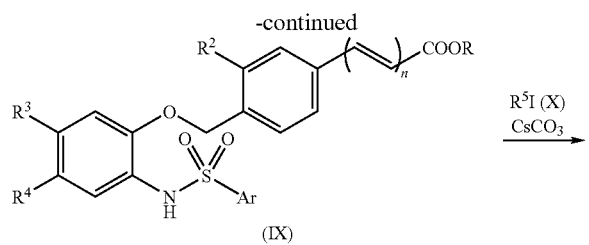
(IX)
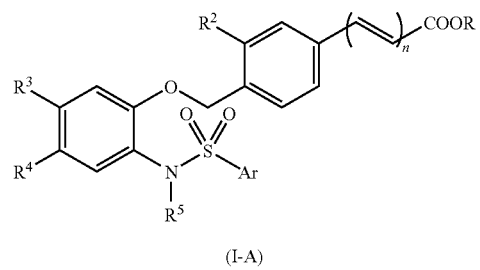
(I-A)
NaOH / Reduction
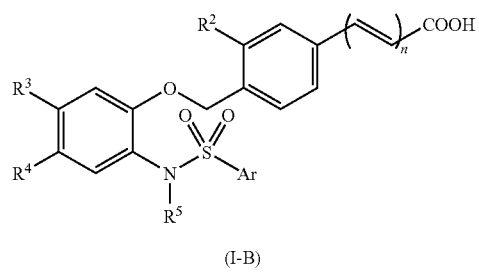
(I-B)
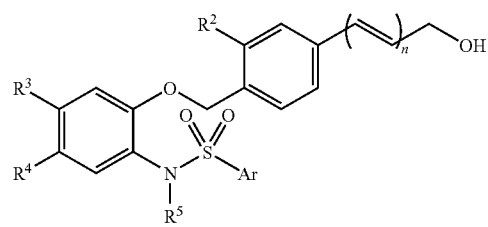
(I-C)
Reaction scheme (B)
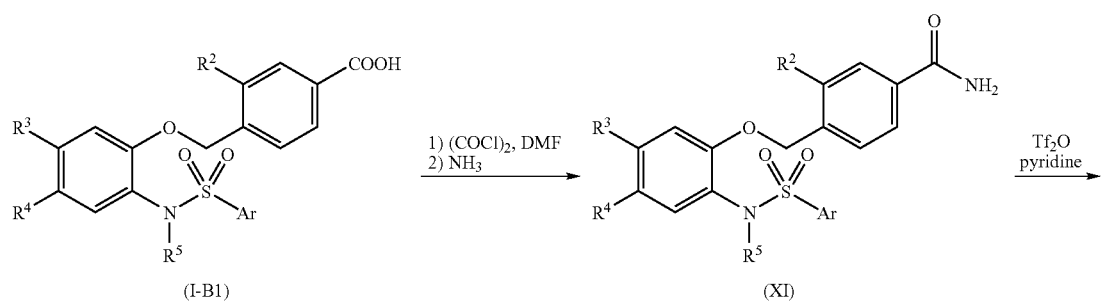

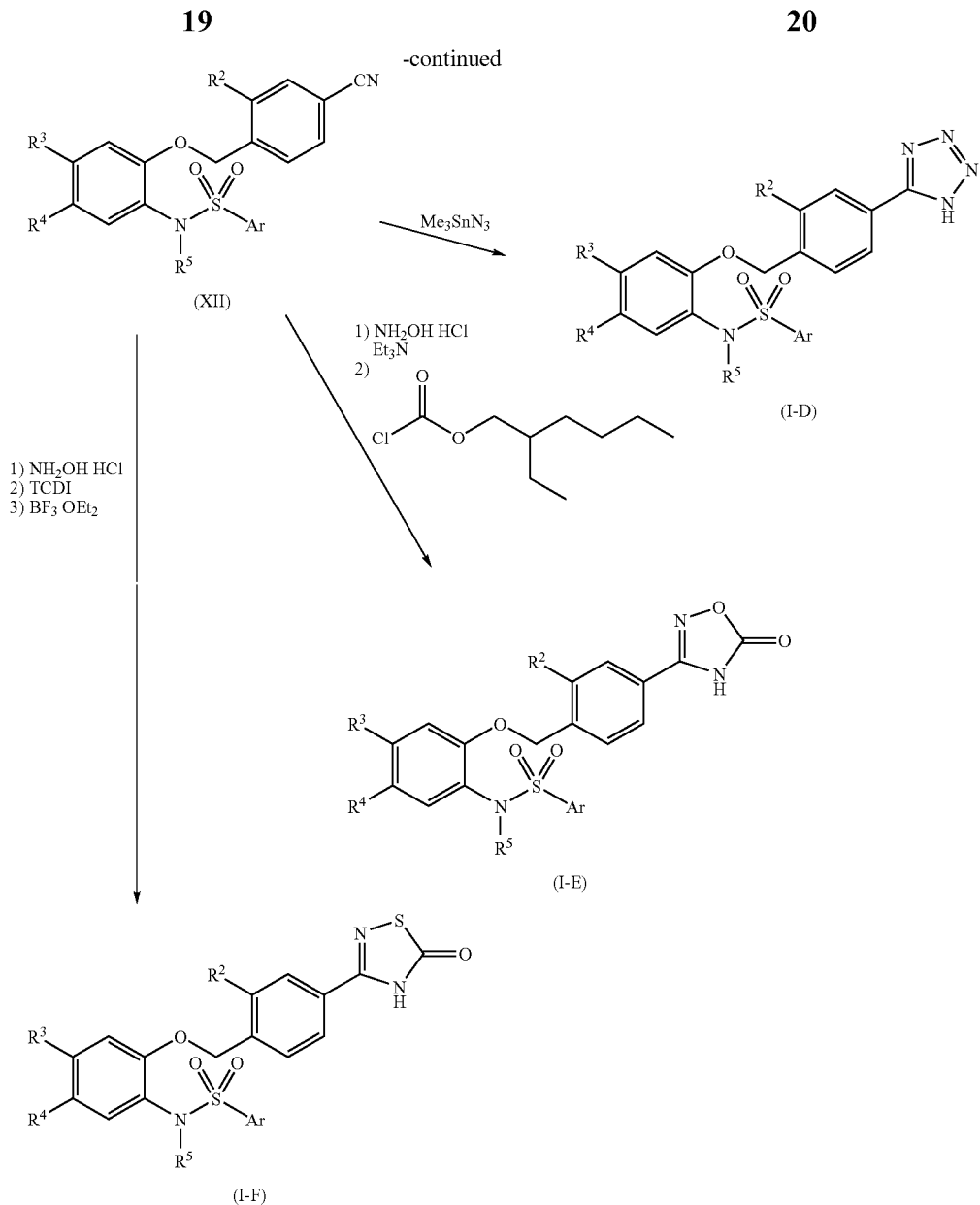

Among the compounds of formula (I), when Ar is a heterocyclic ring having a basic part, its corresponding sulfonyl halide (the compound of formula (VII)) described in the reaction scheme (A) is susceptible to heat, and it was found that it easily decomposed when it is left as it was (see Comparison Example 1).

Particularly, it is easily expected that a sulfonyl halide having a basic part such as a heterocyclic ring containing a nitrogen atom is easily decomposed, since sulfonyl halide compounds are generally unstable to bases.

From these, in preparing a sulfonyl halide having a basic part, it was concerned that (1) it is hard to isolate a sulfonyl halide because the concentrated sulfonyl halide is unstable after evaporation of the solvent after the reaction terminated, and that (2) it was probable that the sulfonyl halide might decompose in the process of preparing a sulfonamide from it, when subjected to temperature higher than ambient temperature for a long time.

As described above, when the sulfonyl halide easily decomposes, it is difficult to determine the actual quantity of the sulfonyl halide, and it is cumbersome to treat it. When the sulfonamide compound is prepared by subjecting to condensation reaction with an amine compound, low yield is concerned due to the decomposition of the sulfonyl halide in the industrial mass production.

As to the method for the preparation of a sulfonamide, condensation reaction with a sulfonyl halide and an amine is generally known.

They disclose a method for transforming a phenylsulfonyl chloride into a sulfonamide or a sulfonic acid ester via an addition of an imidazole to a phenylsulfonyl chloride followed by N-methylation (J. Org. Chem., 57, 4775-4777 (1992)), and it is described that the method is useful in the case of reaction with a nucleophile having low nucleophilicity or sterically hindered one. However, it is not described nor suggested that the methods improve the stability of the sulfonyl halide.

The present inventors have investigated to convert a sulfonyl halide having a heterocyclic ring of formula (III) to a more stable compound to find that the purpose was accomplished by converting it to the compounds of formulae (II-A) and (II-B) according to the method for the preparation as shown in the following reaction scheme (C).

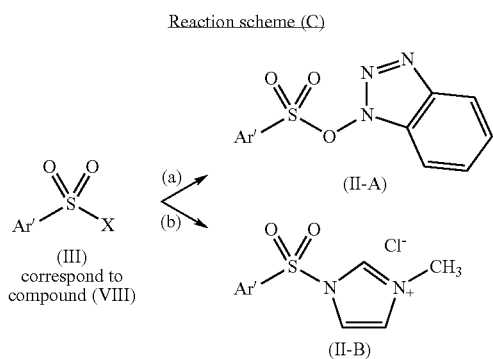

Reaction scheme (C)

In the reaction scheme (C), step (a) is a method of converting to a stable sulfonyl compound with 1-hydroxybenzotriazole. For example, it is carried out with 1-hydroxybenzotriazole, in an organic solvent (an ether (t-butyl methyl ether, diethyl ether, tetrahydrofuran, etc.), a halogen solvent (methylene chloride, chloroform, etc.), etc.) in the presence of a base (triethylamine, diisopropylethylamine, dimethylaminopyridine, pyridine, etc.), at temperature of −20 to 30° C.

The step (b) is also a method for preparing a stable sulfonyl compound; for example, it is carried out in an organic solvent (an ether (t-butyl methyl ether, diethyl ether, tetrahydrofuran, etc.), a halogen solvent (methylene chloride, chloroform, etc.), etc.) with N-methylimidazole at temperature of −20 to 30° C.

The steps (a) and (b) are preferably carried out under an anhydrous condition under the atmosphere of inert gas.

Particularly, when the compound of formula (III) is unstable to heat, the each step (a) and (b) may be carried out without concentrating the prepared sulfonyl halide solution.

Sulfonyl halide of formula (III) is obtained as a solution after preparation, and generally it can be isolated by concentration of the solution. If the materials are exposed to high temperature while concentrating, there is a possibility that a sulfonyl halide may decompose by heating in a large scale, while there is no problem in particular in a small scale (see Comparison Example). Therefore, the transforming into the compound of formulae (II-A) or (II-B) without concentration of solution ensures a low degradability of a sulfonyl chloride with its high reactivity (see Examples 7 and 8).

In the reaction scheme, the sulfonyl halide of formula (III) used as a starting material is known in itself or may be prepared easily in a conventional method from a known compound. The other starting materials and reagents in the present invention are known in themselves or may be prepared according to conventional methods.

The reaction scheme (C) can provide a method for the preparation of the compound of formula (VIII), wherein Ar is a basic heterocyclic ring. The method of the present invention is useful for stabilization of not only an unstable intermediate of the compound of formula (I) but also an unstable sulfonyl chloride with a basic heterocyclic ring.

In the present invention, 5 to 10 membered heterocyclic ring represented by Ar' is, 5 to 10 membered heterocyclic ring comprising 1 to 4 of nitrogen atom(s), 1 to 2 of oxygen atom(s) and/or 1 of sulfur atom; specifically, it represents a basic heterocyclic ring such as thiazole, isothiazole, isoxazole, pyrazine, pyrimidine, pyridazine, pyridine, pyrrole, imidazole, pyrazole, triazole, indole, indoline, purine, quinoline, isoquinoline, phthalazine, naphthyridine, quinoxaline, cinnoline, pyrrolidine, pyrroline, imidazolidine, imidazoline, pyrazoline, etc.

In the present invention, Ar' may be substituted with 1 to 4 of C1-8 alkyl, C1-8 alkoxy, halogen atom, cyano, nitro, C2-8 acyl, dialkylamino, monoalkylamino, monoalkylaminocarbonyl, dialkylaminocarbonyl, C5-10 carbocyclic ring or 5 to 10 membered heterocyclic ring.

In the present invention, C1-8 alkyl as a substituent of Ar' is, methyl, ethyl, propyl, butyl, pentyl, hexyl, heptyl, octyl or isomers thereof.

In the present invention, C1-8 alkoxy is methoxy, ethoxy, propoxy, butoxy, pentyloxy, hexyloxy, heptyloxy, octyloxy or isomers thereof.

In the present invention, halogen atom as a substituent of Ar' is, fluorine, chlorine, bromine or iodine atom.

In the present invention, C3-10 carbocyclic ring as a substituent of Ar' is, cyclopropane, cyclobutane, cyclopentane, cyclohexane, cycloheptane, cyclopentene, cyclohexene, cyclopentadiene, cyclohexadiene, benzene, pentalene, indene, naphthalene, biphenylene, perhydropentalene, perhydroindene, perhydronaphthalene ring, etc.

In the present invention, 5 to 10 membered heterocyclic ring as a substituent of Ar' is, 5 to 10 membered mono- or bi-heterocyclic ring containing 1 to 4 nitrogen atom(s), 1 to 2 oxygen atom(s) and/or 1 sulfur atom, including 5 to 10 membered mono- or bi-heterocyclic aryl, or partially or fully saturated ring thereof.

In the present invention, 5 to 10 membered mono- or bi-heterocyclic aryl containing 1 to 4 nitrogen atom(s), 1 to 2 oxygen atom(s) and/or 1 sulfur atom as a substituent of Ar' is pyrrole, imidazole, triazole, tetrazole, pyrazole, pyridine, pyrazine, pyrimidine, pyridazine, azepine, diazepine, furan, pyran, oxepine, oxazepine, thiophene, thiain (thiopyran), thiepine, oxazole, isoxazole, thiazole, isothiazole, oxadiazole, oxazine, oxadiazine, oxazepine, oxadiazepine, thiadiazole, thiaazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzimidazole ring, etc.

In the present invention, 5 to 10 membered mono- or bi-heterocyclic ring partially or fully saturated one thereof is pyrroline, pyrrolidine, imidazoline, imidazolidine, triazoline, triazolidine, tetrazoline, tetrazolidine, pyrazoline, pyrazolidine, piperidine, piperazine, tetrahydropyridine, tetrahydropyrimidine, tetrahydropyridazine, dihydrofuran, tetrahydrofuran, dihydropyran, tetrahydropyran, dihydrothiophene, tetrahydrothiophene, dihydrothiain(dihydrothiopyran), tetrahydrothiain(tetrahydrothiopyran), oxazoline(dihydrooxazole), oxazolidine(tetrahydrooxazole), dihydroisoxazole, tetrahydroisoxazole, oxadiazoline(dihydrooxadiazole), oxadiazolidine(tetrahydrooxadiazole), thiazoline(dihydrothiazole), thiazolidine(tetrahydrothiazole), dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, benzofurazane, benzothiadiazole, benzotriazole, imidazothiazole, dioxolane, dioxane, dioxadine ring, etc.

In the present invention, Ar' is preferably 5 to 10 membered basic heterocyclic ring containing 1 to 4 nitrogen atom(s), and thiazole, isothiazole, isoxazole, pyrazine, pyrimidine, pyridazine, pyridine, pyrrol, imidazole, pyrazole, triazole, indole, indoline, purine, quinoline, isoquinoline, phthalazine, naphthyridine, quinoxaline, cinnoline, pyrrolidine, pyrroline, imidazolidine, imidazoline and pyrazoline ring are more preferable. Most preferable are pyridine or thiazole ring.

The starting materials and reagents in the present invention are known per se or may be prepared by known methods. The compounds of formulae (III), (IV), (V), (VIII) and (X) are known per se or may be prepared by known methods.

In each reaction in the present specification, obtained products may be purified by known techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

Pharmacological Activity of the Compounds of the Present Invention:

The compound of formula (I) of the present invention can bind strongly to the $EP_1$ receptor which is a subtype of prostaglandin $E_2$ receptor and shows an antagonistic activity. As mentioned hereinbefore, it is known that the $EP_1$ receptor relates to induction pain, pyrexia (induction fever), diuresis or bladder contractive activity. The compound of formula (I), an ester thereof and a non-toxic salt thereof, which can antagonize this receptor, are therefore useful as analgesics, as antipyretic agents or as agents for the prevention and/or treatment of pollakiuria (neurogenic bladder, nervous bladder, stimulated bladder (irritable bladder), detrusor instability, dysuria accompany prostatomegaly), acraturesis (urinary incontinence), lower urinary tract disease syndrome. In addition, the compound of the present invention scarcely binds to the other subtypes of $PGE_2$ and is expected to provide an agent with no side effect.

It has also been known that an $EP_1$ antagonist possesses a suppressive effect on aberrantcryptfoci and formation of intestinal polyps, accordingly it indicates an effective antitumor activity.

The experiment described below shows evidently that the compound of the present invention is less affected by protein binding, so it has a satisfactory in vivo activity.

Pharmacological Experimental Test (i) Binding Assay Using Expression Cell of Prostanoid Receptor Subtype The preparation of membrane fraction was carried out according to the method of Sugimoto et al. (*J. Biol. Chem.*, 267, 6463-6466 (1992)), using expression CHO cell of prostanoid receptor subtype (mouse $EP_1$, $EP_2$, $EP_{3\alpha}$ or $EP_4$).

The standard assay mixture containing membrane fraction (0.5 mg/ml) and $^3H$-$PGE_2$ in a final volume of 200 μl was incubated for 1 hour at room temperature. The reaction was terminated by addition of ice-cold buffer (3 ml). The mixture was rapidly filtered through a glass filter (GF/B). The radioactivity associated with the filter was measured by liquid scintillation counting.

$K_d$ and $B_{max}$ values were determined from Scatchard plots (*Ann. N.Y. Acad. Sci.*, 51, 660 (1949)). Non-specific binding was calculated as the binding in the presence of an excess (2.5 μM) of unlabeled $PGE_2$. In the experiment for competition of specific $^3H$-$PGE_2$ binding by the compound of the present invention, $^3H$-$PGE_2$ (2.5 nM) and the compound of the present invention were added. The following buffer was used in all reaction.

Buffer: potassium phosphate (pH 6.0, 10 mM), EDTA (1 mM), $MgCl_2$ (10 mM) and NaCl (0.1 M).

The dissociation constant $K_i$ (μM) of each compound was calculated by the following equation.

$Ki=IC_{50}/(1+([C]/Kd))$ wherein [C] is concentration of $^3H$-$PGE_2$ used in the reaction The results are shown in Table 1.

TABLE 1

| Compounds | Ki (μM) |
|---|---|
| Compounds of the present invention | |
| Example 2 | 0.0042 |
| Example 2 (6) | 0.00032 |
| Example 2 (32) | 0.0079 |
| Example 2 (33) | 0.0066 |
| Example 2 (41) | 0.0015 |
| Example 2 (87) | 0.0014 |
| Example 2 (94) | 0.0039 |
| Example 3 (11) | 0.0023 |
| Example 3 (30) | 0.0008 |
| Example 4 (14) | 0.0008 |
| Compounds of the related art (WO98/27053) | |
| Example 18 (93) | 0.0008 |
| Example 18 (113) | 0.0055 |
| Example 18 (125) | 0.0013 |
| Example 18 (121) | 0.0010 |

Comments:

It is confirmed that the binding affinity of the compound of formula (I) of the present invention to an $EP_1$ subtype receptor is an equivalent to that of the compound specifically described in above WO98/27053.

(ii) Experimental Measurement of the Activity of Receptor Antagonism Using Cells Expressing Prostanoid Receptor Subtype $EP_1$ in the Presence of BSA (Bovine Serum Albumin)

The cells expressing mouse $EP_1$ receptor were seeded at $1\times10^4$ cells/well in 96 well plates and cultured for 2 days with 10% FBS (fetal bovine serum)/minimum essential medium Eagle alpha modification (αMEM) in the incubator (37° C., 5% $CO_2$). The cells in each well were rinsed with phosphate buffer (PBS(−)), and load buffer was added. After incubation for 1 hour, the load buffer was discarded. After the addition of the assay buffer to each well, the cells were incubated in a dark place at room temperature for 1 hour. After the addition of a compound of the present invention (10 μl) and $PGE_2$ (10 μl) which were prepared with assay buffer, intracellular calcium concentration was measured with Fluorescence drug screening system (FDSS-4000, Hamamatsu Photonics). A pair of fluorescence intensities emitted 500 nm by an excitation wavelength of each 340 nm and 380 nm was measured.

The $EP_1$ antagonist activity was estimated as percent inhibition of the increase of intracellular calcium concentration induced by $PGE_2$ (100 nM).

Load buffer: 10% FBS/αMEM containing 5 μM of Fura 2/AM, 20 μM of indomethacin, 2.5 mM of probenecid Assay buffer: Hank's balanced salt solution (HBSS) containing 1% (w/v) BSA, 2 μM of indomethacin, 2.5 mM of probenecid and 10 mM of HEPES-NaOH The results are shown in Table 2.

TABLE 2

| Compounds | IC$_{50}$ (μM) |
|---|---|
| Compounds of the present invention | |
| Example 2 | 0.0078 |
| Example 2 (6) | 0.0072 |
| Example 2 (32) | 0.021 |
| Example 2 (33) | 0.0041 |
| Example 2 (41) | 0.025 |
| Example 2 (87) | 0.0073 |
| Example 2 (94) | 0.0092 |
| Example 3 (11) | 0.0049 |
| Example 3 (30) | 0.0037 |
| Example 4 (14) | 0.0071 |
| Compounds of the related art (WO98/27053) | |
| Example18 (93) | 0.20 |
| Example18 (113) | 0.47 |
| Example18 (125) | 1.34 |
| Example18 (121) | 0.26 |

Comments:

In the experiment coexistent with proteins (measurement of activity of signaling in cells), the compound of formula (I) of the present invention indicated ten fold as high activity of inhibition of signaling as the compound specifically described in WO98/27053 or more.

It shows that the compound specifically described in WO98/27053 is affected by protein binding to descend its activity in coexistence with serum protein. On the other hand, it also shows that all of the compounds of formula (I) of the present invention are less affected by coexistent protein, and its activity is less lowered.

(iii) Experiment to Assess the Inhibition of Sulprostone-Induced Increase of Intravesical Pressure of Bladder in Rats.

Female rats (Wistar) were anesthetized by urethane and their both ureters were ligated and cut off at the kidney side. The urinary bladder was incised its top and catheter was inserted. The other end of catheter was connected to the pressure transducer and the infusion pump. Repeated micturition reflex, which was induced by the continuous infusion of citrate buffer (pH 3.5) into the bladder, was recorded. The increase of micturition pressure was elicited by the subcutaneous injection of diclofenac (5 mg/kg) and sulprostone (300 μg/kg). Since such an increasing effect was not observed by the treatment of EP$_3$ agonist, it was considered that this increase was caused by the activation of EP$_1$ receptor. The inhibitory effects of the compound of the present invention on this increase of intravesical pressure were measured for 60 minutes after the intraduodenal administration (2 ml/kg).

Table 3 shows the percent inhibition of increase of intravesical pressure at 40 minutes after the administration (1 mg/kg).

TABLE 3

| Compounds | Inhibition (%) (40 minutes later) |
|---|---|
| Example 2 | 68 ± 1 |
| Example 2 (33) | 79 ± 11 |

Comments:

It is confirmed that the compound of formula (I) of the present invention indicated a stronger suppression effect than that of the compound specifically described in WO98/27053 in in vivo experiment, and that it showed effective activity.

(iv) Experiment to Assess the Antagonistic Activity on the Increase in Urination Volume and Number Induced by Sulprostone to Rats.

Male rats (CD (SD) IGS) were used and micturition number and urination volume were measured by means of a Micturition volume measurement system (Neuroscience).

A compound of the present invention was orally administrated (4 ml/kg), and 30 minutes later, sulprostone (200 μg/4 ml/kg) was subcutaneously administered. Number and volume of urination were continuously monitored for 3 hours from the administration of sulprostone.

The percent inhibition of each compound was calculated by the following equation.

$$\text{Inhibition (\%)} = \frac{\left(\begin{array}{c}\text{number of micturitio} \\ \text{in control group}\end{array}\right) - \left(\begin{array}{c}\text{number of micturition in} \\ \text{test compound in the} \\ \text{present invention group}\end{array}\right)}{(\text{number of micturition in control group})} \times 100$$

Comments:

It is confirmed that the compound of formula (I) of the present invention indicated a stronger suppression effect than that of the compound specifically described in WO98/27053 in in vivo experiment.

Toxicity:

The toxicity of the compound of the present invention is very low and therefore, it is confirmed that the compound is safe for medical use.

INDUSTRIAL APPLICABILITY

Application to Pharmaceuticals:

The compound of formula (I) of the present invention, an ester thereof and a non-toxic salt thereof, which antagonize the EP$_1$ receptor, are therefore considered to be useful as analgesics, as antipyretic agents or as agents for the treatment of pollakiuria (neurogenic bladder, nervous bladder, stimulated bladder (irritable bladder), detrusor instability, dysuria accompany prostatomegaly), acraturesis (urinary incontinence), lower urinary tract disease syndrome. In addition, the compound of the present invention scarcely binds to the other subtypes of PGE$_2$ and is expected to provide an agent with little side effect.

It has also been known that an EP$_1$ antagonist possesses a suppressive effect on aberrantcryptfoci and formation of intestinal polyps, accordingly it indicates an effective antitumor activity.

The compound of formula (I) of the present invention and a non-toxic salt thereof may be administered in combination with other medicaments for the purpose of 1) complement and/or enhancement of the prevention and/or treatment effect of the compound,
2) improvement of the pharmacokinetics and/or the absorption of the compound, lowering of dose, and/or
3) alleviation of a side effect of the compound.

The compound of formula (I) may be administered in combination with other medicaments as a composition in one drug product comprising these components, or may be separately administered. In the case of the separated administration, they may be administered simultaneously or with lapse of time. While administration with lapse of time, the compound of formula (I) may be precedently administered, followed by administration of the other medicaments. Alternatively, the other medicaments may be precedently administered, followed by administration of the compound of formula (I). Routes of administration may be either the same or different to each other.

The above combination drug takes effect on whichever disease preventing and/or treatment effect of the compound of formula (I) is complemented and/or enhanced.

For example, the other medicaments which complement and/or enhance the effect of the compound of formula (I) for the prevention and/or treatment for pollakiuria (frequent urination) are anticholinergic drugs, tricyclic anti-depressant agents, α agonists, $\alpha_1$ antagonists, GABA agonists, antidiuretics, anti-androgenic hormones, corpus luteum hormones, $NK_1$ antagonists, $\beta_3$ agonists, P2X antagonists, potassium channel openers, LPA, $EP_3$ antagonists, capsaicin, resiniferatoxin, 5α-reductase inhibitors, etc.

For example, other medicaments which are useful for the complement and/or enhancement of the effect of the compound of formula (I) for the prevention and/or treatment of algia are opioids, gabapentin, pregabalin, $\alpha_2$ antagonists, NMDA antagonists, TTX-resistant sodium channel blockers, VR1 antagonists, nociceptin antagonists, P2X antagonists, IP antagonists, $EP_3$ antagonists, N-type calcium channel blockers, iNOS inhibitors, etc.

A weight ratio of the compound of formula (I) and other medicaments is not limited in particular.

The other medicaments may be administered in combination of arbitrary two or more.

Based on the mechanism, the other medicaments which complement and/or enhance the effect of the compound of formula (I) for the preventing and/or treatment for disorders include not only medicaments which have already found thus far but also ones which will be found in future.

For the purpose above described, the compound of formula (I) of the present invention, an ester thereof, a non-toxic salt thereof or combination of theirs and other medicaments may be normally administered systemically or partially, usually by oral or parenteral administration.

The dosages are determined depending on patient's age, body weight, symptom, a desired therapeutic effect, a route of administration and a duration of the treatment, etc. Generally the doses per person per administration to an adult human are from 1 to 100 mg up to several times per day by oral administration. Alternatively, they are from 1 to 100 mg up to several times per day by parenteral administration (preferred into vein). Or they are administrated into vein continuously for from 1 to 24 hours per day.

As mentioned above, the doses to be used depend on various conditions. So the doses to be administrated may be lower than the dose specified above in some cases and sometimes they may be something over.

The compound of formula (I) of the present invention and a non-toxic salt thereof or a combination of the compound of formula (I) and other medicaments may be administered in the form of, for example, solid compositions, liquid compositions or other compositions for oral administration, or as injections, external medicines or suppositories, etc. for parenteral administration.

Solid compositions for oral administration include tablets, pills, capsules, dispersible powders and granules, etc.

Capsules include hard capsules and soft capsules.

In such solid compositions, one or more of the active compound(s) is or are, admixed with at least one inert diluent e.g. lactose, mannitol, glucose, hydroxypropyl cellulose, microcrystalline cellulose, starch, polyvinylpyrrolidone, magnesium metasilicate aluminate, etc. Such compositions may contain additional substances other than inert diluent, for example, lubricating agents e.g. magnesium stearate, disintegrating agents e.g. cellulose calcium glycolate, agents for stabilizing e.g. lactose, assisting agents for dissolving e.g. glutamic acid, asparaginic acid. Tablets or pills may, if desired, be coated with gastric or enteric films such as sugar, gelatin, hydroxypropyl cellulose or hydroxypropylmethylcellulose phthalate, etc., or be coated with two or more films. And further, the compositions also include capsules of absorbable materials such as gelatin.

Liquid compositions for oral administration include pharmaceutically-acceptable emulsions, solutions, syrups and elixirs, etc. In such liquid compositions, one or more of the active compound(s) is or are comprised in inert diluent(s) commonly used in the art (e.g. purified water, ethanol). Besides inert diluents, such compositions may also comprise adjuvants such as wetting agents, suspending agents, sweetening agents, flavoring agents, perfuming agents, preserving agents.

Other compositions for oral administration include spray compositions which may be prepared by known methods per se and which comprise one or more of the active compound(s). Spray compositions may comprise additional substances other than inert diluents: e.g. stabilizing agents such as sodium hydrogen sulfate, stabilizing agents to give the title compound isotonicity, isotonic buffer such as sodium chloride, sodium citrate and citric acid. For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions. Aqueous solutions or suspensions include, for example, distilled water for injection and physiological salt solution. Non-aqueous solutions or suspensions include, for example, propylene glycol, polyethylene glycol, plant oils such as olive oil, alcohols such as ethanol, POLYSORBATE80 (registered trademark), etc. It may be used by admixing of sterile aqueous or non-aqueous solutions, suspensions and emulsion. Such compositions may comprise additional diluents: e.g. preserving agents, wetting agents, emulsifying agents, dispersing agents, stabilizing agent (for example, lactose), assisting agents such as assisting agents for dissolving (for example, glutamic acid, asparaginic acid). They may be sterilized, for example, by filtration through a bacteria-retaining filter, by incorporation of sterilizing agents in the compositions or by irradiation. They also be manufactured in the form of sterile solid compositions (for example, the freeze-dried compositions) and which can be dissolved in sterile water or some other sterile diluents for injection immediately before usage.

Other compositions for parenteral administration include liquids for external use, and endemic liniments, ointment, suppositories and pessaries which comprise one or more of the active compound(s) and may be prepared by known methods.

BEST MODE FOR CARRYING OUT THE INVENTION

The following Reference examples and Examples are intend to illustrate, but not to limit the present invention.

The solvents in parentheses at chromatographic separations section show the developing or eluting solvents and the ratios of the solvents used are indicated by volume. Without special explanation, NMR data was determined in CDCl₃ solution. And the solvents in parentheses at NMR data section show solvents used in determination.

Reference Example 1

4-(2-nitro-4,5-dimethylphenoxymethyl)-3-methyl-benzoic acid methyl ester

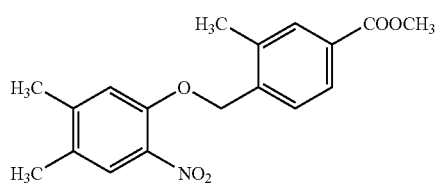

Under atmosphere of argon, a mixture of 2-nitro-4,5-dimethylphenol (4 g), DMF (100 ml), potassium carbonate (6.6 g) and 4-mesyloxymethyl-3-methylbenzoic acid methyl ester (6.8 g) were stirred for 15 minutes at 60° C. After the termination of reaction, the mixture was cooled and poured into iced water. The mixture was extracted with ethyl acetate-hexane. The organic layer was washed, dried, concentrated under reduced pressure to give the title compound (7.22 g) having the following physical data.

TLC: Rf 0.24 (n-hexane:ethyl acetate=4:1).

Reference Example 2

4-(2-amino-4,5-dimethylphenoxymethyl)-3-methyl-benzoic acid methyl ester

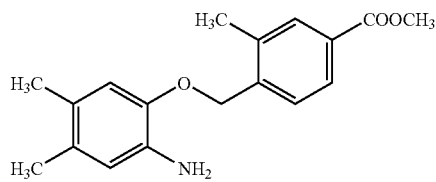

A mixture of 4-(2-nitro-4,5-dimethylphenoxymethyl)-3-methylbenzoic acid methyl ester prepared in Reference Example 1 (7.21 g), acetic acid (88 ml) and water (8.8 ml) was stirred at 50° C. To the reaction solution, iron powder (6.11 g) was gradually added, and the mixture was stirred for 1 hour at 50° C. After cooling, the mixture was filtered and the filtrate was concentrated and azeotroped with toluene. To the residue, ethyl acetate-water (100 ml-100 ml) was added and the mixture was filtrated over Celite (registered trademark). The organic layer was washed, dried, concentrated under reduced pressure to give the title compound (4.66 g) having the following physical data.

TLC: Rf 0.51 (n-hexane:ethyl acetate=2:1).

Reference Example 3

3-methyl-4-[2-[N-(5-methyl-2-furylsulfonyl)amino]-4,5-dimethylphenoxymethyl]benzoic acid methyl ester

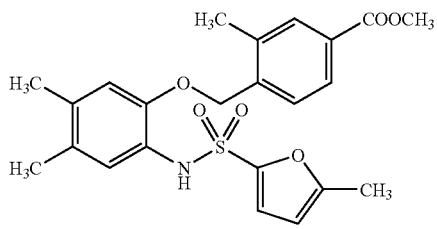

A solution of 4-(2-amino-4,5-dimethylphenoxymethyl)-3-methylbenzoic acid methyl ester prepared in Reference Example 2 (632 mg) in pyridine (4 ml) was cooled to 0° C., then 5-methylfuran-2-sulfonyl chloride (490 mg) was added dropwise thereto. After the solution was stirred for 1 hour at room temperature, the reaction mixture was diluted by ethyl acetate, and poured into water. The organic layer was washed, dried, concentrated under reduced pressure. The residue was washed by mixed solvent of diisopropylether and hexane to give the title compound (875 mg) having the following physical data.

TLC: Rf 0.42 (n-hexane:ethyl acetate=2:1).

Example 1

3-methyl-4-[2-[N-isobutyl-N-(5-methyl-2-furylsulfonyl)amino]-4,5-dimethylphenoxymethyl]benzoic acid methyl ester

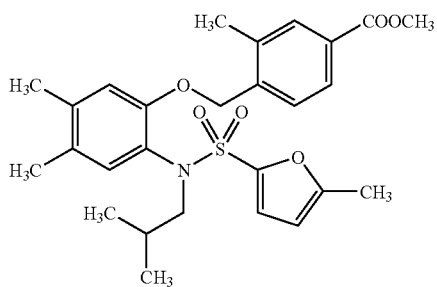

To a solution of 3-methyl-4-[2-[N-(5-methyl-2-furylsulfonyl)amino]-4,5-dimethylphenoxymethyl]benzoic acid methyl ester prepared in Reference Example 3 (870 mg) in N,N-dimethylacetamide (2 ml), cesium carbonate (1.37 g) and isobutyl iodide (0.36 ml) were added and the mixture was stirred for 1 hour at 100° C. The reaction mixture was allowed to cool and poured into ethyl acetate-water (40 ml-40 ml). The organic layer was washed, dried and concentrated under reduced pressure.

The residue was purified by column chromatography on silica gel (toluene-ethyl acetate) to give the title compound (855 mg) having the following physical data.

TLC: Rf 0.51 (n-hexane:ethyl acetate=2:1);

NMR: δ 7.87 (d, J=8.4 Hz, 1H), 7.86 (s, 1H), 7.38 (d, J=8.4 Hz, 1H), 7.04 (s, 1H), 6.70 (m, 2H), 5.93 (m, 1H), 4.91 (brs, 2H), 3.92 (s, 3H), 3.48 (m, 2H), 2.34 (s, 3H), 2.23 (s, 3H), 2.18 (s, 3H), 2.09 (s, 3H), 0.90 (brs, 6H).

Example 2

3-methyl-4-[2-[N-isobutyl-N-(5-methyl-2-furylsulfonyl)amino]-4,5-dimethylphenoxymethyl]benzoic acid

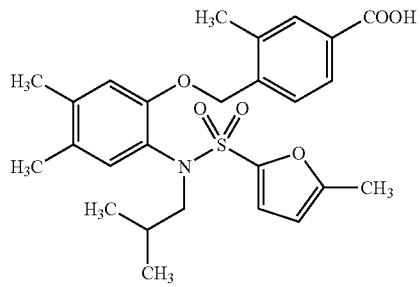

To a solution of 3-methyl-4-[2-[N-isobutyl-N-(5-methyl-2-furylsulfonyl)amino]-4,5-dimethylphenoxymethyl]benzoic acid methyl ester prepared in Example 1 (850 mg) in dioxane (10 ml), 2N aqueous sodium hydroxide (2.5 ml) and methanol (4 ml) were added, and the mixture was stirred for 30 hours at room temperature. To the mixture, 2N hydrochloric acid was added, then ethyl acetate-water (30 ml-15 ml) was also added. The organic layer was washed, dried and concentrated under reduced pressure. The residue was dissolved in hot ethanol (40 ml) and added by hot water (40 ml), then allowed to cool. Precipitation was filtrated, and dried to give the title compound (755 mg) having the following physical data.

TLC: Rf 0.78 (chloroform:methanol:water=8:2:0.2);
NMR: δ 7.94 (d, J=7.8 Hz, 1H), 7.93 (s, 1H), 7.44 (d, J=7.8 Hz, 1H), 7.04 (s, 1H), 6.74-6.70 (m, 2H), 5.94 (dd, J=3.3, 0.9 Hz, 1H), 4.94 (br, 2H), 3.48 (d, J=6.6 Hz, 2H), 2.37 (s, 3H), 2.24 (s, 3H), 2.19 (s, 3H), 2.11 (s, 3H), 1.68 (sep, J=6.6 Hz, 1H), 0.91 (d, J=6.6 Hz, 6H).

Example 2(1) to Example 2(124)

By the same procedures as described in Reference Example 1 to 3, Examples 1 and 2 using corresponding compounds, the title compounds having the following physical data were obtained.

Example 2(1)

4-[2-[N-isobutyl-N-(5-methyl-2-furylsulfonyl)amino]-5-trifluoromethylphenoxymethyl]cinnamic acid

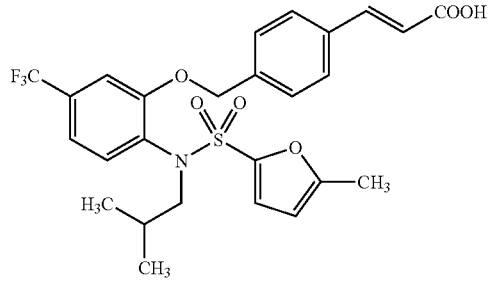

TLC: Rf 0.51 (n-hexane:ethyl acetate:acetic acid=1:1:0.02);
NMR: δ 7.80 (d, J=16.2 Hz, 1H), 7.59 (d, J=8.0 Hz, 2H), 7.45-7.36 (m, 3H), 7.26 (dd, J=8.2, 1.8 Hz, 1H), 7.18 (d, J=1.8 Hz, 1H), 7.00-5.00 (br, 1H), 6.75 (d, J=3.4 Hz, 1H), 6.49 (d, J=16.2 Hz, 1H), 5.98 (dq, J=3.4, 0.8 Hz, 1H), 5.05 (brs, 2H), 3.51 (d, J=7.4 Hz, 2H), 2.16 (s, 3H), 1.75-1.50 (m, 1H), 0.88 (d, J=6.8 Hz, 6H).

Example 2(2)

4-[2-[N-isopropyl-N-(5-methyl-2-furylsulfonyl)amino]-5-trifluoromethylphenoxymethyl]benzoic acid

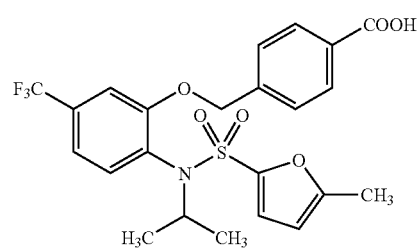

TLC: Rf 0.44 (chloroform:methanol=9:1);
NMR: δ 8.16 (d, J=8.4 Hz, 2H), 7.60 (d, J=8.4 Hz, 2H), 7.21-7.26 (m, 3H), 6.84 (d, J=3.2 Hz, 1H), 6.05 (m, 1H), 5.21 (m, 2H), 4.49 (m, 1H), 2.33 (s, 3H), 1.10 (d, J=6.6 Hz, 6H).

Example 2(3)

4-[2-[N-isobutyl-N-(5-methyl-2-furylsulfonyl)amino]-5-trifluoromethylphenoxymethyl]benzoic acid

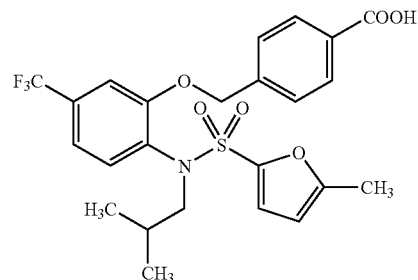

TLC: Rf 0.46 (chloroform:methanol=9:1);
NMR: δ 8.15 (d, J=8.6 Hz, 2H), 7.46 (d, J=8.6 Hz, 2H), 7.41 (m, 1H), 7.29 (m, 1H), 7.18 (m, 1H), 6.76 (d, J=3.4 Hz, 1H), 5.98 (m, 1H), 5.10 (s, 2H), 3.51 (d, J=6.2 Hz, 2H), 2.16 (s, 3H), 1.64 (m, 1H), 0.90 (d, J=6.8 Hz, 6H).

Example 2(4)

4-[2-[N-isobutyl-N-(5-methyl-2-furylsulfonyl)amino]-4-chloro-5-methylphenoxymethyl]benzoic acid

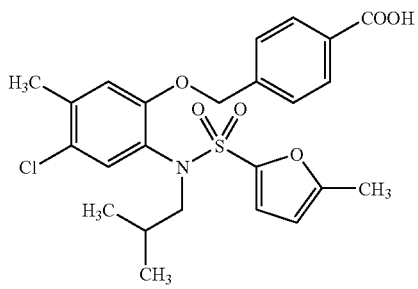

TLC: Rf 0.30 (chloroform:methanol=9:1);
NMR: δ 8.12 and 7.46 (each d, J=8.1 Hz, each 2H), 7.20 (s, 1H), 6.81-6.75 (m, 2H), 6.01-5.98 (m, 1H), 5.12-4.98 (m, 2H), 3.45 (d, J=7.5 Hz, 2H), 2.34 and 2.19 (each s, each 3H), 1.75-1.59 (m, 1H), 0.91 (d, J=6.9 Hz, 6H).

Example 2(5)

4-[2-[N-isopropyl-N-(5-methyl-2-furylsulfonyl)amino]-4,5-dimethylphenoxymethyl]benzoic acid

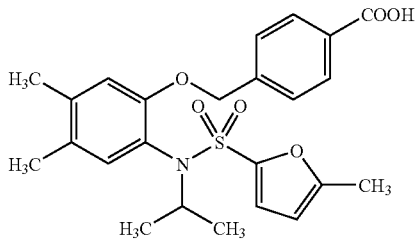

TLC: Rf 0.38 (chloroform:methanol=10:1);
NMR: δ 8.12-8.09 (m, 2H), 7.56 (d, J=8.4 Hz, 2H), 6.81 (s, 1H), 6.79 (d, J=3.3 Hz, 1H), 6.75 (s, 1H), 6.02 (dd, J=3.3, 1.2 Hz, 1H), 5.10 (s, 2H), 4.48 (m, 1H), 2.30 (s, 3H), 2.23 (s, 3H), 2.17 (s, 3H), 1.11 (d, J=6.6 Hz, 6H).

Example 2(6)

4-[2-[N-isobutyl-N-(5-methyl-2-furylsulfonyl)amino]-4,5-dimethylphenoxymethyl]benzoic acid

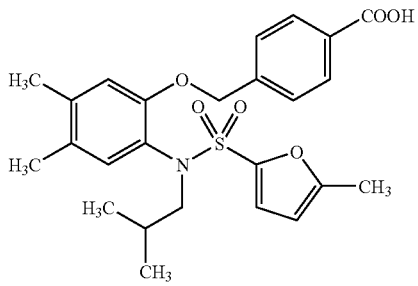

TLC: Rf 0.38 (chloroform:methanol=10:1);
NMR: δ 8.12-8.08 (m, 2H), 7.42 (d, J=8.4 Hz, 2H), 7.03 (s, 1H), 6.71 (d, J=3.3 Hz, 1H), 6.68 (s, 1H), 5.92 (dd, J=3.3, 0.9 Hz, 1H), 5.00 (brs, 2H), 3.52-3.46 (m, 2H), 2.22 (s, 3H), 2.18 (s, 3H), 2.13 (s, 3H), 1.68 (m, 1H), 0.91 (d, J=6.6 Hz, 6H).

Example 2(7)

3-methyl-4-[2-[N-isobutyl-N-(5-methyl-2-furylsulfonyl)amino]-4-methyl-5-chlorophenoxymethyl]benzoic acid

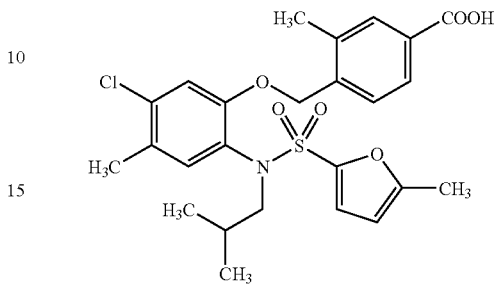

TLC: Rf 0.42 (chloroform:methanol 9:1);
NMR: δ 8.00-7.89 (m, 2H), 7.41 (d, J=8.4 Hz, 1H), 7.16 (s, 1H), 6.95 (s, 1H), 6.74 (d, J=3.3 Hz, 1H), 5.96 (m, 1H), 4.94 (s, 2H), 3.47 (d, J=6.3 Hz, 2H), 2.37 (s, 3H), 2.30 (s, 3H), 2.11 (s, 3H), 1.64 (m, 1H), 0.90 (d, J=6.6 Hz, 6H).

Example 2(8)

3-methyl-4-[2-[N-isobutyl-N-(5-methyl-2-furylsulfonyl)amino]-4-chloro-5-methylphenoxymethyl]benzoic acid

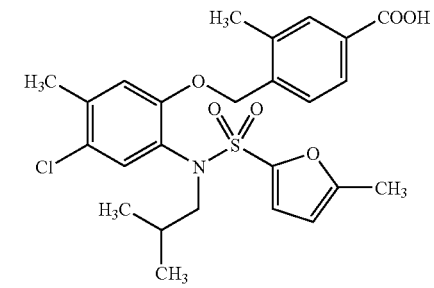

TLC: Rf 0.58 (chloroform:methanol=9:1);
NMR: δ 7.96 (d, J=7.5 Hz, 1H), 7.94 (s, 1H), 7.47 (d, J=7.5 Hz, 1H), 7.20 (s, 1H), 6.81 (s, 1H), 6.77 (d, J=3.3 Hz, 1H), 6.03-5.97 (m, 1H), 4.99 (brs, 2H), 3.44 (d, J=7.5 Hz, 2H), 2.39 (s, 3H), 2.36 (s, 3H), 2.17 (s, 3H), 1.75-1.60 (m, 1H), 0.89 (d, J=6.6 Hz, 6H).

Example 2(9)

3-chloro-4-[2-[N-isobutyl-N-(5-methyl-2-furylsulfonyl)amino]-4-methyl-5-chlorophenoxymethyl]benzoic acid

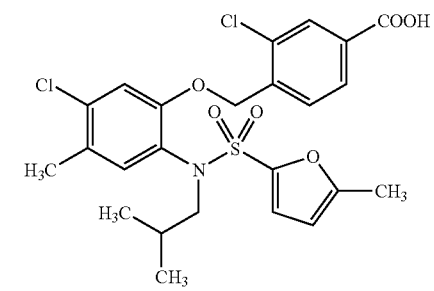

TLC: Rf 0.38 (chloroform:methanol=9:1);

NMR: δ 8.13 (d, J=1.5 Hz, 1H), 8.02 (dd, J=8.4, 1.5 Hz, 1H), 7.58 (d, J=8.4 Hz, 1H), 7.15 (s, 1H), 6.94 (s, 1H), 6.76 (d, J=3.3 Hz, 1H), 5.98 (m, 1H), 5.25-4.90 (br, 2H), 3.48 (d, J=6.6 Hz, 2H), 2.31 (s, 3H), 2.16 (s, 3H), 1.64 (m, 1H), 0.92 (d, J=6.6 Hz, 6H).

Example 2(10)

3-chloro-4-[2-[N-isopropyl-N-(5-methyl-2-furylsulfonyl)amino]-4-methyl-5-chlorophenoxymethyl]benzoic acid

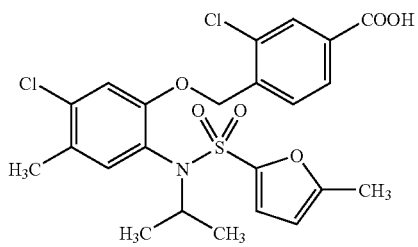

TLC: Rf 0.38 (chloroform:methanol=9:1);
NMR: δ 8.12 (d, J=1.5 Hz, 1H), 8.07 (dd, J=8.4, 1.5 Hz, 1H), 7.88 (d, J=8.4 Hz, 1H), 6.99 (s, 1H), 6.95 (s, 1H), 6.85 (d, J=3.3 Hz, 1H), 6.06 (m, 1H), 5.20 (d, J=14.4 Hz, 1H), 5.15 (d, J=14.4 Hz, 1H), 4.48 (m, 1H), 2.33 (s, 3H), 2.30 (s, 3H), 1.11 (d, J=6.3 Hz, 3H), 1.09 (d, J=6.3 Hz, 3).

Example 2(11)

3-methoxy-4-[2-[N-isopropyl-N-(5-methyl-2-furylsulfonyl)amino]-4-methyl-5-chlorophenoxymethyl]benzoic acid

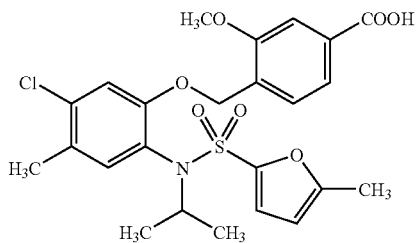

TLC: Rf 0.49 (chloroform:methanol=9:1);
NMR: δ 7.78 (dd, J=8.1, 1.5 Hz, 1H), 7.76 (d, J=1.5 Hz, 1H), 7.59 (d, J=1.5 Hz, 1H), 7.01 (s, 1H), 6.96 (s, 1H), 6.83 (d, J=3.3 Hz, 1H), 6.05-6.00 (m, 1H), 5.11 (d, J=14.1 Hz, 1H), 5.07 (d, J=14.1 Hz, 1H), 4.55-4.40 (m, 1H), 3.94 (s, 3H), 2.30 (s, 3H), 2.29 (s, 3H), 1.12 (d, J=6.9 Hz, 6H).

Example 2(12)

3-methoxy-4-[2-[N-isopropyl-N-(5-methyl-2-furylsulfonyl)amino]-4,5-dimethylphenoxymethyl]benzoic acid

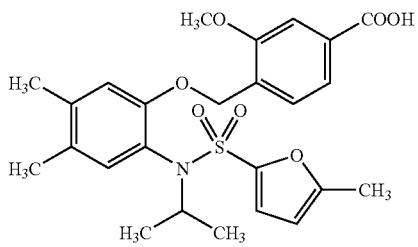

TLC: Rf 0.44 (chloroform:methanol=9:1);
NMR: δ 7.77 (dd, J=8.1, 1.2 Hz, 1H), 7.74 (d, J=8.1 Hz, 1H), 7.58 (d, J=1.2 Hz, 1H), 6.84 (s, 1H), 6.81 (d, J=3.3 Hz, 1H), 6.78 (s, 1H), 6.05-6.00 (m, 1H), 5.09 (s, 2H), 4.60-4.40 (m, 1H), 3.94 (s, 3H), 2.29 (s, 3H), 2.24 (s, 3H), 2.17 (s, 3H), 1.12 (d, J=6.9 Hz, 6H).

Example 2(13)

3-methoxy-4-[2-[N-isobutyl-N-(5-methyl-2-furylsulfonyl)amino]-4,5-dimethylphenoxymethyl]benzoic acid

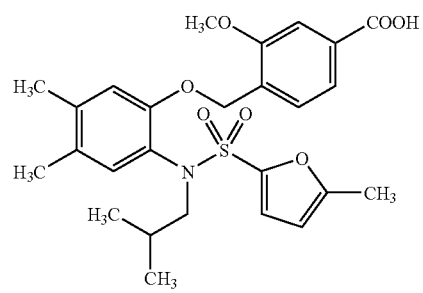

TLC: Rf 0.45 (chloroform:methanol=9:1);
NMR: δ 7.73 (dd, J=8.1, 1.2 Hz, 1H), 7.58 (d, J=1.2 Hz, 1H), 7.40 (d, J=8.1 Hz, 1H), 7.07 (s, 1H), 6.75-6.70 (m, 2H), 5.95-5.90 (m, 1H), 5.15-4.85 (m, 2H), 3.94 (s, 3H), 3.51 (br, 2H), 2.23 (s, 3H), 2.19 (s, 3H), 2.11 (s, 3H), 1.80-1.60 (m, 1H), 0.94 (br, 6H).

Example 2(14)

3-methoxy-4-[2-[N-isopropyl-N-(5-methyl-2-furylsulfonyl)amino]-4-chloro-5-methylphenoxymethyl]benzoic acid

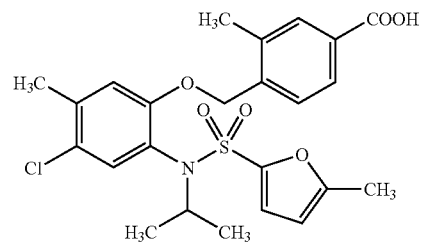

TLC: Rf 0.46 (chloroform:methanol=9:1);
NMR(DMSO-d$_6$): δ 13.02 (s, 1H), 7.58-7.50 (m, 3H), 7.24 (s, 1H), 6.98 (s, 1H), 6.94 (d, J=3.3 Hz, 1H), 6.25 (m, 1H), 5.10 (d, J=13.5 Hz, 1H), 5.04 (d, J=13.5 Hz, 1H), 4.24 (m, 1H), 3.87 (s, 3H), 2.34 (s, 3H), 2.27 (s, 3H), 0.99 (d, J=6.6 Hz, 3H), 0.98 (d, J=6.6 Hz, 3H).

Example 2(15)

3-chloro-4-[2-[N-isobutyl-N-(5-methyl-2-furylsulfonyl)amino]-4,5-dimethylphenoxymethyl]benzoic acid

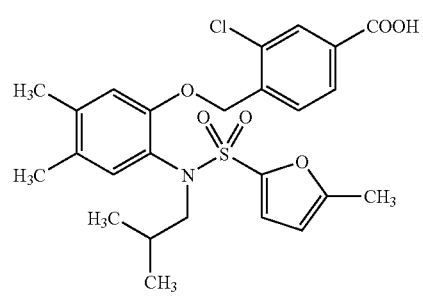

TLC: Rf 0.40 (chloroform:methanol=9:1);

NMR: δ 8.12 (d, J=1.8 Hz, 1H), 8.02 (dd, J=8.1, 1.8 Hz, 1H), 7.61 (d, J=8.1 Hz, 1H), 7.03 (s, 1H), 6.75 (d, J=3.3 Hz, 1H), 6.70 (s, 1H), 5.96 (m, 1H), 5.25-4.85 (br, 2H), 3.50 (d, J=6.6 Hz, 2H), 2.24 (s, 3H), 2.19 (s, 3H), 2.16 (s, 3H), 1.79 (m, 1H), 0.93 (d, J=6.6 Hz, 6H).

Example 2(16)

3-chloro-4-[2-[N-isopropyl-N-(5-methyl-2-furylsulfonyl)amino]-4,5-dimethylphenoxymethyl]benzoic acid

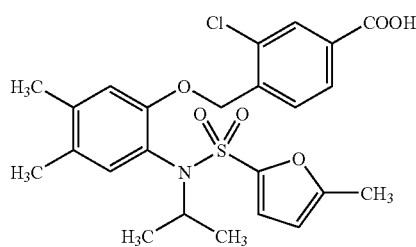

TLC: Rf 0.39 (chloroform:methanol=9:1);

NMR: δ 8.11 (d, J=1.8 Hz, 1H), 8.06 (dd, J=8.1, 1.8 Hz, 1H), 7.90 (d, J=8.1 Hz, 1H), 6.86-6.80 (m, 2H), 6.75 (s, 1H), 6.05 (m, 1H), 5.17 (s, 2H), 4.51 (m, 1H), 2.32 (s, 3H), 2.25 (s, 3H), 2.18 (s, 3H), 1.12 (d, J=6.6 Hz, 3H), 1.11 (d, J=6.6 Hz, 3H).

Example 2(17)

3-methyl-4-[2-[N-isobutyl-N-(5-methyl-2-furylsulfonyl)amino]-4-chloro-5-methylphenoxymethyl]cinnamic acid

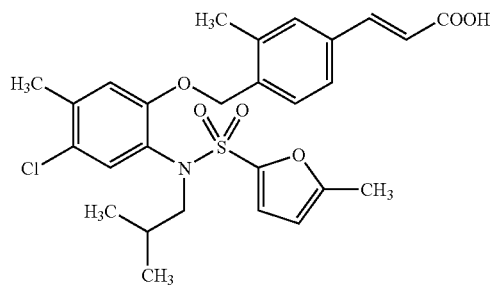

TLC: Rf 0.37 (chloroform:methanol=9:1);

NMR(CD$_3$OD): δ 7.63 (d, J=16.2 Hz, 1H), 7.45 (s) and 7.44 (d, J=8.1 Hz) total 2H, 7.34 (d, J=8.1 Hz, 1H), 7.17 (s, 1H), 7.10 (s, 1H), 6.72 (d, J=3.3 Hz, 1H), 6.50 (d, J=16.2 Hz, 1H), 6.08 (dd, J=3.3, 1.2 Hz, 1H), 4.98 (brs, 2H), 3.44 (d, J=6.9 Hz, 2H), 2.37 (s, 3H), 2.35 (s, 3H), 2.10 (s, 3H), 1.60 (m, 1H), 0.87 (d, J=6.6 Hz, 6H).

Example 2(18)

4-[2-[N-isopropyl-N-(5-methyl-2-furylsulfonyl)amino]-4-methyl-5-chlorophenoxymethyl]cinnamic acid

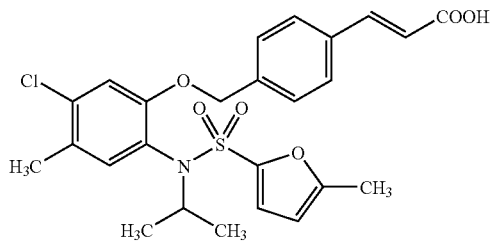

TLC: Rf 0.31 (chloroform:methanol=9:1);

NMR: δ 7.73 (d, J=15.9 Hz, 1H), 7.57 and 7.49 (each d, J=8.1 Hz, each 2H), 6.98 and 6.92 (each s, each 1H), 6.81 (d, J=3.3 Hz, 1H), 6.46 (d, J=15.9 Hz, 1H), 6.03 (d, J=3.3 Hz, 1H), 5.05 (s, 2H), 4.50-4.38 (m, 1H), 2.30 and 2.28 (each s, each 3H), 1.10 and 1.09 (each d, J=6.6 Hz, each 3H).

Example 2(19)

4-[2-[N-isobutyl-N-(5-methyl-2-furylsulfonyl)amino]-4-methyl-5-chlorophenoxymethyl]cinnamic acid

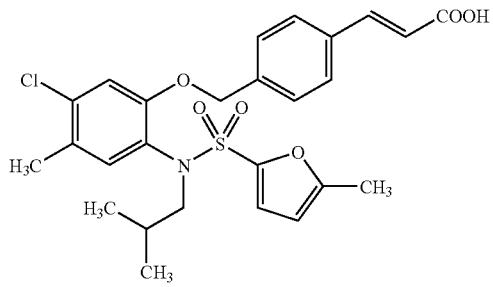

TLC: Rf 0.31 (chloroform:methanol=9:1);

NMR: δ 7.77 (d, J=15.9 Hz, 1H), 7.56 and 7.35 (each d, J=7.8 Hz, each 2H), 7.14 and 6.92 (each s, each 1H), 6.72 (d, J=3.6 Hz, 1H), 6.47 (d, J=15.9 Hz, 1H), 5.95 (d, J=3.6 Hz, 1H), 5.00-4.88 (m, 2H), 3.52-3.42 (m, 2H), 2.29 and 2.13 (each s, each 3H), 1.72-1.60 (m, 1H), 0.90 (d, J=6.3 Hz, 6H).

Example 2(20)

4-[2-[N-isopropyl-N-(5-methyl-2-furylsulfonyl)amino]-4,5-dimethylphenoxymethyl]cinnamic acid

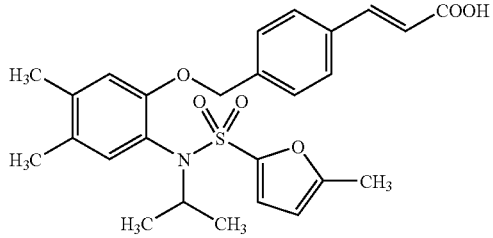

TLC: Rf 0.39 (chloroform:methanol=9:1);

NMR: δ 7.78 (d, J=15.9 Hz, 1H), 7.57 (d, J=8.4 Hz, 2H), 7.50 (d, J=8.4 Hz, 2H), 6.80 (s, 1H), 6.79 (d, J=3.3 Hz, 1H), 6.76 (s, 1H), 6.46 (d, J=15.9 Hz, 1H), 6.01 (m, 1H), 5.06 (s, 2H), 4.47 (sept, J=6.6 Hz, 1H), 2.30 (s, 3H), 2.23 (s, 3H), 2.16 (s, 3H), 1.11 and 1.10 (each d, J=6.6 Hz, each 3H).

Example 2(21)

3-methyl-4-[2-[N-isopropyl-N-(5-methyl-2-furylsulfonyl)amino]-5-trifluoromethylphenoxymethyl]cinnamic acid

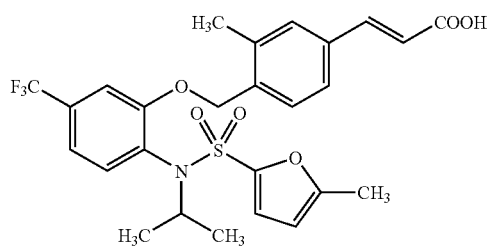

TLC: Rf 0.42 (chloroform:methanol=9:1);

NMR(DMSO-d$_6$): δ 12.36 (br s, 1H), 7.61-7.52 (m, 5H), 7.38 (d, J=8.0 Hz, 1H), 7.24 (d, J=8.0 Hz, 1H), 6.96 (d, J=3.5 Hz, 1H), 6.54 (d, J=16.0 Hz, 1H), 6.28 (d, J=3.5 Hz, 1H), 5.24 (d, J=13.0 Hz, 1H), 5.18 (d, J=13.0 Hz, 1H), 4.26 (septet, J=6.5 Hz, 1H), 2.35 (s, 3H), 2.30 (s, 3H), 0.97 (d, J=6.5 Hz, 6H).

Example 2(22)

3-methyl-4-[2-[N-isopropyl-N-(5-methyl-2-furylsulfonyl)amino]-4,5-dimethylphenoxymethyl]benzoic acid

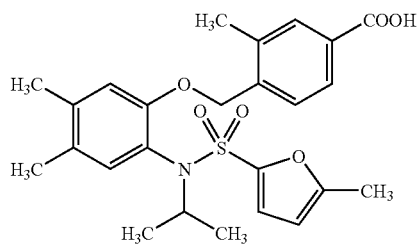

TLC: Rf 0.28 (n-hexane:ethyl acetate=1:1);

NMR: δ 7.97 (d, J=7.8 Hz, 1H), 7.93 (s, 1H), 7.65 (d, J=7.8 Hz, 1H), 6.82 (s, 1H), 6.79 (d, J=3.3 Hz, 1H), 6.77 (s, 1H), 6.01 (dd, J=3.3, 1.2 Hz, 1H), 5.08 (d, J=13.2 Hz, 1H), 5.02 (d, J=13.2 Hz, 1H), 4.47 (quint, J=6.6 Hz, 1H), 2.40 (s, 3H), 2.29 (s, 3H), 2.25 (s, 3H), 2.17 (s, 3H), 1.11 (d, J=6.6 Hz, 6H).

Example 2(23)

3-methyl-4-[2-[N-isopropyl-N-(5-methyl-2-furylsulfonyl)amino]-4,5-dimethylphenoxymethyl]cinnamic acid

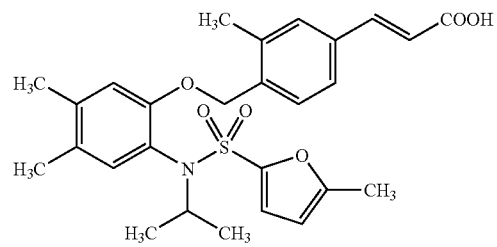

TLC: Rf 0.30 (n-hexane:ethyl acetate=1:2);
MS (FAB, Pos.): 498 (M+H)$^+$.

Example 2(24)

3-methyl-4-[2-[N-isobutyl-N-(5-methyl-2-furylsulfonyl)amino]-4,5-dimethylphenoxymethyl]cinnamic acid

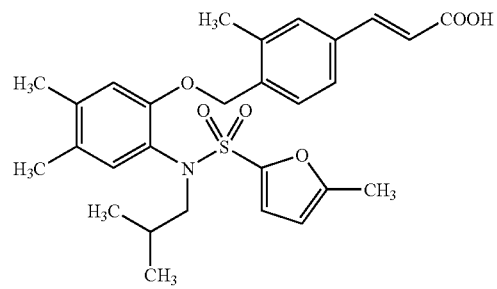

TLC: Rf 0.26 (n-hexane:ethyl acetate=1:2);
MS (FAB, Pos.): 512 (M+H)$^+$.

Example 2(25)

4-[2-[N-isobutyl-N-(5-methyl-2-furylsulfonyl)amino]-4,5-dimethylphenoxymethyl]cinnamic acid

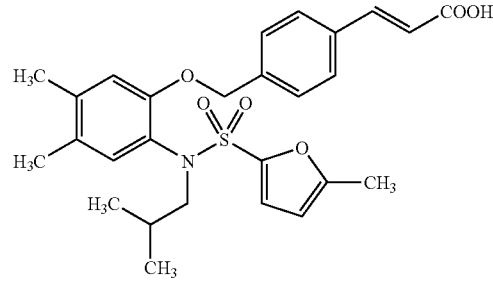

TLC: Rf 0.47 (chloroform:methanol=9:1);

NMR(DMSO-d$_6$): δ 7.69 (d, J=8.1 Hz, 2H), 7.58 (d, J=16.2 Hz, 1H), 7.34 (d, J=8.1 Hz, 2H), 6.93 (s, 1H), 6.90 (s, 1H), 6.79 (d, J=3.3 Hz, 1H), 6.54 (d, J=16.2 Hz, 1H), 6.13 (m, 1H), 5.10-4.80 (m, 2H), 3.40-3.20 (m, 2H, covered with H$_2$O in DMSO-d$_6$), 2.18 (s, 3H), 2.11 (s, 3H), 2.10 (s, 3H), 1.58-1.42 (m, 1H), 0.82 (d, J=6.6 Hz, 6H).

Example 2(26)

3-methoxy-4-[2-[N-isobutyl-N-(5-methyl-2-furylsulfonyl)amino]-4-methyl-5-chlorophenoxymethyl]cinnamic acid

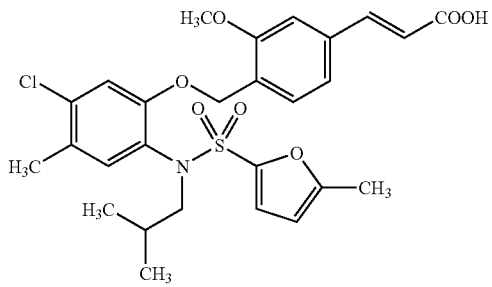

TLC: Rf 0.30 (chloroform:methanol=9:1);
NMR: δ 7.76 (d, J=15.9 Hz, 1H), 7.30 (d, J=8.1 Hz, 1H), 7.26 (s, 1H), 7.20 (d, J=8.1 Hz, 1H), 7.04 (s, 1H), 6.96 (s, 1H), 6.72 (d, J=3.3 Hz, 1H), 6.46 (d, J=15.9 Hz, 1H), 6.00-5.90 (m, 1H), 4.95 (brs, 2H), 3.91 (s, 3H), 3.48 (brs, 2H), 2.29 (s, 3H), 2.13 (s, 3H), 1.75-1.60 (m, 1H), 0.91 (brd, J=6.6 Hz, 6H).

Example 2(27)

4-[6-[N-isobutyl-N-(5-methyl-2-furylsulfonyl)amino]indan-5-yloxymethyl]benzoic acid

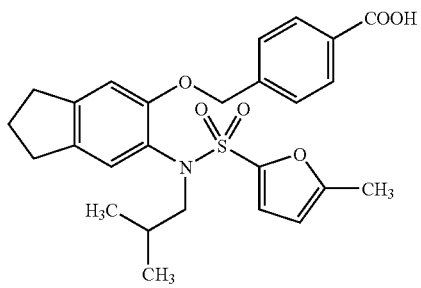

TLC: Rf 0.45 (chloroform:methanol=9:1);
NMR: δ 8.11 (d, J=8.1 Hz, 2H), 7.43 (d, J=8.1 Hz, 2H), 7.12 (s, 1H), 6.77 (s, 1H), 6.73 (d, J=3.3 Hz, 1H), 5.94 (m, 1H), 5.15-4.85 (br, 2H), 3.60-3.40 (br, 2H), 2.86 (t, J=7.2 Hz, 4H), 2.14 (s, 3H), 2.13-2.00 (m, 2H), 1.68 (m, 1H), 1.02-0.82 (br, 6H).

Example 2(28)

4-[6-[N-isopropyl-N-(5-methyl-2-furylsulfonyl)amino]indan-5-yloxymethyl]benzoic acid

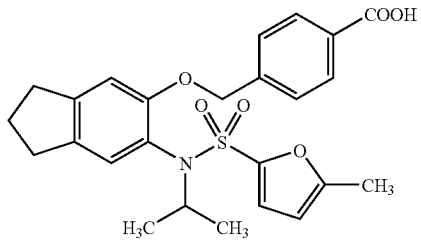

TLC: Rf 0.45 (chloroform:methanol=9:1);
NMR: δ 8.12 (d, J=8.4 Hz, 2H), 7.57 (d, J=8.4 Hz, 2H), 6.90 (s, 1H), 6.83 (s, 1H), 6.81 (d, J=3.3 Hz, 1H), 6.02 (m1H), 5.17-5.05 (m, 2H), 4.49 (m, 1H), 2.93-2.79 (m, 4H), 2.31 (s, 3H), 2.15-2.00 (m, 2H), 1.12 (d, J=6.6 Hz, 3H), 1.11 (d, J=6.6 Hz, 3H).

Example 2(29)

4-[7-[N-isobutyl-N-(5-methyl-2-furylsulfonyl)amino]-1,2,3,4-tetrahydronaphthalen-6-yloxymethyl]benzoic acid

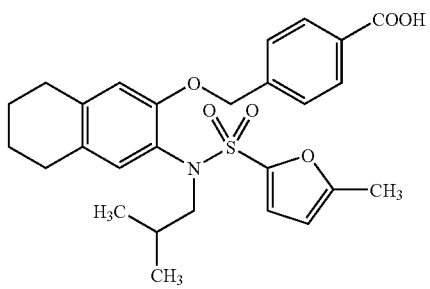

TLC: Rf 0.45 (chloroform:methanol=9:1);
NMR: δ 8.10 (d, J=8.1 Hz, 2H), 7.42 (d, J=8.1 Hz, 2H), 6.95 (s, 1H), 6.73 (d, J=3.3 Hz, 1H), 6.57 (s, 1H), 5.93 (m, 1H), 5.15-4.82 (br, 2H), 3.48 (d, J=7.2 Hz, 2H), 2.77-2.60 (m, 4H), 2.13 (s, 3H), 1.82-1.60 (m, 5H), 0.92 (d, J=6.6 Hz, 6H).

Example 2(30)

4-[7-[N-isopropyl-N-(5-methyl-2-furylsulfonyl)amino]-1,2,3,4-tetrahydronaphthalen-6-yloxymethyl]benzoic acid

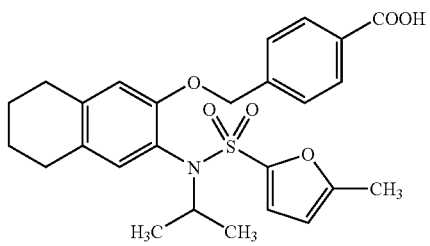

TLC: Rf 0.45 (chloroform:methanol=9:1);
NMR: δ 8.12 (d, J=8.4 Hz, 2H), 7.56 (d, J=8.4 Hz, 2H), 6.80 (d, J=3.3 Hz, 1H), 6.74 (s, 1H), 6.64 (s, 1H), 6.02 (m, 1H), 5.16-5.04 (m, 2H), 4.48 (m, 1H), 2.77-2.58 (m, 4H), 2.30 (s, 3H), 1.82-1.69 (m, 4H), 1.12 (d, J=6.6 Hz, 3H), 1.11 (d, J=6.6 Hz, 3H).

Example 2(31)

3-methyl-4-[2-[N-isobutyl-N-(5-methyl-2-furylsulfonyl)amino]-4-methyl-5-chlorophenoxymethyl]cinnamic acid

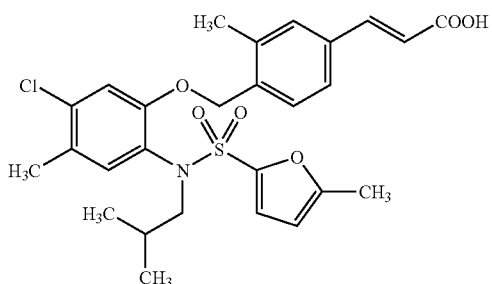

TLC: Rf 0.30 (chloroform:methanol=9:1);

NMR(CD$_3$OD): δ 7.65 (d, J=15.9 Hz, 1H), 7.46 (s) and 7.44 (d, J=7.8 Hz) total 2H, 7.34 (d, J=7.8 Hz, 1H), 7.18 (s, 1H), 7.14 (s, 1H), 6.71 (d, J=3.3 Hz, 1H), 6.50 (d, J=15.9 Hz, 1H), 6.07 (dd, J=3.3, 0.9 Hz, 1H), 4.95 (m, 2H), 3.44 (d, J=7.5 Hz, 2H), 2.35 (s, 3H), 2.28 (s, 3H), 2.09 (s, 3H), 1.61 (m, 1H), 0.87 (d, J=6.6 Hz, 6H).

Example 2(32)

4-[6-[N-isobutyl-N-(5-methyl-2-furylsulfonyl)amino]indan-5-yloxymethyl]cinnamic acid

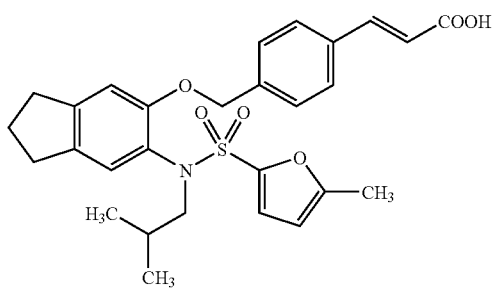

TLC: Rf 0.42 (chloroform methanol=9:1);

NMR: δ 7.79 (d, J=15.9 Hz, 1H), 7.55 (d, J=8.1 Hz, 2H), 7.37 (d, J=8.1 Hz, 2H), 7.11 (s, 1H), 6.78 (s, 1H), 6.71 (d, J=3.3 Hz, 1H), 6.47 (d, J=15.9 Hz, 1H), 5.93 (m, 1H), 5.10-4.80 (br, 2M), 3.60-3.40 (br, 2H), 2.86 (t, J=7.5 Hz, 4H), 2.14 (s, 3H), 2.08 (m, 2H), 1.68 (m, 1H), 1.00-0.82 (br, 6H).

Example 2(33)

3-methyl-4-[6-[N-isobutyl-N-(5-methyl-2-furylsulfonyl)amino]indan-5-yloxymethyl]benzoic acid

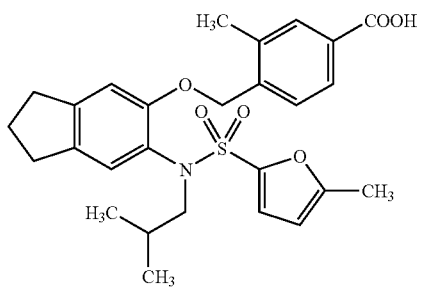

TLC: Rf 0.33 (chloroform:methanol=10:1);

NMR(CDCl$_3$+1 drop of CD$_3$OD): δ 7.89 (d, J=8.4 Hz, 1H), 7.88 (s, 1H), 7.39 (d, J=8.4 Hz, 1H), 7.12 (s, 1H), 6.79 (s, 1H), 6.71 (d, J=3.3 Hz, 1H), 5.94 (m, 1H), 5.06-4.74 (m, 2H), 3.60-3.37 (m, 2H), 2.92-2.82 (m, 4H), 2.34 (s, 3H), 2.17-2.03 (m, 2H), 2.10 (s, 3H), 1.69 (m, 1H), 1.01-0.80 (m, 6H).

Example 2(34)

3-methyl-4-[6-[N-isobutyl-N-(5-methyl-2-furylsulfonyl)amino]indan-5-yloxymethyl]cinnamic acid

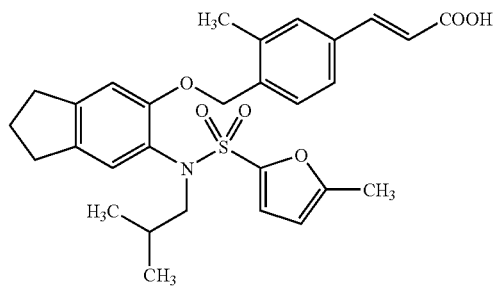

TLC: Rf 0.30 (chloroform:methanol=10:1);

NMR: δ 7.78 (d, J=15.9 Hz, 1H), 7.42-7.36 (m, 3H), 7.10 (s, 1H), 6.80 (s, 1H), 6.72 (d, J=3.3 Hz, 1H), 6.46 (d, J=15.9 Hz, 1H), 5.94 (m, 1H), 5.04-4.77 (m, 2H), 3.59-3.37 (m, 2H), 2.91-2.82 (m, 4H), 2.34 (s, 3H), 2.14-2.05 (m, 2H), 2.12 (s, 3H), 1.68 (m, 1H), 1.00-0.82 (m, 6H).

Example 2(35)

4-[2-[N-(2-methyl-2-propenyl)-N-(5-methyl-2-furylsulfonyl)amino]-4,5-dimethylphenoxymethyl]benzoic acid

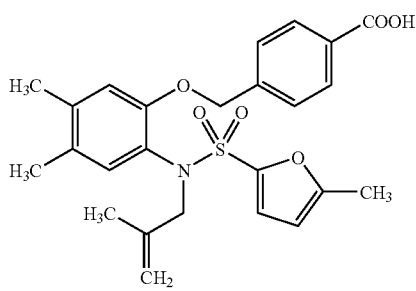

TLC: Rf 0.42 (chloroform:methanol=10:1);

NMR: δ 8.11 (d, J=8.1 Hz, 2H), 7.42 (d, J=8.1 Hz, 2H), 7.02 (s, 1H), 6.74 (d, J=3.3 Hz, 1H), 6.67 (s, 1H), 6.00-5.95 (m, 1H), 5.00 (brs, 2H), 4.77 (s, 2H), 4.26 (brs, 2H), 2.21 (s, 3H), 2.17 (s, 3H), 2.13 (s, 3H), 1.78 (s, 3H).

Example 2(36)

4-[2-[N-isopropyl-N-(2-thiazolylsulfonyl)amino]-5-trifluoromethylphenoxymethyl]benzoic acid

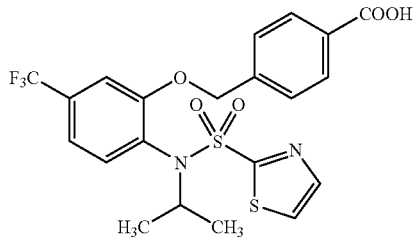

TLC: Rf 0.58 (ethyl acetate);

NMR(CD$_3$OD): δ 8.03 (d, J=8.7 Hz, 2H), 7.92 (d, J=3.3 Hz, 1H), 7.82 (d, J=3.3 Hz, 1H), 7.54 (d, J=8.4 Hz, 2H), 7.43 (brs, 1H), 7.37 (d, J=8.1 Hz, 1H), 7.30 (brd, J=8.1 Hz, 1H), 5.23 (ABd, J=12.6 Hz) and 5.14 (ABd, J=12.6 Hz) total 2H, 4.64 (sept, J=6.9 Hz, 1H), 1.15 (d, J=6.9 Hz) and 1.14 (d, J=6.9 Hz) total 6H.

Example 2(37)

4-[2-[N-isobutyl-N-(2-thiazolylsulfonyl)amino]-5-trifluoromethylphenoxymethyl]benzoic acid

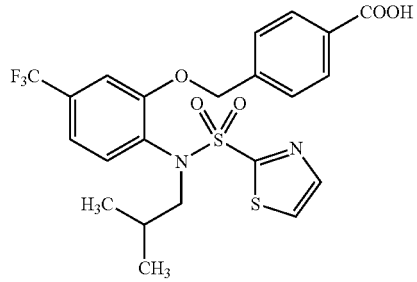

TLC: Rf 0.60 (ethyl acetate);
NMR(CD$_3$OD): δ 8.02 (d, J=8.7 Hz, 2H), 7.74 (m, 2H), 7.52 (d, J=7.2 Hz, 1H), 7.38 (d, J=8.7 Hz) and 7.37 (s) total 3H, 7.32 (brd, J=7.2 Hz, 1H), 5.02 (br, 2H), 3.60 (brd, J=7.5 Hz, 2H), 1.70-1.58 (m, 1H), 0.92 (d, J=6.9 Hz, 6H).

Example 2(38)

4-[2-[N-isopropyl-N-(2-thiazolylsulfonyl)amino]-5-trifluoromethylphenoxymethyl]cinnamic acid

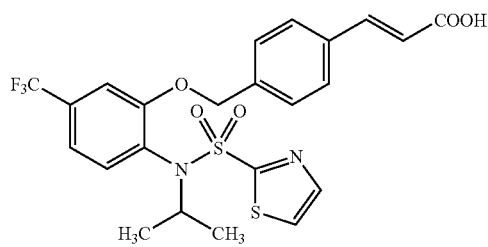

TLC: Rf 0.42 (chloroform:methanol=9:1);
NMR(CD$_3$OD): δ 7.91 (d, J=3 Hz, 1H), 7.81 (d, J=3 Hz, 1H), 7.69 (d, J=15.9 Hz, 1H), 7.63 (d, J=8.4 Hz, 2H), 7.48 (d, J=8.4 Hz, 2H), 7.42 (s, 1H), 7.36 (d, J=8.1 Hz, 1H), 7.29 (brd, J=8.1 Hz, 1H), 6.52 (d, J=15.9 Hz, 1H), 5.18 (ABd, J=12.3 Hz) and 5.09 (ABd, J=12.3 Hz) total 2H, 4.63 (sept, J=6.6 Hz, 1H), 1.15 (d, J=6.6 Hz) and 1.13 (d, J=6.6 Hz) total 6H.

Example 2(39)

4-[2-[N-isobutyl-N-(2-thiazolylsulfonyl)amino]-5-trifluoromethylphenoxymethyl]cinnamic acid

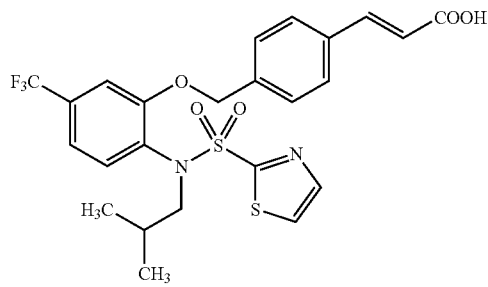

TLC: Rf 0.42 (chloroform:methanol=9:1);
NMR(CD$_3$OD): δ 7.76-7.70 (m, 2H), 7.64 (s) and 7.63 (d, J=15.9 Hz) total 3H, 7.52 (d, J=8.1 Hz, 1H), 7.38-7.28 (m, 4H), 6.53 (d, J=15.9 Hz, 1H), 5.04-4.90 (m, 2H), 3.60 (brd, J=6.9 Hz, 2H), 1.72-1.56 (m, 1H), 0.92 (d, J=6.6 Hz, 6H).

Example 2(40)

4-[2-[N-isobutyl-N-(4-methyl-2-thiazolylsulfonyl)amino]-5-trifluoromethylphenoxymethyl]benzoic acid

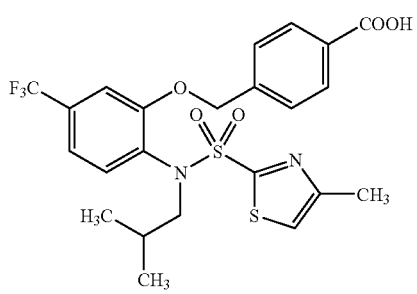

TLC: Rf 0.42 (chloroform:methanol=9:1);
NMR(CD$_3$OD): δ 8.03 (d, J=8.4 Hz, 2H), 7.53 (d, J=8.1 Hz, 1H), 7.42-7.30 (m) and 7.27 (s) total 5H, 5.18-4.90 (m, 2H), 3.63-3.58 (m, 2H), 2.23 (d, J=0.9 Hz, 3H), 1.66 (m, 1H), 0.93 (d, J=6.6 Hz, 6H).

Example 2(41)

4-[2-[N-isobutyl-N-(4-methyl-2-thiazolylsulfonyl)amino]-5-trifluoromethylphenoxymethyl]cinnamic acid

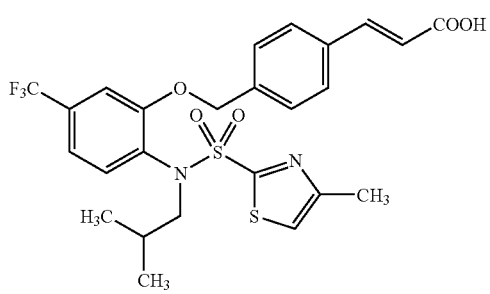

TLC: Rf 0.32 (chloroform:methanol=9:1);
NMR(DMSO-d$_6$): δ 7.70 (d, J=8.1 Hz, 2H), 7.60 (d, J=15.9 Hz, 1H), 7.56-7.46 (m, 3H), 7.38 (d, J=8.7 Hz, 1H), 7.29 (d, J=8.1 Hz, 2H), 6.56 (d, J=15.9 Hz, 1H), 5.20-4.85 (m, 2H), 3.49 (d, J=6.9 Hz, 2H), 2.21 (s, 3H), 1.53 (m, 1H), 0.84 (d, J=6.6 Hz, 6H).

Example 2(42)

4-[2-[N-isopropyl-N-(2-thiazolylsulfonyl)amino]-4-chloro-5-methylphenoxymethyl]benzoic acid

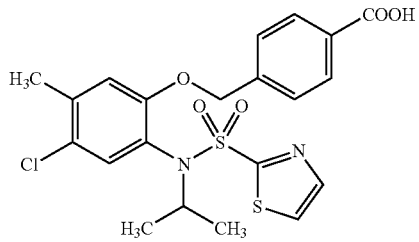

TLC: Rf 0.39 (chloroform:methanol=9:1);

NMR: δ 8.13 (d, J=8.1 Hz, 2H), 7.91 (d, J=3.0 Hz, 1H), 7.52 (d, J=8.1 Hz, 2H), 7.50 (d, J=3.0 Hz, 1H), 7.10 (s, 1H), 6.85 (s, 1H), 5.09 (s, 2H), 4.67 (m, 1H), 2.36 (s, 3H), 1.16 (d, J=6.6 Hz, 3H), 1.15 (d, J=6.6 Hz, 3H).

Example 2(43)

4-[2-[N-isopropyl-N-(4-methyl-2-thiazolylsulfonyl)amino]-4-chloro-5-methylphenoxymethyl]benzoic acid

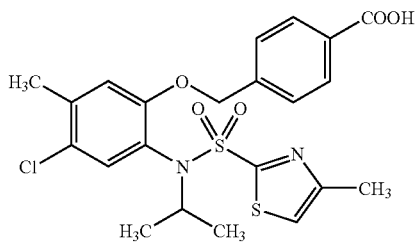

TLC: Rf 0.39 (chloroform:methanol=10:1);
NMR: δ 8.13 (d, J=8.1 Hz, 2H), 7.52 (d, J=8.1 Hz, 2H), 7.09 (s, 1H), 7.04 (m, 1H), 6.85 (s, 1H), 5.10 (s, 2H), 4.68 (m, 1H), 2.49 (d, J=0.6 Hz, 3H), 2.36 (s, 3H), 1.15 (d, J=6.6 Hz, 3H), 1.14 (d, J=6.6 Hz, 3H).

Example 2(44)

4-[2-[N-isobutyl-N-(4-methyl-2-thiazolylsulfonyl)amino]-4-chloro-5-methylphenoxymethyl]benzoic acid

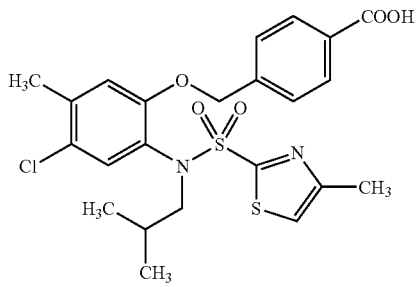

TLC: Rf 0.40 (chloroform:methanol=10:1);
NMR: δ 8.12 (d, J=7.5 Hz, 2H), 7.37 (d, J=7.5 Hz, 2H), 7.27 (d, J=1.2 Hz, 1H), 6.96 (m, 1H), 6.78 (s, 1H), 5.10-4.78 (m, 2H), 3.57 (brs, 2H), 2.35 (s, 3H), 2.34 (s, 3H), 1.70 (m, 1H), 0.94 (d, J=6.6 Hz, 6H).

Example 2(45)

3-chloro-4-[2-[N-isopropyl-N-(4-methyl-2-thiazolylsulfonyl)amino]-4-chloro-5-methylphenoxymethyl]benzoic acid

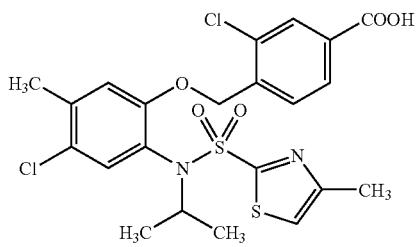

TLC: Rf 0.69 (chloroform:methanol:water=8:2:0.2);
NMR: δ 8.12 (d, J=1.5 Hz, 1H), 8.06 (dd, J=8.1, 1.5 Hz, 1H), 7.83 (d, J=8.1 Hz, 1H), 7.11-7.10 (m, 2H), 6.86 (s, 1H), 5.23 (d, J=14.4 Hz, 1H), 5.15 (d, J=14.4 Hz, 1H), 4.71 (quint, J=6.6 Hz, 1H), 2.52 (d, J=1.2 Hz, 3H), 2.38 (s, 3H), 1.56 (d, J=6.6 Hz, 3H), 1.34 (d, J=6.6 Hz, 3H).

Example 2(46)

3-methyl-4-[2-[N-isobutyl-N-(4-methyl-2-thiazolylsulfonyl)amino]-5-trifluoromethylphenoxymethyl]benzoic acid

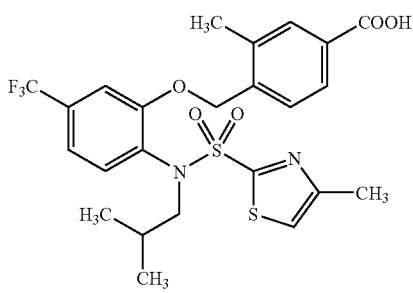

TLC: Rf 0.44 (chloroform:methanol=9:1);
NMR: δ 7.96 (d, J=8.4 Hz, 1H), 7.95 (s, 1H), 7.48 (d, J=8.1 Hz, 1H), 7.35 (d, J=8.4 Hz, 1H), 7.32-7.24 (m, 1H), 7.20 (s, 1H), 6.98 (s, 1H), 5.06-4.85 (m, 2H), 3.70-3.50 (m, 2H), 2.39 (s, 3H), 2.34 (s, 3H), 1.75-1.59 (m, 1H), 0.91 (d, J=6.6 Hz, 6H).

Example 2(47)

3-methyl-4-[2-[N-isobutyl-N-(4-methyl-2-thiazolylsulfonyl)amino]-4-chloro-5-methylphenoxymethyl]benzoic acid

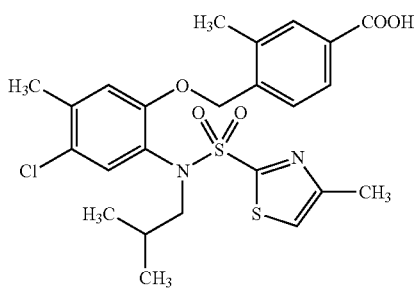

TLC: Rf 0.44 (chloroform:methanol=9:1);
NMR(DMSO-$d_6$): δ 7.79 (s, 1H), 7.76 (d, J=8.1 Hz, 1H), 7.56 (s, 1H), 7.29 (s, 1H), 7.27 (d, J=8.1 Hz, 1H), 7.23 (s, 1H), 5.20-4.65 (m, 2H), 3.55-3.35 (m, 2H), 2.36 (s, 3H), 2.31 (s, 3H), 2.21 (s, 3H), 1.65-1.47 (m, 1H), 0.84 (d, J=6.6 Hz, 6H).

Example 2(48)

3-methoxy-4-[2-[N-isobutyl-N-(4-methyl-2-thiaz-olylsulfonyl)amino]-4-chloro-5-methylphenoxym-ethyl]benzoic acid

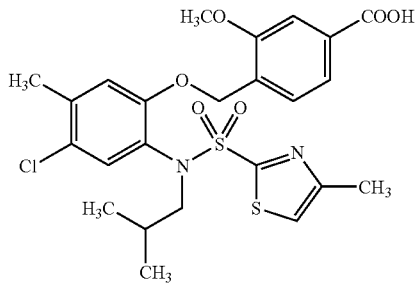

TLC: Rf 0.48 (chloroform:methanol=9:1);
NMR: δ 7.74 (dd, J=7.8, 1.2 Hz, 1H), 7.59 (d, J=1.2 Hz, 1H), 7.31 (d, J=7.8 Hz, 1H), 7.30 (s, 1H), 6.94 (s, 1H), 6.81 (s, 1H), 5.10-4.70 (m, 2H), 3.94 (s, 3H), 3.59 (br, 2H), 2.35 (s, 3H), 2.34 (s, 3H), 1.80-1.60 (m, 1H), 1.12 (d, J=6.9 Hz, 6H).

Example 2(49)

3-methoxy-4-[2-[N-isobutyl-N-(4-methyl-2-thiaz-olylsulfonyl)amino]-5-trifluoromethylphenoxym-ethyl]benzoic acid

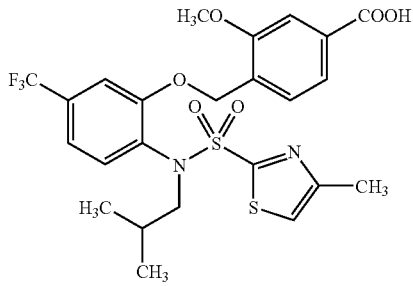

TLC: Rf 0.40 (chloroform:methanol=9:1);
NMR: δ 7.73 (dd, J=8.1, 1.5 Hz, 1H), 7.60 (d, J=1.5 Hz, 1H), 7.50 (d, J=8.1 Hz, 1H), 7.34-7.19 (m, 3H), 6.95 (m, 1H), 5.12-4.80 (m, 2H), 3.95 (s, 3H), 3.77-3.48 (m, 2H), 2.34 (s, 3H), 1.77-1.60 (m, 1H), 0.94 (d, J=6.6 Hz, 6H).

Example 2(50)

4-[2-[N-isobutyl-N-(4-methyl-2-thiazolylsulfonyl)amino]-4-methyl-5-chlorophenoxymethyl]benzoic acid

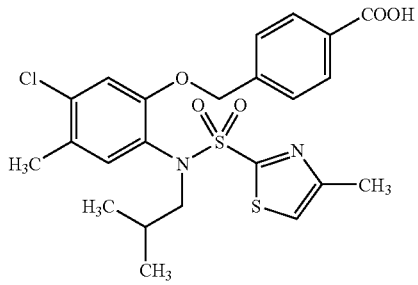

TLC: Rf 0.38 (chloroform:methanol=9:1);
NMR: δ 8.11 and 7.33 (each d, J=8.4 Hz, each 2H), 7.22 (s, 1H), 6.92 and 6.91 (each s, each 1H), 5.10-4.70 (m, 2H), 3.74-3.42 (m, 2H), 2.31 and 2.30 (each s, each 3H), 1.78-1.62 (m, 1H), 1.05-0.83 (m, 6H).

Example 2(51)

3-chloro-4-[2-[N-isobutyl-N-(4-methyl-2-thiazolyl-sulfonyl)amino]-4-methyl-5-chlorophenoxymethyl]benzoic acid

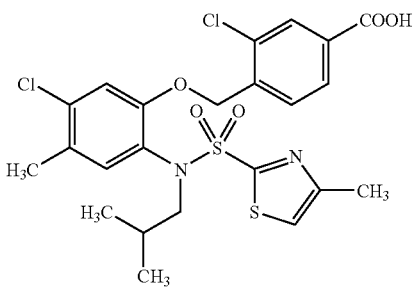

TLC: Rf 0.28 (chloroform:methanol=9:1);
NMR: δ 8.11 (s, 1H), 8.02 and 7.45 (each d, J=8.1 Hz, each 1H), 7.21 (s, 1H), 6.97 (s, 1H), 6.94 (s, 1H), 5.12-4.74 (m, 2H), 3.75-3.45 (m, 2H), 2.32 and 2.31 (each s, each 3H), 1.80-1.62 (m, 1H), 1.05-0.82 (m, 6H).

Example 2(52)

3-methoxy-4-[2-[N-isobutyl-N-(4-methyl-2-thiaz-olylsulfonyl)amino]-4-methyl-5-chlorophenoxym-ethyl]benzoic acid

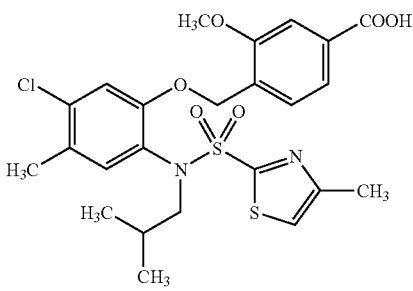

TLC: Rf 0.35 (chloroform:methanol=9:1);
NMR: δ 7.73 (d, J=7.8 Hz, 1H), 7.59 (s, 1H), 7.30-7.20 (m, 2H), 6.95 (s, 1H), 6.91 (s, 1H), 5.09-4.62 (m, 2H), 3.94 (s, 3H), 3.78-3.45 (m, 2H), 2.31 (s, 6H), 1.79-1.63 (m, 1H), 1.08-0.85 (m, 6H).

Example 2(53)

3-methyl-4-[2-[N-isobutyl-N-(4-methyl-2-thiazolyl-sulfonyl)amino]-4,5-dimethylphenoxymethyl]benzoic acid

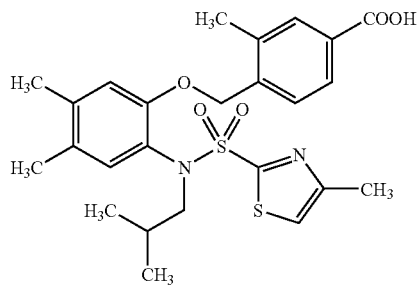

TLC: Rf 0.76 (chloroform:methanol:water=8:2:0.2);
NMR: δ 7.93 (d, J=8.1 Hz, 1H), 7.92 (s, 1H), 7.30 (d, J=8.1 Hz, 1H), 7.08 (s, 1H), 6.90 (d, J=0.9 Hz, 1H), 6.71 (s, 1H), 4.91 (br, 1H), 4.79 (br, 1H), 3.65 (br, 1H), 3.56 (br, 1H), 2.35 (s, 3H), 2.30 (d, J=0.9 Hz, 3H), 2.24 (s, 3H), 2.19 (s, 3H), 1.71 (sep, J=6.9 Hz, 1H), 1.03-0.92 (br, 6H).

Example 2(54)

3-methyl-4-[2-[N-isopropyl-N-(4-methyl-2-thiazolylsulfonyl)amino]-4,5-dimethylphenoxymethyl]benzoic acid

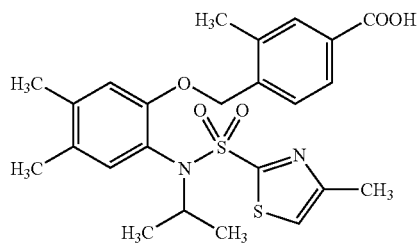

TLC: Rf 0.78 (chloroform:methanol:water=8:2:0.2);
NMR: δ 7.95 (d, J=8.1 Hz, 1H), 7.93 (s, 1H), 7.54 (d, J=8.1 Hz, 1H), 6.98 (d, J=0.9 Hz, 1H), 6.86 (s, 1H), 6.78 (s, 1H), 5.03 (d, J=13.2 Hz, 1H), 4.98 (d, J=13.2 Hz, 1H), 4.69 (quint, J=6.6 Hz, 1H), 2.46 (d, J=0.9 Hz, 3H), 2.39 (s, 3H), 2.25 (s, 3H), 2.16 (s, 3H), 1.17 (d, J=6.6 Hz, 3H), 1.13 (d, J=6.6 Hz, 3H).

Example 2(55)

3-methoxy-4-[2-[N-isobutyl-N-(4-methyl-2-thiazolylsulfonyl)amino]-4,5-dimethylphenoxymethyl]benzoic acid

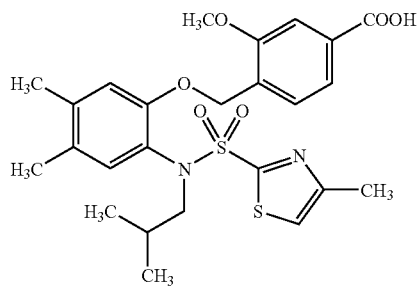

TLC: Rf 0.39 (chloroform:methanol=9:1);
NMR: δ 7.72 (dd, J=8.1, 1.2 Hz, 1H), 7.57 (d, J=1.2 Hz, 1H), 7.26 (d, J=8.1 Hz, 1H), 7.11 (s, 1H), 6.87 (s, 1H), 6.71 (s, 1H), 4.95 (br, 1H), 4.75 (br, 1H), 3.93 (s, 3H), 3.69 (br, 1H), 3.56 (br, 1H), 2.29 (s, 3H), 2.23 (s, 3H), 2.19 (s, 3H), 1.80-1.65 (m, 1H), 0.97 (br, 6H).

Example 2(56)

3-chloro-4-[2-[N-isobutyl-N-(4-methyl-2-thiazolyl-sulfonyl)amino]-4,5-dimethylphenoxymethyl]benzoic acid

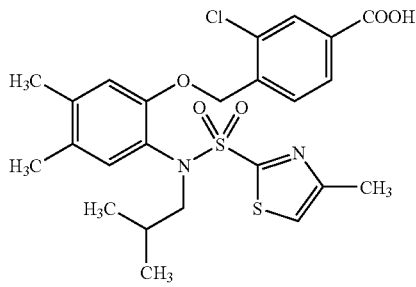

TLC: Rf 0.36 (chloroform:methanol=9:1);
NMR: δ 8.11 (d, J=1.8 Hz, 1H), 8.01 (dd, J=8.1, 1.8 Hz, 1H), 7.49 (d, J=8.1 Hz, 1H), 7.08 (s, 1H), 6.95 (d, J=0.6 Hz, 1H), 6.69 (s, 1H), 5.20-4.70 (br, 2H), 3.80-3.45 (br, 2H), 2.32 (d, J=0.6 Hz, 3H), 2.24 (s, 3H), 2.19 (s, 3H), 1.75 (m, 1H), 1.07-0.85 (br, 6H).

Example 2(57)

3-chloro-4-[2-[N-isopropyl-N-(4-methyl-2-thiazolyl-sulfonyl)amino]-4,5-dimethylphenoxymethyl]benzoic acid

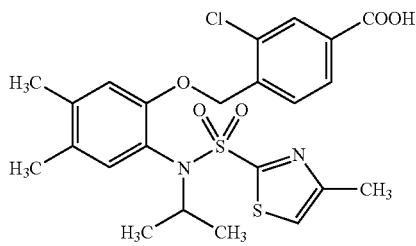

TLC: Rf 0.36 (chloroform:methanol=9:1);
NMR(CDCl$_3$+CD$_3$OD): δ 8.06 (d, J=1.8 Hz, 1H), 7.98 (dd, J=8.1, 1.8 Hz, 1H), 7.70 (d, J=8.1 Hz, 1H), 7.05 (d, J=0.6 Hz, 1H), 6.86 (s, 1H), 6.76 (s, 1H), 5.14 (d, J=14.1 Hz, 1H), 5.08 (d, J=14.1 Hz, 1H), 4.70 (m, 1H), 2.47 (d, J=0.6 Hz, 3H), 2.25 (s, 3H), 2.17 (s, 3H), 1.17 (d, J=6.6 Hz, 3H), 1.15 (d, J=6.6 Hz, 3H).

Example 2(58)

4-[2-[N-isopropyl-N-(4-methyl-2-thiazolylsulfonyl)amino]-4,5-dimethylphenoxymethyl]benzoic acid

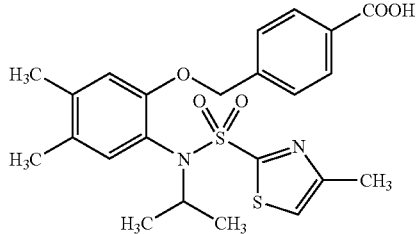

TLC: Rf 0.45 (chloroform:methanol=10:1);

NMR: δ 8.11-8.08 (m, 2H), 7.49 (d, J=8.4 Hz, 2H), 6.97 (d, J=0.9 Hz, 1H), 6.86 (s, 1H), 6.75 (s, 1H), 5.06 (d, J=12.9 Hz, 1H), 5.04 (d, J=12.9 Hz, 1H), 4.71 (m, 1H), 2.46 (d, J=0.9 Hz, 3H), 2.23 (s, 3H), 2.16 (s, 3H), 1.18 (d, J=6.6 Hz, 3H), 1.15 (d, J=6.6 Hz, 3H).

Example 2(59)

4-[2-[N-isobutyl-N-(4-methyl-2-thiazolylsulfonyl)amino]-4,5-dimethylphenoxymethyl]benzoic acid

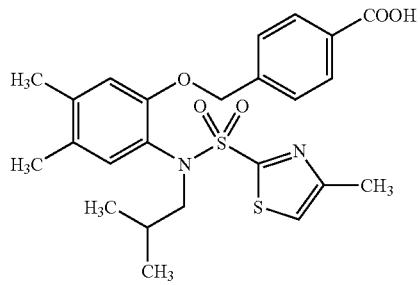

TLC: Rf 0.43 (chloroform:methanol=10:1);
NMR: δ 8.09 (d, J=8.1 Hz, 2H), 7.33 (d, J=8.1 Hz, 2H), 7.08 (s, 1H), 6.89 (d, J=0.9 Hz, 1H), 6.68 (s, 1H), 5.08-4.68 (m, 2H), 3.75-3.45 (m, 2H), 2.30 (s, 3H), 2.23 (s, 3H), 2.18 (s, 3H), 1.71 (m, 1H), 1.04-0.83 (m, 6H).

Example 2(60)

4-[2-[N-isobutyl-N-(4-methyl-2-thiazolylsulfonyl)amino]-4-chloro-5-methylphenoxymethyl]cinnamic acid

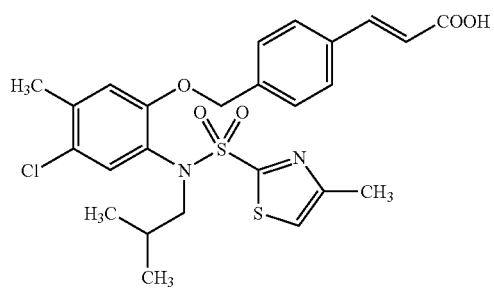

TLC: Rf 0.22 (chloroform:methanol=9:1);
NMR(CD$_3$OD): δ 7.69 (d, J=16.2 Hz, 1H), 7.61 (d, J=8.1 Hz, 2H), 7.32-7.24 (m) and 7.29 (d, J=8.1 Hz) total 4H, 7.05 (s, 1H), 6.52 (d, J=16.2 Hz, 1H), 5.05-4.70 (m, 2H, covered with H$_2$O in CD$_3$OD), 3.63-3.50 (m, 2H), 2.37 (s, 3H), 2.22 (d, J=0.9 Hz, 3H), 1.65 (m, 1H), 0.93 (d, J=6.3 Hz, 6H).

Example 2(61)

3-methyl-4-[2-[N-isobutyl-N-(4-methyl-2-thiazolylsulfonyl)amino]-5-trifluoromethylphenoxymethyl]cinnamic acid

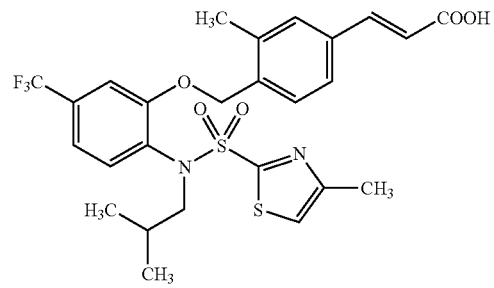

TLC: Rf 0.37 (chloroform:methanol=9:1);
NMR: δ 7.76 (d, J=16.2 Hz, 1H), 7.47 (d, J=7.8 Hz, 1H), 7.45-7.35 (m, 2H), 7.32-7.23 (m, 2H), 7.20 (m, 1H), 6.98 (s, 1H), 6.48 (d, J=16.2 Hz, 1H), 5.03-4.82 (m, 2H), 3.70-3.50 (m, 2H), 2.36 (s, 3H), 2.34 (s, 3H), 1.74-1.58 (m, 1H), 0.91 (d, J=6.9 Hz, 6H).

Example 2(62)

3-chloro-4-[2-[N-isobutyl-N-(4-methyl-2-thiazolylsulfonyl)amino]-5-trifluoromethylphenoxymethyl]cinnamic acid

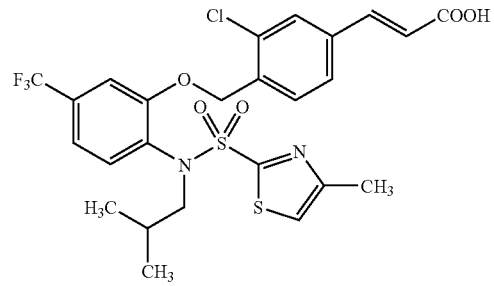

TLC: Rf 0.28 (n-hexane:ethyl acetate=1:2);
NMR: δ 7.71 (d, J=16.2 Hz, 1H), 7.58 (s, 1H), 7.52-7.44 (m, 3H), 7.29 (d, J=8.1 Hz, 1H) 7.19 (s, 1H), 7.01 (d, J=0.9 Hz, 1H), 6.50 (d, J=16.2 Hz, 1H), 5.02 (br, 2H), 3.62 (d, J=6.6 Hz, 2H), 2.35 (s, 3H), 1.68 (sep, J=6.6 Hz, 1H), 0.93 (d, J=6.6 Hz, 6H).

Example 2(63)

3-methyl-4-[2-[N-isopropyl-N-(4-methyl-2-thiazolylsulfonyl)amino]-4,5-dimethylphenoxymethyl]cinnamic acid

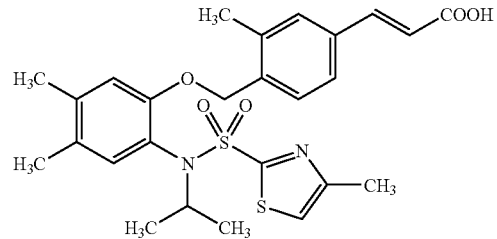

TLC: Rf 0.20 (n-hexane:ethyl acetate=1:2);
MS (FAB, Pos.): 515(M+H)$^+$.

Example 2(64)

3-methyl-4-[2-[N-isobutyl-1-(4-methyl-2-thiazolyl-sulfonyl)amino]-4,5-dimethylphenoxymethyl]cinnamic acid

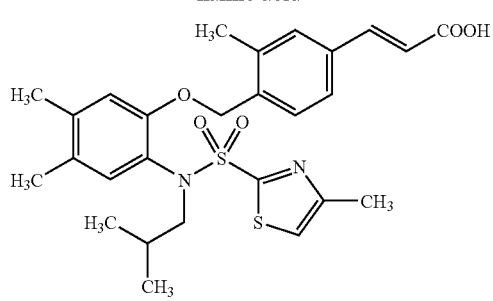

TLC: Rf 0.22 (n-hexane:ethyl acetate=1:2);
MS (FAB, Pos.): 529(M+H)+.

Example 2(65)

4-[2-[N-isobutyl-N-(4-methyl-2-thiazolylsulfonyl)amino]-4-methyl-5-chlorophenoxymethyl]cinnamic acid

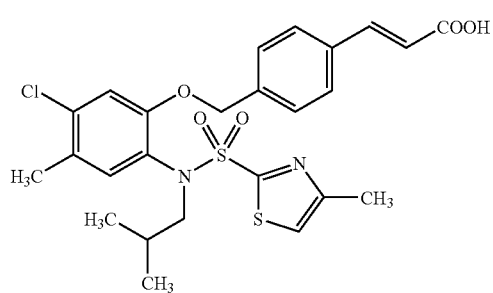

TLC: Rf 0.31 (chloroform:methanol=9:1);
NMR: δ 7.79 (d, J=15.9 Hz, 1H), 7.56 and 7.27 (each d, J=8.1 Hz, each 2H), 7.21 (s, 1H), 6.95-6.88 (m, 2H), 6.48 (d, J=15.9 Hz, 1H), 5.00-4.65 (m, 2H), 3.72-3.42 (m, 2H), 2.33-2.22 (m, 6H), 1.78-1.60 (m, 1H), 1.05-0.83 (m, 6H).

Example 2(66)

3-methyl-4-[2-[N-isobutyl-N-(4-methyl-2-thiazolyl-sulfonyl)amino]-4-methyl-5-chlorophenoxymethyl]cinnamic acid

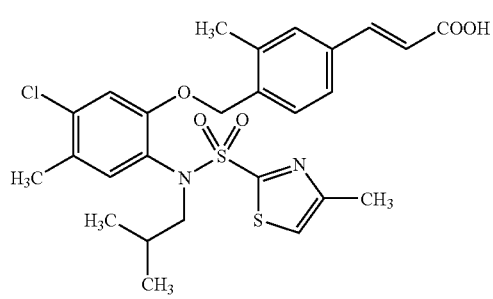

TLC: Rf 0.30 (chloroform:methanol=9:1);
NMR: δ 7.76 (d, J=16.2 Hz, 1H), 7.42-7.37 (m, 2H), 7.30-7.15 (m, 2H), 6.98-6.89 (m, 2H), 6.47 (d, J=16.2 Hz, 1H), 4.95-4.67 (m, 2H), 3.72-3.40 (m, 2H), 2.38-2.22 (m, 9H), 1.77-1.61 (m, 1H), 1.05-0.82 (m, 6H).

Example 2(67)

3-methyl-4-[2-[N-isobutyl-N-(4-methyl-2-thiazolyl-sulfonyl)amino]-4-chloro-5-methylphenoxymethyl]cinnamic acid

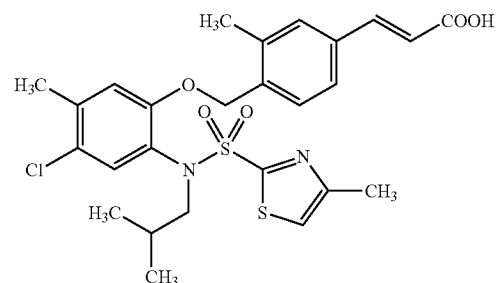

TLC: Rf 0.41 (chloroform:methanol=9:1);
NMR: δ 7.76 (d, J=16.2 Hz, 1H), 7.39 (d, J=8.4 Hz, 1H), 7.38 (s, 1H), 7.27 (d, J=8.4 Hz, 1H), 7.23 (s, 1H), 6.97 (s, 1H), 6.81 (s, 1H), 6.47 (d, J=16.2 Hz, 1H), 5.04-4.66 (m, 2H), 3.65-3.39 (m, 2H), 2.36 (s, 3H), 2.35 (s, 3H), 2.33 (s, 3H), 1.75-1.61 (m, 1H), 0.92 (d, J=6.6 Hz, 6H).

Example 2(68)

4-[2-[N-isobutyl-N-(4-methyl-2-thiazolylsulfonyl)amino]-4,5-dimethylphenoxymethyl]cinnamic acid

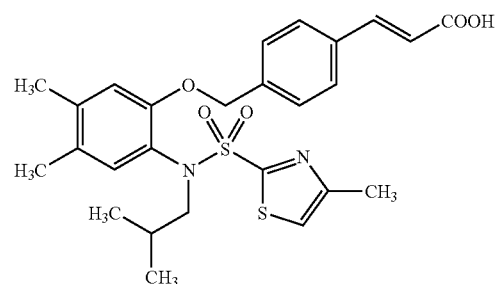

TLC: Rf 0.33 (chloroform:methanol=10:1);
MS (APCI, Neg. 20V): 513 (M−H)−.

Example 2(69)

3-chloro-4-[2-[N-isobutyl-N-(4-methyl-2-thiazolylsulfonyl)amino]-4,5-dimethylphenoxymethyl]cinnamic acid

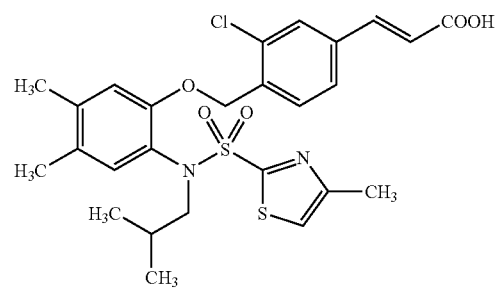

TLC: Rf 0.17 (chloroform:methanol=9:1);
NMR(CD3OD): δ 7.69 (d, J=1.8 Hz, 1H), 7.65 (d, J=15.9 Hz, 1H), 7.59 (dd, J=8.1, 1.5 Hz, 1H), 7.35 (d, J=8.1 Hz, 1H), 7.29 (d, J=1.2 Hz, 1H), 7.04 (s, 1H), 6.88 (s, 1H), 6.57 (d, J=15.9 Hz, 1H), 5.10-4.60 (m, 2H), 3.63-3.50 (m, 2H), 2.28 (s, 3H), 2.21 (d, J=1.2 Hz) and 2.20 (s) total 6H, 1.66 (m, 1H), 1.03-0.85 (m, 6H).

Example 2(70)

3-methoxy-4-[2-[N-isobutyl-N-(4-methyl-2-thiazolylsulfonyl)amino]-4,5-dimethylphenoxymethyl]cinnamic acid

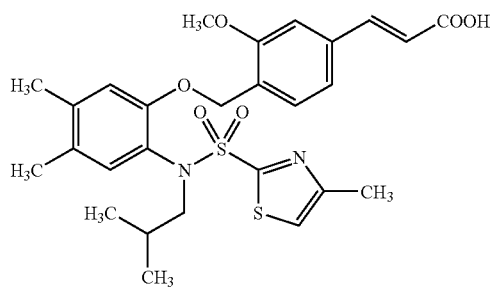

TLC: Rf 0.40 (dichloromethane:methanol=10:1);
MS (FAB, Pos.): 545 (M+H)+.

Example 2(71)

4-[6-[N-isobutyl-N-(4-methyl-2-thiazolylsulfonyl)amino]indan-5-yloxymethyl]benzoic acid

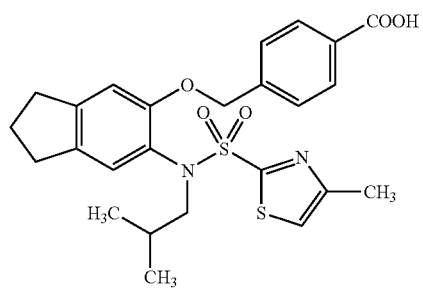

TLC: Rf 0.43 (chloroform:methanol=9:1);
NMR: 8.10 (d, J=8.4 Hz, 2H), 7.34 (d, J=8.4 Hz, 2H), 7.16 (s, 1H), 6.89 (d, J=0.9 Hz, 1H), 6.76 (s, 1H), 5.06-4.70 (br, 2H), 3.78-3.45 (br, 2H), 2.87 (t, J=7.5 Hz, 4H), 2.31 (d, J=0.9 Hz, 3H), 2.09 (m, 2H), 1.74 (m, 1H), 1.04-0.86 (br, 6H).

Example 2(72)

4-[6-[N-isobutyl-N-(4-methyl-2-thiazolylsulfonyl)amino]indan-5-yloxymethyl]cinnamic acid

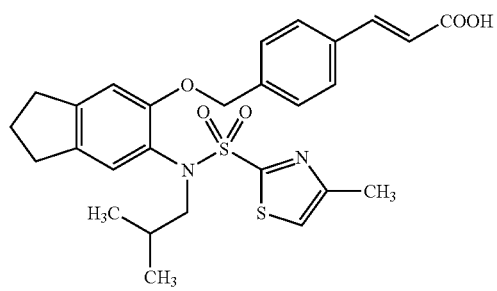

TLC: Rf 0.42 (chloroform:methanol=9:1);

NMR: δ 7.79 (d, J=15.9 Hz, 1H), 7.55 (d, J=8.1 Hz, 2H), 7.28 (d, J=8.1 Hz, 2H), 7.15 (s, 1H), 6.89 (d, J=0.9 Hz, 1H), 6.77 (s, 1H), 6.47 (d, J=15.9 Hz, 1H), 5.05-4.60 (br, 2H), 3.78-3.45 (br, 2H), 2.86 (t, J=7.8 Hz, 4H), 2.30 (d, J=0.9 Hz, 3H), 2.08 (m, 2H), 1.73 (m, 1H), 1.06-0.83 (br, 6H).

Example 2(73)

3-methyl-4-[6-[N-isobutyl-N-(4-methyl-2-thiazolylsulfonyl)amino]indan-5-yloxymethyl]benzoic acid

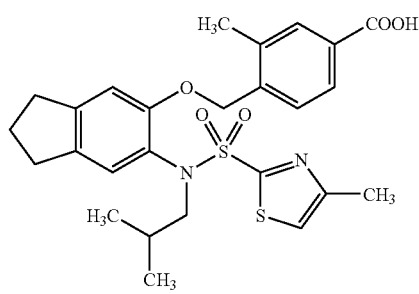

TLC: Rf 0.34 (dichloromethane:methanol=19:1);
NMR: δ 7.95-7.92 (m, 2H), 7.31 (d, J=7.8 Hz, 1H), 7.16 (s, 1H), 6.91 (brs, 1H), 6.79 (s, 1H), 4.93 (brs, 1H), 4.73 (brs, 1H), 3.75-3.45 (m, 2H), 2.92-2.84 (m, 4H), 2.34 (s, 3H), 2.31 (d, J=0.6 Hz, 3H), 2.10 (m, 2H), 1.74 (m, 1H), 1.08-0.80 (brs, 6H).

Example 2(74)

3-methyl-4-[6-[N-isobutyl-N-(4-methyl-2-thiazolylsulfonyl)amino]indan-5-yloxymethyl]cinnamic acid

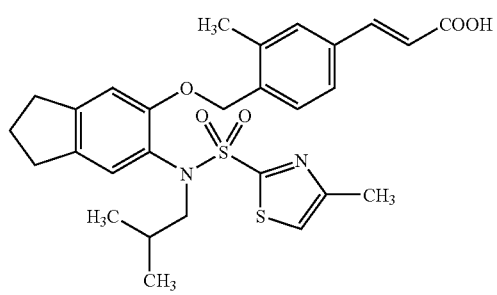

TLC: Rf 0.32 (dichloromethane:methanol=19:1);
NMR: δ 7.76 (d, J=15.9 Hz, 1H), 7.40-7.36 (m, 2H), 7.25 (m, 1H), 7.14 (s, 1H), 6.91 (brs, 1H), 6.80 (s, 1H), 6.46 (d, J=15.9 Hz, 1H), 4.90 (brs, 1H), 4.69 (brs, 1H), 3.75-3.43 (m, 2H), 2.95-2.80 (m, 4H), 2.31 (s, 6H), 2.09 (m, 2H), 1.72 (m, 1H), 1.05-0.85 (brs, 6H).

Example 2(75)

4-[2-[N-isobutyl-N-(2-pyridylsulfonyl)amino]-5-trifluoromethylphenoxymethyl]cinnamic acid

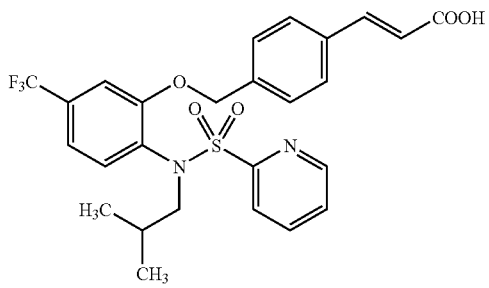

TLC: Rf 0.37 (chloroform:methanol=9:1);
NMR(CD$_3$OD): δ 8.39 (ddd, J=4.5, 1.5, 0.9 Hz, 1H), 7.82 (dt, J=7.5, 1.5 Hz, 1H), 7.72-7.64 (m, 2H), 7.60 (d, J=8.1 Hz, 2H), 7.53 (d, J=7.5 Hz, 1H), 7.38 (ddd, J=7.5, 4.5, 0.9 Hz, 1H), 7.34-7.22 (m, 4H), 6.54 (d, J=15.9 Hz, 1H), 4.95-4.78 (m, 2H), 3.61 (d, J=6.6 Hz, 2H), 1.60 (m, 1H), 0.91 (d, J=6.9 Hz, 6H).

Example 2(76)

4-[2-[N-isobutyl-N-(3-pyridylsulfonyl)amino]-5-trifluoromethylphenoxymethyl]benzoic acid

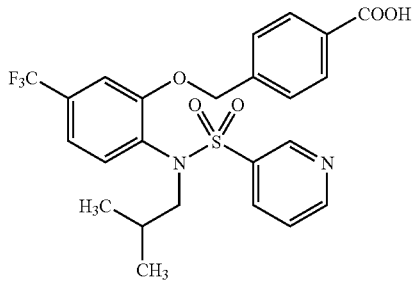

TLC: Rf 0.27 (chloroform:methanol=9:1);
NMR(CD$_3$OD): δ 8.63 (m, 1H), 8.53 (dd, J=5.1, 1.8 Hz, 1H), 7.99 (d, J=8.4 Hz) and 7.94 (m) total 3H, 7.56 (d, J=7.5 Hz, 1H), 7.40-7.29 (m, 3H), 7.23 (d, J=8.4 Hz, 2H), 5.10-4.80 (m, 2H), 3.58-3.40 (m, 2H), 1.61 (m, 1H), 0.92 (brd, J=6 Hz, 6H).

Example 2(77)

3-chloro-4-[2-[N-isopropyl-N-(2-pyridylsulfonyl)amino]-4-chloro-5-methylphenoxymethyl]benzoic acid

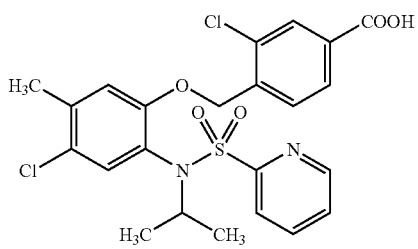

TLC: Rf 0.43 (chloroform:methanol=9:1);
NMR(CD$_3$OD): δ 8.63 (m, 1H), 8.02 (d, J=1.8 Hz, 1H), 7.98-7.84 (m, 3H), 7.70 (d, J=8.1 Hz, 1H), 7.50 (m, 1H), 7.11 (s, 1H), 7.09 (s, 1H), 5.16 (ABd, J=13.5 Hz) and 5.08 (ABd, J=13.5 Hz) total 2H, 4.61 (sept, J=6.6 Hz, 1H), 2.39 (3, 3H), 1.12 (d, J=6.6 Hz) and 1.10 (d, J=6.6 Hz) total 6H.

Example 2(78)

3-methyl-4-[2-[N-isobutyl-N-(2-pyridylsulfonyl)amino]-4-chloro-5-methylphenoxymethyl]benzoic acid

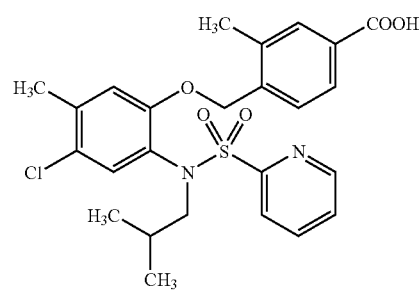

TLC: Rf 0.37 (chloroform:methanol=10:1);
NMR: δ 8.52 (m, 1H), 7.94-7.92 (m, 2H), 7.77-7.68 (m, 2H), 7.31-7.24 (m, 3H), 6.76 (s, 1H), 4.83 (brs, 2H), 3.65-3.50 (m, 2H), 2.34 (s, 6H), 1.66 (m, 1H), 0.91 (d, J=6.6 Hz, 6H).

Example 2(79)

3-methyl-4-[2-[N-isobutyl-N-(3-pyridylsulfonyl)amino]-4-chloro-5-methylphenoxymethyl]benzoic acid

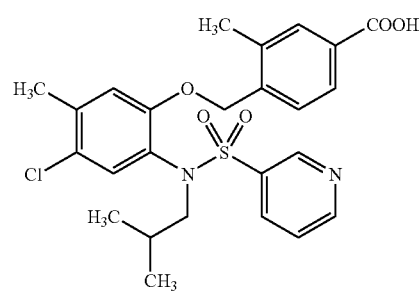

TLC: Rf 0.16 (dichloromethane:methanol=20:1);
NMR: δ 12.90 (s, 1H), 8.67 (d, J=1.8 Hz, 1H), 8.62 (dd, J=4.8, 1.8 Hz, 1H), 7.94 (dt, J=8.1, 1.8 Hz, 1H), 7.74 (s, 1H), 7.68 (d, J=8.1 Hz, 1H), 7.37 (dd, J=8.1, 4.8 Hz, 1H), 7.27 (s, 1H), 7.24 (s, 1H), 7.01 (d, J=8.1 Hz, 1H), 4.95 (br, 1H), 4.76 (br, 1H), 3.45-3.30 (m, 2H), 2.34 (s, 3H), 2.24 (s, 3H), 1.49 (sept, J=6.6 Hz, 1H), 0.90-0.70 (br, 6H).

Example 2(80)

3-methyl-4-[2-[N-isobutyl-N-(2-pyridylsulfonyl)amino]-4-methyl-5-chlorophenoxymethyl]benzoic acid

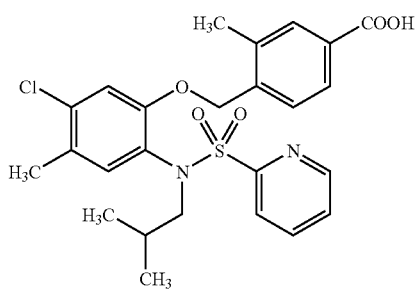

TLC: Rf 0.40 (chloroform:methanol=9:1);
NMR: δ 8.50-8.40 (m, 1H), 7.95-7.85 (m, 2H), 7.75-7.60 (m, 2H), 7.30-7.20 (m, 3H), 6.89 (s, 1H), 4.76 (br, 2H), 3.61 (br, 2H), 2.31 (s, 3H), 2.29 (s, 3H), 1.75-1.55 (m, 1H), 1.00-0.80 (m, 6H).

Example 2(81)

4-[2-[N-isobutyl-N-(3-pyridylsulfonyl)amino]-4-methyl-5-chlorophenoxymethyl]benzoic acid

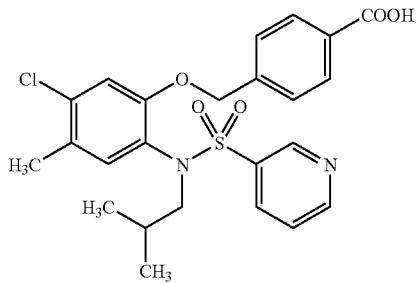

TLC: Rf 0.31 (chloroform:methanol=9:1);
NMR: δ 8.83 (d, J=2.4, 0.6 Hz, 1H), 8.61 (dd, J=5.1, 1.8 Hz, 1H), 8.10 (d, J=8.4 Hz, 2H), 7.78-7.71 (m, 1H), 7.36 (s, 1H), 7.29-7.22 (m, 1H), 7.08 (d, J=8.4 Hz, 2H), 6.90 (s, 1H), 4.94-4.72 and 4.50-4.25 (each m, each 1H), 3.75-3.56 and 3.45-3.24 (each m, each 1H), 2.36 (s, 3H), 1.79-1.63 (m, 1H), 1.16-0.80 (m, 6H).

Example 2(82)

3-chloro-4-[2-[N-isobutyl-N-(3-pyridylsulfonyl)amino]-4-methyl-5-chlorophenoxymethyl]benzoic acid

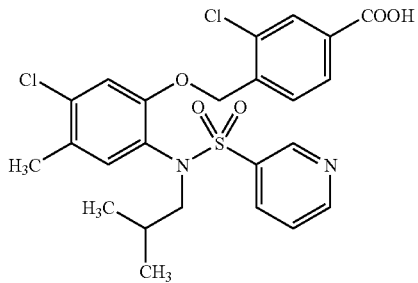

TLC: Rf 0.29 (chloroform:methanol=9:1);

NMR: δ 8.87 (d, J=1.8 Hz, 1H), 8.63 (dd, J=5.1, 1.8 Hz, 1H), 8.13 (d, J=1.8 Hz, 1H), 8.03 (dd, J=8.1, 1.8 Hz, 1H), 7.73-7.66 (m, 1H), 7.40 (s, 1H), 7.36 (dd, J=8.1, 5.1 Hz, 1H), 7.05 (d, J=8.1 Hz, 1H), 6.96 (s, 1H), 4.92-4.74 and 4.54-4.34 (each m, each 1H), 3.72-3.63 and 3.50-3.33 (each m, each 1H), 2.39 (s, 3H), 1.84-1.68 (m, 1H), 1.20-0.92 (m, 6H).

Example 2(83)

3-methyl-4-[2-[N-isobutyl-N-(2-pyridylsulfonyl)amino]-5-trifluoromethylphenoxymethyl]cinnamic acid

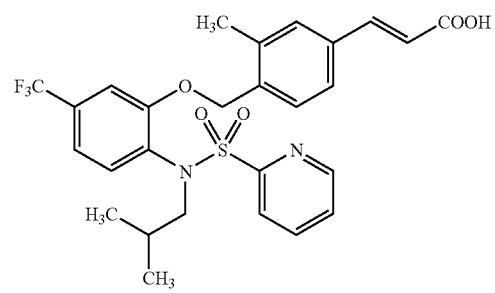

TLC: Rf 0.32 (chloroform:methanol=9:1);
NMR(DMSO-$d_6$): δ 12.39 (br s, 1H), 8.51 (d, J=4.5 Hz, 1H), 7.90 (dd, J=7.5, 7.5 Hz, 1H), 7.70 (d, J=7.5 Hz, 1H), 7.55 (d, J=16.0 Hz, 1H), 7.53-7.46 (m, 5H), 7.35 (d, J=8.0 Hz, 1H), 7.14 (d, J=8.0 Hz, 1H), 6.55 (d, J=16.0 Hz, 1H), 5.00 (br s, 2M, 3.49 (d, J=7.0 Hz, 2H), 2.25 (s, 3H), 1.45 (triple septet, J=7.0, 7.0 Hz, 1H), 0.78 (d, J=7.0 Hz, 6H).

Example 2(84)

3-methoxy-4-[2-[N-isobutyl-N-(2-pyridylsulfonyl)amino]-4,5-dimethylphenoxymethyl]benzoic acid

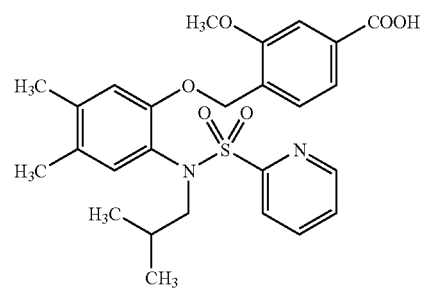

TLC: Rf 0.38 (chloroform:methanol=9:1);
NMR: δ 8.47 (d, J=4.8 Hz, 1H), 7.75-7.60 (m, 3H), 7.56 (d, J=1.5 Hz, 1H), 7.20-7.15 (m, 2H), 7.12 (s, 1H), 6.65 (s, 1H), 4.84 (br, 1H), 4.66 (br, 1H), 3.92 (s, 3H), 3.61 (br, 2H), 2.22 (s, 3H), 2.18 (s, 3H), 1.80-1.60 (m, 1H), 0.96 (br, 6H).

Example 2(85)

3-methoxy-4-[2-[N-isobutyl-N-(3-pyridylsulfonyl)amino]-4,5-dimethylphenoxymethyl]benzoic acid

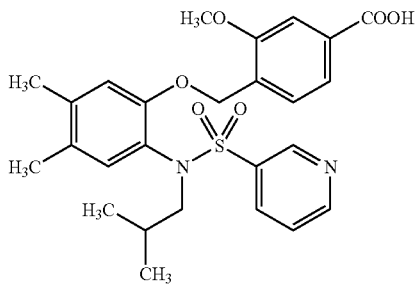

TLC: Rf 0.35 (chloroform:methanol=9:1);
NMR: δ 8.86 (dd, J=2.1, 0.9 Hz, 1H), 8.57 (dd, J=5.1, 1.5 Hz, 1H), 7.75-7.65 (m, 2H), 7.61 (d, J=1.5 Hz, 1H), 7.30-7.20 (m, 2H), 6.92 (d, J=7.8 Hz, 1H), 6.72 (s, 1H), 4.75 (d, J=12.3 Hz, 1H), 4.43 (d, J=12.3 Hz, 1H), 3.93 (s, 3H), 3.75-3.60 (m, 1H), 3.45-3.35 (m, 1H), 2.29 (s, 3H), 2.25 (s, 3H), 1.85-1.65 (m, 1H), 1.09 (d, J=6.3 Hz, 3H), 0.92 (d, J=6.3 Hz, 3H).

Example 2(86)

3-methyl-4-[2-[N-isobutyl-N-(3-pyridylsulfonyl)amino]-4,5-dimethylphenoxymethyl]benzoic acid

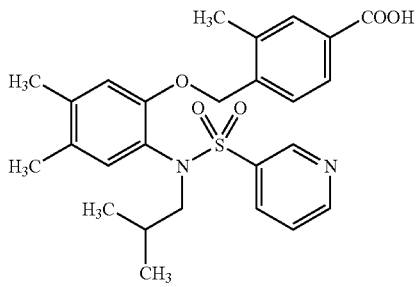

TLC: Rf 0.61 (chloroform:methanol:water=8:2:0.2);
NMR(DMSO-$d_6$): δ 12.87 (brs, 1H), 8.64 (d, J=1.8 Hz, 1H), 8.59 (dd, J=4.8, 1.8 Hz, 1H), 7.91 (dt, J=8.1, 1.8 Hz, 1H), 7.73 (s, 1H), 7.67 (d, J=8.1 Hz, 1H), 7.35 (dd, J=8.1, 4.8 Hz, 1H), 7.04-6.96 (m, 3H), 4.92 (br, 1H), 4.66 (br, 1H), 3.48-3.22 (br, 2H), 2.23 (s, 3H), 2.22 (s, 3H), 2.15 (s, 3H), 1.49 (sep, J=6.9 Hz, 1H), 0.98-0.75 (m, 6H).

Example 2(87)

3-methyl-4-[2-[N-isobutyl-N-(2-pyridylsulfonyl)amino]-4,5-dimethylphenoxymethyl]benzoic acid

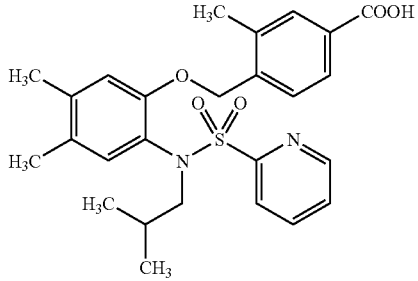

TLC: Rf 0.66 (chloroform:methanol:water=8:2:0.2);
NMR(DMSO-$d_6$): δ 12.88 (s, 1H), 8.47 (d, J=4.5 Hz, 1H), 7.87 (dt, J=1.5, 7.8 Hz, 1H), 7.75 (s, 1H), 7.71 (d, J=7.8 Hz, 1H), 7.63 (d, J=7.8 Hz, 1H), 7.42 (ddd, J=7.8, 4.5, 1.5 Hz, 1H), 7.16 (d, J=7.8 Hz, 1H), 6.93 (s, 1H), 6.91 (s, 1H), 4.80 (br, 2H), 3.57 (d, J=6.6 Hz, 2H), 2.25 (s, 3H), 2.18 (s, 3H), 2.09 (s, 3H), 1.49 (sept, J=6.6 Hz, 1H), 0.81 (d, J=6.6 Hz, 6H).

Example 2(88)

3-methyl-4-[2-[N-isobutyl-N-(3-pyridylsulfonyl)amino]-4-methyl-5-chlorophenoxymethyl]benzoic acid

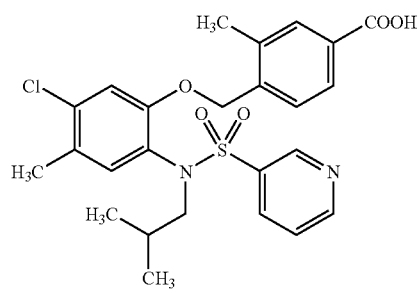

TLC: Rf 0.31 (chloroform:methanol=9:1);
NMR: δ 8.83 (d, J=1.8 Hz, 1H), 8.61 (dd, J=5.4, 1.8 Hz, 1H), 7.93 (d, J=8.1 Hz, 1H), 7.92 (s, 1H), 7.78 (dt, J=8.1, 1.8 Hz 1H), 7.34 (s, 1H), 7.23 (dd, J=8.1, 5.4 Hz, 1H), 6.95 (d, J=8.1 Hz, 1H), 6.94 (s, 1H), 4.88-4.65 and 4.54-4.34 (each m, each 1H), 3.71-3.53 and 3.43-3.24 (each m, each 1H), 2.36 (s, 3H), 2.27 (s, 3H), 1.78-1.63 (m, 1H), 1.08-0.79 (m, 6H).

Example 2(89)

4-[2-[N-isobutyl-N-(2-pyridylsulfonyl)amino]-4,5-dimethylphenoxymethyl]benzoic acid

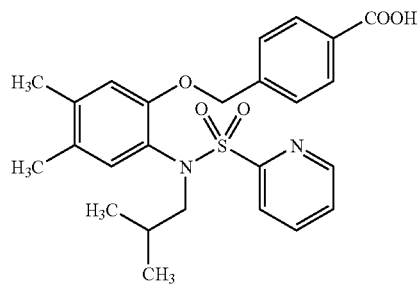

TLC: Rf 0.33 (chloroform:methanol=10:1);
NMR: δ 8.46 (m, 1H), 8.09-8.05 (m, 2H), 7.71-7.60 (m, 2H), 7.28-7.25 (m, 2H), 7.20 (m, 1H), 7.09 (s, 1H), 6.62 (s, 1H), 5.02-4.50 (m, 2H), 3.83-3.43 (m, 2H), 2.21 (s, 3H), 2.17 (s, 3H), 1.67 (m, 1H), 1.04-0.82 (m, 6H).

Example 2(90)

4-[2-[N-isopropyl-N-(2-pyridylsulfonyl)amino]-4-methyl-5-chlorophenoxymethyl]cinnamic acid

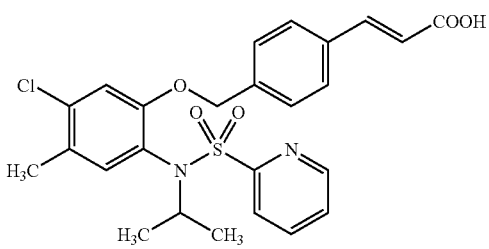

TLC: Rf 0.44 (chloroform:methanol=9:1);
NMR: δ 8.70-8.60 (m, 1H), 7.84 (d, J=7.5 Hz, 1H), 7.79 (d, J=15.9 Hz, 1H), 7.71 (dt, J=1.8, 7.5 Hz, 1H), 7.55 (d, J=8.4 Hz, 2H), 7.39 (d, J=8.4 Hz, 2H), 7.35-7.25 (m, 1H), 6.99 (s, 1H), 6.96 (s, 1H), 6.48 (d, J=15.9 Hz, 1H), 4.96 (d, J=12.3 Hz, 1H), 4.92 (d, J=12.3 Hz, 1H), 4.75-4.60 (m, 1H), 2.26 (s, 3H), 1.14 (d, J=6.9 Hz, 3H), 1.11 (d, J=6.9 Hz, 3H).

Example 2(91)

3-methyl-4-[2-[N-isobutyl-N-(2-pyridylsulfonyl)amino]-4-methyl-5-chlorophenoxymethyl]cinnamic acid

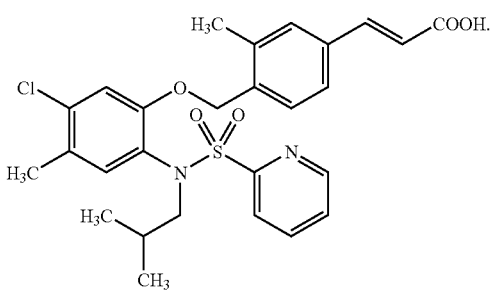

TLC: Rf 0.37 (chloroform:methanol=9:1);
NMR: δ 8.50-8.40 (m, 1H), 7.77 (d, J=15.9 Hz, 1H), 7.75-7.60 (m, 2H), 7.40-7.35 (m, 2H), 7.25-7.20 (m, 2H), 7.15 (d, J=8.4 Hz, 1H), 6.90 (s, 1H), 6.49 (d, J=15.9 Hz, 1H), 4.73 (br, 2H), 3.60 (br, 2H), 2.29 (s, 3H), 2.28 (s, 3H), 1.70-1.55 (m, 1H), 0.91 (d, J=6.6 Hz, 6H).

Example 2(92)

3-methyl-4-[2-[N-isobutyl-N-(2-pyridylsulfonyl)amino]-4,5-dimethylphenoxymethyl]cinnamic acid

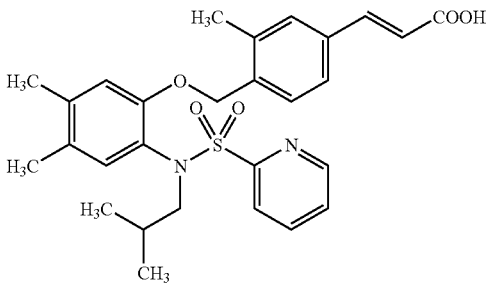

TLC: Rf 0.36 (dichloromethane:methanol=20:1);
MS (FAB, Pos.): 509 (M+H)+.

Example 2(93)

4-[2-[N-isobutyl-N-(3-pyridylsulfonyl)amino]-4,5-dimethylphenoxymethyl]cinnamic acid

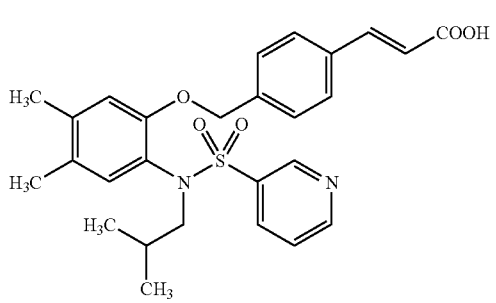

TLC: Rf 0.27 (chloroform:methanol=10:1);
MS (APCI, Neg. 20V): 493 (M−H)−.

Example 2(94)

3-methyl-4-[2-[N-isobutyl-N-(3-pyridylsulfonyl)amino]-4,5-dimethylphenoxymethyl]cinnamic acid

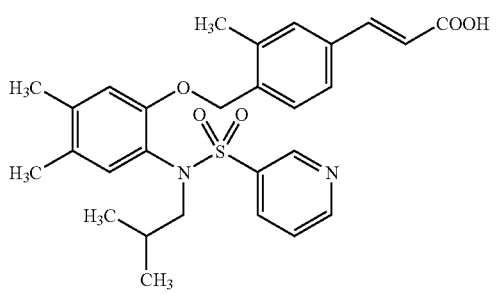

TLC: Rf 0.33 (dichloromethane:methanol=20:1);
MS (FAB, Pos.): 509 (M+H)+.

Example 2(95)

3-chloro-4-[2-[N-isobutyl-N-(3-pyridylsulfonyl)amino]-4,5-dimethylphenoxymethyl]cinnamic acid

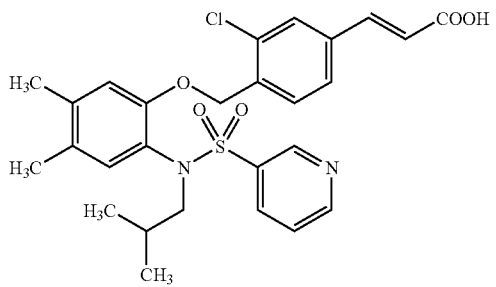

TLC: Rf 0.43 (chloroform:methanol=3:1);
NMR: δ 8.88-8.82 (m, 1H), 8.61-8.52 (m, 1H), 7.75-7.68 (m, 1H), 7.61 (d, J=15.9 Hz, 1H), 7.52 (d, J=1.5 Hz, 1H), 7.47 (d, J=8.1 Hz, 1H), 7.32-7.20 (m, 2H), 6.97 (d, J=8.1 Hz, 1H), 6.70 (s, 1H), 6.50 (d, J=15.9 Hz, 1H), 4.88-4.75 and 4.53-4.41

(each m, each 1H), 3.74-3.58 and 3.48-3.32 (each m, each 1H), 2.29 and 2.25 (each s, each 3H), 1.82-1.63 (m, 1H), 1.15-0.82 (m, 6H).

Example 2(96)

3-methyl-4-[2-[N-isobutyl-N-(3-pyridylsulfonyl)amino]-4-chloro-5-methylphenoxymethyl]cinnamic acid

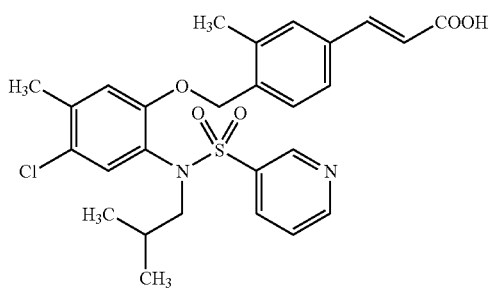

TLC: Rf 0.36 (chloroform:methanol=9:1);
NMR(DMSO-d$_6$): δ 8.65 (m, 2H), 7.94 (m, 1H), 7.54 (d, J=16.2 Hz) and 7.51 (s) total 2H, 7.43 (d, J=8.1 Hz, 1H), 7.38 (dd, J=8.1, 4.8 Hz, 1H), 7.26 (s, 1H), 7.22 (s, 1H), 6.98 (d, J=8.1 Hz, 1H), 6.53 (d, J=16.2 Hz, 1H), 5.00-4.85 (m, 2H), 3.48-3.10 (m, 2H, covered with H$_2$O in DMSO-d$_6$), 2.34 (s, 3H), 2.21 (s, 3H), 1.48 (m, 1H), 0.93 (m, 6H).

Example 2(97)

3-chloro-4-[2-[N-isobutyl-N-(3-pyridylsulfonyl)amino]-5-trifluoromethylphenoxymethyl]cinnamic acid

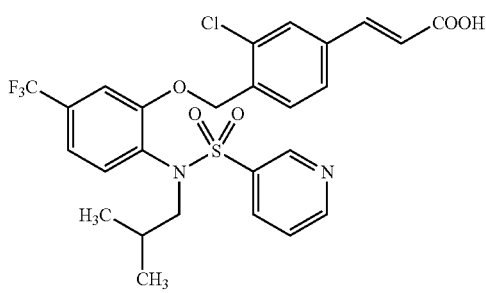

TLC: Rf 0.25 (chloroform:methanol=10:1);
MS (APCI, Neg. 20V): 567 (M−H)$^-$.

Example 2(98)

3-methyl-4-[6-[N-isopropyl-N-(5-methyl-2-furylsulfonyl)amino]indan-5-yloxymethyl]benzoic acid

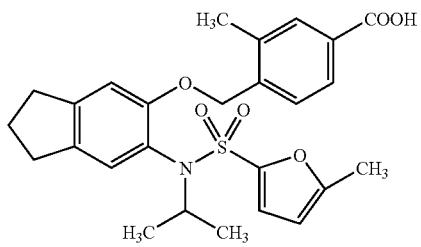

TLC: Rf 0.45 (chloroform:methanol=9:1);

NMR(DMSO-d$_6$): δ 7.79 (s, 1H), 7.75 (d, J=8.0 Hz, 1H), 7.59 (d, J=8.0 Hz, 1H), 7.11 (s, 1H), 6.90 (d, J=3.3 Hz, 1H), 6.82 (s, 1H), 6.30-6.20 (m, 1H), 5.08 (s, 2H), 4.30-4.20 (m, 1H), 2.87 (t, J=7.5 Hz, 2H), 2.79 (t, J=7.5 Hz, 2H), 2.35 (s, 3H), 2.28 (s, 3H), 2.10-1.95 (m, 2H), 0.97 (d, J=6.6 Hz, 6H).

Example 2(99)

3-methyl-4-[6-[N-isopropyl-N-(5-methyl-2-furylsulfonyl)amino]indan-5-yloxymethyl]cinnamic acid

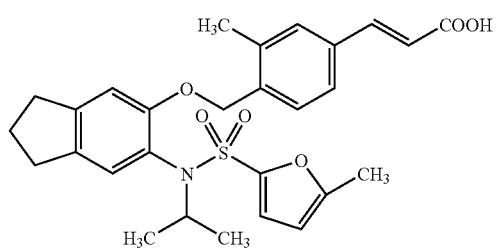

TLC: Rf 0.50 (chloroform:methanol=9:1);
NMR(DMSO-d$_6$): δ 7.60-7.50 (m, 4H), 7.11 (s, 1H), 6.89 (d, J=3.3 Hz, 1H), 6.80 (s, 1H), 6.52 (d, J=16.2 Hz, 1H), 6.30-6.20 (m, 1H), 5.04 (d, J=13.5 Hz, 1H), 5.01 (d, J=13.5 Hz, 1H), 4.30-4.20 (m, 1H), 2.87 (t, J=7.2 Hz, 2H), 2.78 (t, J=7.2 Hz, 2H), 2.32 (s, 3H), 2.28 (s, 3H), 2.10-1.95 (m, 2H), 0.97 (d, J=6.6 Hz, 6H).

Example 2(100)

4-[6-[N-isopropyl-N-(5-methyl-2-furylsulfonyl)amino]indan-5-yloxymethyl]cinnamic acid

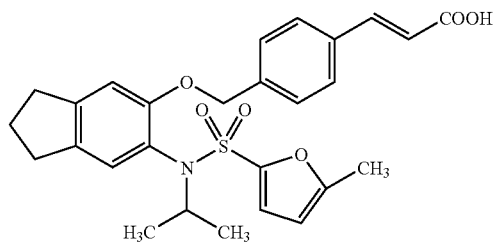

TLC: Rf 0.42 (chloroform:methanol=9:1);
NMR: δ 7.79 (d, J=16.2 Hz, 1H), 7.57 (d, J=8.4 Hz, 2H), 7.51 (d, J=8.4 Hz, 2H), 6.89 (s, 1H), 6.84 (s, 1H), 6.80 (d, J=3.3 Hz, 1H), 6.46 (d, J=16.2 Hz, 1H), 6.02 (m, 1H), 5.14-5.00 (m, 2H), 4.46 (m, 1H), 2.91-2.80 (m, 4H), 2.31 (s, 3H), 2.14-2.02 (m, 2H), 1.11 (d, J=6.6 Hz, 3H), 1.10 (d, J=6.6 Hz, 3H).

Example 2(101)

3-methyl-4-[2-[N-(2-methyl-2-propenyl)-N-(4-methyl-2-thiazolylsulfonyl)amino]-4-chloro-5-methylphenoxymethyl]benzoic acid

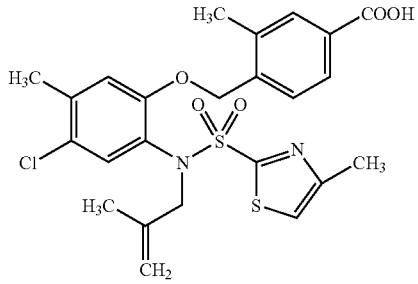

TLC: Rf 0.44 (chloroform:methanol=9:1);
NMR(DMSO-d$_6$): δ 7.79 (s, 1H), 7.77 (d, J=8.4 Hz, 1H), 7.57 (s, 1H), 7.28 (d, J=8.4 Hz, 1H), 7.27 (s, 1H), 7.23 (s, 1H), 4.97 (m, 2H), 4.77 (m, 1H), 4.72 (m, 1H), 4.21 (m, 2H), 2.34 (s, 3H), 2.32 (s, 3H), 2.22 (s, 3H), 1.68 (s, 3H).

Example 2(102)

4-[2-[N-(2-methyl-2-propenyl)-N-(4-methyl-2-thiazolylsulfonyl)amino]-5-trifluoromethylphenoxymethyl]cinnamic acid

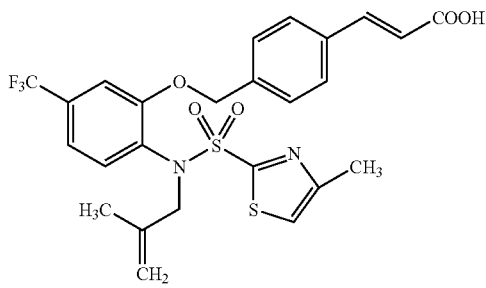

TLC: Rf 0.43 (chloroform:methanol=9:1);
NMR: δ 7.80 (d, J=15.9 Hz, 1H), 7.58 (d, J=8.4 Hz, 2H), 7.45 (d, J=8.1 Hz, 1H), 7.33 (d, J=8.4 Hz, 2H), 7.30-7.20 (m, 1H), 7.15 (s, 1H), 6.99 (s, 1H), 6.50 (d, J=15.9 Hz, 1H), 4.97 (s, 2H), 4.77 (s, 1H), 4.72 (s, 1H), 4.37 (s, 2H), 2.35 (s, 3H), 1.77 (s, 3H).

Example 2(103)

3-methyl-4-[2-[N-(2-methyl-2-propenyl)-N-(4-methyl-2-thiazolylsulfonyl)amino]-4,5-dimethylphenoxymethyl]benzoic acid

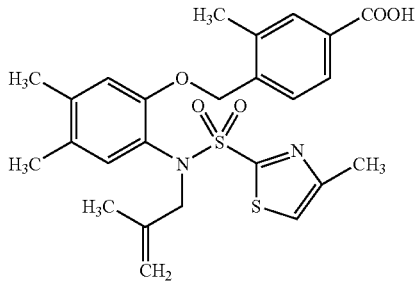

TLC: Rf 0.24 (dichloromethane:methanol=19:1);
NMR(DMSO-d$_6$): δ 7.77-7.73 (m, 2H), 7.50 (brs, 1H), 7.23 (d, J=6.9 Hz, 1H), 6.99 (s, 1H), 6.96 (s, 1H), 4.87 (brs, 2H), 4.74 (brs, 1H), 4.71 (brs, 1H), 4.20 (brs, 2H), 2.28 (s, 3H), 2.19 (s, 3H), 2.16 (d, J=0.6 Hz, 3H), 2.11 (s, 3H), 1.68 (s, 3H).

Example 2(104)

3-methyl-4-[6-[N-isopropyl-N-(2-thiazolylsulfonyl)amino]indan-5-yloxymethyl]benzoic acid

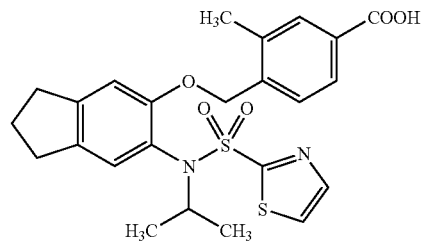

TLC: Rf 0.43 (chloroform:methanol=9:1);
NMR: δ 7.96 (d, J=8.1 Hz, 1H), 7.93 (s, 1H), 7.89 (d, J=3.0 Hz, 1H), 7.58 (d, J=8.1 Hz, 1H), 7.46 (d, J=3.0 Hz, 1H), 6.95 (s, 1H), 6.86 (s, 1H), 5.05 and 4.99 (each d, J=13.5 Hz, each 1H), 4.69 (sept, J=6.6 Hz, 1H), 2.94-2.79 (m, 4H), 2.39 (s, 3H), 2.16-2.02 (m, 2H), 1.18 and 1.15 (each d, J=6.6 Hz, each 3H).

Example 2(105)

3-methyl-4-[6-[N-isobutyl-N-(2-thiazolylsulfonyl)amino]indan-5-yloxymethyl]benzoic acid

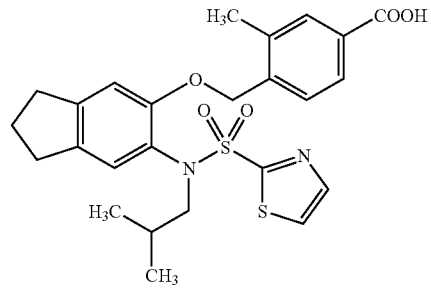

TLC: Rf 0.41 (chloroform:methanol=9:1);
NMR: δ 7.93 (d, J=8.4 Hz, 1H), 7.92 (s, 1H), 7.71 (d, J=3.0 Hz, 1H), 7.35 (d, J=3.0 Hz, 1H), 7.31 (d, J=8.4 Hz, 1H), 7.15 (s, 1H), 6.77 (s, 1H), 5.02-4.64 (m, 2H), 3.81-3.43 (m, 2H), 2.95-2.76 (m, 4H), 2.34 (s, 3H), 2.17-2.01 (m, 2H), 1.82-1.64 (m, 1H), 1.08-0.83 (m, 6H).

Example 2(106)

3-methyl-4-[6-[N-isopropyl-N-(4-methyl-2-thiazolylsulfonyl)amino]indan-5-yloxymethyl]benzoic acid

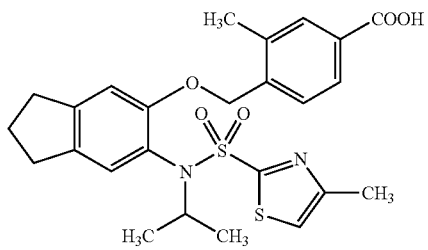

TLC: Rf 0.34 (dichloromethane:methanol=19:1);
NMR: δ 7.97 (d, J=8.1 Hz, 1H), 7.94 (s, 1H), 7.57 (d, J=8.1 Hz, 1H), 7.00 (brs, 1H), 6.94 (s, 1H), 6.86 (s, 1H), 5.05 (d, J=13.5 Hz, 1H), 4.99 (d, J=13.5 Hz, 1H), 4.70 (m, 1H), 2.92-2.81 (m, 4H), 2.47 (s, 3H), 2.39 (s, 3H), 2.09 (m, 2H), 1.18 (d, J=6.6 Hz, 3H), 1.15 (d, J=6.6 Hz, 3H).

Example 2(107)

4-[6-[N-isopropyl-N-(2-thiazolylsulfonyl)amino]indan-5-yloxymethyl]benzoic acid

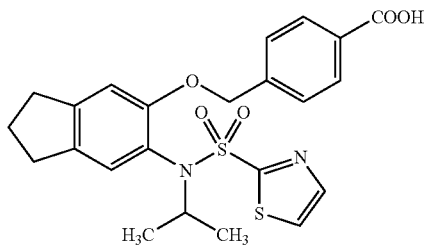

TLC: Rf 0.37 (chloroform:methanol=10:1);
NMR: δ 8.13 (d, J=8.1 Hz, 2H), 7.88 (d, J=3.3 Hz, 1H), 7.51 (d, J=8.1 Hz, 2H), 7.44 (d, J=3.3 Hz, 1H), 6.95 (s, 1H), 6.84 (s, 1H), 5.06 (d, J=13.5 Hz, 1H), 5.05 (d, J=13.5 Hz, 1H), 4.71 (m, 1H), 2.92-2.78 (m, 4H), 2.14-2.02 (m, 2H), 1.18 (d, J=6.6 Hz, 3H), 1.16 (d, J=6.6 Hz, 3H).

Example 2(108)

4-[6-[N-isobutyl-N-(2-thiazolylsulfonyl)amino]indan-5-yloxymethyl]benzoic acid

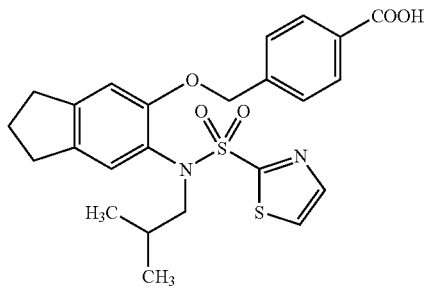

TLC: Rf 0.35 (chloroform:methanol=10:1);
NMR: δ 8.11 (d, J=8.1 Hz, 2H), 7.71 (d, J=3.3 Hz, 1H), 7.35 (d, J=3.3 Hz, 1H), 7.34 (d, J=8.1 Hz, 2H), 7.15 (s, 1H), 6.75 (s, 1H), 4.97 (m, 1H), 4.77 (m, 1H), 3.80-3.47 (m, 2H), 2.89-2.82 (m, 4H), 2.15-2.01 (m, 2H), 1.73 (m, 1H), 1.05-0.85 (m, 6H).

Example 2(109)

4-[6-[N-isopropyl-N-(4-methyl-2-thiazolylsulfonyl)amino]indan-5-yloxymethyl]benzoic acid

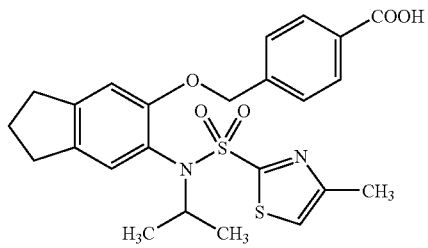

TLC: Rf 0.41 (chloroform:methanol=9:1);
NMR: δ 8.11 (d, J=8.4 Hz, 2H), 7.50 (d, J=8.4 Hz, 2H), 6.98 (d, J=0.9 Hz, 1H), 6.94 (s, 1H), 6.84 (s, 1H), 5.11-5.00 (m, 2H), 4.71 (m, 1H), 2.91-2.79 (m, 4H), 2.47 (d, J=0.9 Hz, 3H), 2.15-2.03 (m, 2H), 1.18 (d, J=6.6 Hz, 3H), 1.15 (d, J=6.6 Hz, 3H).

Example 2(110)

4-[6-[N-isopropyl-N-(4-methyl-2-thiazolylsulfonyl)amino]indan-5-yloxymethyl]cinnamic acid

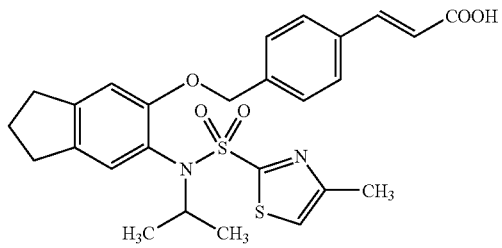

TLC: Rf 0.40 (chloroform:methanol=9:1);
NMR: δ 7.79 (d, J=15.9 Hz, 1H), 7.56 (d, J=8.4 Hz, 2H), 7.45 (d, J=8.4 Hz, 2H), 6.98 (d, J=0.6 Hz, 1H), 6.92 (s, 1H), 6.85 (s, 1H), 6.47 (d, J=15.9 Hz, 1H), 5.06-4.95 (m, 2H), 4.70 (m, 1H), 2.92-2.78 (m, 4H), 2.46 (d, J=0.6 Hz, 3H), 2.16-2.01 (m, 2H), 1.17 (d, J=6.6 Hz, 3H), 1.14 (d, J=6.6 Hz, 3H).

Example 2(111)

3-methyl-4-[6-[N-isopropyl-N-(4-methyl-2-thiazolylsulfonyl)amino]indan-5-yloxymethyl]cinnamic acid

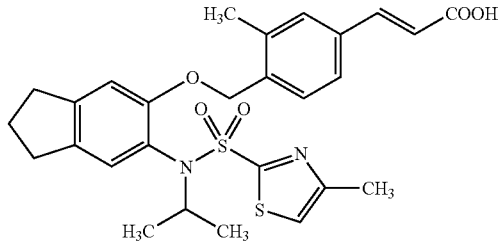

TLC: Rf 0.30 (dichloromethane:methanol=19:1);

NMR(DMSO-d$_6$): δ 12.38 (brs, 1H), 7.57 (brs, 1H), 7.56 (d, J=15.9 Hz, 1H), 7.53 (s, 1H), 7.49 (brd, J=8.1 Hz, 1H), 7.39 (d, J=8.1 Hz, 1H), 7.13 (s, 1H), 6.83 (s, 1H), 6.53 (d, J=15.9 Hz, 1H), 4.99 (brs, 2H), 4.47 (m, 1H), 2.87 (m, 2H), 2.77 (m, 2H), 2.37 (d, J=0.9 Hz, 3H), 2.30 (s, 3H), 2.02 (m, 2H), 1.04 (d, J=6.6 Hz, 3H), 1.00 (d, J=6.6 Hz, 3H).

Example 2(112)

4-[2-[N-isopropyl-N-(2-thiazolylsulfonyl)amino]-4,5-dimethylphenoxymethyl]benzoic acid

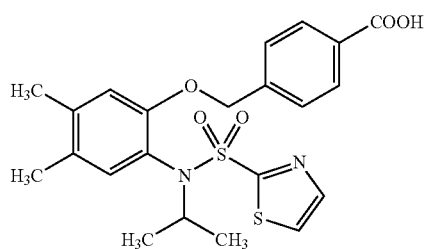

TLC: Rf 0.57 (chloroform:methanol=9:1);
NMR: δ 8.10 (d, J=8.1 Hz, 2H), 7.86 (d, J=3.0 Hz, 1H), 7.49 (d, J=8.1 Hz, 2H), 7.43 (d, J=3.0 Hz, 1H), 6.85 (s, 1H), 6.75 (s, 1H), 5.04 (s, 2H), 4.72 (sept, J=6.9 Hz, 1H), 2.23 (s, 3H), 2.15 (s, 3H), 1.19 (d, J=6.9 Hz, 3H), 1.15 (d, J=6.9 Hz, 3H).

Example 2(113)

4-[2-[N-isobutyl-N-(2-thiazolylsulfonyl)amino]-4,5-dimethylphenoxymethyl]benzoic acid

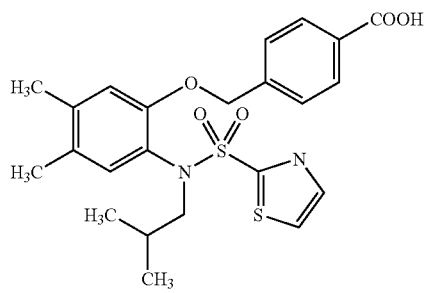

TLC: Rf 0.56 (chloroform:methanol=9:1);
NMR: δ 8.11 (d, J=8.4 Hz, 2H), 7.70 (d, J=3.0 Hz, 1H), 7.36-7.32 (m, 3H), 7.07 (s, 1H), 6.66 (s, 1H), 5.10-4.65 (m, 2H), 3.80-3.45 (m, 2H), 2.22 (s, 3H), 2.18 (s, 3H), 1.71 (sept, J=6.9 Hz, 1H), 1.15-0.95 (m, 6H).

Example 2(114)

4-[2-[N-isopropyl-N-(2-thiazolylsulfonyl)amino]-4,5-dimethylphenoxymethyl]cinnamic acid

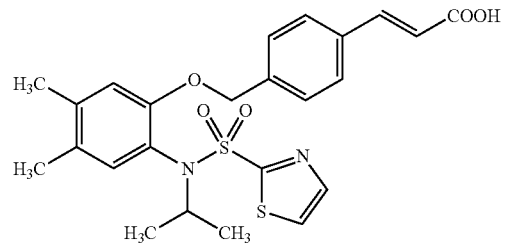

TLC: Rf 0.56 (chloroform:methanol=9:1);
NMR: δ 7.86 (d, J=3.0 Hz, 1H), 7.79 (d, J=15.9 Hz, 1H), 7.56 (d, J=8.4 Hz, 2H), 7.42 (d, J=8.4 Hz, 2H), 7.42 (d, J=3.0 Hz, 1H), 6.84 (s, 1H), 6.76 (s, 1H), 6.46 (d, J=15.9 Hz, 1H), 5.04 (d, J=11.7 Hz, 1H), 4.98 (d, J=11.7 Hz, 1H), 4.71 (sept, J=6.6 Hz, H), 2.23 (s, 3H), 2.13 (s, 3H), 1.18 (d, J=6.6 Hz, 3H), 1.15 (d, J=6.6 Hz, 3H).

Example 2(115)

4-[2-[N-isobutyl-N-(2-thiazolylsulfonyl)amino]-4,5-dimethylphenoxymethyl]cinnamic acid

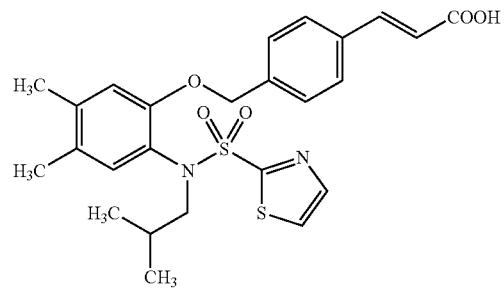

TLC: Rf 0.58 (chloroform:methanol=9:1);
NMR: δ 7.79 (d, J=15.9 Hz, 1H), 7.67 (d, J=3.0 Hz, 1H), 7.55 (d, J=8.4 Hz, 2H), 7.34 (d, J=3.0 Hz, 1H), 7.27 (d, J=8.4 Hz, 2H), 7.05 (s, 1H), 6.67 (s, 1H), 6.47 (d, J=15.9 Hz, 1H), 5.00-4.62 (m, 2H), 3.80-3.45 (m, 2H), 2.22 (s, 3H), 2.17 (s, 3H), 1.70 (sept, J=6.6 Hz, 1H), 1.10-0.96 (m, 6H).

Example 2(116)

4-[6-[N-isopropyl-N-(2-thiazolylsulfonyl)amino]indan-5-yloxymethyl]cinnamic acid

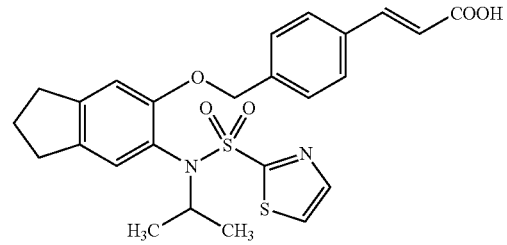

TLC: Rf 0.39 (chloroform:methanol=10:1);
NMR: δ 7.87 (d, J=3.3 Hz, 1H), 7.80 (d, J=15.9 Hz, 1H), 7.56 (d, J=7.8 Hz, 2H), 7.45 (d, J=7.8 Hz, 2H), 7.44 (d, J=3.3 Hz, 1H), 6.94 (s, 1H), 6.85 (s, 1H), 6.48 (d, J=15.9 Hz, 1H), 5.01 (d, J=13.2 Hz, 1H), 5.00 (d, J=13.2 Hz, 1H), 4.70 (m, 1H), 2.91-2.79 (m, 4H), 2.14-2.01 (m, 2H), 1.17 (d, J=6.6 Hz, 3H), 1.15 (d, J=6.6 Hz, 3H).

Example 2(117)

4-[6-[N-isobutyl-N-(2-thiazolylsulfonyl)amino]indan-5-yloxymethyl]cinnamic acid

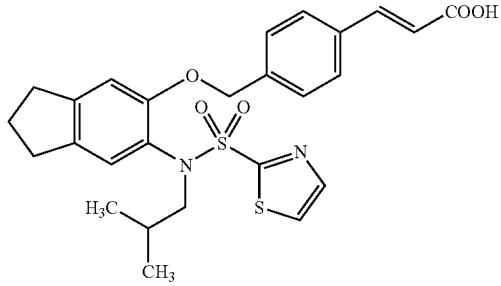

TLC: Rf 0.40 (chloroform:methanol=10:1);
NMR: δ 7.80 (d, J=15.9 Hz, 1H), 7.69 (d, J=3.3 Hz, 1H), 7.55 (d, J=8.4 Hz, 2H), 7.34 (d, J=3.3 Hz, 1H), 7.27 (d, J=8.4 Hz, 2H), 7.14 (s, 1H), 6.75 (s, 1H), 6.48 (d, J=15.9 Hz, 1H), 4.92 (m, 1H), 4.70 (m, 1H), 3.78-3.46 (m, 2H), 2.90-2.80 (m, 4H), 2.14-2.01 (m, 2H), 1.72 (m, 1H), 1.02-0.83 (m, 6H).

Example 2(118)

3-methyl-4-[2-[N-isopropyl-N-(2-thiazolylsulfonyl)amino]-4,5-dimethylphenoxymethyl]benzoic acid

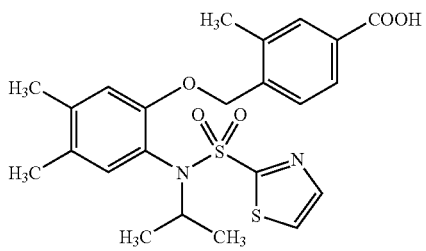

TLC: Rf 0.27 (chloroform:methanol=9:1);
NMR: δ 8.00-7.90 (m, 2H), 7.87 (d, J=3.0 Hz, 1H), 7.55 (d, J=7.8 Hz, 1H), 7.44 (d, J=3.0 Hz, 1H), 6.85 and 6.77 (each s, each 1H), 5.09-4.92 (m, 2H), 4.78-4.62 (m, 1H), 2.39 (s, 3H), 2.25 (s, 3H), 2.16 (s, 3H), 1.19 and 1.15 (each d, J=6.6 Hz, each 3H).

Example 2(119)

3-methyl-4-[2-[N-isobutyl-N-(2-thiazolylsulfonyl)amino]-4,5-dimethylphenoxymethyl]benzoic acid

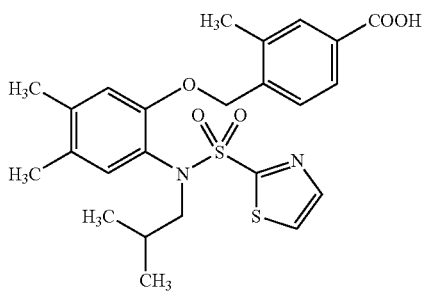

TLC: Rf 0.27 (chloroform:methanol=9:1);

NMR: δ 7.95-7.89 (m, 2H), 7.70 and 7.34 (each d, J=3.3 Hz, each 1H), 7.32-7.29 (m, 1H), 7.06 and 6.69 (each s, each 1H), 5.00-4.68 (m, 2H), 3.78-3.48 (m, 2H), 2.34 (s, 3H), 2.23 (s, 3H), 2.18 (s, 3H), 1.80-1.65 (m, 1H), 1.08-0.82 (m, 6H).

Example 2(120)

3-methyl-4-[2-[N-isopropyl-N-(2-thiazolylsulfonyl)amino]-4,5-dimethylphenoxymethyl]cinnamic acid

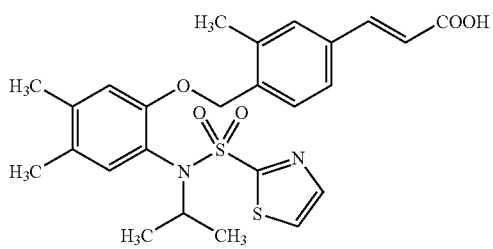

TLC: Rf 0.25 (chloroform:methanol=9:1);
NMR: δ 7.87 (d, J=3.0 Hz, 1H), 7.77 (d, J=16.2 Hz, 1H), 7.52-7.32 (m, 4H), 6.83 and 6.79 (each s, each 1H), 6.46 (d, J=16.2 Hz, 1H), 5.05-4.87 (m, 2H), 4.75-4.62 (m, 1H), 2.36 (s, 3H), 2.25 (s, 3H), 2.15 (s, 3H), 1.17 and 1.13 (each d, J=6.6 Hz, each 3H).

Example 2(121)

3-methyl-4-[2-[N-isobutyl-N-(2-thiazolylsulfonyl)amino]-4,5-dimethylphenoxymethyl]cinnamic acid

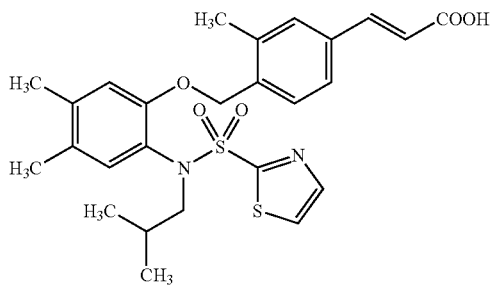

TLC: Rf 0.25 (chloroform:methanol=9:1);
NMR: δ 7.76 (d, J=16.2 Hz, 1H), 7.69 (d, J=3.0 Hz, 1H), 7.42-7.35 (m, 2H), 7.34 (d, J=3.0 Hz, 1H), 7.25-7.19 (m, 1H), 7.05 and 6.70 (each s, each 1H), 6.47 (d, J=16.2 Hz, 1H), 4.95-4.62 (m, 2H), 3.75-3.48 (m, 2H), 2.31 (s, 3H), 2.24 (s, 3H), 2.18 (s, 3H), 1.78-1.62 (m, 1H), 1.78-1.62 (m, 6H).

Example 2(122)

3-methyl-4-[6-[N-isopropyl-N-(2-thiazolylsulfonyl)amino]indan-5-yloxymethyl]cinnamic acid

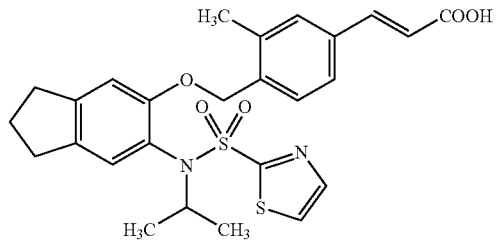

TLC: Rf 0.44 (chloroform:methanol=9:1);

NMR: δ 7.88 (d, J=3.0 Hz, 1H), 7.77 (d, J=16.2 Hz, 1H), 7.51 (d, J=8.1 Hz, 1H), 7.45 (d, J=3.0 Hz, 1H), 7.42 (d, J=8.1 Hz, 1H), 7.38 (s, 1H), 6.93 (s, 1H), 6.87 (s, 1H), 6.46 (d, J=16.2 Hz, 1H), 5.02 and 4.95 (each d, J=12.9 Hz, each 1H), 4.68 (sept, J=6.6 Hz, 1H), 2.94-2.78 (m, 4H), 2.36 (s, 3H), 2.16-2.02 (m, 2H), 1.17 and 1.14 (each d, J=6.6 Hz, each 3H).

Example 2(123)

3-methyl-4-[6-[N-isobutyl-N-(2-thiazolylsulfonyl) amino]indan-5-yloxymethyl]cinnamic acid

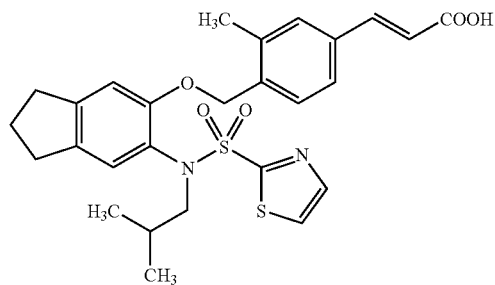

TLC: Rf 0.39 (chloroform:methanol=9:1);
NMR(DMSO-$d_6$): δ 7.98 (d, J=3.0 Hz, 1H), 7.87 (d, J=3.0 Hz, 1H), 7.56 (d, J=16.2 Hz, 1H), 7.52 (s, 1H), 7.50 (d, J=8.1 Hz, 1H), 7.18 (d, J=8.1 Hz, 1H), 7.06 (s, 1H), 7.00 (s, 1H), 6.54 (d, J=16.2 Hz, 1H), 5.04-4.66 (m, 2H), 3.57-3.37 (m, 2H), 2.93-2.68 (m, 4H), 2.27 (s, 3H), 2.11-1.93 (m, 2H), 1.64-1.46 (m, 1H), 0.94-0.74 (m, 6H).

Example 2(124)

4-[3-[N-isobutyl-N-(5-methyl-2-furyl sulfonyl) amino]-2-naphthyloxymethyl]benzoic acid

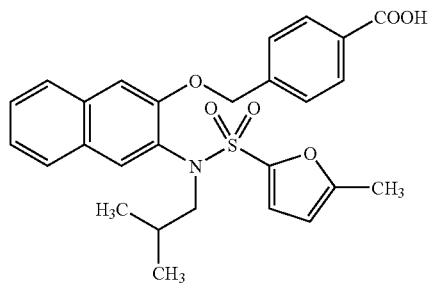

TLC: Rf 0.33 (chloroform:methanol=9:1);
NMR(CD$_3$OD): δ 8.05 (d, J=8.4 Hz, 2H), 7.82-7.75 (m, 3H), 7.53 (d, J=8.4 Hz, 2H), 7.51-7.35 (m, 3H), 6.71 (d, J=3.3 Hz, 1H), 6.05 (m, 1H), 5.42-4.95 (br, 2H), 3.62 (d, J=7.5 Hz, 2H), 2.13 (s, 3H), 1.79-1.61 (, 1H), 0.94 (d, J=6.3 Hz, 6H).

Reference Example 4

N-[4,5-dimethyl-2-(2-methyl-4-cyanophenylmethyloxy)phenyl]-N-isobutyl-(5-methyl-2-furyl)sulfonylamide

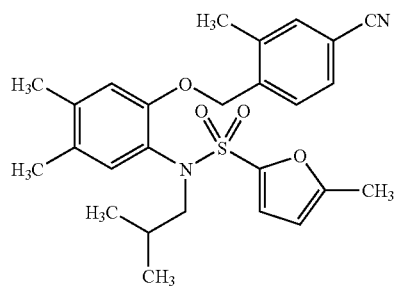

Under atmosphere of argon, a solution of 3-methyl-4-[2-[N-isobutyl-N-(5-methyl-2-furylsulfonyl)amino]-4,5-dimethylphenoxymethyl]benzoic acid prepared in Example 2 (178 mg) in dichloromethane (1.5 ml) was cooled to 0° C., then oxalyl chloride (48 µl) and a catalytic amount of N,N-dimethylformamide was added thereto. After the solution was stirred for 1 hour at room temperature, the reaction mixture was concentrated under reduced pressure, and azeotroped with toluene. Under atmosphere of argon, the residue was dissolved in dichloromethane (1.5 ml), and cooled to 0° C. The solution was added by 28% aqueous ammonia (1 ml) and stirred for 5 minutes. The solution was added by water and ethyl acetate. The organic layer was washed, dried and concentrated under reduced pressure. Under atmosphere of argon, the residue was dissolved in dichloromethane (1.5 ml), and cooled to 0° C. The solution was added by pyridine (0.18 ml) and trifluoromethanesulfonic acid anhydride (0.12 ml) and stirred for 50 minutes. The reaction mixture was poured into water, then it was added by ethyl acetate. The organic layer was washed, dried and concentrated under reduced pressure. The residue was purified by column chromatography on silica gel (hexane-ethyl acetate) to give the title compound (149 mg) having the following physical data.

TLC: Rf 0.74 (n-hexane:ethyl acetate=1:1).

Example 3

N-[4,5-dimethyl-2-[2-methyl-4-(5-tetrazolyl)phenylmethyloxy]phenyl]-N-isobutyl-(5-methyl-2-furyl)sulfonylamide

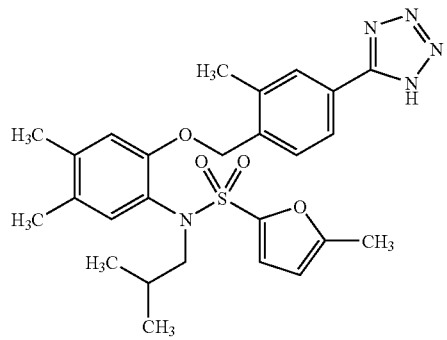

To N-[4,5-dimethyl-2-(2-methyl-4-cyanophenylmethyloxy)phenyl]-N-isobutyl-(5-methyl-2-furyl)sulfonylamide prepared in Reference Example 4 (79 mg), trimethyltin azide (43 mg) was added, and mixture was refluxed for 7 hours, then stirred for 1 day at room temperature. The reaction mixture was added by methanol (3 ml) and 2N hydrochloric acid (2 ml), then stirred for 2 hours. The solution was added by water and ethyl acetate. The organic layer was washed, dried and concentrated under reduced pressure. The residue was washed by hexane-ethyl acetate to give the title compound (81 mg) having the following physical data.

TLC: Rf 0.52 (chloroform:methanol:water=8:2:0.2);
MS (FAB, Pos.): 510 (M+H)$^+$.

Example 3(1) to Example 3(38)

By the same procedures as described in Reference Examples 1 to 3 and Example 3, the title compounds having the following physical data were obtained.

Example 3(1)

N-[4-chloro-5-methyl-2-[2-methyl-4-(5-tetrazolyl)phenylmethyloxy]phenyl]-N-isobutyl-(5-methyl-2-furyl)sulfonylamide

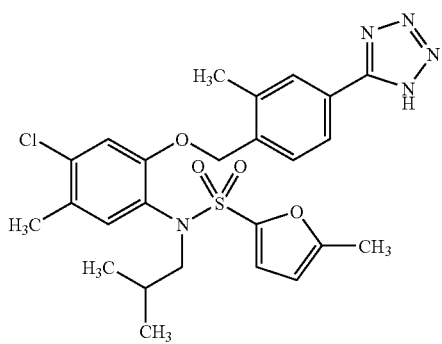

TLC: Rf 0.40 (dichloromethane:methanol=10:1);
MS (FAB, Pos.): 530 (M)$^+$.

Example 3(2)

N-[4,5-dimethyl-2-[2-methyl-4-(5-tetrazolyl)phenylmethyloxy]phenyl]-N-isopropyl-(5-methyl-2-furyl)sulfonylamide

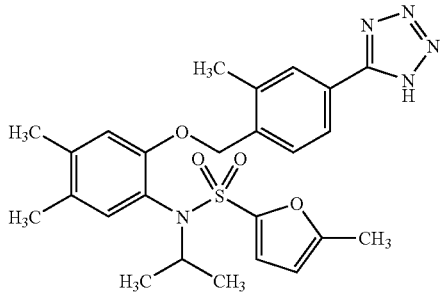

TLC: Rf 0.52 (chloroform:methanol:water=8:2:0.2);
MS (FAB, Pos.): 496 (M+H)$^+$.

Example 3(3)

N-[4-chloro-5-methyl-2-[4-(5-tetrazolyl)phenylmethyloxy]phenyl]-N-isobutyl-(5-methyl-2-furyl)sulfonylamide

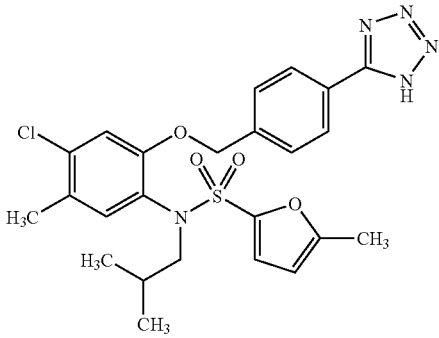

TLC: Rf 0.39 (chloroform:methanol:water=8:2:0.2);
NMR: δ 8.05 (d, J=8.1 Hz, 2H), 7.47 (d, J=8.1 Hz, 2H), 7.08 (s, 1H), 6.93 (s, 1H), 6.80 (d, J=3.3 Hz, 1H), 6.01 (m, 1H), 5.15-4.80 (br, 2H), 3.46 (d, J=7.2 Hz, 2H), 2.27 (s, 3H), 2.19 (s, 3H), 1.64 (m, 1H), 0.88 (d, J=6.9 Hz, 6H).

Example 3(4)

N-[4,5-dimethyl-2-[4-(5-tetrazolyl)phenylmethyloxy]phenyl]-N-isopropyl-(5-methyl-2-furyl)sulfonylamide

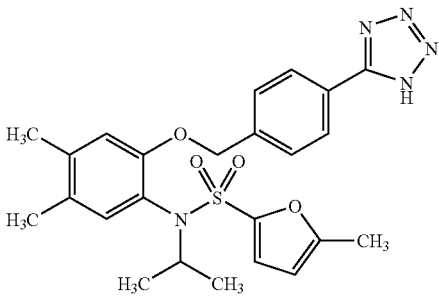

TLC: Rf 0.41 (chloroform:methanol:water=8:2:0.2);
NMR(DMSO-d$_6$): δ 8.04 (d, J=8.1 Hz, 2H), 7.66 (d, J=8.1 Hz, 2H), 7.01 (s, 1H), 6.91 (d, J=3.3 Hz, 1H), 6.76 (s, 1H), 6.29-6.23 (m, 1H), 5.18 and 5.12 (each d, J=13.5 Hz, each 1H), 4.30 (sept, J=6.6 Hz, 1H), 2.30 (s, 3H), 2.23 (s, 3H), 2.14 (s, 3H), 1.02 and 1.00 (each d, J=6.6 Hz, each 3H).

Example 3(5)

N-[4,5-dimethyl-2-[4-(5-tetrazolyl)phenylmethyloxy]phenyl]-N-isobutyl-(5-methyl-2-furyl)sulfonylamide

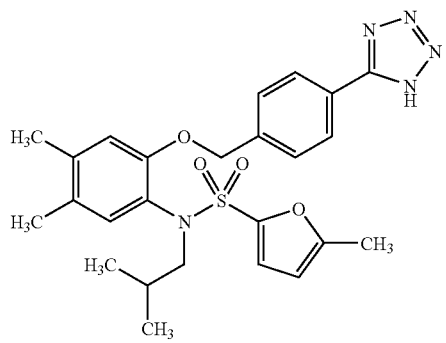

TLC: Rf 0.37 (chloroform:methanol:water=8:2:0.2);
NMR(DMSO-d$_6$): δ 8.04 (d, J=8.4 Hz, 2H), 7.53 (d, J=8.4 Hz, 2H), 6.96 (s, 1H), 6.92 (s, 1H), 6.82 (d, J=3.3 Hz, 1H), 6.19-6.13 (m, 1H), 5.28-4.82 (m, 2H), 3.38 (d, J=6.9 Hz, 2H), 2.21 (s, 3H), 2.14 (s, 6H), 1.64-1.44 (m, 1H), 0.85 (d, J=6.6 Hz, 6H).

Example 3(6)

N-[4-trifluoromethyl-2-[4-(5-tetrazolyl)phenylmethyloxy]phenyl]-N-isobutyl-2-thiazolylsulfonylamide

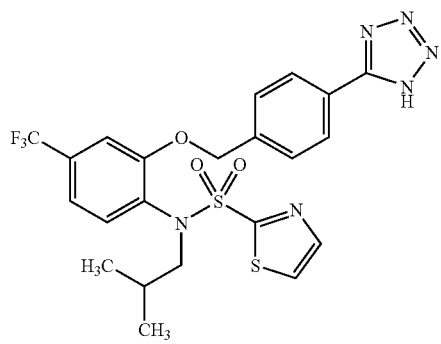

TLC: Rf 0.46 (chloroform:methanol:water=8:2:0.2);
NMR: δ 8.09 (d, J=8.4 Hz, 2H), 7.76 (d, J=2.7 Hz, 1H), 7.49-7.44 (m, 4H), 7.27 (m, 1H), 7.19 (s, 1H), 5.01 (br, 2H), 3.63 (d, J=7.2 Hz, 2H), 1.67 (m, 1H), 0.97 (d, J=7.2 Hz, 6H).

Example 3(7)

N-[4-trifluoromethyl-2-[4-(5-tetrazolyl)phenylmethyloxy]phenyl]-N-isopropyl-2-thiazolylsulfonylamide

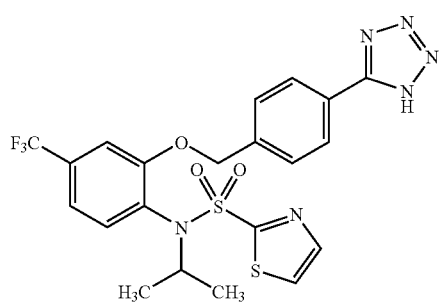

TLC: Rf 0.31 (chloroform:methanol:water=8:2:0.2);
NMR: δ 8.07 (d, J=8.1 Hz, 2H), 7.94 (d, J=3.3 Hz, 1H), 7.60 (d, J=8.1 Hz, 2H), 7.56 (d, J=3.3 Hz, 1H), 7.36-7.20 (m, 3H), 5.17 and 5.13 (each d, J=12.0 Hz, each 1H), 4.68 (sept, J=6.6 Hz, 1H), 1.15 and 1.14 (each d, J=6.6 Hz, each 3H).

Example 3(8)

N-[4-trifluoromethyl-2-[4-(5-tetrazolyl)phenylmethyloxy]phenyl]-N-isobutyl-(4-methyl-2-thiazolyl)sulfonylamide

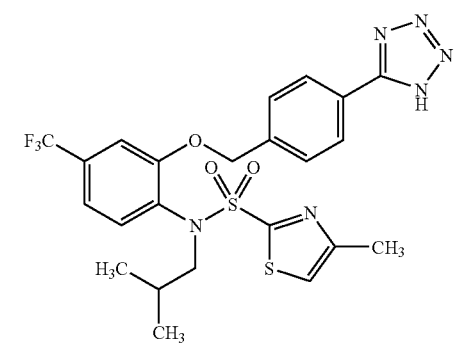

TLC: Rf 0.31 (chloroform:methanol:water=8:2:0.2);
NMR: δ 8.04 (d, J=8.1 Hz, 2H), 7.42 (d, J=8.1 Hz, 1H), 7.37 (d, J=8.1 Hz, 2H), 7.23 (m, 1H), 7.16 (s, 1H), 6.99 (s, 1H), 4.95 (br, 2H), 3.56 (d, J=6.6 Hz, 2H), 2.26 (s, 3H), 1.59 (sept, J=6.6 Hz, 1H), 0.84 (d, J=6.6 Hz, 6H).

Example 3(9)

N-[4-trifluoromethyl-2-[4-(5-tetrazolyl)phenylmethyloxy]phenyl]-N-isopropyl-(4-methyl-2-thiazolyl)sulfonylamide

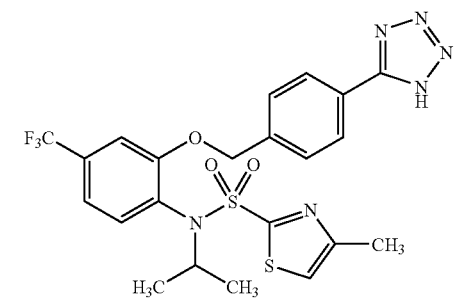

TLC: Rf 0.42 (chloroform:methanol:water=8:2:0.2);
NMR: δ 7.93 (d, J=8.1 Hz, 2H), 7.41 (d, J=8.1 Hz, 2H), 7.24-7.16 (m, 3H), 7.02 (s, 1H), 5.10-4.92 (m, 2H), 4.57 (quint, J=6.6 Hz, 1H), 2.39 (s, 3H), 1.04 (d, J=6.6 Hz, 3H), 1.02 (d, J=6.6 Hz, 3H).

Example 3(10)

N-[4-chloro-5-methyl-2-[2-methyl-4-(5-tetrazolyl)phenylmethyloxy]phenyl]-N-isobutyl-(4-methyl-2-thiazolyl)sulfonylamide

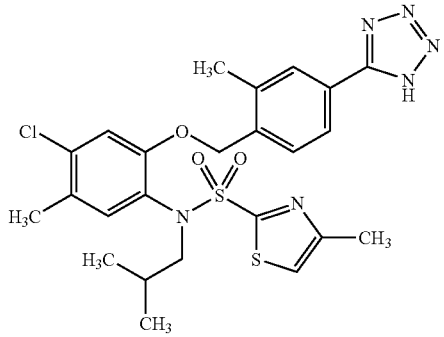

TLC: Rf 0.24 (dichloromethane:methanol=10:1);
MS (FAB, Pos.): 547 (M)$^+$.

Example 3(11)

N-[4-chloro-5-methyl-2-[2-methyl-4-(5-tetrazolyl)phenylmethyloxy]phenyl]-N-isopropyl-(4-methyl-2-thiazolyl)sulfonylamide

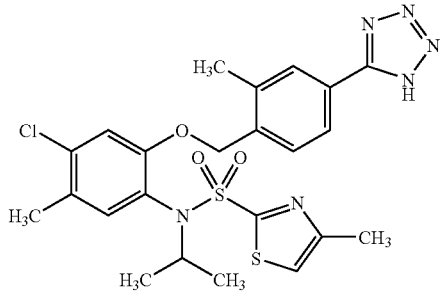

TLC: Rf 0.24 (dichloromethane:methanol=10:1);
MS (FAB, Pos.): 533 (M)$^+$.

Example 3(12)

N-[4-trifluoromethyl-2-[2-methyl-4-(5-tetrazolyl)phenylmethyloxy]phenyl]-N-isopropyl-(4-methyl-2-thiazolyl)sulfonylamide

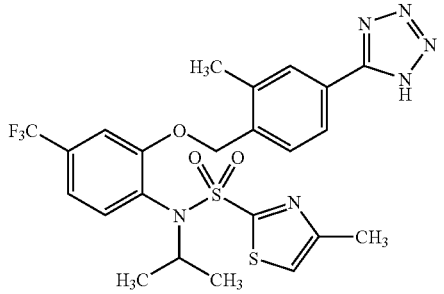

TLC: Rf 0.38 (chloroform:methanol:water=8:2:0.2);
NMR: δ 7.91 (s, 1H), 7.82 (d, J=7.8 Hz, 1H), 7.64 (d, J=7.8 Hz, 1H), 7.33-7.20 (m, 3H), 7.12 (s, 1H), 5.11 (s, 2H), 4.65 (sept, J=6.6 Hz, 1H), 2.49 (s, 3H), 2.43 (s, 3H), 1.12 (d, J=6.6 Hz, 6H).

Example 3(13)

N-[4-trifluoromethyl-2-[2-methyl-4-(5-tetrazolyl)phenylmethyloxy]phenyl]-N-isobutyl-(4-methyl-2-thiazolyl)sulfonylamide

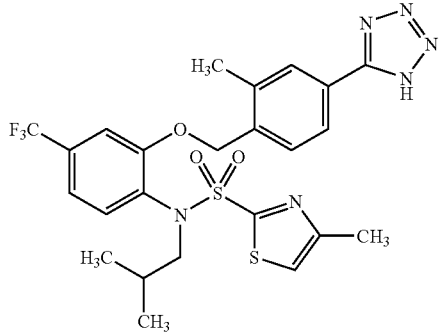

TLC: Rf 0.34 (chloroform:methanol:water=8:2:0.2);
NMR: δ 7.97 (s, 1H), 7.89 (d, J=8.1 Hz, 1H), 7.48-7.38 (m, 2H), 7.34-7.18 (m, 2H), 7.05 (s, 1H), 5.12-4.84 (m, 2H), 3.59 (d, J=7.2 Hz, 2H), 2.41 (s, 3H), 2.34 (s, 3H), 1.74-1.58 (m, 1H), 0.89 (d, J=6.6 Hz, 6H).

Example 3(14)

N-[4,5-dimethyl-2-[2-methyl-4-(5-tetrazolyl)phenylmethyloxy]phenyl]-N-isobutyl-(4-methyl-2-thiazolyl)sulfonylamide

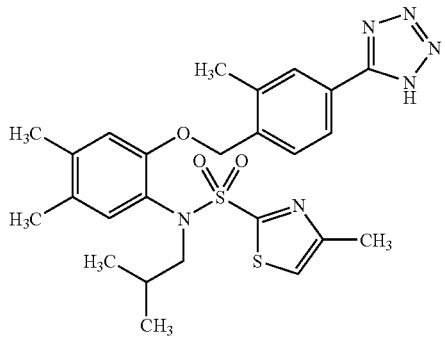

TLC: Rf 0.46 (chloroform:methanol:water=8:2:0.2);
MS (FAB, Pos.): 527 (M+H)$^+$.

Example 3(15)

N-[4,5-dimethyl-2-[2-methyl-4-(5-tetrazolyl)phenylmethyloxy]phenyl]-N-isopropyl-(4-methyl-2-thiazolyl)sulfonylamide

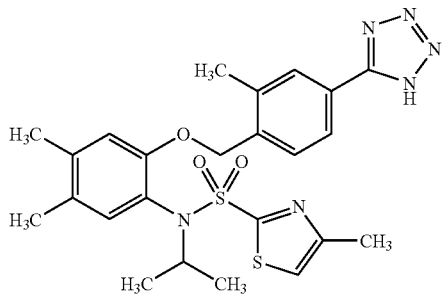

TLC: Rf 0.52 (chloroform:methanol:water=8:2:0.2);
MS (FAB, Pos.): 513 (M+H)$^+$.

Example 3(16)

N-[4,5-dimethyl-2-[4-(5-tetrazolyl)phenylmethyloxy]phenyl]-N-isopropyl-(4-methyl-2-thiazolyl)sulfonylamide

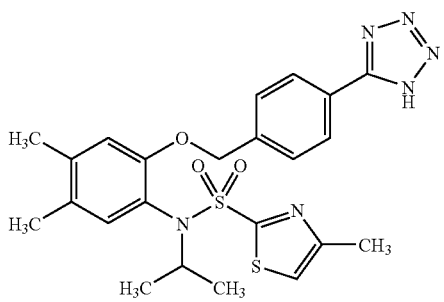

TLC: Rf 0.29 (chloroform:methanol=5:1);
MS (APCI, Neg. 20V): 497 (M−H)⁻.

Example 3(17)

N-[4,5-dimethyl-2-[4-(5-tetrazolyl)phenylmethyloxy]phenyl]-N-isobutyl-(4-methyl-2-thiazolyl)sulfonylamide

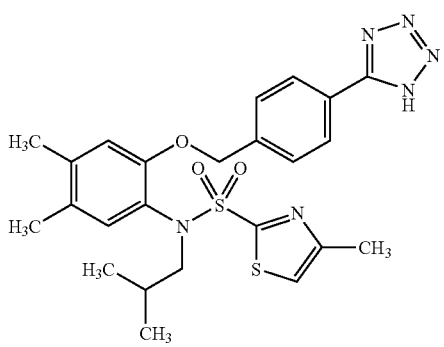

TLC: Rf 0.26 (chloroform:methanol=5:1);
MS (APCI, Neg. 20V): 511 (M−H)⁻.

Example 3(18)

N-[4-chloro-5-methyl-2-[4-(5-tetrazolyl)phenylmethyloxy]phenyl]-N-isopropyl-(4-methyl-2-thiazolyl)sulfonylamide

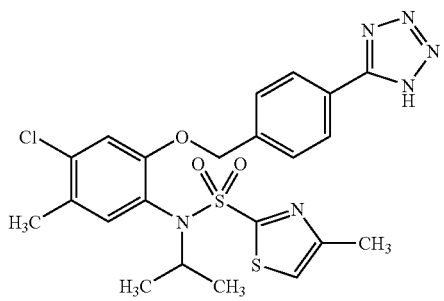

TLC: Rf 0.31 (chloroform:methanol:water=8:2:0.2);
NMR: δ 8.02 (d, f=8.4 Hz, 2H), 7.51 (d, J=8.4 Hz, 2H), 7.10 (s, 1H), 6.98 (s, 2H), 5.03 and 4.95 (each d, J=12.6 Hz, each 1H), 4.65 (sept, J=6.6 Hz, 1H), 2.46 (s, 3H), 2.26 (s, 3H), 1.13 and 1.12 (each d, J=6.6 Hz, each 3H).

Example 3(19)

N-[4-chloro-5-methyl-2-[4-(5-tetrazolyl)phenylmethyloxy]phenyl]-N-isobutyl-(4-methyl-2-thiazolyl)sulfonylamide

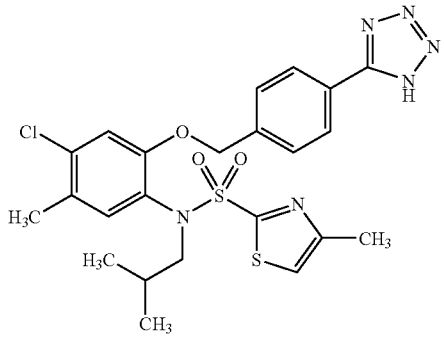

TLC: Rf 0.29 (chloroform:methanol:water=8:2:0.2);
NMR(DMSO-$d_6$): δ 8.05 (d, J=8.4 Hz, 2H), 7.52 (s, 1H), 7.45 (d, J=8.4 Hz, 2H), 7.26 (s, 1H), 7.25 (s, 1H), 5.25-4.73 (m, 2H), 3.62-3.40 (m, 2H), 2.26 (s, 3H), 2.22 (s, 3H), 1.66-1.50 (m, 1H), 0.88 (d, J=6.6 Hz, 6H).

Example 3(20)

N-[4,5-dimethyl-2-[2-methoxy-4-(5-tetrazolyl)phenylmethyloxy]phenyl]-N-isopropyl-(4-methyl-2-thiazolyl)sulfonylamide

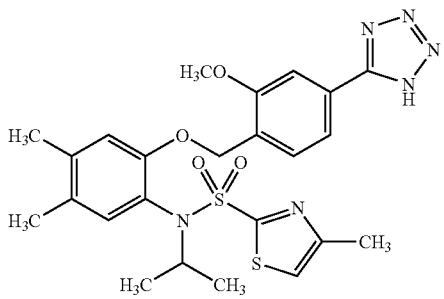

TLC: Rf 0.31 (chloroform:methanol=5:1);
NMR(CDCl₃+1 drop of CD₃OD) δ 7.71 (d, J=7.5 Hz, 1H), 7.70 (d, J=1.5 Hz, 1H), 7.51 (dd, J=7.5, 1.5 Hz, 1H), 7.07 (d, J=0.9 Hz, 1H), 6.83 (s, 1H), 6.82 (s, 1H), 5.09 (d, J=13.8 Hz, 1H), 5.04 (d, J=13.8 Hz, 1H), 4.68 (m, 1H), 3.97 (s, 3H), 2.46 (d, J=0.9 Hz, 3H), 2.25 (s, 3H), 2.16 (s, 3H), 1.15 (d, J=6.6 Hz, 3H), 1.14 (d, J=6.6 Hz, 3H).

Example 3(21)

N-[4-trifluoromethyl-2-[4-(5-tetrazolyl)phenylmethyloxy]phenyl]-N-isopropyl-3-pyridylsulfonylamide

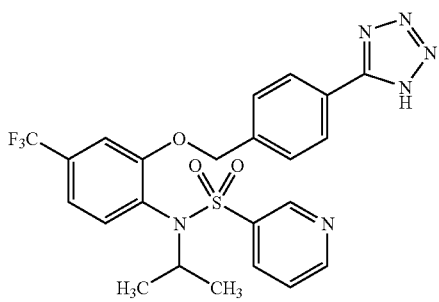

TLC: Rf 0.47 (chloroform:methanol=3:1);

NMR(DMSO-d₆): δ 8.91 (dd, J=2.4, 0.6 Hz, 1H), 8.73 (dd, J=4.5, 1.8 Hz, 1H), 8.14 (ddd, J=8.4, 2.4, 1.8 Hz, 1H), 8.04 (d, J=8.4 Hz, 2H), 7.57 (s, 1H), 7.55 (d, J=8.4 Hz, 2H), 7.47 (ddd, J=8.4, 4.5, 0.6 Hz, 1H), 7.43-7.38 (m, 2H), 5.28 (d, J=12.3 Hz, 1H), 5.21 (d, J=12.3 Hz, 1H), 4.45-4.25 (m, 1H), 1.04 (d, J=6.6 Hz, 3H), 1.00 (d, J=6.6 Hz, 3H).

Example 3(22)

N-[4-trifluoromethyl-2-[4-(5-tetrazolyl)phenylmethyloxy]phenyl]-N-isobutyl-3-pyridylsulfonylamide

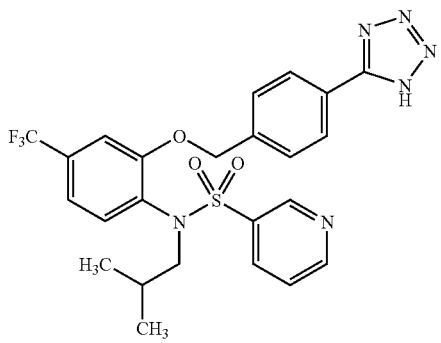

TLC: Rf 0.47 (chloroform:methanol=3:1);

NMR: δ 8.89 (d, J=1.5 Hz, 1H), 8.46 (dd, J=4.8, 1.5 Hz, 1H), 8.00 (d, J=8.4 Hz, 2H), 7.83 (dt, J=8.1, 1.5 Hz, 1H), 7.59 (d, J=8.4 Hz, 1H), 7.35 (dd, J=8.4, 0.9 Hz, 1H), 7.26-7.20 (m, 1H), 7.19 (d, J=0.9 Hz, 1H), 7.14 (d, J=8.4 Hz, 2H), 4.95 (brs, 1H), 4.77 (brs, 1H), 3.56 (brs, 1H), 3.40 (brs, 1H), 1.70-1.60 (m, 1H), 0.94 (brs, 6H).

Example 3(23)

N-[4-trifluoromethyl-2-[4-(5-tetrazolyl)phenylmethyloxy]phenyl]-N-isopropyl-2-pyridylsulfonylamide

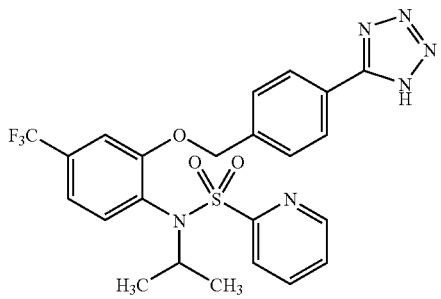

TLC: Rf 0.47 (chloroform:methanol=3:1);

NMR: δ 8.69 (d, J=4.8 Hz, 1H), 8.02 (d, J=8.4 Hz, 2H), 7.92-7.76 (m, 2H), 7.52 (d, J=8.4 Hz, 2H), 7.46-7.38 (m, 1H), 7.30-7.26 (m, 3H), 5.08 (d, J=12.0 Hz, 1H), 5.01 (d, J=12.0 Hz, 1H), 4.75-4.55 (m, 1H), 1.11 (d, J=7.5 Hz, 3H), 1.08 (d, J=7.5 Hz, 3H).

Example 3(24)

N-[4-trifluoromethyl-2-[4-(5-tetrazolyl)phenylmethyloxy]phenyl]-N-isobutyl-2-pyridylsulfonylamide

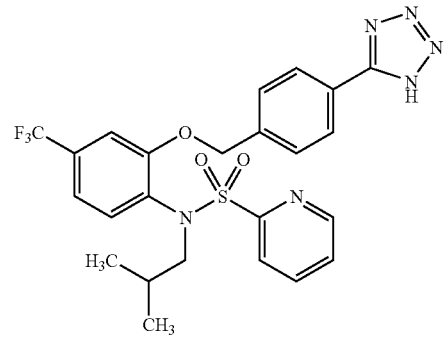

TLC: Rf 0.38 (chloroform:methanol=3:1);

NMR: δ 8.60-8.45 (m, 1H), 8.10 (d, J=8.4 Hz, 2H), 7.80-7.70 (m, 2H), 7.49 (d, J=8.1 Hz, 1H), 7.38 (d, J=8.4 Hz, 2H), 7.38-7.31 (m, 1H), 7.30-7.20 (m, 1H), 7.14 (d, J=1.8 Hz, 1H), 4.91 (brs, 2H), 3.63 (brd, J=6.3 Hz, 2H), 1.70-1.55 (m, 1H), 0.89 (d, J=6.6 Hz, 6H).

Example 3(25)

N-[4-trifluoromethyl-2-[2-methyl-4-(5-tetrazolyl)phenylmethyloxy]phenyl]-N-isopropyl-2-pyridylsulfonylamide

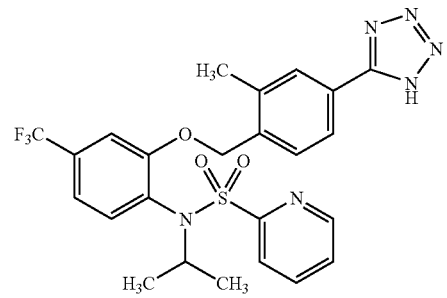

TLC: Rf 0.24 (chloroform:methanol=3:1);

NMR: δ 8.69 (d, J=4.8 Hz, 1H), 7.92-7.75 (m, 4H), 7.58 (d, J=7.8 Hz, 1H), 7.48-7.39 (m, 1H), 7.31-7.18 (m, 3H), 5.03 (s, 2H), 4.72-4.58 (m, 1H), 2.37 (s, 3H), 1.11 and 1.09 (each d, J=6.6 Hz, each 3H).

Example 3(26)

N-[4,5-dimethyl-2-[2-methyl-4-(5-tetrazolyl)phenyl-methyloxy]phenyl]-N-isobutyl-2-pyridylsulfonylamide

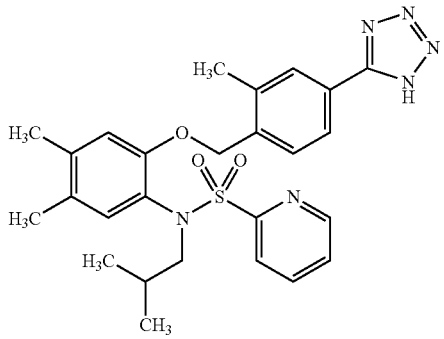

TLC: Rf 0.40 (chloroform:methanol:water=8:2:0.2);
MS (FAB, Pos.): 507 (M+H)$^+$.

Example 3(27)

N-[4,5-dimethyl-2-[2-methyl-4-(5-tetrazolyl)phenyl-methyloxy]phenyl]-N-isobutyl-3-pyridylsulfonylamide

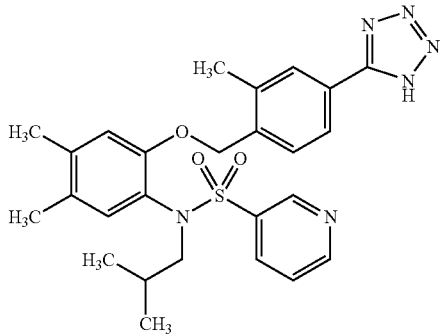

TLC: Rf 0.44 (chloroform:methanol:water=8:2:0.2);
MS (FAB, Pos.): 507 (M+H)$^+$.

Example 3(28)

N-[4-chloro-5-methyl-2-[4-(5-tetrazolyl)phenylmethyloxy]phenyl]-N-isobutyl-3-pyridylsulfonylamide

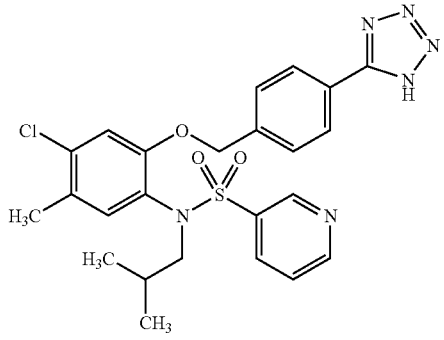

TLC: Rf 0.28 (chloroform:methanol:water=8:2:0.2);
NMR(DMSO-d$_6$): δ 8.69 (d, J=1.8 Hz, 1H), 8.64 (dd, J=4.8, 1.8 Hz, 1H), 8.00 (d, J=8.1 Hz, 2H), 7.98-7.92 (m, 1H), 7.40 (dd, J=8.1, 4.8 Hz, 1H), 7.30 (d, J=8.4 Hz, 2H), 7.27 (s, 1H), 7.24 (s, 1H), 5.17-4.68 (m, 2H), 3.46-3.16 (m, 2H), 2.28 (s, 3H), 1.60-1.42 (m, 1H), 1.00-0.73 (m, 6H).

Example 3(29)

N-[4,5-dimethyl-2-[2-chloro-4-(5-tetrazolyl)phenyl-methyloxy]phenyl]-N-isobutyl-2-pyridylsulfonylamide

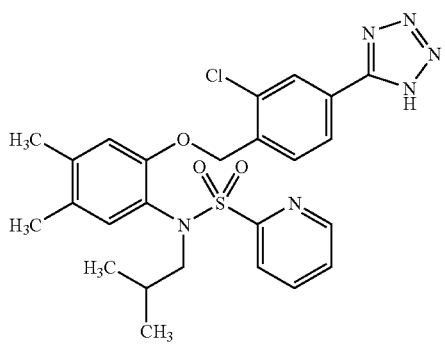

TLC: Rf 0.22 (chloroform:methanol:water=40:10:1);
NMR: δ 8.52 (d, J=4.5 Hz, 1H), 8.20 (d, J=1.5 Hz, 1H), 7.98 (d, J=7.8 Hz, 1H), 7.79 (dt, J=1.5, 8.1 Hz, 1H), 7.71 (d, J=8.1 Hz, 1H), 7.47 (d, J=7.8 Hz, 1H), 7.35-7.30 (m, 1H), 7.04 (s, 1H), 6.63 (s, 1H), 4.90 (br, 1H), 4.64 (br, 1H), 3.67 (br, 1H), 3.57 (br, 1H), 2.21 (s, 3H), 2.15 (s, 3H), 1.80-1.60 (m, 1H), 0.91 (br, 6H).

Example 3(30)

N-[4,5-dimethyl-2-[2-chloro-4-(5-tetrazolyl)phenyl-methyloxy]phenyl]-N-isopropyl-3-pyridylsulfonylamide

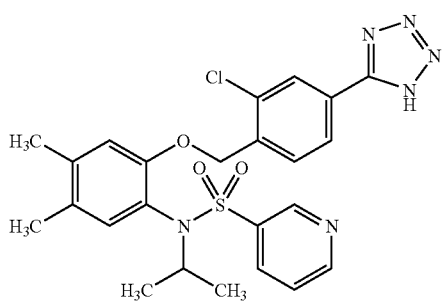

TLC: Rf 0.22 (chloroform:methanol:water=40:10:1);
NMR: δ 9.11 (d, J=1.8 Hz, 1H), 8.61 (dd, J=4.8, 1.5 Hz, 1H), 8.20-8.10 (m, 2H), 7.88 (dd, J=7.8, 1.5 Hz, 1H), 7.42 (dd, J=8.1, 4.8 Hz, 1H), 7.33 (d, J=7.8 Hz, 1H), 7.01 (s, 1H), 6.79 (s, 1H), 4.96 (d, J=13.5 Hz, 1H), 4.93 (d, J=13.5 Hz, 1H), 4.60-4.45 (m, 1H), 2.29 (s, 3H), 2.23 (s, 3H), 1.25 (d, J=6.6 Hz, 3H), 1.11 (d, J=6.6 Hz, 3H).

Example 3(31)

N-[4,5-dimethyl-2-[2-chloro-4-(5-tetrazolyl)phenyl-methyloxy]phenyl]-N-isobutyl-3-pyridylsulfonyla-mide

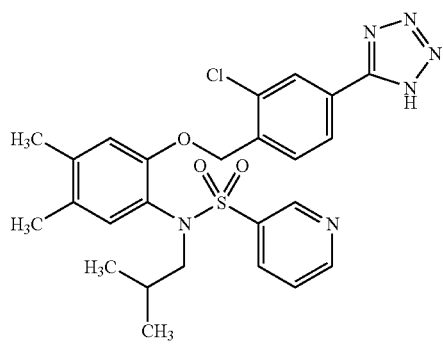

TLC: Rf 0.22 (chloroform:methanol:water=40:10:1);
NMR: δ 8.97 (d, J=1.8 Hz, 1H), 8.55-8.45 (m, 1H), 8.15 (d, J=1.5 Hz, 1H), 7.89 (d, J=7.8 Hz, 1H), 7.83 (dt, J=8.1, 1.8 Hz, 1H), 7.31 (dd, J=8.1, 4.8 Hz, 1H), 7.24 (s, 1H), 7.07 (d, J=7.8 Hz, 1H), 6.75 (s, 1H), 4.89 (d, J=12.5 Hz, 1H), 4.63 (d, J=12.5 Hz, 1H), 3.70-3.60 (m, 1H), 3.45-3.30 (m, 1H), 2.30 (s, 3H), 2.26 (s, 3H), 1.80-1.60 (m, 1H), J=6.6 Hz, 3H), 0.93 (d, J=6.6 Hz, 3H).

Example 3(32)

N-[4,5-dimethyl-2-[4-(5-tetrazolyl)phenylmethy-loxy]phenyl]-N-isopropyl-2-pyridylsulfonylamide

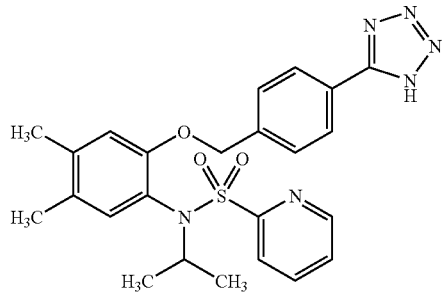

TLC: Rf 0.23 (chloroform:methanol=5:1);
MS (APCI, Neg. 20V): 477 (M−H)⁻.

Example 3(33)

N-[4,5-dimethyl-2-[4-(5-tetrazolyl)phenylmethy-loxy]phenyl]-N-isobutyl-2-pyridylsulfonylamide

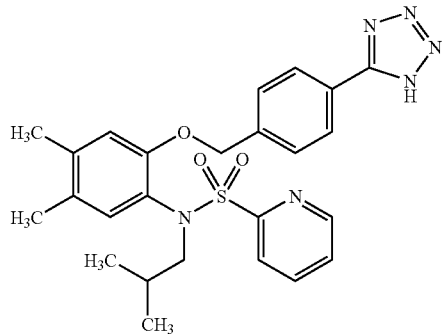

TLC: Rf 0.23 (chloroform:methanol=5:1);
MS (APCI, Neg. 20V): 491 (M−H)⁻.

Example 3(34)

N-[4,5-dimethyl-2-[4-(5-tetrazolyl)phenylmethy-loxy]phenyl]-N-isobutyl-3-pyridylsulfonylamide

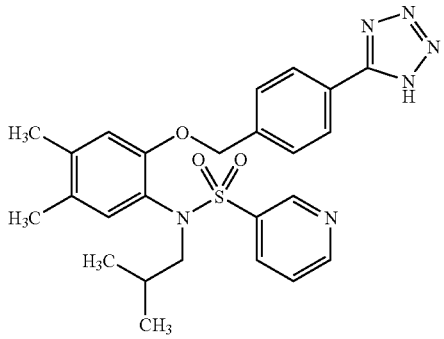

TLC: Rf 0.23 (chloroform:methanol=5:1);
MS (APCI, Neg. 20V): 491 (M−H)⁻.

Example 3(35)

N-[4-chloro-5-methyl-2-[2-methyl-4-(5-tetrazolyl)phenylmethyloxy]phenyl]-N-isopropyl-2-pyridylsul-fonylamide

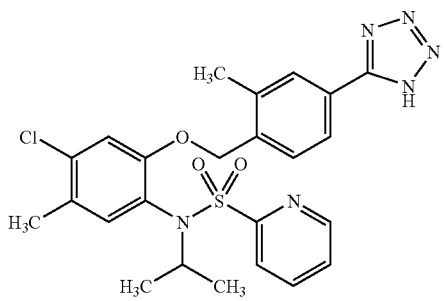

TLC: Rf 0.30 (chloroform:methanol:water=8:2:0.2);
NMR(DMSO-d₆): δ 8.67 (d, J=3.6 Hz, 1H), 7.98-7.88 (m, 2H), 7.85-7.78 (m, 2H), 7.55-7.48 (m, 2H), 7.37 (s, 1H), 7.04 (s, 1H), 5.10 (ABd, J=13.2 Hz) and 5.04 (ABd, J=13.2 Hz) total 2H, 4.49 (sept, J=6.9 Hz, 1H), 2.36 (s, 3H), 2.23 (s, 3H), 1.02 (d, J=6.9 Hz) and 0.99 (d, J=6.9 Hz) total 6H.

Example 3(36)

N-[4-chloro-5-methyl-2-[2-methyl-4-(5-tetrazolyl)phenylmethyloxy]phenyl]-N-isobutyl-2-pyridylsulfo-nylamide

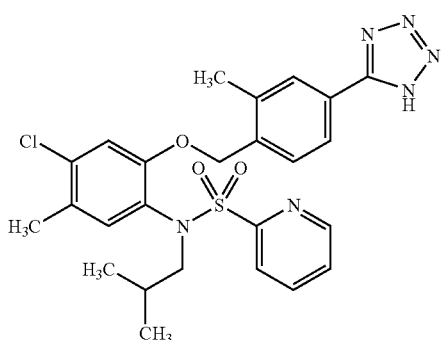

TLC: Rf 0.26 (chloroform:methanol:water=8:2:0.2);

NMR(DMSO-$d_6$): δ 8.48 (m, 1H), 7.93-7.85 (m) and 7.90 (dd, J=7.8, 1.8 Hz) total 2H, 7.81 (d, J=8.1 Hz, 1H), 7.68 (d, J=8.1 Hz, 1H), 7.44 (ddd, J=7.8, 4.8, 1.2 Hz, 1H), 7.29 (s) and 7.27 (d, J=7.8 Hz) total 2H, 7.20 (s, 1H), 4.92 (m, 2H), 3.47 (m, 2H), 2.31 (s, 3H), 2.23 (s, 3H), 1.50 (m, 1H), 0.81 (d, J=6.6 Hz, 6H).

Example 3(37)

N-[4,5-dimethyl-2-[2-methoxy-4-(5-tetrazolyl)phenylmethyloxy]phenyl]-N-isobutyl-2-pyridylsulfonylamide

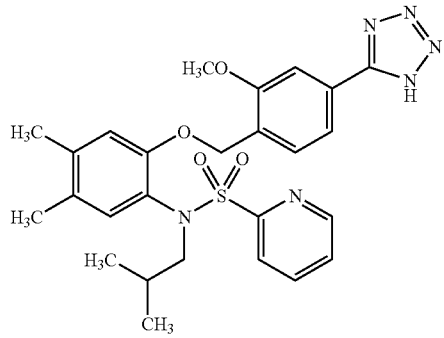

TLC: Rf 0.23 (dichloromethane:methanol=10:1);
MS (FAB, Pos.): 523 (M+H)$^+$.

Example 3(38)

N-[4,5-dimethyl-2-[2-methoxy-4-(5-tetrazolyl)phenylmethyloxy]phenyl]-N-isopropyl-2-pyridylsulfonylamide

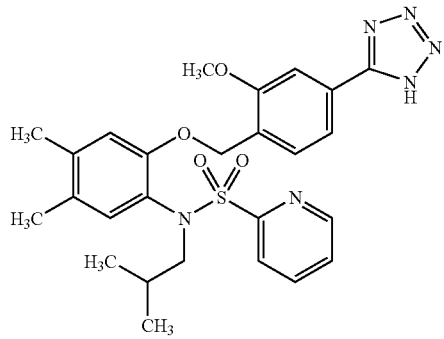

TLC: Rf 0.23 (chloroform:methanol=10:1);

Reference Example 5

N-[4,5-dimethyl-2-[2-methyl-4-(N-hydroxyamidino)phenylmethyloxy]phenyl]-N-isobutyl-(5-methyl-2-furyl)sulfonylamide

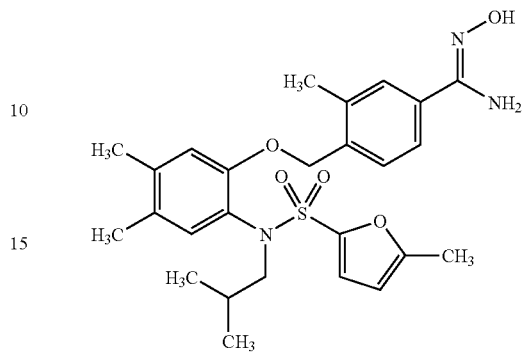

To a solution of N-[4,5-dimethyl-2-(2-methyl-4-cyanophenylmethyloxy)phenyl]-N-isobutyl-(5-methyl-2-furyl)sulfonylamide prepared in Reference Example 4 (70 mg) in ethanol (2 ml), triethylamine (42 μl) and hydroxylamine hydrogen chloride salt (21 mg) were added at room temperature, then mixture was refluxed for 5 hours. After termination of reaction, the reaction mixture was poured into ethyl acetate-water. The organic layer was washed, dried and concentrated under reduced pressure to give the title compound (80 mg) having the following physical data.
TLC: Rf 0.38 (n-hexane:ethyl acetate=2:3).

Example 4

N-[4,5-dimethyl-2-[2-methyl-4-(5-oxo-1,2,4-oxadiazol-3-yl)phenylmethyloxy]phenyl]-N-isobutyl-(5-methyl-2-furyl)sulfonylamide

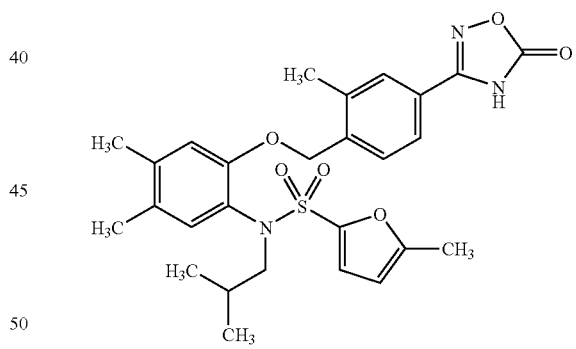

To a solution of N-[4,5-dimethyl-2-[2-methyl-4-(N-hydroxyamidino)phenylmethyloxy]phenyl]-N-isobutyl-(5-methyl-2-furyl)sulfonylamide prepared in Reference Example 5 (78 mg) in N,N-dimethylformamide (1 ml), pyridine (16 μl) and chloro formic acid 2-ethylhexyl ester (30 μl) were added and the mixture was stirred for 1 hour at 0° C. After termination of reaction, the reaction mixture was poured into ethyl acetate-water. The organic layer was washed, dried and concentrated under reduced pressure. To the residue, xylenes (2 ml) were added, and the mixture was refluxed for 6 hours at 140° C. After termination of reaction, the reaction mixture was concentrated under reduced pressure. The residue was purified by column chromatography on silica gel (hexane-ethyl acetate) to give the title compound (42 mg) having the following physical data.

TLC: Rf 0.43 (chloroform:methanol=19:1);

NMR: δ 10.69 (br, 1H), 7.62 (s, 1H), 7.59 (d, J=8.1 Hz, 1H), 7.54 (d, J=8.1 Hz, 1H), 6.97 (s, 1H), 6.78 (d, J=3.3 Hz, 1H), 6.71 (s, 1H), 6.00 (d, J=3.3 Hz, 1H), 4.94 (br, 2H), 3.46 (d, J=7.5 Hz, 2H), 2.39 (s, 3H), 2.24 (s, 3H), 2.19 (s, 3H), 2.18 (s, 3H), 1.70-1.55 (m, 1H), 0.89 (d, J=6.6 Hz, 6H).

Example 4(1) to Example 4(22)

By the same procedures as described in Reference Examples 1 to 5 and Example 4, the compounds having the following physical data were obtained.

Example 4(1)

N-[4-chloro-5-methyl-2-[4-(5-oxo-1,2,4-oxadiazol-3-yl)phenylmethyloxy]phenyl]-N-isopropyl-(5-methyl-2-furyl)sulfonylamide

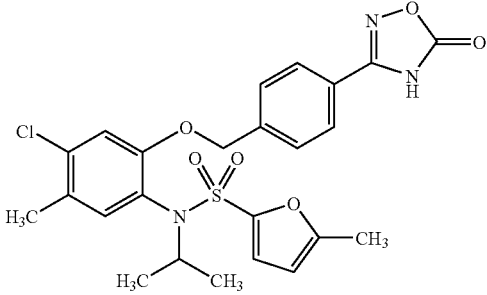

TLC: Rf 0.40 (chloroform:methanol=19:1);

NMR: δ 10.81 (br, 1H), 7.79 (d, J=8.3 Hz, 2H), 7.63 (d, J=8.3 Hz, 2H), 6.97 (s, 1H), 6.92 (s, 1H), 6.84 (d, J=3.3 Hz, 1H), 6.10-6.00 (m, 1H), 5.07 (s, 2H), 4.55-4.35 (m, 1H), 2.34 (s, 3H), 2.28 (s, 3H), 1.10 (d, J=6.6 Hz, 3H), 1.07 (d, J=6.6 Hz, 3H).

Example 4(2)

N-[4-chloro-5-methyl-2-[4-(5-oxo-1,2,4-oxadiazol-3-yl)phenylmethyloxy]phenyl]-N-isobutyl-(5-methyl-2-furyl)sulfonylamide

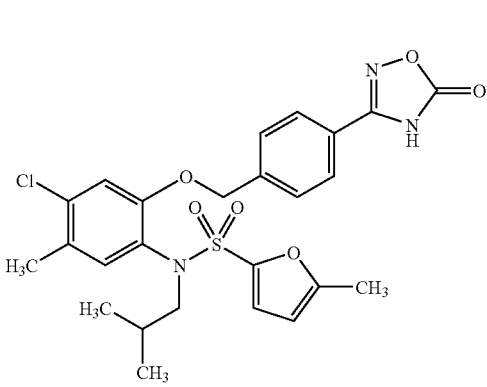

TLC: Rf 0.38 (chloroform:methanol=19:1);

NMR: δ 11.01 (br, 1H), 7.80 (d, J=8.3 Hz, 2H), 7.52 (d, J=8.3 Hz, 2H), 7.10 (s, 1H), 6.92 (s, 1H), 6.78 (d, J=3.3 Hz, 1H), 6.05-5.95 (m, 1H), 5.02 (br, 2H), 3.45 (d, J=7.2 Hz, 2H), 2.29 (s, 3H), 2.20 (s, 3H), 1.70-1.55 (m, 1H), 0.90 (d, J=6.9 Hz, 6H).

Example 4(3)

N-[4,5-dimethyl-2-[2-methyl-4-(5-oxo-1,2,4-oxadiazol-3-yl)phenylmethyloxy]phenyl]-N-isopropyl-(5-methyl-2-furyl)sulfonylamide

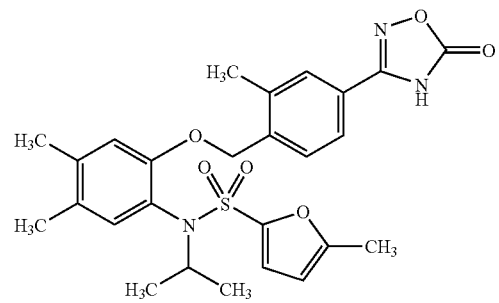

TLC: Rf 0.43 (chloroform:methanol=19:1);

NMR: δ 10.34 (br, 1H), 7.71 (d, J=8.1 Hz, 1H), 7.65-7.55 (m, 2H), 6.86 (d, J=3.3 Hz, 1H), 6.79 (s, 1H), 6.74 (s, 1H), 6.10-6.05 (m, 1H), 4.93 (s, 2H), 4.50-4.40 (m, 1H), 2.37 (s, 3H), 2.34 (s, 3H), 2.26 (s, 3H), 2.17 (s, 3H), 1.09 (d, J=6.6 Hz, 3H), 1.07 (d, J=6.6 Hz, 3H).

Example 4(4)

N-[4,5-dimethyl-2-[4-(5-oxo-1,2,4-oxadiazol-3-yl)phenylmethyloxy]phenyl]-N-isobutyl-(5-methyl-2-furyl)sulfonylamide

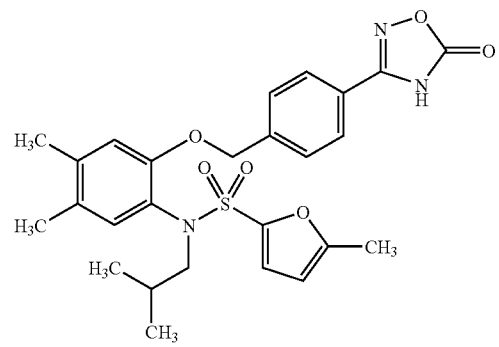

TLC: Rf 0.53 (chloroform:methanol=9:1);

NMR: δ 11.10-10.50 (br, 1H, NH), 7.78 (d, J=8.7 Hz, 2H), 7.52 (d, J=8.7 Hz, 2H), 6.97 (s, 1H), 6.78 (d, J=3.3 Hz, 1H), 6.69 (s, 1H), 6.01-5.98 (m, 1H), 5.15-4.85 (m, 2H), 3.46 (d, J=7.2 Hz, 2H), 2.22 (s, 3H), 2.20 (s, 3H), 2.17 (s, 3H), 1.73-1.60 (m, 1H), 0.90 (d, J=6.9 Hz, 6H).

Example 4(5)

N-[4,5-dimethyl-2-[2-methoxy-4-(5-oxo-1,2,4-oxadiazol-3-yl)phenylmethyloxy]phenyl]-N-isobutyl-(5-methyl-2-furyl)sulfonylamide

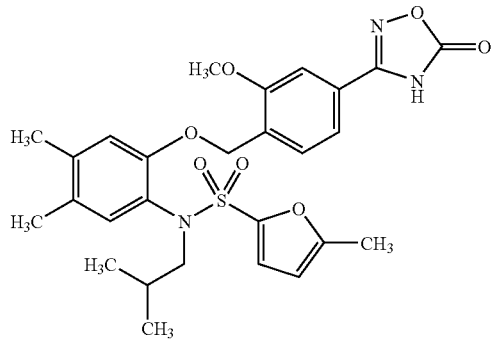

TLC: Rf 0.46 (dichloromethane:methanol=10:1);
MS (FAB, Pos.): 542 (M+H)$^+$.

Example 4(6)

N-[4,5-dimethyl-2-[2-methoxy-4-(5-oxo-1,2,4-oxadiazol-3-yl)phenylmethyloxy]phenyl]-N-isopropyl-(5-methyl-2-furyl)sulfonylamide

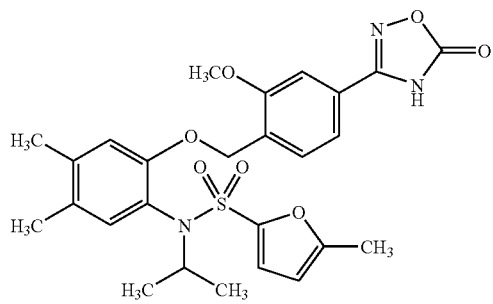

TLC: Rf 0.44 (dichloromethane:methanol=19:1);
NMR: δ 7.68 (d, J=8.1 Hz, 1H), 7.35 (dd, J=8.1, 1.5 Hz, 1H), 7.24 (d, J=1.5 Hz, 1H), 6.91 (d, J=3.3 Hz, 1H), 6.77 (s, 1H), 6.72 (s, 1H), 6.11 (dd, J=3.3, 0.6 Hz, 1H), 4.92 (d, J=14.7 Hz, 1H), 4.83 (d, J=14.7 Hz, 1H), 4.49 (m, 1H), 3.93 (s, 3H), 2.37 (s, 3H), 2.25 (s, 3H), 2.17 (s, 3H), 1.09 (d, J=6.9 Hz, 3H), 1.07 (d, J=6.9 Hz, 3H).

Example 4(7)

N-[4-trifluoromethyl-2-[4-(5-oxo-1,2,4-oxadiazol-3-yl)phenylmethyloxy]phenyl]-N-isopropyl-2-thiazolylsulfonylamide

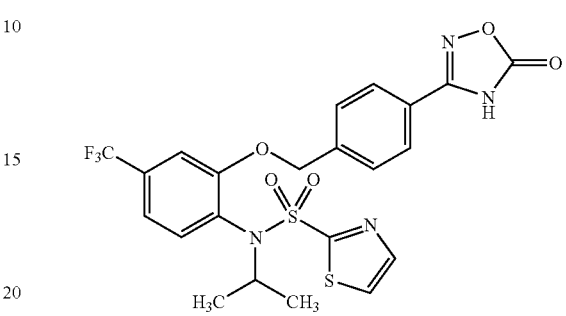

TLC: Rf 0.23 (n-hexane:ethyl acetate=1:1);
NMR: 7.96 (d, J=3.3 Hz, 1H), 7.82 (d, J=8.4 Hz, 2H), 7.65 (d, J=8.4 Hz, 2H), 7.57 (d, J=3.3 Hz, 1H), 7.34-7.22 (m, 3H), 5.19 (s, 2H), 4.68 (sept, J=6.6 Hz, 1H), 1.15 and 1.14 (each d, J=6.6 Hz, each 3H).

Example 4(8)

N-[4-trifluoromethyl-2-[4-(5-oxo-1,2,4-oxadiazol-3-yl)phenylmethyloxy]phenyl]-N-isopropyl-(4-methyl-2-thiazolyl)sulfonylamide

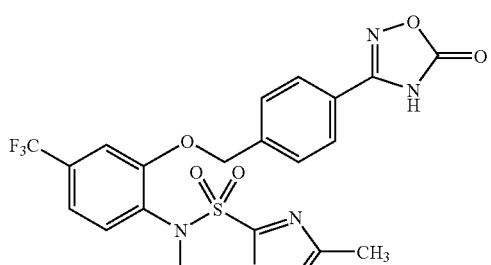

TLC: Rf 0.60 (chloroform:methanol:water=8:2:0.2);
NMR: δ 7.82 (d, J=8.4 Hz, 2H), 7.64 (d, J=8.4 Hz, 2H), 7.32-7.24 (m, 3H), 7.11 (d, J=0.9 Hz, 1H), 5.19 (s, 2H), 4.68 (quint, J=6.6 Hz, 1H), 2.51 (d, J=0.9 Hz, 3H), 1.14 (d, J=6.6 Hz, 6H).

Example 4(9)

N-[4-trifluoromethyl-2-[4-(5-oxo-1,2,4-oxadiazol-3-yl)phenylmethyloxy]phenyl]-N-isobutyl-(4-methyl-2-thiazolyl)sulfonylamide

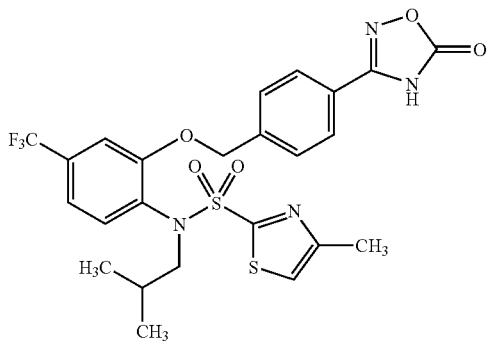

TLC: Rf 0.60 (chloroform:methanol:water=8:2:0.2);

NMR: δ 7.83 (d, J=8.4 Hz, 2H), 7.48 (d, J=8.4 Hz, 2H), 7.45 (d, J=7.8 Hz, 1H), 7.27 (m, 1H), 7.18 (d, J=1.5 Hz, 1H), 7.04 (d, J=0.6 Hz, 1H), 5.05 (br, 2H), 3.60 (d, J=6.9 Hz, 2H), 2.38 (d, J=0.6 Hz, 3H), 1.66 (sep, J=6.9 Hz, 1H), 0.92 (d, J=6.9 Hz, 6H).

Example 4(10)

N-[4-chloro-5-methyl-2-[4-(5-oxo-1,2,4-oxadiazol-3-yl)phenylmethyloxy]phenyl]-N-isobutyl-(4-methyl-2-thiazolyl)sulfonylamide

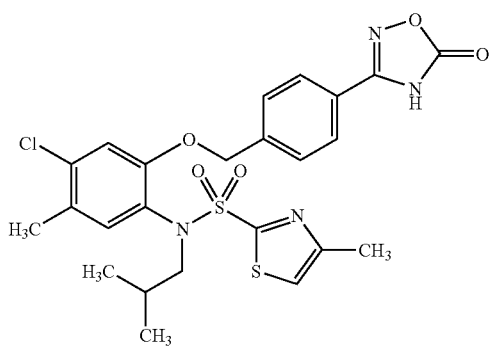

TLC: Rf 0.37 (chloroform:methanol=19:1);

NMR: δ 10.89 (br, 1H), 7.79 (d, J=8.4 Hz, 2H), 7.44 (d, J=8.4 Hz, 2H), 7.17 (s, 1H), 7.01 (s, 1H), 6.92 (s, 1H), 4.99 (br, 1H), 4.87 (br, 1H), 3.57 (br, 2H), 2.36 (s, 3H), 2.27 (s, 3H), 1.80-1.60 (m, 1H), 0.93 (d, J=6.6 Hz, 6H).

Example 4(11)

N-[4-chloro-5-methyl-2-[2-methyl-4-(5-oxo-1,2,4-oxadiazol-3-yl)phenylmethyloxy]phenyl]-N-isobutyl-(4-methyl-2-thiazolyl)sulfonylamide

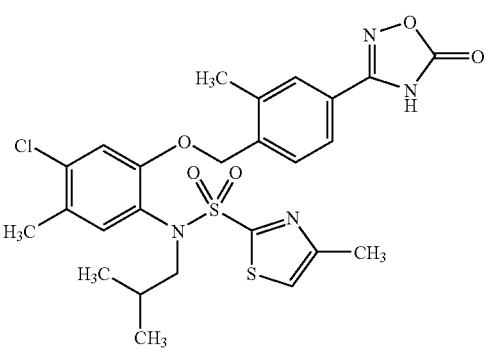

TLC: Rf 0.43 (ethyl acetate);

NMR(DMSO-$d_6$): δ 7.67 (s, 1H), 7.64 (d, J=8.1 Hz, 1H), 7.50 (s, 1H), 7.34 (s, 1H), 7.32 (d, J=8.1 Hz, 1H), 7.21 (s, 1H), 5.06 (brs, 1H), 4.87 (brs, 1H), 3.45 (brs, 2H), 2.33 (s, 3H), 2.27 (s, 3H), 2.22 (s, 3H), 1.70-1.50 (m, 1H), 0.86 (brd, J=6.3 Hz, 6H).

Example 4(12)

N-[4,5-dimethyl-2-[2-methyl-4-(5-oxo-1,2,4-oxadiazol-3-yl)phenylmethyloxy]phenyl]-N-isopropyl-(4-methyl-2-thiazolyl)sulfonylamide

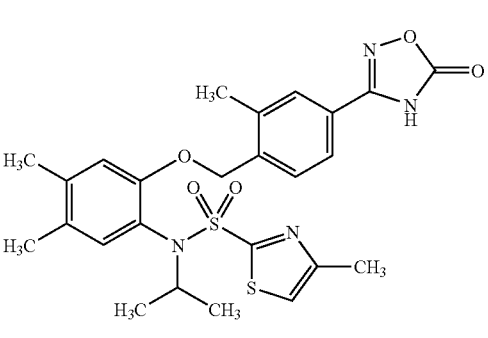

TLC: Rf 0.45 (chloroform:methanol=19:1);

NMR: δ 10.56 (br, 1H), 7.64 (d, J=8.1 Hz, 1H), 7.62 (s, 1H), 7.57 (dd, J=8.1, 1.8 Hz, 1H), 7.07 (s, 1H), 6.83 (s, 1 μl), 6.77 (s, 1H), 4.98 (s, 2H), 4.75-4.60 (m, 1H), 2.49 (s, 3H), 2.39 (s, 3H), 2.25 (s, 3H), 2.16 (s, 3H), 1.14 (d, J=6.6 Hz, 3H), 1.13 (d, J=6.6 Hz, 3H).

Example 4(13)

N-[4,5-dimethyl-2-[2-methyl-4-(5-oxo-1,2,4-oxadiazol-3-yl)phenylmethyloxy]phenyl]-N-isobutyl-(4-methyl-2-thiazolyl)sulfonylamide

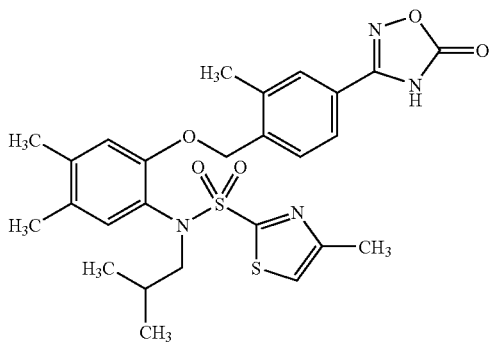

TLC: Rf 0.45 (chloroform:methanol=19:1);

NMR: δ 10.95 (br, 1H), 7.62 (s, 1H), 7.59 (d, J=8.1 Hz, 1H), 7.40 (d, J=8.1 Hz, 1H), 7.03 (s, 1H), 6.99 (s, 1H), 6.71 (s, 1H), 4.91 (br, 1H), 4.82 (br, 1H), 3.57 (br, 2H), 2.37 (s, 3H), 2.34 (s, 3H), 2.24 (s, 3H), 2.17 (s, 3H), 1.80-1.60 (m, 1H), 0.93 (br, 6H).

Example 4(15)

N-[4,5-dimethyl-2-[4-(5-oxo-1,2,4-oxadiazol-3-yl)phenylmethyloxy]phenyl]-N-isobutyl-(4-methyl-2-thiazolyl)sulfonylamide

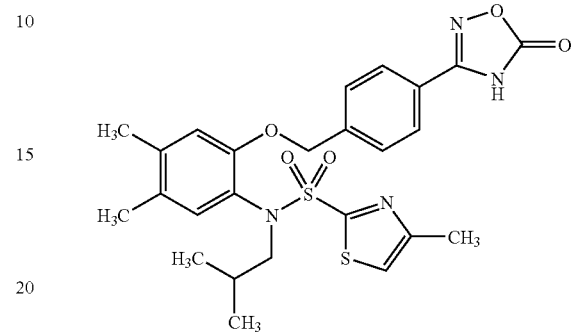

TLC: Rf 0.39 (chloroform:methanol 10:1);

NMR: δ 7.78 (d, J=8.4 Hz, 2H), 7.43 (d, J=8.4 Hz, 2H), 7.03 (s, 1H), 6.97 (d, J=0.9 Hz, 1H), 6.68 (s, 1H), 5.12-4.68 (m, 2H), 3.73-3.42 (m, 2H), 2.35 (d, J=0.9 Hz, 3H), 2.23 (s, 3H), 2.17 (s, 3H), 1.69 (m, 1H), 1.03-0.86 (m, 6H).

Example 4(14)

N-[4,5-dimethyl-2-[4-(5-oxo-1,2,4-oxadiazol-3-yl)phenylmethyloxy]phenyl]-N-isopropyl-(4-methyl-2-thiazolyl)sulfonylamide

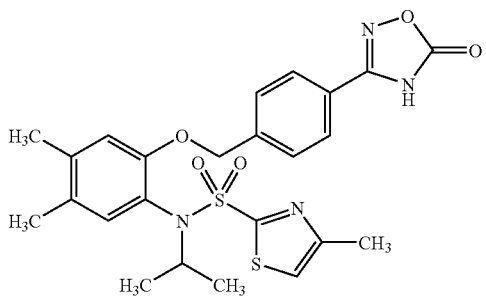

TLC: Rf 0.42 (chloroform:methanol=10:1);

NMR: δ 7.77 (d, J=8.4 Hz, 2H), 7.57 (d, J=8.4 Hz, 2H), 7.06 (d, J=0.9 Hz, 1H), 6.83 (s, 1H), 6.74 (s, 1H), 5.05 (d, J=12.9 Hz, 1H), 5.00 (d, J=12.9 Hz, 1H), 4.68 (m, 1H), 2.49 (d, J=0.9 Hz, 3H), 2.24 (s, 3H), 2.15 (s, 3H), 1.15 (d, J=6.6 Hz, 3H), 1.13 (d, J=6.6 Hz, 3H).

Example 4(16)

N-[4,5-dimethyl-2-[2-methoxy-4-(5-oxo-1,2,4-oxadiazol-3-yl)phenylmethyloxy]phenyl]-N-isopropyl-(4-methyl-2-thiazolyl)sulfonylamide

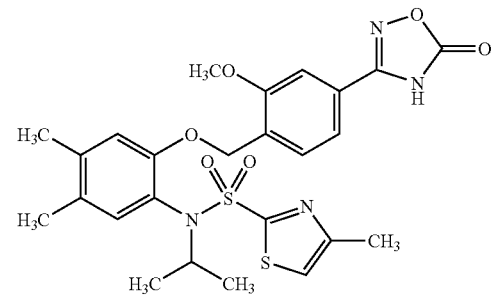

TLC: Rf 0.37 (dichloromethane:methanol=19:1);

NMR: δ 7.63 (d, J=7.8 Hz, 1H), 7.33 (dd, J=7.8, 1.5 Hz, 1H), 7.30 (d, J=1.5 Hz, 1H), 7.08 (brs, 1H), 6.83 (s, 1H), 6.76 (s, 1H), 5.02 (d, J=14.4 Hz, 1H), 4.93 (d, J=14.4 Hz, 1H), 4.69 (m, 1H), 3.93 (s, 3H), 2.49 (d, J=1.2 Hz, 3H), 2.25 (s, 3H), 2.16 (s, 3H), 1.14 (d, J=6.9 Hz, 3H), 1.13 (d, J=6.9 Hz, 3H).

Example 4(17)

N-[4-trifluoromethyl-2-[4-(5-oxo-1,2,4-thiadiazol-3-yl)phenylmethyloxy]phenyl]-N-isopropyl-2-thiazolylsulfonylamide

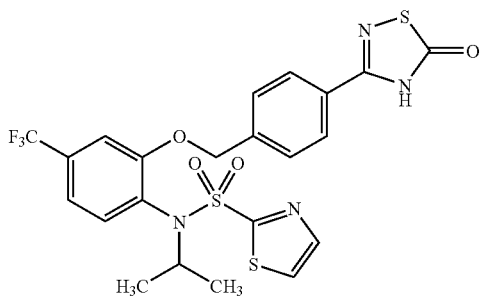

TLC: Rf 0.44 (n-hexane:ethyl acetate=1:1);
NMR: δ 11.41 (brs, 1H), 7.94 (d, J=8.4 Hz, 2H), 7.94 (d, J=3.0 Hz, 1H), 7.60 (d, J=8.4 Hz, 2H), 7.54 (d, J=3.0 Hz, 1H), 7.34-7.20 (m, 3H), 5.16 (s, 2H), 4.69 (sept, J=6.6 Hz, 1H), 1.15 (d, J=6.6 Hz, 6H).

Example 4(18)

N-[4-trifluoromethyl-2-[4-(5-oxo-1,2,4-oxadiazol-3-yl)phenylmethyloxy]phenyl]-N-isobutyl-2-pyridylsulfonylamide

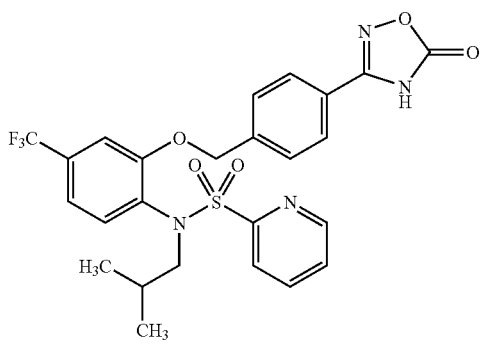

TLC: Rf 0.46 (chloroform:methanol=9:1);
NMR(DMSO-d$_6$): δ 8.60-8.50 (m, 1H), 7.90 (dt, J=1.8, 7.8 Hz, 1H), 7.81 (d, J=8.4 Hz, 2H), 7.72 (d, J=7.5 Hz, 1H), 7.55-7.35 (m, 6H), 5.08 (brs, 2H), 3.52 (brd, J=7.5 Hz, 2H), 1.60-1.40 (m, 1H), 0.83 (d, J=6.6 Hz, 6H).

Example 4(19)

N-[4,5-dimethyl-2-[2-methyl-4-(5-oxo-1,2,4-oxadiazol-3-yl)phenylmethyloxy]phenyl]-N-isopropyl-2-pyridylsulfonylamide

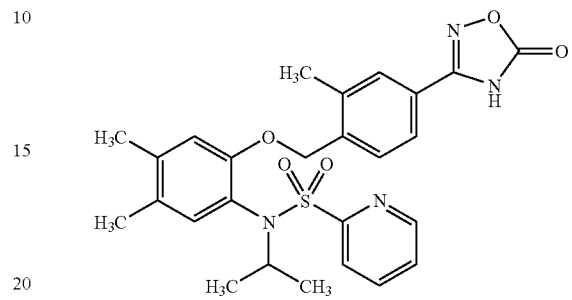

TLC: Rf 0.33 (chloroform:methanol=19:1);
NMR: δ 10.41 (br, 1H), 8.75-8.70 (m, 1H), 7.90 (dd, J=7.8, 0.9 Hz, 1H), 7.80 (dt, J=0.9, 7.8 Hz, 1H), 7.65-7.50 (m, 3H), 7.41 (ddd, J=7.8, 4.8, 0.9 Hz, 1H), 6.78 (s, 1H), 6.72 (s, 1H), 4.87 (d, J=13.4 Hz, 1H), 4.83 (d, J=13.4 Hz, 1H), 4.75-4.60 (m, 1H), 2.34 (s, 3H), 2.25 (s, 3H), 2.13 (s, 3H), 1.10 (d, J=6.6 Hz, 6H).

Example 4(20)

N-[4,5-dimethyl-2-[2-methyl-4-(5-oxo-1,2,4-oxadiazol-3-yl)phenylmethyloxy]phenyl]-N-isobutyl-3-pyridylsulfonylamide

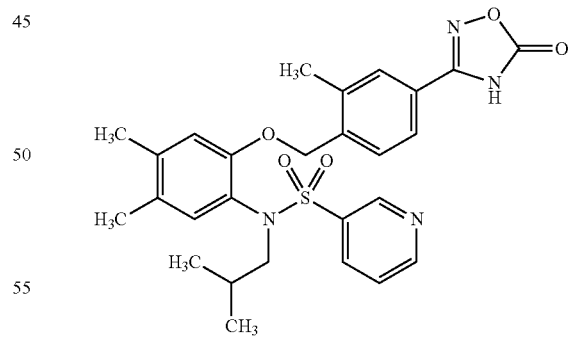

TLC: Rf 0.30 (chloroform:methanol=19:1);
NMR: δ 11.28 (br, 1H), 8.84 (d, J=1.8 Hz, 1H), 8.49 (dd, J=4.8, 1.8 Hz, 1H), 7.87 (dt, J=8.1, 1.8 Hz, 1H), 7.62 (s, 1H), 7.47 (d, J=7.8 Hz, 1H), 7.19 (dd, J=8.1, 4.8 Hz, 1H), 7.15 (s, 1H), 6.97 (d, J=7.8 Hz, 1H), 6.69 (s, 1H), 4.82 (br, 1H), 4.62 (br, 1H), 3.53 (br, 1H), 3.34 (br, 1H), 2.30 (s, 3H), 2.27 (s, 3H), 2.22 (s, 3H), 1.80-1.60 (m, 1H), 1.00 (br, 3H), 0.87 (br, 3H).

Example 4(21)

N-[4,5-dimethyl-2-[2-methoxy-4-(5-oxo-1,2,4-oxadiazol-3-yl)phenylmethyloxy]phenyl]-N-isobutyl-2-pyridylsulfonylamide

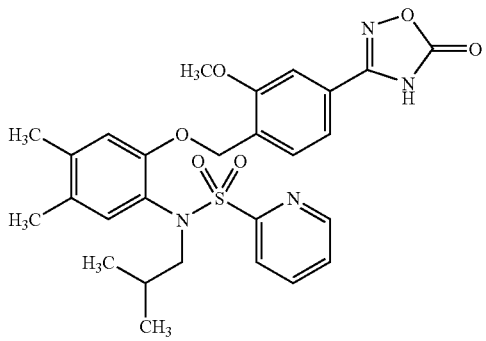

TLC: Rf 0.36 (dichloromethane:methanol=10:1);
MS (FAB, Pos.): 539 (M+H)+.

Example 4(22)

N-[4,5-dimethyl-2-[2-methoxy-4-(5-oxo-1,2,4-oxadiazol-3-yl)phenylmethyloxy]phenyl]-N-isopropyl-2-pyridylsulfonylamide

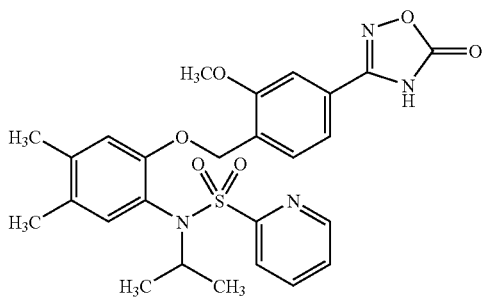

TLC: Rf 0.37 (dichloromethane:methanol=19:1);
NMR: δ 8.73 (ddd, J=4.8, 1.5, 0.9 Hz, 1H), 7.91 (ddd, J=7.8, 1.2, 0.9 Hz, 1H), 7.82 (ddd, J=7.8, 7.8, 1.5 Hz, 1H), 7.57 (d, J=7.8 Hz, 1H), 7.43 (ddd, J=7.8, 4.8, 1.2 Hz, 1H), 7.32 (dd, J=7.8, 1.5 Hz, 1H), 7.26 (m, 1H), 6.76 (s, 1H), 6.72 (s, 1H), 4.88 (d, J=14.1 Hz, 1H), 4.78 (d, J=14.1 Hz, 1H), 4.71 (m, 1H), 3.91 (s, 3H), 2.24 (s, 3H), 2.13 (s, 3H), 1.10 (d, J=6.6 Hz, 3H), 1.09 (d, J=6.6 Hz, 3H).

Example 5(1) to Example 5(63)

By the same procedure as described in Reference Examples 1 to 3 and Example 2, the compounds of the present invention having the following physical data were obtained.

Example 5(1)

3,5-dimethyl-4-[2-[N-isobutyl-N-(5-methyl-2-furylsulfonyl)amino]-5-trifluoromethylphenoxymethyl]benzoic acid

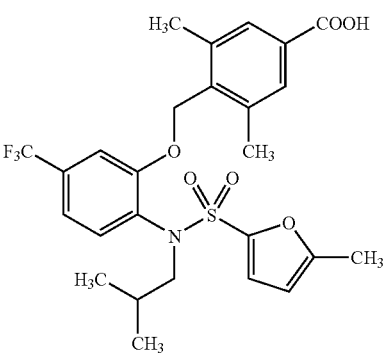

TLC: Rf 0.49 (chloroform:methanol=10:1);
NMR: δ 7.82 (s, 2H), 7.40-7.20 (m, 3H), 6.70 (d, J=3.3 Hz, 1H), 6.00-5.95 (m, 1H), 5.07 (s, 2H), 3.35 (d, J=7.5 Hz, 2H), 2.43 (s, 6H), 2.19 (s, 3H), 1.60-1.45 (m, 1H), 0.79 (d, J=6.6 Hz, 6H).

Example 5(2)

3-methyl-4-[6-[N-(5-methyl-2-furylsulfonyl)-N-(2-methyl-2-propenyl)amino]indan-5-yloxymethyl]benzoic acid

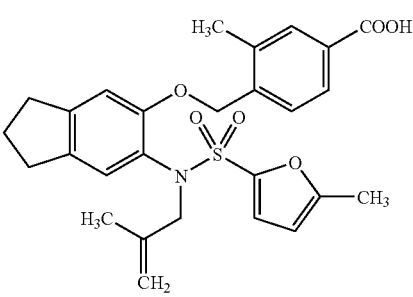

TLC: Rf 0.54 (chloroform:methanol=9:1);
NMR(DMSO-d6): δ 7.80-7.70 (m, 2H), 7.37 (d, J=7.8 Hz, 1H), 7.05 (s, 1H), 6.99 (s, 1H), 6.87 (d, J=3.3 Hz, 1H), 6.17 (d, J=3.3 Hz, 1H), 4.99 (br, 2H), 4.72 (s, 2H), 4.13 (br, 2H), 2.83 (t, J=7.4 Hz, 2H), 2.77 (t, J=7.4 Hz, 2H), 2.32 (s, 3H), 2.08 (s, 3H), 2.05-1.90 (m, 2H), 1.65 (s, 3H).

Example 5(3)

4-[6-[N-cyclopropylmethyl-N-(5-methyl-2-furylsulfonyl)amino]indan-5-yloxymethyl]-3-methylbenzoic acid

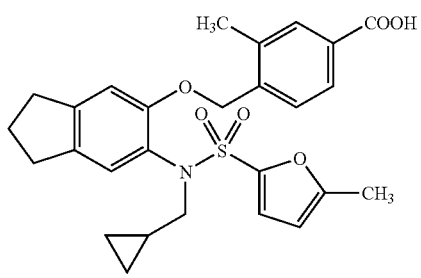

TLC: Rf 0.54 (chloroform:methanol=9:1);

NMR(DMSO-d$_6$): δ 7.77 (s, 1H), 7.74 (d, J=8.1 Hz, 1H), 7.38 (d, J=8.1 Hz, 1H), 7.09 (s, 1H), 7.02 (s, 1H), 6.85 (d, J=3.3 Hz, 1H), 6.20-6.15 (m, 1H), 5.01 (br, 2H), 3.41 (br, 2H), 2.86 (t, J=7.4 Hz, 2H), 2.79 (t, J=7.4 Hz, 2H), 2.32 (s, 3H), 2.10 (s, 3H), 2.10-1.95 (m, 2H), 0.90-0.70 (m, 1H), 0.35-0.25 (m, 2H), 0.05-(−0.05) (m, 2H).

Example 5(4)

4-[3-[N-isobutyl-N-(4-methyl-2-thiazolylsulfonyl)amino]naphthalen-2-yloxymethyl]benzoic acid

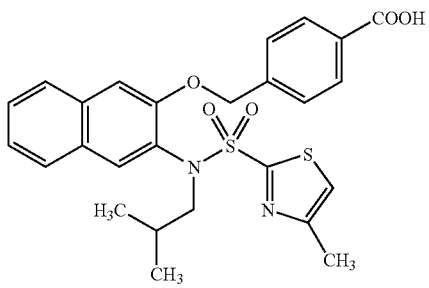

TLC: Rf 0.55 (ethyl acetate:methanol=9:1);

NMR: δ 8.14 (d, J=8.4 Hz, 2H), 7.85 (s, 1H), 7.78 (d, J=8.1 Hz, 1H), 7.70 (d, J=8.1 Hz, 1H), 7.51-7.37 (m, 4H), 7.18 (s, 1H), 6.93 (s, 1H), 5.17 and 4.96 (each br-m, total 2H), 3.85-3.62 (br-m, 2H), 2.34 (s, 3H), 1.82-1.69 (m, 1H), 0.97 (br-s, 6H).

Example 5(5)

4-[3-[N-isopropyl-N-(4-methyl-2-thiazolylsulfonyl)amino]naphthalen-2-yloxymethyl]benzoic acid

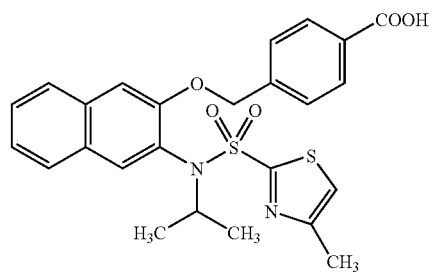

TLC: Rf 0.55 (ethyl acetate:methanol=9:1);

NMR: δ 8.15 (d, J=8.4 Hz, 2H), 7.72 (d, J=9.0 Hz, 2H), 7.61 (s, 1H), 7.60 (d, J=9.0 Hz, 2H), 7.51-7.46 (m, 1H), 7.44-7.35 (m, 1H), 7.24 (s, 1H), 7.03 (s, 1H), 5.24 (s, 2H), 4.84-4.75 (m, 1H), 2.52 (s, 3H), 1.26 (d, J=6.6 Hz, 3H), 1.17 (d, J=6.6 Hz, 3H).

Example 5(6)

4-[3-[N-isobutyl-N-(4-methyl-2-thiazolylsulfonyl)amino]naphthalen-2-yloxymethyl]-3-methylbenzoic acid

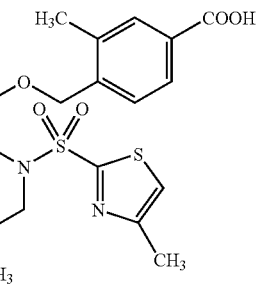

TLC: Rf 0.63 (ethyl acetate:methanol=9:1);

NMR: δ 7.98-7.96 (m, 2H), 7.84 (s, 1H), 7.78 (d, J=8.1 Hz, 1H), 7.72 (d, J=8.1 Hz, 1H), 7.52-7.47 (m, 1H), 7.42-7.37 (m, 2H), 7.21 (s, 1H), 6.95 (s, 1H), 5.10 and 4.96 (each br-m, total 2H), 3.84-3.60 (br-m, 2H), 2.41 (s, 3H), 2.34 (s, 3H), 1.82-1.68 (m, 1H), 0.96 (br-s, 6H).

Example 5(7)

4-[3-[N-isopropyl-N-[2-(4-methylthiazolyl)sulfonyl]amino]naphthalen-2-yloxymethyl]-3-methylbenzoic acid

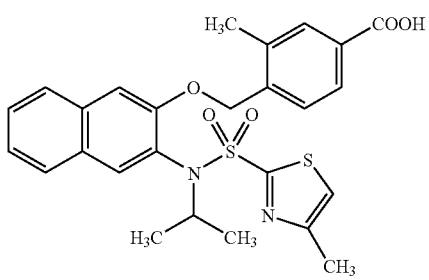

TLC: Rf 0.56 (ethyl acetate:methanol=9:1);
NMR: δ 8.00-7.97 (m, 2H), 7.76-7.65 (m, 3H), 7.61 (s, 1H), 7.52-7.47 (m, 1H), 7.40-7.35 (m, 1H), 7.26 (s, 1H), 7.04 (s, 1H), 5.22 (d, J=15.0 Hz, 1H), 5.17 (d, J=15.0 Hz, 1H), 4.83-4.73 (m, 1H), 2.53 (s, 3H), 2.46 (s, 3H), 1.25 (d, J=6.6 Hz, 3H), 1.16 (d, J=6.6 Hz, 3H).

Example 5(8)

4-[3-[N-isobutyl-N-(4-methyl-2-thiazolylsulfonyl)amino]naphthalen-2-yloxymethyl]cinnamic acid

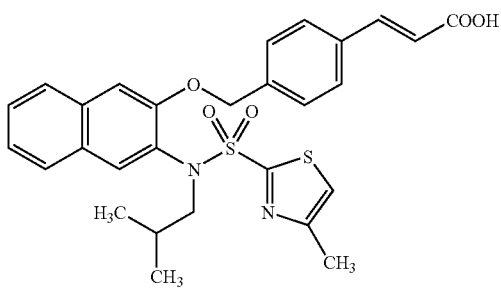

TLC: Rf 0.67 (ethyl acetate:methanol=9:1);
NMR: δ 7.84-7.69 (m, 4H), 7.58 (d, J=8.1 Hz, 2H), 7.51-7.45 (m, 1H), 7.41-7.35 (m, 3H), 7.18 (s, 1H), 6.93 (s, 1H), 6.49 (d, J=16.2 Hz, 1H), 5.02 and 4.91 (each br-m, total 2H), 3.84-3.62 (br-m, 2H), 2.33 (s, 3H), 1.82-1.68 (m, 1H), 0.91 (br-s, 6H).

Example 5(9)

4-[3-[N-isopropyl-N-(4-methyl-2-thiazolylsulfonyl)amino]naphthalen-2-yloxymethyl]cinnamic acid

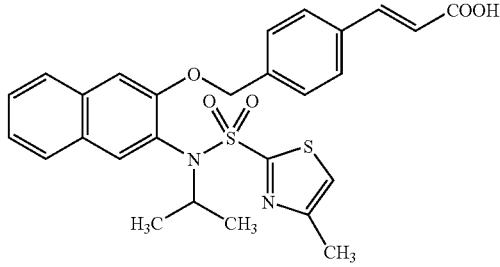

TLC: Rf 0.61 (ethyl acetate:methanol=9:1);
NMR: δ 7.80 (d, J=16.9 Hz, 1H), 7.71 (d, J=8.7 Hz, 2H), 7.61-7.46 (m, 6H), 7.39-7.34 (m, 1H), 7.24 (s, 1H), 7.03 (s, 1H), 6.48 (d, J=16.9 Hz, 1H), 5.19 (s, 2H), 4.85-4.72 (m, 1H), 2.51 (s, 3H), 1.25 (d, J=6.6 Hz, 3H), 1.16 (d, J=6.6 Hz, 3H).

Example 5(10)

3-methyl-4-[6-[N-methyl-N-(5-methyl-2-furylsulfonyl)amino]indan-5-yloxymethyl]benzoic acid

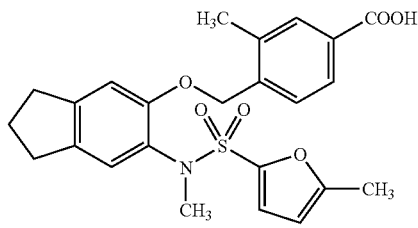

TLC: Rf 0.58 (chloroform:methanol=9:1);
NMR(DMSO-$d_6$): δ 7.77 (s, 1H), 7.74 (d, J=7.8 Hz, 1H), 7.36 (d, J=7.8 Hz, 1H), 7.09 (s, 1H), 6.99 (s, 1H), 6.90 (d, J=3.3 Hz, 1H), 6.25-6.15 (m, 1H), 5.02 (s, 2H), 3.15 (s, 3H), 2.84 (t, J=7.4 Hz, 2H), 2.78 (t, J=7.4 Hz, 2H), 2.32 (s, 3H), 2.12 (s, 3H), 2.10-1.95 (m, 2H).

Example 5(11)

4-[6-[N-ethyl-N-(5-methyl-2-furylsulfonyl)amino]indan-5-yloxymethyl]-3-methylbenzoic acid

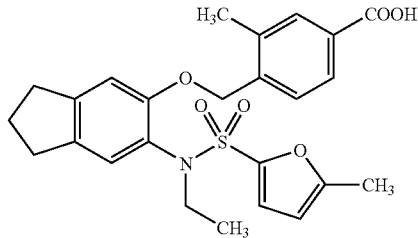

TLC: Rf 0.59 (chloroform:methanol=9:1);
NMR(DMSO-$d_6$): δ 7.77 (s, 1H), 7.74 (d, J=7.8 Hz, 1H), 7.38 (d, J=7.8 Hz, 1H), 7.10 (s, 1H), 6.95 (s, 1H), 6.86 (d, J=3.3 Hz, 1H), 6.16 (d, J=3.3 Hz, 1H), 5.01 (br, 2H), 3.58 (br, 2H), 2.86 (t, J=7.4 Hz, 2H), 2.79 (t, J=7.4 Hz, 2H), 2.32 (s, 3H), 2.10 (s, 3H), 2.10-1.95 (m, 2H), 0.99 (t, J=7.2 Hz, 3H).

Example 5(12)

4-[6-[N-methyl-N-(5-methyl-2-furylsulfonyl)amino]indan-5-yloxymethyl]cinnamic acid

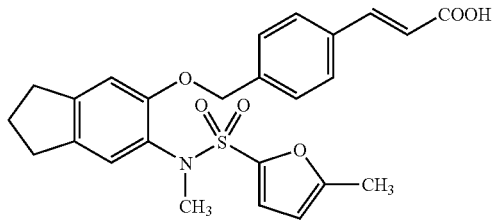

TLC: Rf 0.53 (chloroform:methanol=9:1);
NMR: δ 7.77 (d, J=15.9 Hz, 1H), 7.55 (d, J=8.4 Hz, 2H), 7.37 (d, J=8.4 Hz, 2H), 7.14 (s, 1H), 6.80 (s, 1H), 6.79 (d, J=3.6 Hz, 1H), 6.47 (d, J=15.9 Hz, 1H), 5.97 (d, J=3.6 Hz, 1H), 4.98 (s, 2H), 3.31 (s, 3H), 2.90-2.80 (m, 4H), 2.17 (s, 3H), 2.08 (quint, J=7.5 Hz, 2H).

Example 5(13)

4-[6-[N-ethyl-N-(5-methyl-2-furylsulfonyl)amino]indan-5-yloxymethyl]cinnamic acid

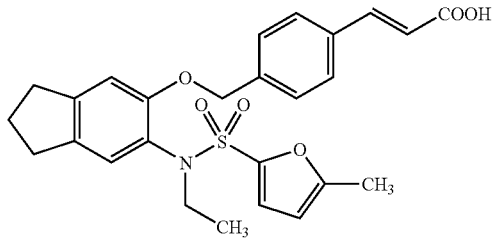

TLC: Rf 0.53 (chloroform:methanol=9:1);
NMR: δ 7.77 (d, J=16.2 Hz, 1H), 7.55 (d, J=8.4 Hz, 2H), 7.37 (d, J=8.4 Hz, 2H), 7.08 (s, 1H), 6.80 (s, 1H), 6.75 (d, J=3.3 Hz, 1H), 6.47 (d, J=16.2 Hz, 1H), 5.94 (d, J=3.3 Hz, 1H), 4.97 (s, 2H), 3.82-3.65 (m, 2H), 2.90-2.80 (m, 4H), 2.15 (s, 3H), 2.08 (quint, J=7.2 Hz, 2H), 1.14 (t, J=7.2 Hz, 3H).

Example 5(14)

4-[6-[N-(5-methyl-2-furylsulfonyl)-N-propylamino]indan-5-yloxymethyl]cinnamic acid

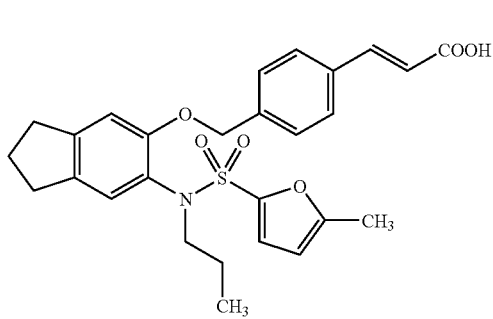

TLC: Rf 0.54 (chloroform:methanol=9:1);
NMR: δ 7.78 (d, J=15.9 Hz, 1H), 7.55 (d, J=8.1 Hz, 2H), 7.37 (d, J=8.1 Hz, 2H), 7.08 (s, 1H), 6.79 (s, 1H), 6.74 (d, J=3.3 Hz, 1H), 6.46 (d, J=15.9 Hz, 1H), 5.94 (brd, J=3.3 Hz, 1H), 4.97 (br s, 2H), 3.65-3.61 (m, 2H), 2.90-2.80 (m, 4H), 2.15 (s, 3H), 2.08 (quint, J=7.5 Hz, 2H), 1.53 (sext, J=7.2 Hz, 2H), 0.89 (t, J=7.2 Hz, 3H).

Example 5(15)

4-[4,5-dimethyl-2-[N-(5-methyl-2-furylsulfonyl)-N-(2-methyl-2-propenyl)amino]phenoxymethyl]-3-methylbenzoic acid

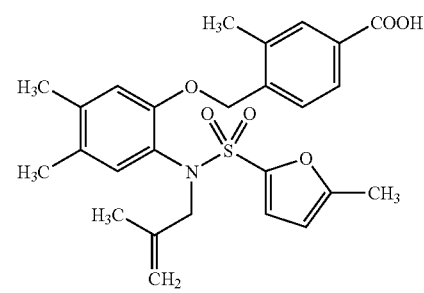

TLC: Rf 0.45 (chloroform:methanol=9:1);
NMR: δ 8.00-7.93 (m, 2H), 7.44 (d, J=8.1 Hz, 1H), 7.02 (s, 1H), 6.75 (d, J=3.3 Hz, 1H), 6.69 (s, 1H), 5.96 (m, 1H), 4.94 (s, 2H), 4.77 (s, 2H), 4.27 (s, 2H), 2.38 (s, 3H), 2.22 (s, 3H), 2.18 (s, 3H), 2.12 (s, 3H), 1.78 (s, 3H).

Example 5(16)

4-[6-[N-(5-methyl-2-furylsulfonyl)-N-(2-methyl-2-propenyl)amino]indan-5-yloxymethyl]cinnamic acid

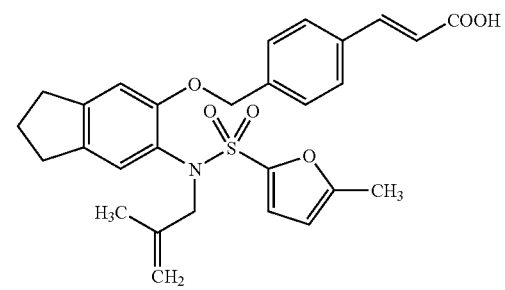

TLC: Rf 0.61 (chloroform:methanol=9:1);
NMR: δ 7.78 (d, J=15.9 Hz, 1H), 7.56 (d, J=8.4 Hz, 2H), 7.36 (d, J=8.4 Hz, 2H), 7.09 (s, 1H), 6.76 (s, 1H), 6.74 (d, J=3.0 Hz, 1H), 6.47 (d, J=15.9 Hz, 1H), 5.94 (d, J=3.0 Hz, 1H), 4.95 (brs, 2H), 4.77 (s, 2H), 4.38-4.18 (m, 2H), 2.90-2.75 (m, 4H), 2.14 (s, 3H), 2.07 (quint, J=7.5 Hz, 2H), 1.78 (s, 3H).

Example 5(17)

4-[6-[N-cyclopropylmethyl-N-(5-methyl-2-furylsulfonyl)amino]indan-5-yloxymethyl]cinnamic acid

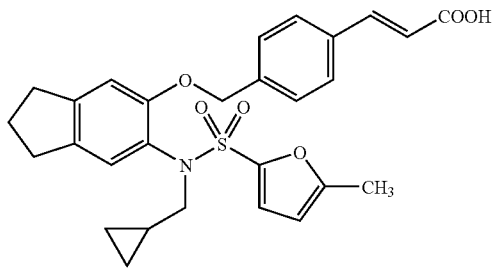

TLC: Rf 0.51 (chloroform:methanol=9:1);
NMR: δ 7.79 (d, J=15.9 Hz, 1H), 7.55 (d, J=8.4 Hz, 2H), 7.38 (d, J=8.4 Hz, 2H), 7.15 (s, 1H), 6.79 (s, 1H), 6.74 (d, J=3.3 Hz, 1H), 6.47 (d, J=15.9 Hz, 1H), 5.94 (d, J=3.3 Hz, 1H), 4.97 (brs, 2H), 3.65-3.50 (m, 2H), 2.92-2.70 (m, 4H), 2.15 (s, 3H), 2.08 (quint, J=7.5 Hz, 2H), 1.00-0.85 (m, 1H), 0.45-0.36 (m, 2H), 0.20-0.05 (m, 2H).

Example 5(18)

4-[6-[N-(5-methyl-2-furylsulfonyl)-N-(2-propenyl)amino]indan-5-yloxymethyl]cinnamic acid

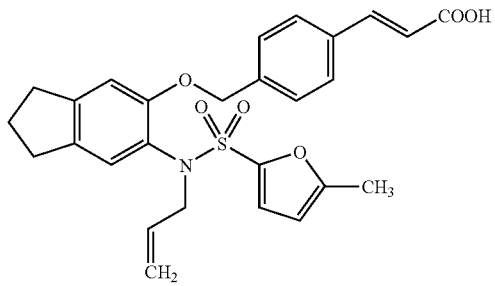

TLC: Rf 0.57 (chloroform:methanol=9:1);
NMR: δ 7.79 (d, J=15.9 Hz, 1H), 7.56 (d, J=8.4 Hz, 2H), 7.38 (d, J=8.4 Hz, 2H), 7.07 (s, 1H), 6.78 (s, 1H), 6.76 (d, J=3.3 Hz, 1H), 6.47 (d, J=15.9 Hz, 1H), 5.96 (d, J=3.3 Hz, 1H), 5.96-5.77 (m, 1H), 5.13-5.03 (m, 2H), 4.97 (s, 2H), 4.42-4.20 (m, 2H), 2.90-2.80 (m, 4H), 2.16 (s, 3H), 2.07 (quint, J=7.5 Hz, 2H).

Example 5(19)

3-methyl-4-[6-[N-(5-methyl-2-furylsulfonyl)-N-propylamino]indan-5-yloxymethyl]benzoic acid

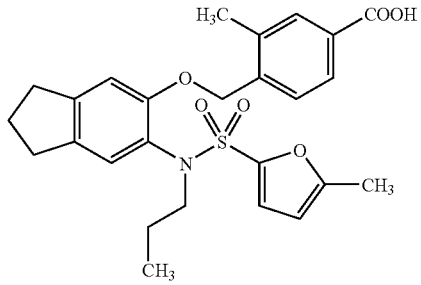

TLC: Rf 0.40 (chloroform:methanol=10:1);
NMR: δ 7.95 (d, J=7.8 Hz, 1H), 7.93 (s, 1H), 7.46 (d, J=7.8 Hz, 1H), 7.10 (s, 1H), 6.81 (s, 1H), 6.75 (d, J=3.3 Hz, 1H), 5.95 (dd, J=3.3, 0.9 Hz, 1H), 4.96 (s, 2H), 3.76-3.47 (m, 2H), 2.92-2.82 (m, 4H), 2.37 (s, 3H), 2.13 (s, 3H), 2.15-2.03 (m, 2H), 1.60-1.47 (m, 2H), 0.89 (t, J=7.5 Hz, 3H).

Example 5(20)

3-methyl-4-[6-[N-(5-methyl-2-furylsulfonyl)-N-(2-propenyl)amino]indan-5-yloxymethyl]benzoic acid

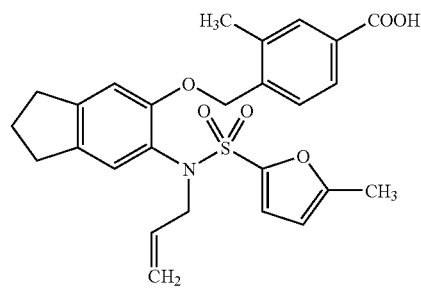

TLC: Rf 0.41 (chloroform:methanol=10:1);
NMR: 7.95 (d, J=7.8 Hz, 1H), 7.94 (s, 1H), 7.47 (d, J=7.8 Hz, 1H), 7.08 (s, 1H), 6.80 (s, 1H), 6.78 (d, J=3.3 Hz, 1H), 5.97 (d, J=3.3 Hz, 1H), 5.85 (m, 1H), 5.10 (dd, J=16.8, 1.2 Hz, 1H), 5.05 (dd, J=9.9, 1.2 Hz, 1H), 4.97 (s, 2H), 4.43-4.18 (m, 2H), 2.91-2.81 (m, 4H), 2.37 (s, 3H), 2.15 (s, 3H), 2.13-2.03 (m, 2H).

Example 5(21)

4-[4,5-dimethyl-2-[N-methyl-N-(4-methyl-2-thiazolylsulfonyl)amino]phenoxymethyl]-3-methylbenzoic acid

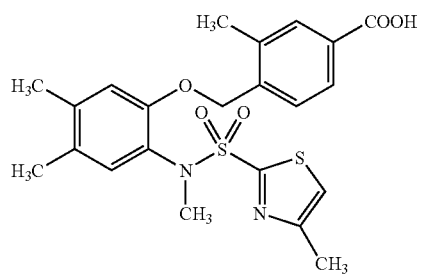

TLC: Rf 0.49 (dichloromethane:methanol=10:1);
NMR: δ 7.94-7.90 (m, 2H), 7.31 (d, J=9.0 Hz, 1H), 7.13 (s, 1H), 6.94 (m, 1H), 6.73 (s, 1H), 4.88 (s, 2H), 3.42 (s, 3H), 2.35 (s, 3H), 2.34 (d, J=0.9 Hz, 3H), 2.24 (s, 3H), 2.19 (s, 3H).

Example 5(22)

4-[4,5-dimethyl-2-[N-ethyl-N-(4-methyl-2-thiazolyl-sulfonyl)amino]phenoxymethyl]-3-methylbenzoic acid

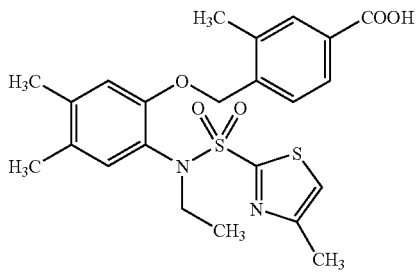

TLC: Rf 0.49 (dichloromethane:methanol=10:1);
NMR: δ 7.96-7.90 (m, 2H), 7.32 (d, J=8.1 Hz, 1H), 7.06 (s, 1H), 6.90 (m, 1H), 6.74 (s, 1H), 4.87 (brs, 2H), 3.85 (br, 2H), 2.34 (s, 3H), 2.32 (d, J=0.9 Hz, 3H), 2.25 (s, 3H), 2.19 (s, 3H), 1.18 (t, J=7.2 Hz, 3H).

Example 5(23)

4-[4,5-dimethyl-2-[N-(4-methyl-2-thiazolylsulfonyl)-N-propylamino]phenoxymethyl]-3-methylbenzoic acid

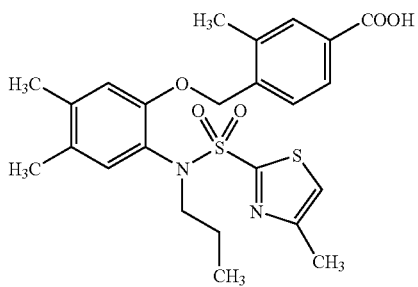

TLC: Rf 0.49 (dichloromethane:methanol=10:1);
NMR(DMSO-$d_6$): δ 12.88 (s, 1H), 7.78-7.72 (m, 2H), 7.49 (m, 1H), 7.25 (d, J=7.8 Hz, 1H), 7.03 (s, 1H), 6.95 (s, 1H), 4.88 (br, 2H), 3.59 (br, 2H), 2.28 (s, 3H), 2.22 (s, 3H), 2.18 (s, 3H), 2.13 (s, 3H), 1.44-1.35 (m, 2H), 0.81 (t, J=7.2 Hz, 3H).

Example 5(24)

4-[4,5-dimethyl-2-[N-(4-methyl-2-thiazolylsulfonyl)-N-(2-propenyl)amino]phenoxymethyl]-3-methylbenzoic acid

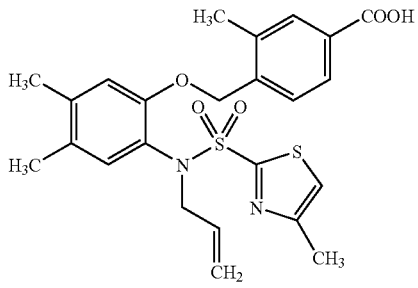

TLC: Rf 0.49 (dichloromethane:methanol=10:1);
NMR(DMSO-$d_6$): δ 12.88 (s, 1H), 7.78-7.72 (m, 2H), 7.50 (s, 1H), 7.26 (d, J=7.5 Hz, 1H), 7.01 (s, 1H), 6.95 (s, 1H), 5.74 (m, 1H), 5.09 (d, J=17.1 Hz, 1H), 5.04 (d, J=9.9 Hz, 1H), 4.89 (br, 2H), 4.27 (br, 2H), 2.29 (s, 3H), 2.21 (s, 3H), 2.18 (s, 3H), 2.12 (s, 3H).

Example 5(25)

4-[2-[N-cyclopropylmethyl-N-(4-methyl-2-thiazolyl-sulfonyl)amino-4,5-dimethyl]phenoxymethyl]-3-methylbenzoic acid

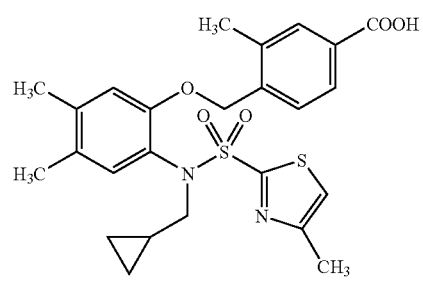

TLC: Rf 0.49 (dichloromethane:methanol=10:1);
NMR(DMSO-$d_6$): δ 12.87 (br, 1H), 7.78-7.72 (m, 2H), 7.48 (s, 1H), 7.25 (d, J=7.5 Hz, 1H), 7.03 (s, 1H), 7.00 (s, 1H), 4.90 (br, 2H), 3.45 (br, 2H), 2.27 (s, 3H), 2.23 (s, 3H), 2.17 (s, 3H), 2.14 (s, 3H), 0.82 (m, 1H), 0.38-0.30 (m, 2H), 0.10-0.02 (m, 2H).

Example 5(26)

4-[4,5-dimethyl-2-[N-(2-hydroxy-2-methylpropyl)-N-(4-methyl-2-thiazolylsulfonyl)amino]phenoxymethyl]-3-methylbenzoic acid

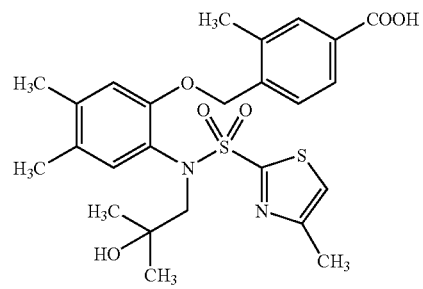

TLC: Rf 0.49 (dichloromethane:methanol=10:1);
NMR: δ 7.99-7.94 (m, 2H), 7.47 (d, J=8.1 Hz, 1H), 7.04 (m, 1H), 6.79 (s, 1H), 6.77 (s, 1H), 5.06 (d, J=12.3 Hz, 1H), 4.95 (d, J=12.3 Hz, 1H), 3.95 (d, J=15.3 Hz, 1H), 3.73 (d, J=15.3 Hz, 1H), 2.420 (s, 3H), 2.417 (s, 3H), 2.23 (s, 3H), 2.11 (s, 3H), 1.25 (s, 3H), 1.21 (s, 3H).

Example 5(27)

4-[4,5-dimethyl-2-[N-methyl-N-(5-methyl-2-furyl-sulfonyl)amino]phenoxymethyl]benzoic acid

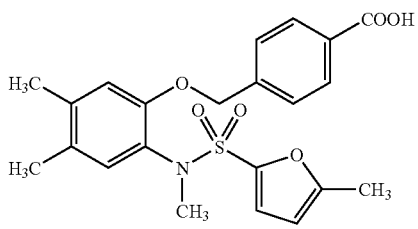

TLC: Rf 0.46 (chloroform:methanol=9:1);

NMR: δ 8.11 (d, J=8.4 Hz, 2H), 7.42 (d, J=8.4 Hz, 2H), 7.08 (s, 1H), 6.79 (d, J=3.3 Hz, 1H), 6.71 (s, 1H), 5.99-5.95 (m, 1H), 5.03 (s, 2H), 3.31 (s, 3H), 2.22 (s, 3H), 2.18 (s, 3H), 2.16 (s, 3H).

Example 5(28)

4-[4,5-dimethyl-2-[N-ethyl-N-(5-methyl-2-furylsul-fonyl)amino]phenoxymethyl]benzoic acid

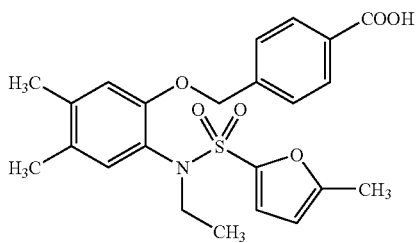

TLC: Rf 0.41 (chloroform:methanol=9:1);

NMR: δ 8.10 (d, J=8.4 Hz, 2H), 7.43 (d, J=8.4 Hz, 2H), 7.01 (s, 1H), 6.76 (d, J=3.3 Hz, 1H), 6.71 (s, 1H), 5.96-5.93 (m, 1H), 5.02 (s, 2H), 3.83-3.65 (m, 2H), 2.23 (s, 3H), 2.18 (s, 3H), 2.14 (s, 3H), 1.14 (t, J=7.2 Hz, 3H).

Example 5(29)

4-[4,5-dimethyl-2-[N-(5-methyl-2-furylsulfonyl)-N-propylamino]phenoxymethyl]benzoic acid

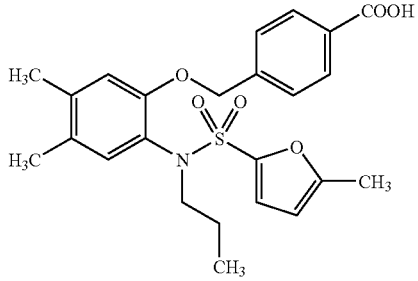

TLC: Rf 0.43 (chloroform:methanol=9:1);

NMR: δ 8.11 (d, J=8.4 Hz, 2H), 7.43 (d, J=8.4 Hz, 2H), 7.02 (s, 1H), 6.74 (d, J=3.0 Hz, 1H), 6.70 (s, 1H), 5.96-5.93 (m, 1H), 5.01 (s, 2H), 3.75-3.53 (m, 2H), 2.22 (s, 3H), 2.18 (s, 3H), 2.14 (s, 3H), 1.60-1.46 (m, 2H), 0.90 (t, J=7.2 Hz, 3H).

Example 5(30)

4-[6-[N-(2-methyl-2-propenyl)-N-(4-methyl-2-thiaz-olylsulfonyl)amino]indan-5-yloxymethyl]benzoic acid

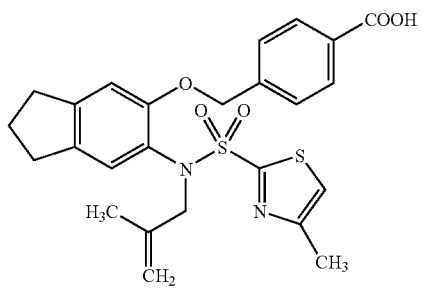

TLC: Rf 0.36 (dichloromethane:methanol=19:1);

NMR: δ 8.11 (d, J=8.7 Hz, 2H), 7.35 (d, J=8.7 Hz, 2H), 7.14 (s, 1H), 6.92 (brs, 1H), 6.74 (s, 1H), 5.10-4.70 (brs, 2H), 4.80 (brs, 2H), 4.60-4.20 (brs, 2H), 2.88-2.82 (m, 4H), 2.32 (d, J=0.9 Hz, 3H), 2.07 (m, 2H), 1.83 (s, 3H).

Example 5(31)

4-[6-[N-(4-methyl-2-thiazolylsulfonyl)-N-(2-prope-nyl)amino]indan-5-yloxymethyl]benzoic acid

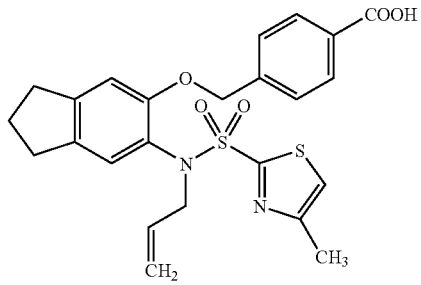

TLC: Rf 0.34 (dichloromethane:methanol=19:1);

NMR: 8.11 (d, J=8.7 Hz, 2H), 7.35 (d, J=8.7 Hz, 2H), 7.13 (s, 1H), 6.93 (brs, 1H), 6.76 (s, 1H), 5.89 (ddt, J=17.1, 10.2, 6.3 Hz, 1H), 5.17-5.06 (m, 2H), 4.92 (brs, 2H), 4.70-4.10 (brs, 2H), 2.89-2.83 (m, 4H), 2.34 (d, J=0.9 Hz, 3H), 2.08 (m, 2H).

Example 5(32)

4-[6-[N-cyclopropylmethyl-N-(4-methyl-2-thiazolyl-sulfonyl)amino]indan-5-yloxymethyl]benzoic acid

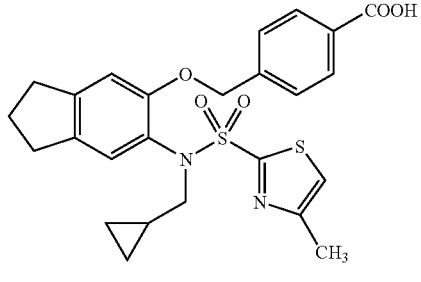

TLC: Rf 0.36 (dichloromethane:methanol=19:1);

NMR: δ 8.10 (d, J=8.7 Hz, 2H), 7.35 (d, J=8.7 Hz, 2H), 7.22 (s, 1H), 6.89 (brs, 1H), 6.78 (s, 1H), 5.10-4.70 (m, 2H), 3.90-3.50 (m, 2H), 2.90-2.85 (m, 4H), 2.32 (d, J=0.9 Hz, 3H), 2.09 (m, 2H), 1.00 (m, 1H), 0.43 (m, 2H), 0.20 (brs, 2H).

Example 5(33)

4-[3-[N-isopropyl-N-(5-methyl-2-furylsulfonyl)amino]naphthalen-2-yloxymethyl]-3-methylbenzoic acid

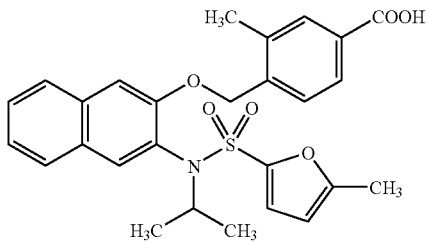

TLC: Rf 0.52 (chloroform:methanol=9:1);

NMR(DMSO-$d_6$): δ 7.92-7.80 (m, 3H), 7.77 (d, J=8.1 Hz, 1H), 7.69 (d, J=8.1 Hz, 1H), 7.63 (s, 1H), 7.60 (s, 1H), 7.57-7.50 (m, 1H), 7.45-7.36 (m, 1H), 6.95 (d, J=3.3 Hz, 1H), 6.29 (d, J=3.3 Hz, 1H), 5.26 and 5.24 (each d, J=13.5 Hz, each 1H), 4.34 (sept, J=6.6 Hz, 1H), 2.42 (s, 3H), 2.34 (s, 3H), 1.06 and 1.00 (each d, J=6.6 Hz, each 3H).

Example 5(34)

4-[3-[N-isobutyl-N-(5-methyl-2-furylsulfonyl)amino]naphthalen-2-yloxymethyl]-3-methylbenzoic acid

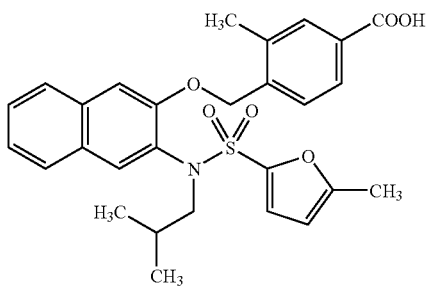

TLC: Rf 0.50 (chloroform:methanol=9:1);

NMR(DMSO-$d_6$): δ 7.88 (d, J=7.8 Hz, 1H), 7.86-7.74 (m, 4H), 7.59 (s, 1H), 7.56-7.36 (m, 3H), 6.86 (d, J=3.3 Hz, 1H), 6.19 (d, J=3.3 Hz, 1H), 5.40-4.90 (br, 2H), 3.47 (brd, J=6.9 Hz, 2H), 2.39 (s, 3H), 2.12 (s, 3H), 1.65-1.50 (m, 1H), 0.83 (brd, J=6.3 Hz, 6H).

Example 5(35)

4-[3-[N-isopropyl-N-(5-methyl-2-furylsulfonyl)amino]naphthalen-2-yloxymethyl]cinnamic acid

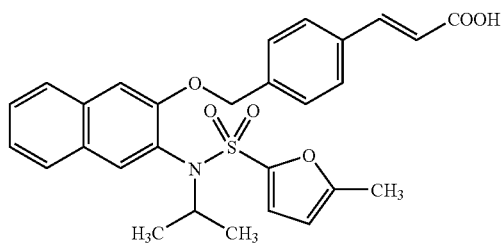

TLC: Rf 0.45 (chloroform:methanol=9:1);

NMR(DMSO-$d_6$): δ 7.87 (d, J=7.8 Hz, 1H), 7.82 (d, J=7.8 Hz, 1H), 7.73 (d, J=8.4 Hz, 2H), 7.67-7.46 (m, 6H), 7.44-7.34 (m, 1H), 6.94 (d, J=3.3 Hz, 1H), 6.56 (d, J=15.9 Hz, 1H), 6.28 (d, J=3.3 Hz, 1H), 5.27 and 5.21 (each d, J=13.2 Hz, each 1H), 4.36 (sept, J=6.6 Hz, 1H), 2.33 (s, 3H), 1.08 and 1.03 (each d, J=6.6 Hz, each 3H).

Example 5(36)

4-[3-[N-isobutyl-N-(5-methyl-2-furylsulfonyl)amino]naphthalen-2-yloxymethyl]cinnamic acid

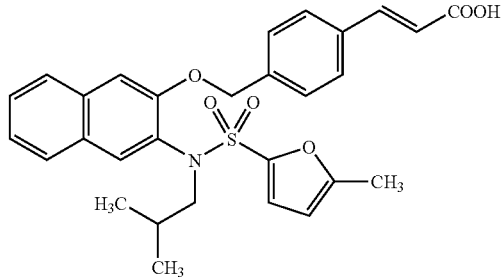

TLC: Rf 0.45 (chloroform:methanol=9:1);

NMR(DMSO-$d_6$): δ 7.88 (d, J=8.4 Hz, 1H), 7.81 (s, 1H), 7.80 (d, J=8.1 Hz, 1H), 7.72 (d, J=7.8 Hz, 2H), 7.61 (d, J=15.9 Hz, 1H), 7.55-7.34 (m, 2H), 7.50 (s, 1H), 7.44 (d, J=7.8 Hz, 2H), 6.82 (d, J=3.6 Hz, 1H), 6.56 (d, J=15.9 Hz, 1H), 6.16 (d, J=3.6 Hz, 1H), 5.40-4.90 (br, 2H), 3.49 (d, J=6.6 Hz, 2H), 2.13 (s, 3H), 1.64-1.48 (m, 1H), 0.85 (d, J=6.6 Hz, 6H).

Example 5(37)

4-[3-[N-isopropyl-N-(5-methyl-2-furylsulfonyl)amino]naphthalen-2-yloxymethyl]-3-methylcinnamic acid

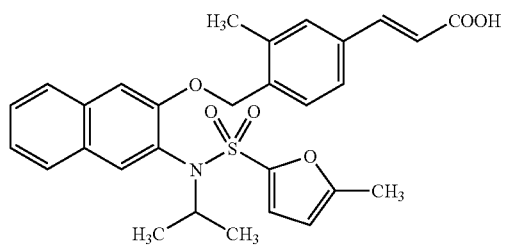

TLC: Rf 0.46 (chloroform:methanol=9:1);

NMR(DMSO-$d_6$): δ 7.87 (d, J=8.1 Hz, 1H), 7.86 (d, J=8.4 Hz, 1H), 7.64-7.48 (m, 7H), 7.44-7.36 (m, 1H), 6.93 (d, J=3.6 Hz, 1H), 6.54 (d, J=15.9 Hz, 1H), 6.29 (d, J=3.6 Hz, 1H), 5.23 and 5.18 (each d, J=14.4 Hz, each 1H), 4.33 (sept, J=6.6 Hz, 1H), 2.39 (s, 3H), 2.34 (s, 3H), 1.06 and 1.00 (each d, J=6.6 Hz, each 3H).

Example 5(38)

4-[3-[N-isobutyl-N-(5-methyl-2-furylsulfonyl)amino]naphthalen-2-yloxymethyl]-3-methylcinnamic acid

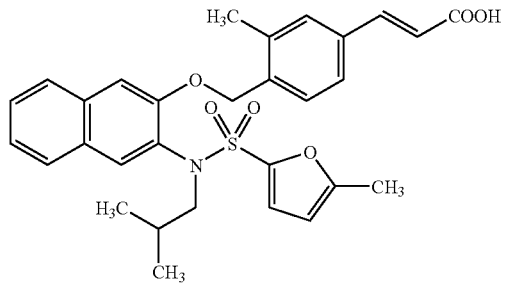

TLC: Rf 0.46 (chloroform:methanol=9:1);

NMR(DMSO-$d_6$): δ 7.88 (d, J=8.1 Hz, 1H), 7.84 (d, J=8.4 Hz, 1H), 7.78 (s, 1H), 7.62-7.47 (m, 5H), 7.44-7.35 (m, 2H), 6.84 (d, J=3.6 Hz, 1H), 6.54 (d, J=16.2 Hz, 1H), 6.20 (d, J=3.6 Hz, 1H), 5.35-4.90 (br, 2H), 3.47 (d, J=7.2 Hz, 2H), 2.35 (s, 3H), 2.14 (s, 3H), 1.63-1.49 (m, 1H), 0.83 (d, J=6.3 Hz, 6H).

Example 5(39)

4-[3-[N-isobutyl-N-[2-(4-methylthiazolyl)sulfonyl]amino]naphthalen-2-yloxymethyl]-3-methylcinnamic acid

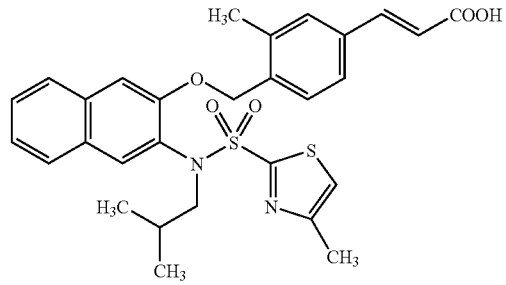

TLC: Rf 0.71 (ethyl acetate:methanol=9:1);

NMR: δ 7.82-7.71 (m, 4H), 7.51-7.46 (m, 1H), 7.43-7.32 (m, 4H), 7.21 (s, 1H), 6.95 (s, 1H), 6.48 (d, J=16.2 Hz, 1H), 5.04 and 4.91 (each br-m, total 2H), 3.83-3.60 (br-m, 2H), 2.38 (s, 3H), 2.34 (s, 3H), 1.81-1.67 (m, 1H), 0.95 (br-s, 6H).

Example 5(40)

4-[3-[N-isopropyl-N-(4-methyl-2-thiazolylsulfonyl)amino]naphthalen-2-yloxymethyl]-3-methylbenzoic acid

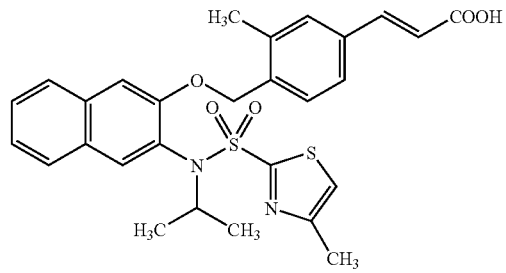

TLC: Rf 0.71 (ethyl acetate:methanol=9:1);

NMR(DMSO-$d_6$): δ 7.88-7.83 (m, 2H), 7.65-7.47 (m, 8H), 7.42-7.37 (m, 1H), 6.55 (d, J=15.9 Hz, 1H), 5.16 (s, 2H), 4.62-4.49 (m, 1H), 2.42 (s, 3H), 2.36 (s, 3H), 1.13 (d, J=6.6 Hz, 3H), 1.03 (d, J=6.6 Hz, 3H).

Example 5(41)

4-[6-[N-ethyl-N-(4-methyl-2-thiazolylsulfonyl)amino]indan-5-yloxymethyl]benzoic acid

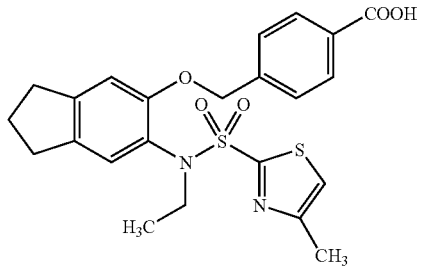

TLC: Rf 0.34 (dichloromethane:methanol=19:1);

NMR: δ 8.10 (d, J=8.4 Hz, 2H), 7.35 (d, J=8.4 Hz, 2H), 7.14 (s, 1H), 6.90 (brs, 1H), 6.79 (s, 1H), 4.92 (m, 2H), 4.20-3.60 (m, 2H), 2.90-2.83 (m, 4H), 2.33 (s, 3H), 2.09 (m, 2H), 1.20 (t, J=7.2 Hz, 3H).

Example 5(42)

4-[6-[N-(4-methyl-2-thiazolylsulfonyl)-N-propylamino]indan-5-yloxymethyl]benzoic acid

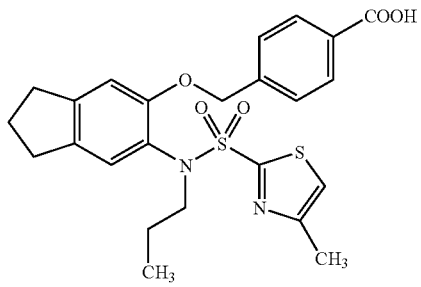

TLC: Rf 0.34 (dichloromethane:methanol=19:1);

NMR: δ 8.11 (d, J=8.4 Hz, 2H), 7.35 (d, J=8.4 Hz, 2H), 7.15 (s, 1H), 6.90 (brs, 1H), 6.78 (s, 1H), 5.10-4.70 (m, 2H), 4.00-3.50 (m, 2H), 2.90-2.84 (m, 4H), 2.32 (s, 3H), 2.09 (m, 2H), 1.58 (m, 2H), 0.93 (t, J=7.5 Hz, 3H).

Example 5(43)

4-[4,5-dimethyl-2-[N-(5-methyl-2-furylsulfonyl)-N-(2-propenyl)amino]phenoxymethyl]benzoic acid

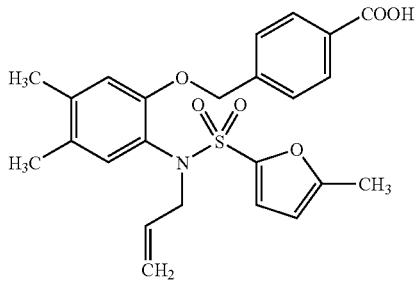

TLC: Rf 0.44 (chloroform:methanol=9:1);

NMR: δ 8.12 (d, J=8.4 Hz, 2H), 7.43 (d, J=8.4 Hz, 2H), 7.01 (s, 1H), 6.77 (d, J=3.0 Hz, 1H), 6.68 (s, 1H), 5.99-5.94 (m, 1H), 5.92-5.75 (m, 1H), 5.16-5.03 (m, 2H), 5.02 (s, 2H), 4.42-4.20 (m, 2H), 2.21 (s, 3H), 2.17 (s, 3H), 2.15 (s, 3H).

Example 5(44)

4-[4,5-dimethyl-2-[N-methyl-N-(5-methyl-2-furylsulfonyl)amino]phenoxymethyl]-3-methylbenzoic acid

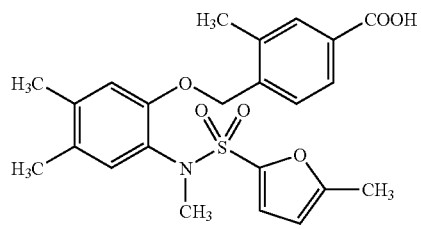

TLC: Rf 0.42 (chloroform:methanol=9:1);

NMR: δ 7.98-7.91 (m, 2H), 7.43 (d, J=8.7 Hz, 1H), 7.08 (s, 1H), 6.79 (d, J=3.3 Hz, 1H), 6.74 (s, 1H), 5.98 (m, 1H), 4.98 (s, 2H), 3.30 (s, 3H), 2.38 (s, 3H), 2.24 (s, 3H), 2.19 (s, 3H), 2.15 (s, 3H).

Example 5(45)

4-[4,5-dimethyl-2-[N-ethyl-N-(5-methyl-2-furylsulfonyl)amino]phenoxymethyl]-3-methylbenzoic acid

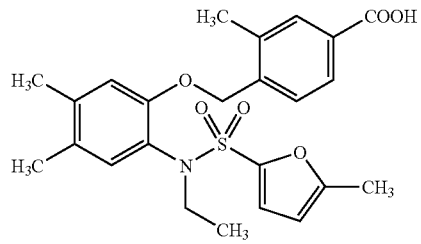

TLC: Rf 0.42 (chloroform:methanol=9:1);

NMR: δ 7.97-7.90 (m, 2H), 7.45 (d, J=8.1 Hz, 1H), 7.01 (s, 1H), 6.76 (s, 1H), 6.75 (d, J=3.3 Hz, 1H), 5.95 (m, 1H), 4.96 (s, 2H), 3.82-3.66 (br, 2H), 2.37 (s, 3H), 2.25 (s, 3H), 2.19 (s, 3H), 2.13 (s, 3H), 1.14 (t, J=7.2 Hz, 3H).

Example 5(46)

4-[4,5-dimethyl-2-[N-(5-methyl-2-furylsulfonyl)-N-propylamino]phenoxymethyl]-3-methylbenzoic acid

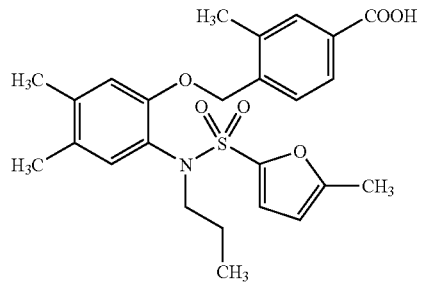

TLC: Rf 0.42 (chloroform:methanol=9:1);

NMR: δ 7.98-7.90 (m, 2H), 7.45 (d, J=8.1 Hz, 1H), 7.02 (s, 1H), 6.78-6.70 (m, 2H), 5.95 (m, 1H), 4.95 (s, 2H), 3.71-3.55

(br, 2H), 2.37 (s, 3H), 2.24 (s, 3H), 2.19 (s, 3H), 2.12 (s, 3H), 1.60-1.44 (m, 2H), 0.88 (t, J=7.5 Hz, 3H).

Example 5(47)

4-[4,5-dimethyl-2-[N-(5-methyl-2-furylsulfonyl)-N-(2-propenyl)amino]phenoxymethyl]-3-methylbenzoic acid

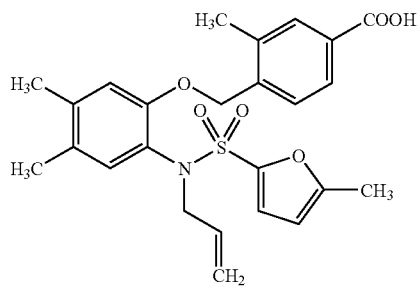

TLC: Rf 0.45 (chloroform:methanol=9:1);

NMR: δ 7.98-7.90 (m, 2H), 7.45 (d, J=8.1 Hz, 1H), 7.01 (s, 1H), 6.77 (d, J=3.3 Hz, 1H), 6.71 (s, 1H), 5.96 (m, 1H), 5.83 (m, 1H), 5.15-5.00 (m, 2H), 4.96 (s, 2H), 4.40-4.20 (br, 2H), 2.38 (s, 3H), 2.23 (s, 3H), 2.18 (s, 3H), 2.14 (s, 3H).

Example 5(48)

4-[4,5-dimethyl-2-[N-(2-hydroxy-2-methylpropyl)-N-(5-methyl-2-furylsulfonyl)amino]phenoxymethyl]-3-methylbenzoic acid

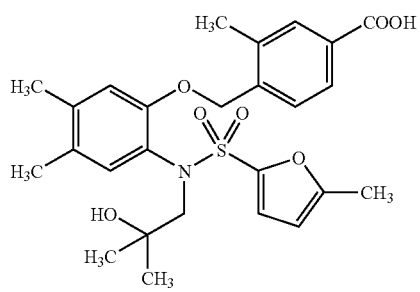

TLC: Rf 0.41 (chloroform:methanol=9:1);

NMR: δ 8.00-7.94 (m, 2H), 7.53 (d, J=7.8 Hz, 1H), 6.80 (s, 1H), 6.77 (s, 1H), 6.75 (d, J=3.3 Hz, 1H), 6.01 (m, 1H), 5.08 (d, J=12.3 Hz, 1H), 5.00 (d, J=12.3 Hz, 1H), 3.84 (d, J=14.4 Hz, 1H), 3.56 (d, J=14.4 Hz, 1H), 2.42 (s, 3H), 2.23 (s, 3H), 2.21 (s, 3H), 2.14 (s, 3H), 1.25 (s, 3H), 1.18 (s, 3H).

Example 5(49)

4-[6-[N-methyl-N-(4-methyl-2-thiazolylsulfonyl)amino]indan-5-yloxymethyl]benzoic acid

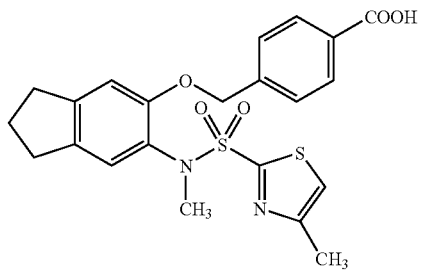

TLC: Rf 0.34 (dichloromethane:methanol=19:1);

NMR: δ 8.11 (d, J=8.7 Hz, 2H), 7.35 (d, J=8.7 Hz, 2H), 7.20 (s, 1H), 6.94 (brs, 1H), 6.78 (s, 1H), 4.92 (brs, 2H), 3.44 (s, 3H), 2.89-2.83 (m, 4H), 2.35 (d, J=0.9 Hz, 3H), 2.08 (m, 2H).

Example 5(50)

4-[6-[N-(2-hydroxy-2-methylpropyl)-N-(5-methyl-2-furylsulfonyl)amino]indan-5-yloxymethyl]-3-methylbenzoic acid

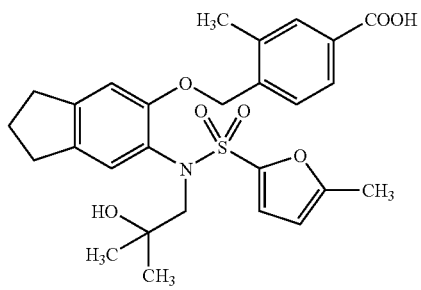

TLC: Rf 0.32 (chloroform:methanol=10:1);

NMR: 7.97 (d, J=7.8 Hz, 1H), 7.95 (s, 1H), 7.53 (d, J=7.8 Hz, 1H), 6.89 (s, 1H), 6.86 (s, 1H), 6.75 (d, J=3.3 Hz, 1H), 6.01 (dd, J=3.3, 0.9 Hz, 1H), 5.08 (d, J=12.9 Hz, 1H), 5.02 (d, J=12.9 Hz, 1H), 3.85 (d, J=14.7 Hz, 1H), 3.58 (d, J=14.7 Hz, 1H), 2.90-2.78 (m, 4H), 2.42 (s, 3H), 2.21 (s, 3H), 2.13-2.01 (m, 2H), 1.25 (s, 3H), 1.18 (s, 3H).

Example 5(51)

3-methyl-4-[6-[N-methyl-N-(4-methyl-2-thiazolylsulfonyl)amino]indan-5-yloxymethyl]cinnamic acid

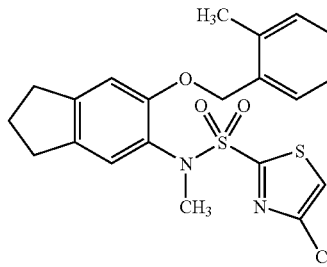

TLC: Rf 0.45 (chloroform:methanol=9:1);

NMR(DMSO-d$_6$): δ 7.60-7.50 (m, 3H), 7.49 (d, J=8.1 Hz, 1H), 7.20 (d, J=8.1 Hz, 1H), 7.09 (s, 1H), 7.04 (s, 1H), 6.53 (d, J=15.9 Hz, 1H), 4.87 (br, 2H), 3.24 (s, 3H), 2.85 (t, J=7.4 Hz, 2H), 2.77 (t, J=7.4 Hz, 2H), 2.25 (s, 3H), 2.23 (s, 3H), 2.10-1.95 (m, 2H).

Example 5(52)

4-[6-[N-ethyl-N-(4-methyl-2-thiazolylsulfonyl)amino]indan-5-yloxymethyl]-3-methylcinnamic acid

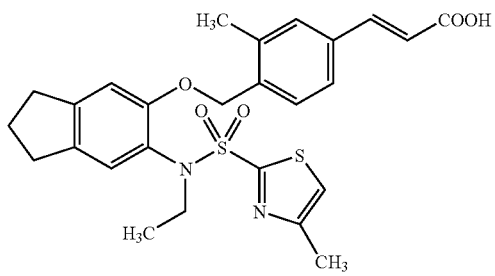

TLC: Rf 0.44 (chloroform:methanol=9:1);

NMR(DMSO-d$_6$): δ 7.55 (d, J=16.0 Hz, 1H), 7.50-7.40 (m, 3H), 7.19 (d, J=8.1 Hz, 1H), 7.09 (s, 1H), 6.98 (s, 1H), 6.52 (d, J=16.0 Hz, 1H), 4.84 (br, 2H), 3.66 (br, 2H), 2.85 (t, J=7.4 Hz, 2H), 2.77 (t, J=7.4 Hz, 2H), 2.23 (s, 3H), 2.19 (s, 3H), 2.10-1.90 (m, 2H), 1.01 (t, J=7.0 Hz, 3H).

Example 5(53)

4-[2-[N-cyclopropylmethyl-N-(5-methyl-2-furylsulfonyl)amino]-4,5-dimethylphenoxymethyl]benzoic acid

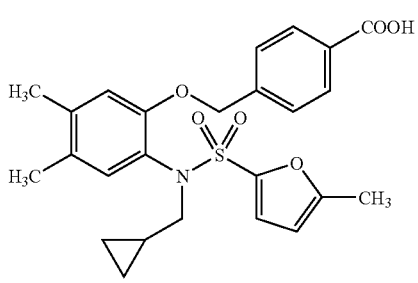

TLC: Rf 0.41 (chloroform:methanol=9:1);

NMR: δ 8.11 (d, J=8.4 Hz, 2H), 7.43 (d, J=8.4 Hz, 2H), 7.09 (s, 1H), 6.74 (d, J=3.0 Hz, 1H), 6.70 (s, 1H), 5.96-5.92 (m, 1H), 5.02 (brs, 2H), 3.68-3.40 (m, 2H), 2.23 (s, 3H), 2.19 (s, 3H), 2.14 (s, 3H), 1.03-0.86 (m, 1H), 0.46-0.35 (m, 2H), 0.21-0.06 (m, 2H).

Example 5(54)

4-[4,5-dimethyl-2-[N-(2-hydroxy-2-methylpropyl)-N-(5-methyl-2-furylsulfonyl)amino]phenoxymethyl]benzoic acid

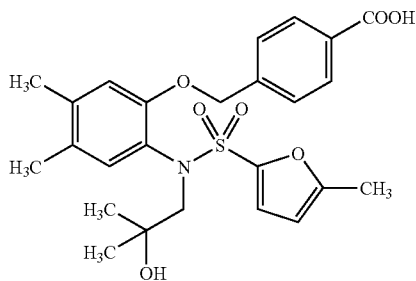

TLC: Rf 0.34 (chloroform:methanol=9:1);

NMR: δ 8.13 (d, J=8.4 Hz, 2H), 7.52 (d, J=8.4 Hz, 2H), 6.81 (s, 1H), 6.75 (s, 1H), 6.74 (d, J=3.0 Hz, 1H), 6.03-5.98 (m, 1H), 5.22-4.96 (m, 2H), 3.92-3.76 and 3.64-3.48 (each m, total 2H), 2.21 (s, 6H), 2.13 (s, 3H), 1.28 and 1.19 (each brs, each 3H).

Example 5(55)

3-methyl-4-[6-[N-(2-methyl-2-propenyl)-N-(4-methyl-2-thiazolylsulfonyl)amino]indan-5-yloxymethyl]cinnamic acid

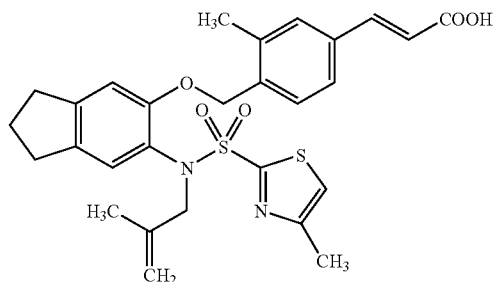

TLC: Rf 0.60 (chloroform:methanol=9:1);

NMR: δ 7.76 (d, J=15.9 Hz, 1H), 7.42-7.34 (m, 2H), 7.27-7.22 (m, 1H), 7.12 (s, 1H), 6.92 (d, J=0.9 Hz, 1H), 6.78 (s, 1H), 6.47 (d, J=15.9 Hz, 1H), 4.90-4.72 (m, 4H), 4.50-4.14 (m, 2H), 2.92-2.80 (m, 4H), 2.31 (s, 6H), 2.18-2.00 (m, 2H), 1.81 (s, 3H).

Example 5(56)

4-[6-[N-cyclopropylmethyl-N-(4-methyl-2-thiazolyl-sulfonyl)amino]indan-5-yloxymethyl]-3-methylcinnamic acid

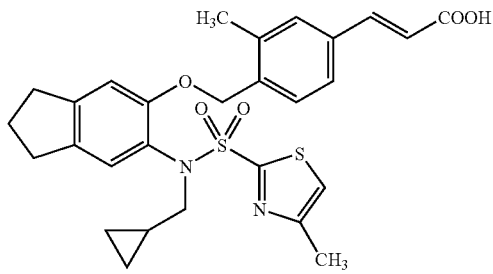

TLC: Rf 0.60 (chloroform:methanol=9:1);

NMR: δ 7.77 (d, J=15.9 Hz, 1H), 7.42-7.38 (m, 2H), 7.30-7.25 (m, 1H), 7.21 (s, 1H), 6.89 (d, J=0.9 Hz, 1H), 6.82 (s, 1H), 6.46 (d, J=15.9 Hz, 1H), 4.92-4.64 (m, 2H), 3.84-3.42 (m, 2H), 2.95-2.76 (m, 4H), 2.31 (s, 3H), 2.31 (s, 3H), 2.18-2.02 (m, 2H), 1.08-0.90 (m, 1H), 0.46-0.40 (m, 2H), 0.26-0.08 (m, 2H).

Example 5(58)

3-methyl-4-[6-[N-(4-methyl-2-thiazolylsulfonyl)-N-(2-propenyl)amino]indan-5-yloxymethyl]cinnamic acid

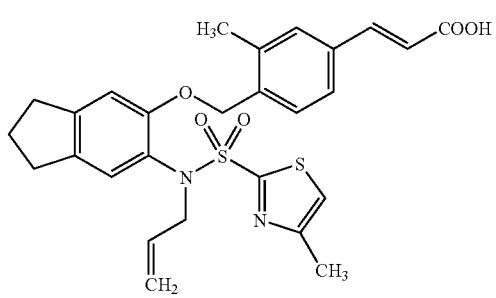

TLC: Rf 0.42 (dichloromethane:methanol=10:1);

NMR: δ 7.76 (d, J=15.9 Hz, 1H), 7.42-7.36 (m, 2H), 7.28 (m, 1H), 7.11 (s, 1H), 6.92 (m, 1H), 6.80 (s, 1H), 6.47 (d, J=15.9 Hz, 1H), 5.87 (m, 1H), 5.11 (dd, J=17.1, 1.5 Hz, 1H), 5.07 (dd, J=8.7, 1.5 Hz, 1H), 4.83 (br, 2H), 4.32 (br, 2H), 2.92-2.82 (m, 4H), 2.33 (d, J=0.6 Hz, 3H), 2.32 (s, 3H), 2.16-2.04 (m, 2H).

Example 5(57)

4-[6-[N-(2-hydroxy-2-methylpropyl)-N-(5-methyl-2-furylsulfonyl)amino]indan-5-yloxymethyl]cinnamic acid

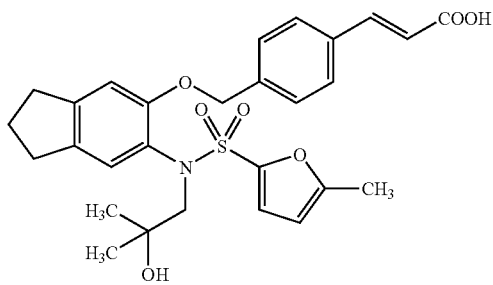

TLC: Rf 0.46 (chloroform:methanol=9:1);

NMR: δ 7.78 (d, J=15.9 Hz, 1H), 7.58 (d, J=8.1 Hz, 2H), 7.47 (d, J=8.1 Hz, 2H), 6.85 (d, J=3.6 Hz, 2H), 6.74 (d, J=3.6 Hz, 1H), 6.47 (d, J=15.9 Hz, 1H), 6.01 (d, J=2.1 Hz, 1H), 5.10 (d, J=12.0 Hz, 1H), 4.99 (d, J=12.0 Hz, 1H), 3.85 (d, J=14.1 Hz, 1H), 3.53 (d, J=14.1 Hz, 1H), 2.90-2.77 (m, 4H), 2.23 (s, 3H), 2.07 (m, 2H), 1.27 (s, 3H), 1.16 (s, 3H).

Example 5(59)

4-[6-[N-(2-hydroxy-2-methylpropyl)-N-(4-methyl-2-thiazolylsulfonyl)amino]indan-5-yloxymethyl]-3-methylcinnamic acid

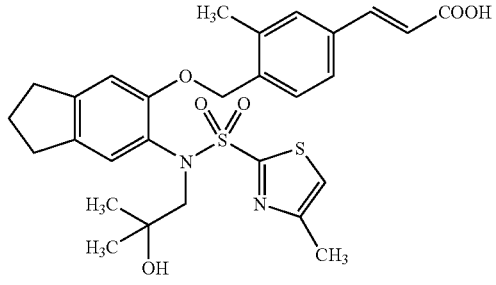

TLC: Rf 0.42 (dichloromethane:methanol=10:1);

NMR: δ 7.76 (d, J=15.9 Hz, 1H), 7.44-7.38 (m, 3H), 7.05 (m, 1H), 6.88 (s, 1H), 6.82 (s, 1H), 6.46 (d, J=15.9 Hz, 1H), 5.03 (d, J=12.0 Hz, 1H), 4.93 (d, J=12.0 Hz, 1H), 3.96 (d, J=14.4 Hz, 1H), 3.69 (d, J=14.4 Hz, 1H), 2.87 (t, J=7.5 Hz, 2H), 2.77 (t, J=7.5 Hz, 2H), 2.43 (s, 3H), 2.40 (s, 3H), 2.13-2.00 (m, 2H), 1.23 (s, 3H), 1.18 (s, 3H).

Example 5(60)

4-[4,5-dimethyl-2-[N-cyclopropylmethyl-N-(5-methyl-2-furylsulfonyl)amino]phenoxymethyl]-3-methylbenzoic acid

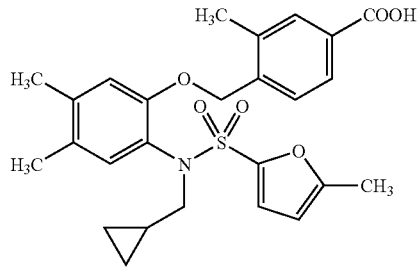

TLC: Rf 0.45 (chloroform:methanol=9:1);
NMR: δ 8.00-7.92 (m, 2H), 7.47 (d, J=7.8 Hz, 1H), 7.09 (s, 1H), 6.78-6.71 (m, 2H), 5.94 (m, 1H), 4.96 (s, 2H), 3.63-3.45 (br, 2H), 2.37 (s, 3H), 2.25 (s, 3H), 2.19 (s, 3H), 2.13 (s, 3H), 0.95 (m, 1H), 0.44-0.35 (m, 2H), 0.15-0.22 (m, 2H).

Example 5(61)

3-methyl-4-[6-[N-(4-methyl-2-thiazolylsulfonyl)-N-propylamino]indan-5-yloxymethyl]cinnamic acid

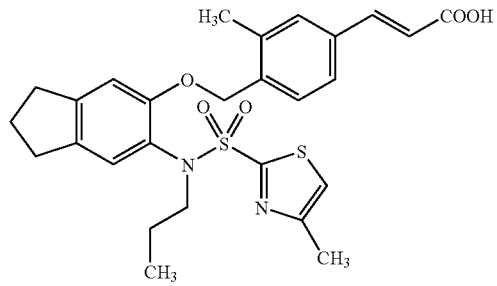

TLC: Rf 0.41 (chloroform:methanol=9:1);
NMR: δ 7.76 (d, J=16.2 Hz, 1H), 7.44-7.34 (m, 2H), 7.32-7.20 (m, 1H), 7.13 (s, 1H), 6.90 (s, 1H), 6.82 (s, 1H), 6.46 (d, J=16.2 Hz, 1H), 4.90-4.70 (m, 2H), 3.90-3.50 (m, 2H), 2.89 (t, J=7.5 Hz) and 2.86 (t, J=7.5 Hz) total 4H, 2.31 (s) and 2.30 (s) total 6H, 2.09 (quint, J=7.5 Hz, 2H), 1.58 (m, 2H), 0.91 (t, J=7.5 Hz, 3H).

Example 5(62)

4-[6-[N-(2-hydroxy-2-methylpropyl)-N-(4-methyl-2-thiazolylsulfonyl)amino]indan-5-yloxymethyl]benzoic acid

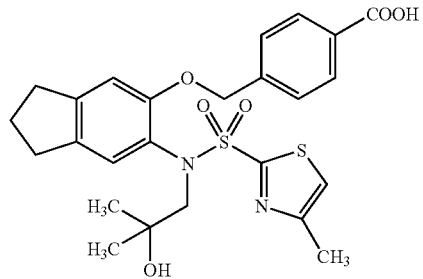

TLC: Rf 0.29 (dichloromethane:methanol=19:1);

NMR: δ 8.13 (d, J=7.8 Hz, 2H), 7.48 (d, J=7.8 Hz, 2H), 7.02 (brs, 1H), 6.90 (s, 1H), 6.83 (s, 1H), 5.12 (d, J=12.6 Hz, 1H), 4.95 (d, J=12.6 Hz, 1H), 3.96 (d, J=15.0 Hz, 1H), 3.77 (d, J=15.0 Hz, 1H), 2.88-2.75 (m, 4H), 2.42 (s, 3H), 2.06 (m, 2H), 1.29 (s, 3H), 1.22 (s, 3H).

Example 6

3-methyl-4-[6-[N-isobutyl-N-(4-methyl-2-thiazolylsulfonyl)amino]indan-5-yloxymethyl]cinnamic acid sodium salt

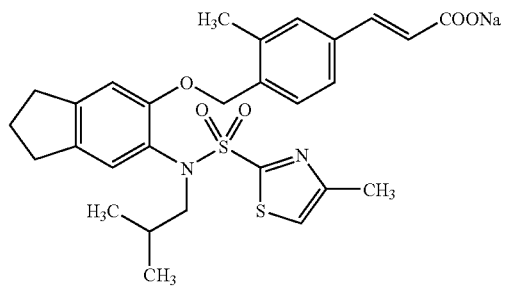

To a suspension of the compound prepared in Example 2(74) (213 g) in ethanol (2 L), 5N aqueous solution of sodium hydroxide (74.7 ml) was added and the mixture was stirred for 0.5 hour at 80° C. The reaction solution was filtered under heating to remove the insolubles, then the mixture was cooled, and the precipitate was collected. The mother liquor was concentrated and the residue was dissolved in ethanol (500 ml) and water (25 ml) under heating. The mixture was filtered under heating to remove the insolubles, then the mixture was cooled, and the precipitate was collected. Under heating, all collected solids were dried under reduced pressure to give the compound of the present invention (165 g) having the following physical data.

TLC: Rf 0.52 (chloroform:methanol=9:1);
NMR(DMSO-$d_6$): δ 7.49 (s, 1H), 7.29 (s, 1H), 7.26 (d, J=8.1 Hz, 1H), 7.10-7.00 (m, 4H), 6.38 (d, J=15.9 Hz, 1H), 4.89 (br-d, J=10.5 Hz, 1H), 4.63 (br-d, J=10.5 Hz, 1H), 3.55-3.25 (m, 2H), 2.85 (t, J=7.2 Hz, 2H), 2.78 (t, J=7.2 Hz, 2H), 2.21 (s, 3H), 2.18 (s, 3H), 2.10-1.90 (m, 2H), 1.60-1.45 (m, 1H), 1.00-0.70 (m, 6H).

Example 6(1)

4-[2-[N-isopropyl-N-(5-methyl-2-furylsulfonyl)amino]-5-trifluoromethylphenoxymethyl]benzoic acid sodium salt

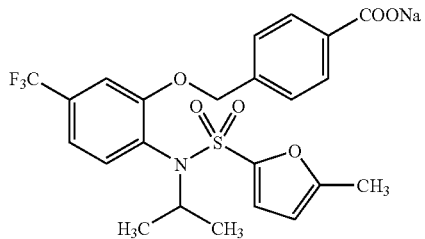

TLC: Rf 0.50 (chloroform:methanol=9:1);

NMR: δ 7.84 (d, J=8.1 Hz, 2H), 7.20-6.95 (m, 5H), 6.65 (d, J=3.3 Hz, 1H), 5.84 (d, J=3.3 Hz, 1H), 4.75 (brs, 2H), 4.30-4.10 (m, 1H), 2.12 (s, 3H), 0.86 (brd, J=3.9 Hz, 6H).

Example 6(2)

4-[2-[N-isobutyl-N-(5-methyl-2-furylsulfonyl) amino]-4,5-dimethylphenoxymethyl]benzoic acid sodium salt

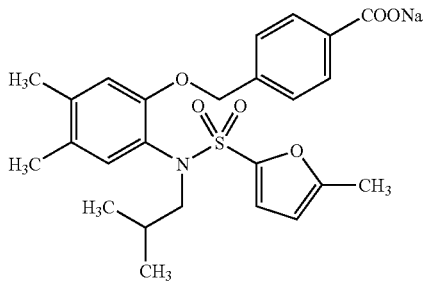

TLC: Rf 0.40 (chloroform:methanol=9:1);
NMR: δ 7.83 (d, J=8.1 Hz, 2H), 7.00 (d, J=8.1 Hz, 2H), 6.88 (s, 1H), 6.59 (s, 1H), 6.54 (d, J=3.0 Hz, 1H), 5.74 (s, 1H), 4.90-4.50 (m, 2H), 3.33 (brd, J=6.3 Hz, 2H), 2.09 (s, 3H), 2.05 (s, 3H), 1.93 (s, 3H), 1.60-1.40 (m, 1H), 0.73 (d, J=6.3 Hz, 6H).

Example 6(3)

3-methyl-4-[2-[N-isobutyl-N-(5-methyl-2-furylsulfonyl)amino]-4,5-dimethylphenoxymethyl]benzoic acid sodium salt

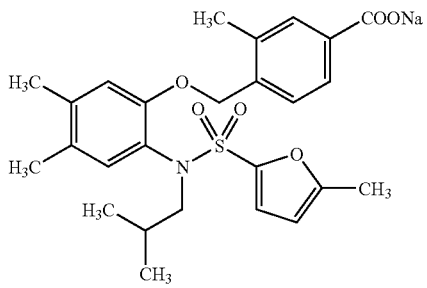

TLC: Rf 0.41 (chloroform:methanol=9:1);
NMR(DMSO-$d_6$): δ 7.70 (s, 1H), 7.66 (d, J=7.8 Hz, 1H), 7.13 (d, J=7.8 Hz, 1H), 6.99 (s, 1H), 6.91 (s, 1H), 6.76 (d, J=3.3 Hz, 1H), 6.14 (d, J=3.3 Hz, 1H), 4.88 (brs, 2H), 3.36 (d, J=6.9 Hz, 2H), 2.26 (s, 3H), 2.22 (s, 3H), 2.14 (s, 3H), 2.10 (s, 3H), 1.60-1.45 (m, 1H), 0.81 (brd, J=6.3 Hz, 6H).

Example 6(4)

4-[6-[N-isobutyl-N-(4-methyl-2-thiazolylsulfonyl)amino]indan-5-yloxymethyl]benzoic acid sodium salt

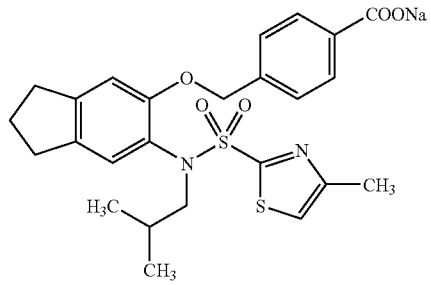

TLC: Rf 0.40 (chloroform:methanol=9:1);
NMR(CD$_3$OD): δ 7.91 (d, J=8.1 Hz, 2H), 7.19 (s, 1H), 7.18 (d, J=8.1 Hz, 2H), 7.13 (s, 1H), 6.93 (s, 1H), 5.00-4.80 (m, 1H), 4.65-4.58 (m, 1H), 3.65-3.48 (m, 2H), 2.95-2.80 (m, 4H), 2.21 (d, J=0.9 Hz, 3H), 2.09 (quint, J=7.5 Hz, 2H), 1.66 (m, 1H), 1.03-0.85 (m, 6H).

Example 6(5)

4-[6-[N-isobutyl-N-(4-methyl-2-thiazolylsulfonyl)amino]indan-5-yloxymethyl]benzoic acid potassium salt

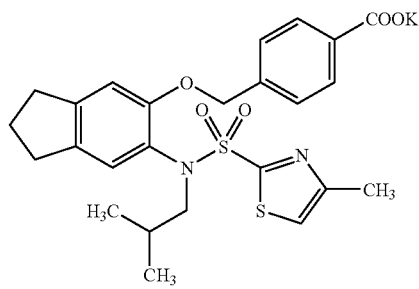

TLC: Rf 0.37 (chloroform:methanol=9:1);
NMR(DMSO-$d_6$): δ 7.81 (d, J=8.0 Hz, 2H), 7.47 (q, J=0.4 Hz, 1H), 7.06 (d, J=8.0 Hz, 1H), 7.03 (s, 2H), 6.95 (s, 1H), 5.10-4.80 (m, 1H), 4.80-4.50 (m, 1H), 3.43 (brs, 2H), 2.80 (q, J=7.0 Hz, 4H), 2.23 (d, J=0.4 Hz, 3H), 2.01 (qn, J=7.0 Hz, 2H), 1.53 (sept, J=6.6 Hz, 1H), 0.85 (brs, 6H).

Example 6(6)

4-[6-[N-isobutyl-N-(5-methyl-2-furylsulfonyl)amino]indan-5-yloxymethyl]cinnamic acid sodium salt

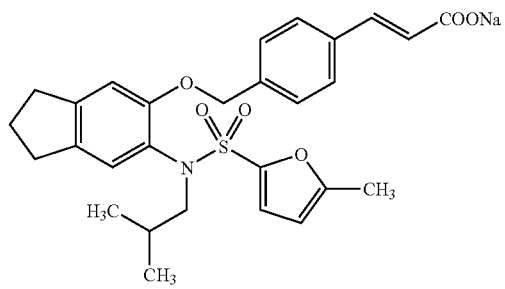

TLC: Rf 0.51 (chloroform:methanol=9:1);

NMR: δ 7.37 (d, J=15.9 Hz, 1H), 7.17 (d, J=7.5 Hz, 2H), 7.10-6.90 (m, 3H), 6.67 (s, 1H), 6.55 (s, 1H), 6.45 (d, J=15.9 Hz, 1H), 5.74 (s, 1H), 4.80-4.45 (m, 2H), 3.35 (d, J=6.3 Hz, 2H), 2.85-2.55 (m, 4H), 2.10-1.80 (m, 5H), 1.65-1.40 (m, 1H), 0.74 (brs, 6H).

Example 6(7)

3-methyl-4-[6-[N-isobutyl-N-(5-methyl-2-furylsulfonyl)amino]indan-5-yloxymethyl]benzoic acid sodium salt

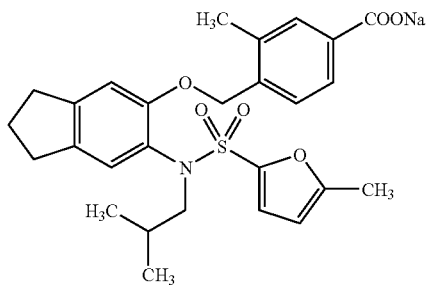

TLC: Rf 0.60 (chloroform:methanol=9:1);

NMR(CD$_3$OD): δ 7.78 (s) and 7.75 (d, J=8.1 Hz) total 2H, 7.24 (d, J=8.1 Hz, 1H), 7.07 (s, 1H), 6.97 (s, 1H), 6.64 (d, J=3.3 Hz, 1H), 6.03 (dd, J=3.3, 0.9 Hz, 1H), 5.08-4.75 (m, 2H), 3.48 (d, J=7.5 Hz, 2H), 2.94-2.80 (m, 4H), 2.32 (s, 3H), 2.15-2.00 (m) and 2.04 (s) total 5H, 1.87 (m, 1H), 0.98-0.80 (m, 6H).

Example 6(8)

4-[6-[N-isopropyl-N-(4-methyl-2-thiazolylsulfonyl)amino]indan-5-yloxymethyl]cinnamic acid potassium salt

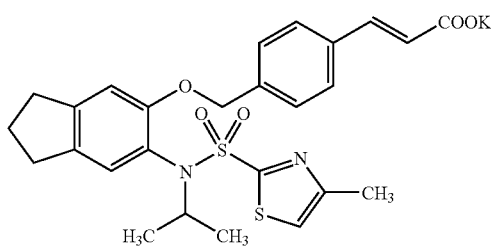

TLC: Rf 0.36 (chloroform:methanol=9:1);

NMR: δ 7.27 (d, J=15.9 Hz, 1H), 7.21 (d, J=7.5 Hz, 2H), 6.98 (d, J=7.5 Hz, 2H), 6.84 (s, 1H), 6.78 (s, 1H), 6.70 (s, 1H), 6.41 (d, J=15.9 Hz, 1H), 4.70-4.40 (m, 3H), 2.85-2.60 (m, 4H), 2.24 (s, 3H), 2.05-1.90 (m, 2H), 1.01 (d, J=6.6 Hz, 3H), 0.95 (d, J=6.6 Hz, 3H).

Example 6(9)

4-[2-[N-isobutyl-N-(2-thiazolylsulfonyl)amino]-4,5-dimethylphenoxymethyl]benzoic acid potassium salt

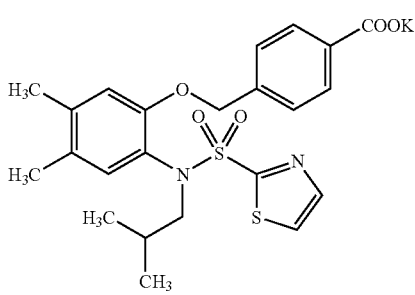

TLC: Rf 0.32 (chloroform:methanol=9:1);

NMR: δ 7.82 (d, J=8.1 Hz, 2H), 7.33 (d, J=3.0 Hz, 1H), 7.15 (d, J=3.0 Hz, 1H), 6.94 (s, 1H), 6.89 (d, J=8.1 Hz, 2H), 6.56 (s, 1H), 4.70-4.55 (m, 1H), 4.45-4.25 (m, 1H), 3.60-3.30 (m, 2H), 2.09 (s, 6H), 1.60-1.45 (m, 1H), 0.78 (brs, 3H), 0.72 (brs, 3H).

Example 6(10)

3-methyl-4-[2-[N-isobutyl-N-(2-thiazolylsulfonyl)amino]-4,5-dimethylphenoxymethyl]benzoic acid sodium salt

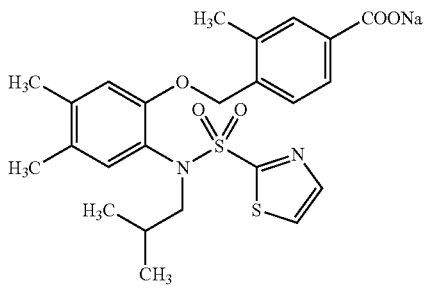

TLC: Rf 0.37 (chloroform:methanol=10:1);

NMR(DMSO-d$_6$): δ 7.98 (d, J=3.0 Hz, 1H), 7.82 (d, J=3.0 Hz, 1H), 7.64 (s, 1H), 7.60 (d, J=7.8 Hz, 1H), 6.99 (d, J=7.8 Hz, 1H), 6.97 (s, 1H), 6.91 (s, 1H), 5.00-4.54 (m, 2H), 3.42 (d, J=6.3 Hz, 2H), 2.20 (s, 3H), 2.20 (s, 3H), 2.11 (s, 3H), 1.50 (m, 1H), 0.90-0.73 (m, 6H).

Example 7

4-[6-[N-isobutyl-N-(5-methyl-2-furylsulfonyl)amino]indan-5-yloxymethyl]-3-methylbenzylalcohol

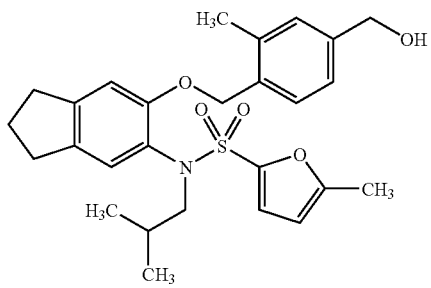

To a suspension of the compound prepared in Example 2(33) (1.20 g) in tetrahydrofuran (10 ml), borohydride-dimethylthiol complex (2M tetrahydrofuran solution, 6.0 ml) was added and the mixture was stirred for 1 hour. To the reaction mixture, methanol, water and 1N hydrochloric acid were added, and was extracted with ethyl acetate twice. The combined organic layer was washed with 1N hydrochloric acid, water and a saturated aqueous solution of sodium chloride successively, dried over an anhydrous sodium sulfate and was purified by column chromatography on silica gel (n-hexane:ethyl acetate=from 8:1 to 2:1) to give the compound of the present invention (947 mg) having the following physical data.

TLC: Rf 0.57 (n-hexane:ethyl acetate=1:1);

NMR: δ 7.20 (d, J=7.8 Hz, 1H), 7.13 (s, 1H), 7.10 (d, J=7.8 Hz, 1H), 7.07 (s, 1H), 6.95 (s, 1H), 6.79 (d, J=3.3 Hz, 1H), 6.20-6.15 (m, 1H), 4.94 (br, 1H), 4.83 (br, 1H), 4.45 (s, 2H), 3.32 (d, J=6.9 Hz, 2H), 2.84 (t, J=7.4 Hz, 2H), 2.78 (t, J=7.4 Hz, 2H), 2.25 (s, 3H), 2.13 (s, 3H), 2.10-1.90 (m, 2H), 1.55-1.40 (m, 1H), 0.90-0.70 (m, 6H).

Reference Example 5

Methyl t-butyl ether solution of 4-methyl-2-thiazolylsulfonylchloride

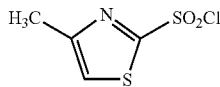

Under atmosphere of argon, to a solution of 4-methylthiazole (3.0 g) in methyl t-butyl ether (45 ml), n-butyl lithium (1.58 M hexane solution, 19.1 ml) was added under stirring at −78° C., and the mixture was stirred for 1 hour. 5.72M solution of sulfur dioxide in tetrahydrofuran (5.3 ml) was added dropwise to the mixture, and the mixture was stirred for 1 hour. To the mixture, N-chlorosuccinimide (4.44 g) was added. Then the mixture was warmed to 0° C. and stirred for another 1 hour. Water was added to the reaction mixture, and the organic layer was washed with water twice, with a saturated aqueous solution of sodium chloride once, and was dried over an anhydrous magnesium sulfate to give the title compound, as methyl t-butyl ether solution (92 ml). The concentration of this solution was 0.20 M. The conversion yield of the title compound was 3.69 g.

Example 8

1-(4-methylthiazol-2-ylsulfonyloxy)-1,2,3-benzotriazole

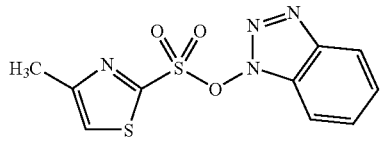

Under atmosphere of argon, to a solution of 4-methylthiazol-2-sulfonyl chloride in methyl t-butyl ether (0.20 M, 20 ml), 1-hydroxybenzotriazole (549 mg) and triethylamine (0.57 ml) were added under stirring with cooled on ice bath, and the mixture was stirred for 1 hour at room temperature. To the reaction mixture, ethyl acetate was added. The organic layer was washed with water three times, with a saturated aqueous solution of sodium chloride once successively, dried over an anhydrous magnesium sulfate and concentrated to give the compound of the present invention (1.1 g) having the following physical data.

NMR: δ 8.03 (dt, J=8.4, 1.0 Hz, 1H), 7.70-6.57 (m, 2H), 7.53 (d, J=1.0 Hz, 1H), 7.46 (ddd, J=8.4, 5.8, 2.0 Hz, 1H), 2.62 (d, J=1.0 Hz, 3H).

Example 9

1-(4-methylthiazol-2-ylsulfonyl)-3-methylimidazol-1-onium hydrogen chloride salt

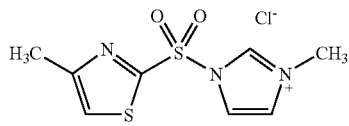

Under atmosphere of argon, a solution of 4-methylthiazol-2-sulfonyl chloride in methyl t-butyl ether (0.14 M, 30 ml) was cooled to 0° C., then 1-methylimidazole (0.68 ml) was added and the mixture was stirred for 1 hour. The white precipitate appeared was collected and dried to give the compound of the present invention (1.56 g) having the following physical data.

NMR(DMSO-d$_6$): δ 9.08 (brs, 1H), 7.69 (t, J=1.8 Hz, 1H), 7.63 (t, J=1.8 Hz, 1H), 7.20-7.17 (m, 1H), 3.96 (s, 3H), 2.31 (d, J=1.8 Hz, 3H).

Among the compounds of formula (I) of the present invention, the compounds wherein Ar is thiazole (prepared in Examples 2(36) to (74), (101) to (123), Examples 3(6) to (20), Examples 4(7) to (17), Examples 5(5) to (10), (22) to (27), (31) to (33), (40) to (43), (50), (52), (53), (56), (57), (59), (60), (62), (63), Example 6, Examples 6(4), (5), (8) to (10)), the compounds wherein Ar is pyridine (prepared in Examples 2(75) to (97), Examples 3(21) to (38), Examples 4(18) to (22))) may be prepared by the same procedures of Reference Example 3 using the compound prepared in Examples 8 and 9 or a corresponding compound in place of a corresponding sulfonyl chloride, followed by corresponding procedures.

Comparison Example 1

A Comparison of the Stability of 4-methyl-2-thiazolylsulfonyl chloride with that of the Compound Prepared in Examples 8 and 9

The solution prepared in Reference Example 1 was concentrated under reduced pressure to give 4-methyl-2-thiazolylsulfonyl chloride. The stability of this compound and the compounds prepared in Examples 8 and 9 was measured on HPLC. The conditions of HPLC were as follows.

Column: YMC-Pack ODS-AM-302(4.6 mm*150 mm)
Eluting solvent: MeCN/3 mM tetra-n-butylammonium phosphate=40/60
Flow rate: 1 ml/min
Detected by UVabs 220 nm
The results are shown in table 4.

TABLE 4

| Compounds | Temperature (° C.) | Time (hour) | Residual Rate (%) |
|---|---|---|---|
| 4-methyl-2-thiazolylsulfonyl chloride | 1 | 24 | 102.0 |
|  | 1 | 48 | 96.3 |
|  | 1 | 72 | 98.6 |
|  | 20 | 24 | 71.4 |
|  | 20 | 48 | 20.6 |
|  | 20 | 66 | 2.0 |
|  | 40 | 16 | 60.9 |
|  | 40 | 24 | 7.6 |
| Compound prepared in ex. 8 | 40 | 24 | 99.8 |
| Compound prepared in ex. 9 | 40 | 24 | 99.6 |

Table 4 shows that 4-methyl-2-thiazolylsulfonyl chloride is stable at low temperature, but when subjected to room temperature or higher, it is hard to assure the stability.

On the other hand, the compounds prepared in Examples 8 and 9 are stable even at high temperature, since the residual rate thereof hardly changed when they were left at 40° C. for one day.

Therefore, the compound of formula (II), given in the present invention, is useful as an intermediate for a sulfonamide compound, since its stability is improved compared with the corresponding sulfonyl halide compound.

Formulation Example 1

The following compounds were admixed in conventional method and punched out to obtain 100 tablets each containing 5 mg of active ingredient.

| | |
|---|---|
| 3-Methyl-4-[2-[N-isobutyl-N-(5-methyl-2-furylsulfonyl)amino]-4,5-dimethylphenoxymethyl]benzoic acid | 500 mg |
| Cellulose calcium glycolate (disintegrant) | 200 mg |
| Magnesium stearate (lubricant) | 100 mg |
| Microcrystalline cellulose | 9.2 g |

Formulation Example 2

The following compounds were admixed in conventional method and solution is sterilized, filled into vials each containing 1 ml and lyophilized to obtain 100 vials each containing 5 mg of active ingredient.

| | |
|---|---|
| 3-Methyl-4-[2-[N-isobutyl-N-(5-methyl-2-furylsulfonyl)amino]-4,5-dimethylphenoxymethyl]benzoic acid | 500 mg |
| Mannit | 50 g |
| Distilled water | 100 ml |

The invention claimed is:
1. An N-phenylarylsulfonylamide compound of formula (I):

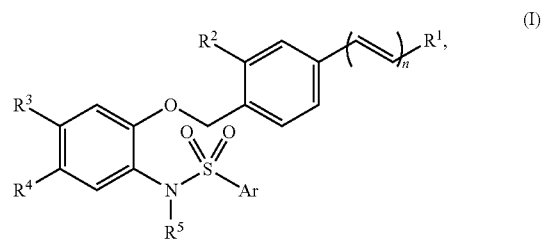

wherein $R^1$ is COOH, 5-tetrazolyl, 5-oxo-1,2,4-oxadiazolyl, $CH_2OH$ or 5-oxo-1,2,4-thiadiazolyl;
$R^2$ is hydrogen, methyl, methoxy or chloro;
$R^3$ and $R^4$ are a combination of (1) methyl and methyl, (2) methyl and chloro, (3) chloro and methyl, or (4) trifluoromethyl and hydrogen; or $R^3$ and $R^4$ are taken together with the carbon to which $R^3$ and $R^4$ are attached to form (5) cyclopentene, (6) cyclohexene or (7) benzene ring;
$R^5$ is isopropyl, isobutyl, 2-methyl-2-propenyl, cyclopropylmethyl, methyl, ethyl, propyl, 2-propenyl or 2-hydroxy-2-methylpropyl;
Ar is pyridyl or 5-methyl-2-furyl; and n is zero or 1, and when $R^1$ is 5-tetrazolyl, 5-oxo-1,2,4-oxadiazolyl or 5-oxo-1,2,4-thiadiazolyl, n is zero, an alkyl ester thereof or a non-toxic salt thereof.
2. The compound according to claim 1, wherein Ar is 5-methyl-2-furyl, 2-pyridyl or 3-pyridyl.
3. The compound according to claim 1, wherein Ar is 5-methyl-2-furyl.
4. The compound according to claim 1, which is selected from the group consisting of
(1) 4-[2-[N-isobutyl-N-(5-methyl-2-furylsulfonyl)amino]-5-trifluoromethylphenoxymethyl]cinnamic acid,
(2) 4-[2-[N-isopropyl-N-(5-methyl-2-furylsulfonyl)amino]-5-trifluoromethylphenoxymethyl]benzoic acid,
(3) 4-[2-[N-isobutyl-N-(5-methyl-2-furylsulfonyl)amino]-5-trifluoromethylphenoxymethyl]benzoic acid,
(4) 4-[2-[N-isobutyl-N-(5-methyl-2-furylsulfonyl)amino]-4-chloro-5-methylphenoxymethyl]benzoic acid,
(5) 4-[2-[N-isopropyl-N-(5-methyl-2-furylsulfonyl)amino]-4,5-dimethylphenoxymethyl]benzoic acid,
(6) 4-[2-[N-isobutyl-N-(5-methyl-2-furylsulfonyl)amino]-4,5-dimethylphenoxymethyl]benzoic acid,
(7) 3-methyl-4-[2-[N-isobutyl-N-(5-methyl-2-furylsulfonyl)amino]-4-methyl-5-chlorophenoxymethyl]benzoic acid,
(8) 3-methyl-4-[2-[N-isobutyl-N-(5-methyl-2-furylsulfonyl)amino]-4-chloro-5-methylphenoxymethyl]benzoic acid,
(9) 3-chloro-4-[2-[N-isobutyl-N-(5-methyl-2-furylsulfonyl)amino]-4-methyl-5-chlorophenoxymethyl]benzoic acid,
(10) 3-chloro-4-[2-[N-isopropyl-N-(5-methyl-2-furylsulfonyl)amino]-4-methyl-5-chlorophenoxymethyl]benzoic acid,
(11) 3-methoxy-[4-[2N-isopropyl-N-(5-methyl-2-furylsulfonyl)amino]-4-methyl-5-chlorophenoxymethyl]benzoic acid,

(12) 3-methyl-4-[2-[N-isobutyl-N-(5-methyl-2-furylsulfonyl)amino]-4,5-dimethylphenoxymethyl]benzoic acid,
(13) 3-methyl-4-[2-[N-isopropyl-N-(5-methyl-2-furylsulfonyl)amino]-4,5-dimethylphenoxymethyl]benzoic acid,
(14) 3-methoxy-442-[N-isobutyl-N-(5-methyl-2-furylsulfonyl)amino]-4,5-dimethylphenoxymethyl]benzoic acid,
(15) 3-methoxy-[4-[2N-isopropyl-N-(5-methyl-2-furylsulfonyl)amino]-4-chloro-5-methylphenoxymethyl]benzoic acid,
(16) 3-chloro-4-[2-[N-isobutyl-N-(5-methyl-2-furylsulfonyl)amino]-4,5-dimethylphenoxymethyl]benzoic acid,
(17) 3-chloro-4-[2-[N-isopropyl-N-(5-methyl-2-furylsulfonyl)amino)-4,5-dimethylphenoxymethyl]benzoic acid,
(18) 3-methyl-4-[2-[N-isobutyl-N-(5-methyl-2-furylsulfonyl)amino]-4-chloro-5-methylphenoxymethyl]cinnamic acid,
(19) 4-[2-[N-isopropyl-N-(5-methyl-2-furylsulfonyl)amino]-4-methyl-5-chlorophenoxymethyl]cinnamic acid,
(20) 4-[2-[N-isobutyl-N-(5-methyl-2-furylsulfonyl)amino]-4-methyl-5-chlorophenoxymethyl]cinnamic acid,
(21) 4-[2-[N-isopropyl-N-(5-methyl-2-furylsulfonyl)amino]-4,5-dimethylphenoxymethyl]cinnamic acid,
(22) 3-methyl-4-[2-[N-isopropyl-N-(5-methyl-2-furylsulfonyl)amino]-5-trifluoromethylphenoxymethyl]cinnamic acid,
(23) 3-methyl-4-[2-[N-isopropyl-N-(5-methyl-2-furylsulfonyl)amino)-4,5-dimethylphenoxymethyl]benzoic acid,
(24) 3-methyl-4-[2-[N-isopropyl-N-(5-methyl-2-furylsulfonyl)amino]-4,5-dimethylphenoxymethyl]cinnamic acid,
(25) 3-methyl-4-[2-[N-isobutyl-N-(5-methyl-2-furylsulfonyl)amino]-4,5-dimethylphenoxymethyl]cinnamic acid,
(26) 4-[2-[N-isobutyl-N-(5-methyl-2-furylsulfonyl)amino]-4,5-dimethylphenoxymethyl]cinnamic acid
(27) N-[4-chloro-5-methyl-2-[2-methyl-4-(5-tetrazolyl)phenylmethyloxy]phenyl]-N-isobutyl-(5-methyl-2-furyl)sulfonylamide,
(28) 3-methoxy-4-[2-[N-isobutyl-N-(5-methyl-2-furylsulfonyl)amino]-4-methyl-5-chlorophenoxymethyl]cinnamic acid,
(29) N-[4,5-dimethyl-2-[2-methyl-4-(5-tetrazolyl)phenylmethyloxy)phenyl]-N-isobutyl-(5-methyl-2-furyl)sulfonylamide,
(30) N-[4,5-dimethyl-2-[2-methyl-4-(5-tetrazolyl)phenylmethyloxy]phenyl]-N-isopropyl-(5-methyl-2-furyl)sulfonylamide,
(31) N-[4-chloro-5-methyl-2-[4-(5-tetrazolyl)phenylmethyloxy]phenyl]-N-isobutyl-(5-methyl-2-furyl)sulfonylamide,
(32) N-[4-chloro-5-methyl-2-[4-(5-oxo-1,2,4-oxadiazol-3-yl)phenylmethyloxy]phenyl]-N-isopropyl-(5-methyl-2-furyl)sulfonylamide,
(33) N-[4-chloro-5-methyl-2-[4-(5-oxo-1,2,4-oxadiazol-3-yl)phenylmethyloxy]phenyl]-N-isobutyl-(5-methyl-2-furyl)sulfonylamide,
(34) 4-[6-[N-isobutyl-N-(5-methyl-2-furylsulfonyl)amino]indan-5-yloxymethyl]benzoic acid,
(35) 4-[6-[N-isopropyl-N-(5-methyl-2-furylsulfonyl)amino]indan-5-yloxymethyl]benzoic acid,
(36) 4-[7-[N-isobutyl-N-(5-methyl-2-furylsulfonyl)amino]-1,2,3,4-tetrahydronaphthalen-6-yloxymethyl]benzoic acid,
(37) 4474N-isopropyl-N-(5-methyl-2-furylsulfonyl)amino]-1,2,3,4-tetrahydronaphthalen-6-yloxymethyl]benzoic acid,
(38) N-[4,5-dimethyl-2-[2-methyl-4-(5-oxo-1,2,4-oxadiazol-3-yl)phenylmethyloxy]phenyl]-N-isopropyl-(5-methyl-2-furyl)sulfonylamide,
(39) N-[4,5-dimethyl-2-[2-methyl-4-(5-oxo-1,2,4-oxadiazol-3-yl)phenylmethyloxy]phenyl]-N-isobutyl-(5-methyl-2-furyl)sulfonylamide,
(40) N-[4,5-dimethyl-2-[4-(5-tetrazolyl)phenylmethyloxyl]phenyl]-N-isopropyl-(5-methyl-2-furyl)sulfonylamide,
(41) N-[4,5-dimethyl-2-[4-(5-tetrazolyl)phenylmethyloxy]phenyl]-N-isobutyl-(5-methyl-2-furyl)sulfonylamide,
(42) N-[4,5-dimethyl-2-[4-(5-oxo-1,2,4-oxadiazol-3-yl)phenylmethyloxy]phenyl]-N-isobutyl-(5-methyl-2-furyl)sulfonylamide,
(43) 3-methyl-4-[2-[N-isobutyl-N-(5-methyl-2-furylsulfonyl)amino]-4-methyl-5-chlorophenoxymethyl]cinnamic acid,
(44) N-[4,5-dimethyl-2-[2-methoxy-4-(5-oxo-1,2,4-oxadiazol-3-yl)phenylmethyloxy]phenyl]-N-isobutyl-(5-methyl-2-furyl)sulfonylamide,
(45) N-[4,5-dimethyl-2-[2-methoxy-4-(5-oxo-1,2,4-oxadiazol-3-yl)phenylmethyloxy)phenyl]-N-isopropyl-(5-methyl-2-furyl)sulfonylamide,
(46) 4-[6-[N-isobutyl-N-(5-methyl-2-furylsulfonyl)amino)indan-5-yloxymethyl]cinnamic acid,
(47) 3-methyl-4-[6-[N-isobutyl-N-(5-methyl-2-furylsulfonyl)amino]indan-5-yloxymethyl]benzoic acid,
(48) 3-methyl-4-[6-[N-isobutyl-N-(5-methyl-2-furylsulfonyl)amino]indan-5-yloxymethyl]cinnamic acid,
(49) 4-(2-[4N-(2-methyl-2-propenyl)-N-(5-methyl-2-furylsulfonyl)amino)-4,5-dimethylphenoxymethyl]benzoic acid,
(50) 3-methyl-4-[6-[N-isopropyl-N-(5-methyl-2-furylsulfonyl)amino]indan-5-yloxymethyl]benzoic acid,
(51) 3-methyl-4-[6-[N-isopropyl-N-(5-methyl-2-furylsulfonyl)amino]indan-5-yloxymethyl]cinnamic acid,
(52) 4-[6-[N-isopropyl-N-(5-methyl-2-furylsulfonyl)amino)indan-5-yloxymethyl]cinnamic acid,
(53) 4-[3-(N-isobutyl-N-(5-methyl-2-furylsulfonyl)amino]-2-naphthyloxymethyl]benzoic acid,
(54) 3,5-dimethyl-[4-[2N-isobutyl-N-(5-methyl-2-furylsulfonyl)amino]-5-trifluoromethylphenoxymethyl]benzoic acid,
(55) 3-methyl-4-[6-[N-(2-methyl-2-propenyl)-N-(5-methyl-2-furylsulfonyl)amino]indan-5-yloxymethyl]benzoic acid,
(56) 4-[6-[N-cyclopropylmethyl-N-(5-methyl-2-furylsulfonyl)amino)indan-5-yloxymethyl]-3-methylbenzoic acid,
(57) 4-[6-[N-isobutyl-N-(5-methyl-2-furylsulfonyl)amino]indan-5-yloxymethyl]-3-methylbenzylalcohol,
(58) 3-methyl-4-[6-[N-methyl-N-(5-methyl-2-furylsulfonyl)amino]indan-5-yloxymethyl]benzoic acid,
(59) 4-[6-[N-ethyl-N-(5-methyl-2-furylsulfonyl)amino]indan-5-yloxymethyl]-3-methylbenzoic acid,
(60) 4-[6-[N-methyl-N-(5-methyl-2-furylsulfonyl)amino]indan-5-yloxymethyl]cinnamic acid,
(61) 4-[6-[N-ethyl-N-(5-methyl-2-furylsulfonyl)amino]indan-5-yloxymethyl)cinnamic acid,

(62) 4-[6-[N-propyl-N-(5-methyl-2-furylsulfonyl)amino]indan-5-yloxymethyl)cinnamic acid,
(63) 4-[4,5-dimethyl-2-[N-(2-methyl-2-propenyl)-N-(5-methyl-2-furylsulfonyl)amino]phenoxymethyl]-3-methylbenzoic acid,
(64) 4-[6-N-(2-methyl-2-propenyl)-N-(5-methyl-2-furylsulfonyl)amino]indan-5-yloxymethyl]cinnamic acid,
(65) 4-[6-[N-cyclopropylmethyl-N-(5-methyl-2-furylsulfonyl)amino]indan-5-yloxymethyl]cinnamic acid,
(66) 4-[6-[N-(2-propenyl)-N-(5-methyl-2-furylsulfonyl)amino]indan-5-yloxymethyl]cinnamic acid,
(67) 3-methyl-4-[6-[N-propyl-N-(5-methyl-2-furylsulfonyl)amino]indan-5-yloxymethyl)benzoic acid,
(68) 3-methyl-4-[6-[N-(2-propenyl)-N-(5-methyl-2-furylsulfonyl)amino]indan-5-yloxymethyl]benzoic acid,
(69) 4-[4,5-dimethyl-2-[N-methyl-N-(5-methyl-2-furylsulfonyl)amino]phenoxymethyl]benzoic acid,
(70) 4-[4,5-dimethyl-2-[N-ethyl-N-(5-methyl-2-furylsulfonyl)amino]phenoxymethyl]benzoic acid,
(71) 4-[4,5-dimethyl-2-[N-(5-methyl-2-furylsulfonyl)-N-propylamino]phenoxymethyl]benzoic acid,
(72) 4-[3-[N-isopropyl-N-(5-methyl-2-furylsulfonyl)amino]naphthalen-2-yloxymethyl]-3-methylbenzoic acid,
(73) 4-[3-[N-isobutyl-N-(5-methyl-2-furylsulfonyl)amino]naphthalen-2-yloxymethyl]-3-methylbenzoic acid,
(74) 4-[3-[N-isopropyl-N-(5-methyl-2-furylsulfonyl)amino]naphthalen-2-yloxymethyl]cinnamic acid,
(75) 4-[3-[N-isobutyl-N-(5-methyl-2-furylsulfonyl)amino]naphthalen-2-yloxymethyl]cinnamic acid,
(76) 3-methyl-4-[3-N-isopropyl-N-(5-methyl-2-furylsulfonyl)amino)naphthalen-2-yloxymethyl]cinnamic acid,
(77) 3-methyl-4-[3-[N-isobutyl-N-(5-methyl-2-furylsulfonyl)amino]naphthalen-2-yloxymethyl]cinnamic acid,
(78) 4-[4,5-dimethyl-2-[N-[(5-methyl-2-furyl)sulfonyl]-N-2-propenylamino]phenoxymethyl]benzoic acid,
(79) 4-[4,5-dimethyl-2-[N-methyl-N-(5-methyl-2-furylsulfonyl)amino]phenoxymethyl]-3-methylbenzoic acid,
(80) 4-[4,5-dimethyl-2-[N-ethyl-N-(5-methyl-2-furylsulfonyl)amino]phenoxymethyl]-3-methylbenzoic acid,
(81) 4-[4,5-dimethyl-2-[N-(5-methyl-2-furylsulfonyl)-N-propylamino]phenoxymethyl]-3-methylbenzoic acid,
(82) 4-[4,5-dimethyl-2-[N-(5-methyl-2-furylsulfonyl)-N-(2-propenyl)amino]phenoxymethyl]-3-methylbenzoic acid,
(83) 4-[4,5-dimethyl-2-[N-(2-hydroxy-2-methylpropyl)-N-(5-methyl-2-furylsulfonyl)amino]phenoxymethyl]-3-methylbenzoic acid,
(84) 4-[6-[N-(2-hydroxy-2-methylpropyl)-N-(5-methyl-2-furylsulfonyl)amino]indan-5-yloxymethyl]-3-methylbenzoic acid,
(85) 4-[4,5-dimethyl-2-[N-cyclopropylmethyl-N-(5-methyl-2-furylsulfonyl)amino]phenoxymethyl]benzoic acid,
(86) 4-[4,5-dimethyl-2-[N-(2-hydroxy-2-methylpropyl)-N-(5-methyl-2-furylsulfonyl)amino]phenoxymethyl]benzoic acid,
(87) 4-[6-[N-(2-hydroxy-2-methylpropyl)-N-(5-methyl-2-furylsulfonyl)amino]indan-5-yloxymethyl]cinnamic acid, and
(88) 4-[4,5-dimethyl-2-[N-cyclopropylmethyl-N-(5-methyl-2-furylsulfonyl)amino)phenoxymethyl]-3-methylbenzoic acid.

5. The compound according to claim 1, wherein Ar is 2-pyridyl or 3-pyridyl.

6. The compound according to claim 1, which is selected from the group consisting of
(1) 4-[2-[N-isobutyl-N-(2-pyridylsulfonyl)amino]-5-trifluoromethylphenoxymethyl]cinnamic acid,
(2) 4-[2-[N-isobutyl-N-(3-pyridylsulfonyl)amino]-5-trifluoromethylphenoxymethyl]benzoic acid,
(3) 3-chloro-4-[2-[N-isopropyl-N-(2-pyridylsulfonyl)amino]-4-chloro-5-methylphenoxymethyl]benzoic acid,
(4) 3-methyl-4-[2-[N-isobutyl-N-(2-pyridylsulfonyl)amino]-4-chloro-5-methylphenoxymethyl]benzoic acid,
(5) 3-methyl-4-[2-[N-isobutyl-N-(3-pyridylsulfonyl)amino]-4-chloro-5-methylphenoxymethyl]benzoic acid,
(6) 3-methyl-4-[2-[N-isobutyl-N-(2-pyridylsulfonyl)amino]-4-methyl-5-chlorophenoxymethyl]benzoic acid,
(7) N-[4-trifluoromethyl-2-[4-(5-tetrazolyl)phenylmethyloxy]phenyl]-N-isopropyl-3-pyridylsulfonylamide,
(8) N-[4-trifluoromethyl-2-[4-(5-tetrazoyl)phenylmethyloxy]phenyl]-N-isobutyl-3-pyridylsulfonylamide,
(9) 4-[2-[N-isobutyl-N-(3-pyridylsulfonyl)amino]-4-methyl-5-chlorophenoxymethyl]benzoic acid,
(10) 3-chloro-4-[2-[N-isobutyl-N-(3-pyridylsulfonyl)amino]-4-methyl-5-chlorophenoxymethyl]benzoic acid,
(11) 3-methyl-4-[2-[N-isobutyl-N-(2-pyridylsulfonyl)amino)-5-trifluoromethylphenoxymethyl]cinnamic acid,
(12) 3-methoxy-4-[2-[N-isobutyl-N-(2-pyridylsulfonyl)amino]-4,5-dimethylphenoxymethyl]benzoic acid,
(13) 3-methoxy-4-[2-[N-isobutyl-N-(3-pyridylsulfonyl)amino]-4,5-dimethylphenoxymethyl]benzoic acid,
(14) 3-methyl-4-[2-[N-isobutyl-N-(3-pyridylsulfonyl)amino]-4,5-dimethylphenoxymethyl]benzoic acid,
(15) 3-methyl-4-[2-[N-isobutyl-N-(2-pyridylsulfonyl)amino]-4,5-dimethylphenoxymethyl]benzoic acid,
(16) N-[4-trifluoromethyl-2-[4-(5-tetrazolyl)phenylmethyloxy)phenyl]-N-isopropyl-2-pyridylsulfonylamide,
(17) N-[4-trifluoromethyl-2-[4-(5-tetrazolyl)phenylmethyloxy]phenyl]-N-isobutyl-2-pyridylsulfonylamide,
(18) 3-methyl-4-[2-[N-isobutyl-N-(3-pyridylsulfonyl)amino]-4-methyl-5-chlorophenoxymethyl]benzoic acid,
(19) 4-[2-[N-isobutyl-N-(2-pyridylsulfonyl)amino]-4,5-dimethylphenoxymethyl]benzoic acid,
(20) N-[4-trifluoromethyl-2-[4-(5-oxo-1,2,4-oxadiazol-3-yl)phenylmethyloxy]phenyl]-N-isobutyl-2-pyridylsulfonylamide,
(21) 4-[2-[N-isopropyl-N-(2-pyridylsulfonyl)amino]-4-methyl-5-chlorophenoxymethyl]cinnamic acid,
(22) 3-methyl-4-[2-[N-(2-pyridylsulfonyl)amino]-4-methyl-5-chlorophenoxymethyl]cinnamic acid,
(23) 3-methyl-4-[2-[N-isobutyl-N-(2-pyridylsulfonyl)amino]-4,5-dimethylphenoxymethyl]cinnamic acid,
(24) 4-[2-[N-isobutyl-N-(3-pyridylsulfonyl)amino]-4,5-dimethylphenoxymethyl]cinnamic acid,
(25) 3-methyl-4-[2-[N-isobutyl-N-(3-pyridylsulfonyl)amino]-4,5-dimethylphenoxymethyl]cinnamic acid,
(26) N-[4-trifluoromethyl-2-[2-methyl-4-(5-tetrazolyl)phenylmethyloxy]phenyl]-N-isopropyl-2-pyridylsulfonylamide,
(27) 3-chloro-4-[2-[N-isobutyl-N-(3-pyridylsulfonyl)amino]-4,5-dimethylphenoxymethyl]cinnamic acid,

(28) N-[4,5-dimethyl-2-[2-methyl-4-(5-tetrazolyl)phenylmethyloxy]phenyl]-N-isobutyl-2-pyridylsulfonylamide,
(29) N-[4,5-dimethyl-2-[2-methyl-4-(5-tetrazolyl)phenylmethyloxy]phenyl]-N-isobutyl-3-pyridylsulfonylamide,
(30) N-[4-chloro-5-methyl-2-[4-(5-tetrazolyl)phenylmethyloxy]phenyl]-N-isobutyl-3-pyridylsulfonylamide,
(31) N-[4,5-dimethyl-2-[2-chloro-4-(5-tetrazolyl)phenylmethyloxy]phenyl]-N-isobutyl-2-pyridylsulfonylamide,
(32) N-[4,5-dimethyl-2-[2-chloro-4-(5-tetrazolyl)phenylmethyloxy]phenyl]-N-isopropyl-3-pyridylsulfonylamide,
(33) N-[4,5-dimethyl-2-[2-chloro-4-(5-tetrazolyl)phenylmethyloxy]phenyl]-N-isobutyl-3-pyridylsulfonylamide,
(34) 3-methyl-4-[2-[N-isobutyl-N-(3-pyridylsulfonyl)amino]-4-chloro-5-methylphenoxymethyl]cinnamic acid,
(35) N-[4,5-dimethyl-2-[4-(5-tetrazolyl)phenylmethyloxy]phenyl]-N-isopropyl-2-pyridylsulfonylamide,
(36) N-[4,5-dimethyl-2-[4-(5-tetrazolyl)phenylmethyloxy]phenyl]-N-isobutyl-2-pyridylsulfonylamide,
(37) N-[4,5-dimethyl-2-[4-(5-tetrazolyl)phenylmethyloxy]phenyl]-N-isobutyl-3-pyridylsulfonylamide,
(38) 3-chloro-4-[2-N-isobutyl-N-(3-pyridylsulfonyl)amino]-5-trifluoromethylphenoxymethyl]cinnamic acid,
(39) N-[4-chloro-5-methyl-2-[2-methyl-4-(5-tetrazolyl)phenylmethyloxy]phenyl]-N-isopropyl-2-pyridylsulfonylamide,
(40) N-[4-chloro-5-methyl-2-[2-methyl-4-(5-tetrazolyl)phenylmethyloxy]phenyl]-N-isobutyl-2-pyridylsulfonylamide,
(41) N-[4,5-dimethyl-2-[2-methyl-4-(5-oxo-1,2,4-oxadiazol-3-yl)phenylmethyloxy]phenyl]-N-isopropyl-2-pyridylsulfonylamide,
(42) N-[4,5-dimethyl-2-[2-methyl-4-(5-oxo-1,2,4-oxadiazol-3-yl)phenylmethyloxy]phenyl]-N-isobutyl-3-pyridylsulfonylamide,
(43) N-[4,5-dimethyl-2-[2-methoxy-4-(5-tetrazolyl)phenylmethyloxy]phenyl]-N-isobutyl-2-pyridylsulfonylamide,
(44) N-[4,5-dimethyl-2-[2-methoxy-4-(5-tetrazolyl)phenylmethyloxy]phenyl)-N-isopropyl-2-pyridylsulfonylamide,
(45) N-[4,5-dimethyl-2-[2-methoxy-4-(5-oxo-1,2,4-oxadiazol-3-yl)phenylmethyloxy]phenyl]-N-isobutyl-2-pyridylsulfonylamide, and
(46) N-[4,5-dimethyl-2-[2-methoxy-4-(5-oxo-1,2,4-oxadiazol-3-yl)phenylmethyloxy]phenyl]-N-isopropyl-2-pyridylsulfonylamide.

7. An antagonist of EP 1 receptor which is a prostaglandin E2 receptor subtype, wherein the antagonist is an N-phenylarylsulfonylamide compound of formula (I):

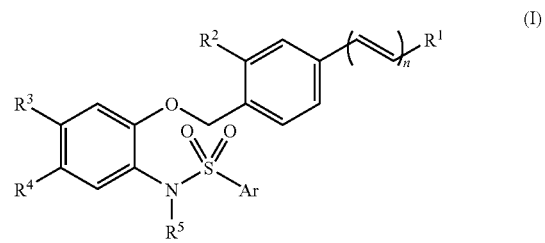

wherein $R^1$ is COOH, 5-tetrazolyl, 5-oxo-1,2,4-oxadiazolyl, $CH_2OH$ or 5-oxo-1,2,4-thiadiazolyl;
$R^2$ is hydrogen, methyl, methoxy or chloro;
$R^3$ and $R^4$ are a combination of (1) methyl and methyl, (2) methyl and chloro, (3) chloro and methyl, or (4) trifluoromethyl and hydrogen; or $R^3$ and $R^4$ are taken together with the carbon to which $R^3$ and $R^4$ are attached to form (5) cyclopentene, (6) cyclohexene or (7) benzene ring;
$R^5$ is isopropyl, isobutyl, 2-methyl-2-propenyl, cyclopropylmethyl, methyl, ethyl, propyl, 2-propenyl or 2-hydroxy-2-methylpropyl;
Ar is pyridyl or 5-methyl-2-furyl; and n is zero or 1, and when $R^1$ is 5-tetrazolyl, 5-oxo-1,2,4-oxadiazolyl or 5-oxo-1,2,4-thiadiazolyl, n is zero, an ester thereof or a non-toxic salt thereof as an active ingredient.

8. A pharmaceutical composition, which comprises the N-phenylarylsulfonylamide compound of formula (I):

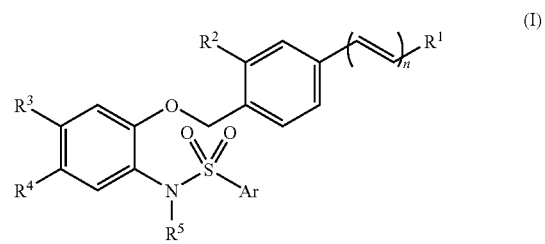

wherein $R^1$ is COOH, 5-tetrazolyl, 5-oxo-1,2,4-oxadiazolyl, $CH_2OH$ or 5-oxo-1,2,4-thiadiazolyl;
$R^2$ is hydrogen, methyl, methoxy or chloro;
$R^3$ and $R^4$ are a combination of (1) methyl and methyl, (2) methyl and chloro, (3) chloro and methyl, or (4) trifluoromethyl and hydrogen; or $R^3$ and $R^4$ are taken together with the carbon to which $R^3$ and $R^4$ are attached to form (5) cyclopentene, (6) cyclohexene or (7) benzene ring;
$R^5$ is isopropyl, isobutyl, 2-methyl-2-propenyl, cyclopropylmethyl, methyl, ethyl, propyl, 2-propenyl or 2-hydroxy-2-methylpropyl;
Ar is pyridyl or 5-methyl-2-furyl; and n is zero or 1, and when $R^1$ is 5-tetrazolyl, 5-oxo-1,2,4-oxadiazolyl or 5-oxo-1,2,4-thiadiazolyl, n is zero, an ester thereof or a non-toxic salt thereof as an active ingredient.

* * * * *